(12) United States Patent
Ziemann et al.

(10) Patent No.: US 9,371,374 B2
(45) Date of Patent: Jun. 21, 2016

(54) HCV CORE LIPID BINDING DOMAIN MONOCLONAL ANTIBODIES

(71) Applicant: Abbott Laboratories, Abbott Park, IL (US)

(72) Inventors: Robert Ziemann, Abbott Park, IL (US); April Ahlberg, Abbott Park, IL (US); David Hawksworth, Abbott Park, IL (US); Bryan Tieman, Abbott Park, IL (US); A. Scott Muerhoff, Abbott Park, IL (US); Christopher Marohnic, Abbott Park, IL (US); Kathy Otis, Abbott Park, IL (US)

(73) Assignee: ABBOTT LABORATORIES, Abbot Park, IL (US)

( * ) Notice: Subject to any disclaimer, the term of this patent is extended or adjusted under 35 U.S.C. 154(b) by 0 days.

(21) Appl. No.: 14/138,991

(22) Filed: Dec. 23, 2013

(65) Prior Publication Data

US 2014/0272931 A1    Sep. 18, 2014

Related U.S. Application Data

(60) Provisional application No. 61/783,529, filed on Mar. 14, 2013.

(51) Int. Cl.
G01N 33/569 (2006.01)
C07K 16/10 (2006.01)
G01N 33/576 (2006.01)

(52) U.S. Cl.
CPC .......... *C07K 16/109* (2013.01); *G01N 33/5767* (2013.01); *C07K 2317/34* (2013.01); *C07K 2317/92* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,338,397 A | 7/1982 | Gilbert et al. |
| 4,425,437 A | 1/1984 | Riggs |
| 4,431,739 A | 2/1984 | Riggs |
| 4,526,938 A | 7/1985 | Churchill |
| 4,554,101 A | 11/1985 | Hopp |
| 4,816,397 A | 3/1989 | Boss |
| 4,816,567 A | 3/1989 | Cabilly |
| 4,880,078 A | 11/1989 | Inoue et al. |
| 4,946,778 A | 8/1990 | Ladner |
| 5,006,309 A | 4/1991 | Khalil |
| 5,063,081 A | 11/1991 | Cozzette |
| 5,089,424 A | 2/1992 | Khalil |
| 5,128,326 A | 7/1992 | Balazs et al. |
| 5,135,875 A | 8/1992 | Meucci |
| 5,223,409 A | 6/1993 | Ladner |
| 5,225,539 A | 7/1993 | Winter |
| 5,241,070 A | 8/1993 | Law |
| 5,242,828 A | 9/1993 | Bergstrom |
| 5,258,498 A | 11/1993 | Huston |
| 5,290,540 A | 3/1994 | Prince et al. |
| 5,294,404 A | 3/1994 | Grandone |
| 5,350,671 A | 9/1994 | Houghton et al. |
| 5,352,803 A | 10/1994 | Mattingly |
| 5,359,093 A | 10/1994 | Adamczyk |
| 5,399,346 A | 3/1995 | Anderson et al. |
| 5,403,484 A | 4/1995 | Ladner |
| 5,427,908 A | 6/1995 | Dower |
| 5,468,646 A | 11/1995 | Mattingly |
| 5,496,925 A | 3/1996 | Mattingly |
| 5,516,637 A | 5/1996 | Huang |
| 5,530,101 A | 6/1996 | Queen |
| 5,543,524 A | 8/1996 | Mattingly |
| 5,565,332 A | 10/1996 | Hoogenboom |
| 5,565,352 A | 10/1996 | Hochstrasser |
| 5,571,698 A | 11/1996 | Ladner |
| 5,573,904 A | 11/1996 | Mattingly |
| 5,580,717 A | 12/1996 | Dower |
| 5,585,089 A | 12/1996 | Queen |
| 5,593,896 A | 1/1997 | Adamczyk |
| 5,624,821 A | 4/1997 | Winter |
| 5,627,052 A | 5/1997 | Schrader |
| 5,641,870 A | 6/1997 | Rinderknecht |
| 5,648,260 A | 7/1997 | Winter |
| 5,658,727 A | 8/1997 | Barbas |
| 5,679,377 A | 10/1997 | Bernstein et al. |
| 5,688,688 A | 11/1997 | Luciw et al. |
| 5,693,762 A | 12/1997 | Queen |
| 5,698,426 A | 12/1997 | Huse |
| 5,705,330 A | 1/1998 | Shah et al. |
| 5,714,350 A | 2/1998 | Co et al. |
| 5,714,352 A | 2/1998 | Jakobovits |
| 5,723,323 A | 3/1998 | Kauffman |

(Continued)

FOREIGN PATENT DOCUMENTS

| | | |
|---|---|---|
| CA | 2450710 | 1/2003 |
| EP | 086631 | 8/1983 |

(Continued)

OTHER PUBLICATIONS

Shavinskaya et al. (The Journal of Biological Chemistry 2007, p. 37158-37169).*
Kuo et al., "An assay for circulating antibodies to a major etiologic virus of human non-A, non-B hepatitis," Science, 244(4902):362-364 (1989).
Kyte et al., "A simple method for displaying the hydropathic character of a protein," J. Mol. Biol., 157(1):105-132 (1982).
Lee et al., "Increased detection of hepatitis C virus infection in commercial plasma donors by a third-generation screening assay," Transfusion, 35(10):845-849 (1995).
Little et al., "Of mice and men: hybridoma and recombinant antibodies," Immunol. Today, 21(8):364-370 (2000).
MacCallum et al., "Antibody-antigen interactions: contact analysis and binding site topography," J. Mol. Biol., 262(5):732-745 (1996).

(Continued)

*Primary Examiner* — Agnieszka Boesen
(74) *Attorney, Agent, or Firm* — Irene M. Reininger

(57) ABSTRACT

The present invention relates to monoclonal antibodies for the detection of HCV antigen. More specifically, the invention describes antibodies against HCV core antigen lipid binding domain and immunoassay methods, kits and compositions for use in detecting HCV infection.

16 Claims, 3 Drawing Sheets

(56) References Cited

U.S. PATENT DOCUMENTS

Figure 1:

| | | |
|---|---|---|
| 5,733,743 A | 3/1998 | Johnson |
| 5,750,753 A | 5/1998 | Kimae |
| 5,753,430 A * | 5/1998 | Mehta et al. ............... 435/5 |
| 5,763,192 A | 6/1998 | Kauffman |
| 5,766,886 A | 6/1998 | Studnicka |
| 5,780,225 A | 7/1998 | Wigler |
| 5,783,699 A | 7/1998 | Mattingly |
| 5,795,784 A | 8/1998 | Arnquist et al. |
| 5,807,715 A | 9/1998 | Morrison et al. |
| 5,814,476 A | 9/1998 | Kauffman |
| 5,817,483 A | 10/1998 | Kauffman |
| 5,821,047 A | 10/1998 | Garrard |
| 5,824,514 A | 10/1998 | Kauffman |
| 5,855,913 A | 1/1999 | Hanes et al. |
| 5,856,194 A | 1/1999 | Arnquist et al. |
| 5,874,064 A | 2/1999 | Edwards et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hori |
| 5,934,272 A | 8/1999 | Lloyd et al. |
| 5,939,598 A | 8/1999 | Kucherlapati |
| 5,969,108 A | 10/1999 | McCafferty |
| 5,976,862 A | 11/1999 | Kauffman |
| 5,985,309 A | 11/1999 | Edwards et al. |
| 5,985,320 A | 11/1999 | Edwards et al. |
| 5,985,615 A | 11/1999 | Jakobovits |
| 5,989,463 A | 11/1999 | Tracy et al. |
| 5,989,905 A | 11/1999 | Houghton et al. |
| 5,998,209 A | 12/1999 | Jokobovits |
| 6,019,968 A | 2/2000 | Platz et al. |
| 6,075,181 A | 6/2000 | Kucherlapati |
| 6,091,001 A | 7/2000 | Jakobovits |
| 6,096,319 A | 8/2000 | Seidel |
| 6,114,598 A | 9/2000 | Kucherlapati |
| 6,130,364 A | 10/2000 | Jakobovits |
| 6,172,189 B1 | 1/2001 | Devare |
| 6,180,370 B1 | 1/2001 | Queen |
| 6,194,222 B1 | 2/2001 | Buechler et al. |
| 6,204,023 B1 | 3/2001 | Robinson |
| 6,225,047 B1 | 5/2001 | Hutchens |
| 6,306,579 B1 | 10/2001 | Seidel |
| 6,329,209 B1 | 12/2001 | Wagner |
| 6,350,861 B1 | 2/2002 | Co et al. |
| 6,555,114 B1 * | 4/2003 | Leroux-Roels et al. ... 424/228.1 |
| 6,623,921 B2 | 9/2003 | Aoyagi |
| 6,699,658 B1 | 3/2004 | Wittrup |
| 6,727,092 B2 | 4/2004 | Shah |
| 6,846,905 B2 | 1/2005 | Hackett et al. |
| 6,914,128 B1 | 7/2005 | Salfeld |
| 7,285,418 B2 | 10/2007 | Katrukha et al. |
| 7,371,383 B2 | 5/2008 | Reed et al. |
| 7,462,354 B2 | 12/2008 | Sette et al. |
| 7,521,542 B2 | 4/2009 | Johnson et al. |
| 7,612,181 B2 | 11/2009 | Wu |
| 7,858,752 B2 | 12/2010 | Tu |
| 7,888,004 B2 | 2/2011 | Coit et al. |
| 8,030,026 B2 | 10/2011 | Brophy et al. |
| 8,193,318 B2 | 6/2012 | Koenig et al. |
| 2002/0037868 A1 | 3/2002 | Budkowska |
| 2002/0137134 A1 | 9/2002 | Gerngross |
| 2003/0170881 A1 | 9/2003 | Davis |
| 2003/0186374 A1 | 10/2003 | Hufton |
| 2004/0018577 A1 | 1/2004 | Campbell |
| 2004/0018590 A1 | 1/2004 | Gerngross et al. |
| 2005/0054078 A1 | 3/2005 | Miller |
| 2006/0018897 A1 | 1/2006 | Lee et al. |
| 2006/0160164 A1 | 7/2006 | Miller |
| 2008/0020401 A1 | 1/2008 | Grenier |
| 2008/0113339 A1 | 5/2008 | Rodgers et al. |
| 2008/0248493 A1 | 10/2008 | Mattingly |
| 2010/0297607 A1 | 11/2010 | Zheng |
| 2012/0009196 A1 | 1/2012 | Muerhoff |
| 2014/0272932 A1 | 9/2014 | Muerhoff |
| 2014/0272933 A1 | 9/2014 | Dawson et al. |
| 2015/0024457 A1 | 1/2015 | Brophy |

FOREIGN PATENT DOCUMENTS

| | | |
|---|---|---|
| EP | 0229246 | 7/1987 |
| EP | 0239400 | 9/1987 |
| EP | 0424634 | 5/1991 |
| EP | 0425633 | 5/1991 |
| EP | 0471293 | 2/1992 |
| EP | 0519596 | 12/1992 |
| EP | 0592106 | 4/1994 |
| EP | 1176195 | 1/2002 |
| EP | 2014302 | 1/2009 |
| FR | 2779526 | 12/1999 |
| WO | 90/01443 | 2/1990 |
| WO | 90/05144 | 5/1990 |
| WO | 90/05370 | 5/1990 |
| WO | 90/14424 | 11/1990 |
| WO | 90/14430 | 11/1990 |
| WO | 90/14443 | 11/1990 |
| WO | WO 91/05548 | 5/1991 |
| WO | 91/09967 | 7/1991 |
| WO | 91/10741 | 7/1991 |
| WO | WO 91/09630 | 7/1991 |
| WO | 91/17271 | 11/1991 |
| WO | 92/01047 | 1/1992 |
| WO | 92/02551 | 2/1992 |
| WO | 92/03461 | 3/1992 |
| WO | 92/09690 | 6/1992 |
| WO | 92/11272 | 7/1992 |
| WO | 92/15679 | 9/1992 |
| WO | 92/18619 | 10/1992 |
| WO | 92/20791 | 11/1992 |
| WO | WO 92/19244 | 11/1992 |
| WO | 92/22324 | 12/1992 |
| WO | 93/01288 | 1/1993 |
| WO | WO 93/00365 | 1/1993 |
| WO | 93/06213 | 4/1993 |
| WO | 93/11236 | 6/1993 |
| WO | WO 94/01778 | 1/1994 |
| WO | 94/02602 | 2/1994 |
| WO | 94/18219 | 8/1994 |
| WO | 95/15982 | 6/1995 |
| WO | 95/20401 | 8/1995 |
| WO | WO 96/20698 | 7/1996 |
| WO | 96/33735 | 10/1996 |
| WO | 96/34096 | 10/1996 |
| WO | 97/20032 | 6/1997 |
| WO | 97/29131 | 8/1997 |
| WO | WO 97/32572 | 9/1997 |
| WO | WO 97/44013 | 11/1997 |
| WO | 98/16654 | 4/1998 |
| WO | 98/24893 | 6/1998 |
| WO | 98/31700 | 7/1998 |
| WO | WO 98/31346 | 7/1998 |
| WO | 98/50433 | 11/1998 |
| WO | 99/06834 | 2/1999 |
| WO | WO 99/15154 | 4/1999 |
| WO | WO 99/20253 | 4/1999 |
| WO | 99/45031 | 9/1999 |
| WO | 99/51773 | 10/1999 |
| WO | 99/53049 | 10/1999 |
| WO | WO 99/51773 | 10/1999 |
| WO | WO 99/54342 | 10/1999 |
| WO | WO 99/66903 | 12/1999 |
| WO | 00/09560 | 2/2000 |
| WO | WO 00/07023 | 2/2000 |
| WO | 00/37504 | 6/2000 |
| WO | 00/56772 | 9/2000 |
| WO | 00/56934 | 9/2000 |
| WO | WO 00/56934 | 9/2000 |
| WO | WO 01/38360 | 5/2001 |
| WO | 01/83525 | 11/2001 |
| WO | WO 02/072636 | 9/2002 |
| WO | WO 03/016466 | 2/2003 |
| WO | WO 03/035835 | 5/2003 |
| WO | WO 03/086458 | 10/2003 |

(56) References Cited

FOREIGN PATENT DOCUMENTS

| WO | WO 2005/000901 | 1/2005 |
|---|---|---|
| WO | WO 2005/010049 | 2/2005 |
| WO | WO 2005/035575 | 4/2005 |
| WO | WO 2005/068503 | 7/2005 |
| WO | WO 2005/100584 | 10/2005 |
| WO | WO 2008/028686 | 3/2008 |
| WO | WO 2008/070727 | 6/2008 |
| WO | WO 2008/120202 | 10/2008 |
| WO | WO 2010/060186 | 6/2010 |

OTHER PUBLICATIONS

Marchalonis et al., "Evolutionary factors in the emergence of the combinatorial germline antibody repertoire," Adv. Exp. Med. Biol., 484:13-30 (2001).
Marks et al., "By-passing immunization: building high affinity human antibodies by chain shuffling," Biotechnology (NY), 10(7):779-783 (1992).
Mattingly, "Chemiluminescent 10-methyl-acridinium-9-(N-sulphonylcarboxamide) salts. Synthesis and kinetics of light emission," J. Biolumin. Chemilumin., 6(2):107-114 (1991).
McCafferty et al., "Phage antibodies: filamentous phage displaying antibody variable domains," Nature, 348(6301):552-554 (1990).
McCapra et al., "Chemiluminescence Involving Peroxide Decompositions," Photochemistry and Photobiology, 4:1111-1121 (1965).
Mendez et al., "Functional transplant of megabase human immunoglobulin loci recapitulates human antibody response in mice," Nat. Genet., 15(2):146-156 (1997).
Mimms et al., "Specificity of anti-HCV ELISA assessed by reactivity to three immunodominant HCV regions," Lancet, 336(8730):1590-1591 (1990).
Morota et al., "A new sensitive and automated chemiluminescent microparticle immunoassay for quantitative determination of hepatitis C virus core antigen," J. Virol. Methods, 157(1):8-14 (2009).
Morrison, "Transfectomas provide novel chimeric antibodies," Science, 229(4719):1202-1207 (1985).
Mullinax et al., "Expression of a heterodimeric Fab antibody protein in one cloning step," Biotechniques, 12(6):864-869 (1992).
Oellerich, "Enzyme-immunoassay: a review," J. Clin. Chem. Clin. Biochem., 22(12):895-904 (1984).
Oi et al., "Chimeric Antibodies," BioTechniques, 4(3):214 (1986).
Padlan et al., "A possible procedure for reducing the immunogenicity of antibody variable domains while preserving their ligand-binding properties," Mol. Immunol., 28(4-5):489-498 (1991).
Panina-Bordignon et al., "Universally immunogenic T cell epitopes: promiscuous binding to human MHC class II and promiscuous recognition by T cells," Eur. J. Immunol., 19(12):2237-2242 (1989).
Persic et al., "An integrated vector system for the eukaryotic expression of antibodies or their fragments after selection from phage display libraries," Gene, 187(1):9-18 (1997).
Poljak, "Production and structure of diabodies," Structure, 2(12):1121-1123 (1994).
Presta et al., "Humanization of an antibody directed against IgE," J. Immunol., 151(5):2623-2632 (1993).
Razavi et al., "Stable and versatile active acridinium esters I," Luminescence, 15(4):239-244 (2000).
Razavi et al., "Stable and versatile active acridinium esters II," Luminescence, 15(4):245-249 (2000).
Riechmann et al., "Reshaping human antibodies for therapy," Nature, 332(6162):323-327 (1988).
Sawai et al., "Direct production of the Fab fragment derived from the sperm immobilizing antibody using polymerase chain reaction and cDNA expression vectors," Am. J. Reprod. Immunol., 34(1):26-34 (1995).
Schier et al., "Identification of functional and structural amino-acid residues by parsimonious mutagenesis," Gene, 169 (2):147-155 (1996).
Seligmann et al., Immunochemical Study of a Human Myeloma IgG1 Half Molecule (*), Ann. Immunol., 129:855-870 (1978).

Shapiro et al., "DNA target motifs of somatic mutagenesis in antibody genes," Crit. Rev. Immunol., 22(3):183-200 (2002).
Sims et al., "A humanized CD18 antibody can block function without cell destruction," J. Immunol., 151(4):2296-2308 (1993).
Skerra et al., "Assembly of a functional immunoglobulin Fv fragment in *Escherichia coli*," Science, 240 (4855):1038-1041 (1988).
Studnicka et al., "Human-engineered monoclonal antibodies retain full specific binding activity by preserving non-CDR complementarity-modulating residues," Protein Eng., 7(6):805-814 (1994).
Tamura et al., "MEGA5: molecular evolutionary genetics analysis using maximum likelihood, evolutionary distance, and maximum parsimony methods," Mol. Biol. Evol., 28(10):2731-2739 (2011).
Taylor et al., "A transgenic mouse that expresses a diversity of human sequence heavy and light chain immunoglobulins," Nucleic Acids Res., 20(23):6287-6295 (1992).
Thies et al., "Folding and association of the antibody domain CH3: prolyl isomerization preceeds dimerization," J. Mol. Biol., 293(1):67-79 (1999).
Thompson et al., "CLUSTAL W: improving the sensitivity of progressive multiple sequence alignment through sequence weighting, position-specific gap penalties and weight matrix choice," Nucleic Acids Res., 22(22):4673-4680 (1994).
Verhoeyen et al., "Reshaping human antibodies: grafting an antilysozyme activity," Science, 239(4847):1534-1536 (1988).
Ward et al., "Binding activities of a repertoire of single immunoglobulin variable domains secreted from *Escherichia coli*," Nature, 341(6242):544-546 (1989).
West et al., "Crystal structure and immunoglobulin G binding properties of the human major histocompatibility complex-related Fc receptor(,)," Biochemistry, 39(32):9698-9708 (2000).
Yelton et al., "Affinity maturation of the BR96 anti-carcinoma antibody by codon-based mutagenesis," J. Immunol., 155(4):1994-2004 (1995).
Zapata et al., "Engineering linear F(ab')2 fragments for efficient production in *Escherichia coli* and enhanced antiproliferative activity," Protein Eng., 8(10):1057-1062 (1995).
Patent Cooperation Treaty, Notification of the International Search Report and the Written Opinion of the International Searching Authority, or the Declaration, in International application No. PCT/US13/77499, dated May 20, 2014 (21 pages).
Hope et al. Sequence motifs required for lipid droplet association and protein stability are 1, 6-9, and 19 unique to the hepatitis C virus core protein. J Gen Virol. 2000, vol. 81(Pt 8), p. 1913-25. Abstract; p. 1914, Fig 1; p. 1915, col. 2, last para and Table 1; p. 1916, col. 1 and Fig 2; p. 1917, col. 2, top and middle para; p. 1918, col. 1, para 1; and p. 1919, Fig 3 (13 pages).
Ferns at al. Characterisation of a panel of monoclonal antibodies raised against recombinant 1, 6-9, and 19 HCV core protein. J Med Virol. 1996, vol. 50(3), p. 221-9. Abstract (9 pages).
Laperche at al. Simultaneous Detection of Hepatitis C Virus (HCV) Core Antigen and Anti-1, 6-9, and 19 HCV Antibodies Improves the Early Detection of HCV Infection. J Clin Microbiol. 2005, vol. 43(8), p. 3877-83. Entire documentation, especially Abstract (8 pages).
Aach et al., "Hepatitis C virus infection in post-transfusion hepatitis. An analysis with first- and second-generation assays," N. Engl. J. Med., 325(19):1325-1329 (1991).
Alter et al., "The natural history of community-acquired hepatitis C in the United States. The Sentinel Counties Chronic non-A, non-B Hepatitis Study Team," N. Engl. J. Med., 327(27):1899-1905 (1992).
Anthony et al., "Recapitulation of IVIG anti-inflammatory activity with a recombinant IgG Fc," Science, 320(5874):373-376 (2008).
Babcook et al., "A novel strategy for generating monoclonal antibodies from single, isolated lymphocytes producing antibodies of defined specificities," Proc. Natl. Acad. Sci. USA, 93(15):7843-7848 (1996).
Barbas et al., "Assembly of combinatorial antibody libraries on phage surfaces: the gene III site," Proc. Natl. Acad. Sci. USA, 88(18):7978-7982 (1991).
Barbas et al., "In vitro evolution of a neutralizing human antibody to human immunodeficiency virus type 1 to enhance affinity and broaden strain cross-reactivity," Proc. Natl. Acad. Sci. USA, 91(9):3809-3813 (1994).

(56) References Cited

OTHER PUBLICATIONS

Biewenga et al., "IgA1 half molecules in human multiple myeloma and the in vitro production of similar fragments from intact IgA1 molecules," Clin. Exp. Immunol., 51(2):395-400 (1983).
Boulant et al., "Hepatitis C virus core protein is a dimeric alpha-helical protein exhibiting membrane protein features," J. Virol., 79(17):11353-11365 (2005).
Carter et al., "Humanization of an anti-p185HER2 antibody for human cancer therapy," Proc. Natl. Acad. Sci. USA, 89(10):4285-4289 (1992).
Eng et al., "Internal initiation stimulates production of p8 minicore, a member of a newly discovered family of hepatitis C virus core protein isoforms," J. Virol., 83(7):3104-3114 (2009).
Gram et al., "In vitro selection and affinity maturation of antibodies from a naive combinatorial immunoglobulin library," Proc. Natl. Acad. Sci. USA, 89(8):3576-3580 (1992).
Green et al., "Regulation of B cell development by variable gene complexity in mice reconstituted with human immunoglobulin yeast artificial chromosomes," J. Exp. Med., 188(3):483-495 (1998).
Griffiths et al., "Human anti-self antibodies with high specificity from phage display libraries," EMBO J., 12(2):725-734 (1993).
Holliger et al., "'Diabodies': small bivalent and bispecific antibody fragments," Proc. Natl. Acad. Sci. USA, 90(14):6444-6448 (1993).
Huston et al., "Protein engineering of antibody binding sites: recovery of specific activity in an anti-digoxin single-chain Fv analogue produced in *Escherichia coli*," Proc. Natl. Acad. Sci. USA, 85(16):5879-5883 (1988).
Padlan et al., "Identification of specificity-determining residues in antibodies," FASEB J., 9(1):133-139 (1995).
Roberts et al., "RNA-peptide fusions for the in vitro selection of peptides and proteins," Proc. Natl. Acad. Sci. USA, 94(23):12297-12302 (1997).
Roguska et al, "Humanization of murine monoclonal antibodies through variable domain resurfacing," Proc. Natl. Acad. Sci. USA, 91(3):969-973 (1994).
Shu et al., "Secretion of a single-gene-encoded immunoglobulin from myeloma cells," Proc. Natl. Acad. Sci. USA, 90(17):7995-7999 (1993).
Wallemacq et al., "Evaluation of the new AxSYM cyclosporine assay: comparison with TDx monoclonal whole blood and Emit cyclosporine assays," Clin. Chem., 45(3):432-435 (1999).
Yatscoff et al., "Abbott TDx monoclonal antibody assay evaluated for measuring cyclosporine in whole blood," Clin. Chem., 36(11):1969-1973 (1990).
Adamczyk et al., "Modulation of the Chemiluminescent Signal from N10-(3-Sulfopropyl)-N-Sulfonylacridinium-9-carboxamides," Tetrahedron, 55:10899-10914 (1999).
Adamczyk et al., "Chemiluminescence quenching of pteroic acid-N-sulfonyl-acridinium-9-carboxamide conjugates by folate binding protein," Bioorg. Med. Chem. Lett., 14(9):2313-2317 (2004).
Adamczyk et al., "Chemiluminescent acridinium-9-carboxamide boronic acid probes: application to a homogeneous glycated hemoglobin assay," Bioorg. Med. Chem. Lett., 16(5):1324-1328 (2006).
Adamczyk et al., "Homogeneous chemiluminescent assays for free choline in human plasma and whole blood," Anal. Chim. Acta, 579(1):61-67 (2006).
Adamczyk et al., "Intrinsic factor-mediated modulation of cyanocobalamin-N-sulfonyl-acridinium-9-carboxamide chemiluminescence," Bioorg. Med. Chem. Lett., 14(15):3917-3921 (2004).
Adamczyk et al., "Linker-mediated modulation of the chemiluminescent signal from N(10)-(3-Sulfopropyl)-N-sulfonylacridinium-9-carboxamide tracers," Bioconjug. Chem., 11(5):714-724 (2000).
Adamczyk et al., "Regiodependent luminescence quenching of biotinylated N-sulfonyl-acridinium-9-carboxamides by avidin," Org. Lett., 5(21):3779-3782 (2003).
Adamczyk et al., "Synthesis of a chemiluminescent acridinium hydroxylamine (AHA) for the direct detection of abasic sites in DNA," Org. Lett. 1(5):779-781 (1999).
Adamczyk et al., "Neopentyl 3-Triflyloxypropanesulfonate. A Reactive Sulfopropylation Reagent for the Preparation of Chemiluminescent Labels," J. Org. Chem., 63:5636-5639 (1998).
Ames et al., "Conversion of murine Fabs isolated from a combinatorial phage display library to full length immunoglobulins," J. Immunol. Methods, 184(2):177-186 (1995).
Azzazy et al., "Phage display technology: clinical applications and recent innovations," Clin. Biochem., 35(6):425-445 (2002).
Better et al., "*Escherichia coli* secretion of an active chimeric antibody fragment," Science, 240(4855):1041-1043 (1988).
Biedler et al., "Cloning and high level expression of a chimeric antibody with specificity for human carcinoembryonic antigen," J. Immunol., 141(11):4053-4060 (1988).
Bird et al., "Single-chain antigen-binding proteins," Science, 242(4877):423-426 (1988).
Bresters et al., "Enhanced sensitivity of a second generation ELISA for antibody to hepatitis C virus," Vox Sang, 62 (4):213-217 (1992).
Brinkmann et al., "Phage display of disulfide-stabilized Fv fragments," J. Immunol. Methods, 182(1):41-50 (1995).
Burton et al., "Human antibodies from combinatorial libraries," Adv. Immunol., 57:191-280 (1994).
Busch et al., "Committee report. Nucleic acid amplification testing of blood donors for transfusion-transmitted infectious diseases: Report of the Interorganizational Task Force on Nucleic Acid Amplification Testing of Blood Donors," Transfusion, 40(2):143-159 (2000).
Choo et al., "Isolation of a cDNA clone derived from a blood-borne non-A, non-B viral hepatitis genome," Science, 244 (4902):359-362 (1989).
Chothia et al., "Canonical structures for the hypervariable regions of immunoglobulins," J. Mol. Biol., 196(4):901-917 (1987).
Chothia et al., "Conformations of immunoglobulin hypervariable regions," Nature, 342(6252):877-883 (1989).
Clackson et al., "Making antibody fragments using phage display libraries," Nature, 352(6336):624-628 (1991).
Courouce et al., "Anti-hepatitis C virus (anti-HCV) seroconversion in patients undergoing hemodialysis: comparison of second- and third-generation anti-HCV assays," Transfusion, 34(9):790-795 (1994).
Courouce et al., "Significance of NS3 and NS5 antigens in screening for HCV antibody," Lancet, 343(8901):853-854 (1994).
Dall'Acqua et al., "Contribution of domain interface residues to the stability of antibody CH3 domain homodimers," Biochemistry, 37(26):9266-9273 (1998).
Fuchs et al., "Targeting Recombinant Antibodies to the Surface of *Echerichia coli*: Fusion to a Peptidoglycan Associated Lipoprotein," Biotechnology, 9:1370-1372 (1991).
Garrard et al., FAB Assembly and Enrichment in a Monovalent Phage Display System, Biotechnology, 9:1373-1377 (1991).
Gavilondo et al., "Antibody engineering at the millennium," Biotechniques, 29(1):128-132, 134-136, 138 passim (2000).
Green et al., "Antigen-specific human monoclonal antibodies from mice engineered with human Ig heavy and light chain YACs," Nat. Genet., 7(1):13-21 (1994).
Hawkins et al., "Selection of phage antibodies by binding affinity. Mimicking affinity maturation," J. Mol. Biol., 226 (3):889-896 (1992).
Hay et al., "Bacteriophage cloning and *Escherichia coli* expression of a human IgM Fab," Hum. Antibodies Hybridomas, 3(2):81-85 (1992).
Hino, "Diagnosis of hepatitis C," Intervirology, 37(2):77-86 (1994).
Hoogenboom et al., "Multi-subunit proteins on the surface of filamentous phage: methodologies for displaying antibody (Fab) heavy and light chains," Nucleic Acids Res., 19(15):4133-4137 (1991).
Hoogenboom et al., "Natural and designer binding sites made by phage display technology," Immunol. Today, 21(8):371-378 (2000).
Hoogenboom, "Designing and optimizing library selection strategies for generating high-affinity antibodies," Trends Biotechnol., 15(2):62-70 (1997).
Huber et al., "Crystallographic structure studies of an IgG molecule and an Fc fragment," Nature, 264(5585):415-420 (1976).
Huse et al., "Generation of a large combinatorial library of the immunoglobulin repertoire in phage lambda," Science, 246(4935):1275-1281 (1989).

(56) References Cited

OTHER PUBLICATIONS

Huston et al., "Protein engineering of single-chain Fv analogs and fusion proteins," Methods Enzymol., 203:46-88 (1991).
Jackson et al., "In vitro antibody maturation. Improvement of a high affinity, neutralizing antibody against IL-1 beta," J. Immunol., 154(7):3310-3319 (1995).
Johnsson et al., "Comparison of methods for immobilization to carboxymethyl dextran sensor surfaces by analysis of the specific activity of monoclonal antibodies," J. Mol. Recognit., 8(1-2):125-131 (1995).
Johnsson et al., "Immobilization of proteins to a carboxymethyldextran-modified gold surface for biospecific interaction analysis in surface plasmon resonance sensors," Anal. Biochem., 198(2):268-277 (1991).
Jones et al., "Replacing the complementarity-determining regions in a human antibody with those from a mouse," Nature, 321(6069):522-525 (1986).
Jonsson et al., "Introducing a biosensor based technology for real-time biospecific interaction analysis," Ann. Biol. Clin. (Paris), 51(1):19-26 (1993).
Jonsson et al., "Real-time biospecific interaction analysis using surface plasmon resonance and a sensor chip technology," Biotechniques, 11(5):620-627 (1991).
Kabat et al., "Attempts to locate complementarity-determining residues in the variable positions of light and heavy chains," Ann. NY Acad. Sci., 190:382-393 (1971).
Kellermann et al., "Antibody discovery: the use of transgenic mice to generate human monoclonal antibodies for therapeutics," Curr. Opin. Biotechnol., 13(6):593-597 (2002).
Kettleborough et al., "Isolation of tumor cell-specific single-chain Fv from immunized mice using phage-antibody libraries and the reconstruction of whole antibodies from these antibody fragments," Eur. J. Immunol., 24(4):952-958 (1994).
Kim et al., "Identifying amino acid residues that influence plasma clearance of murine IgG1 fragments by site-directed mutagenesis," Eur. J. Immunol., 24(3):542-548 (1994).
Kleinman et al., "Increased detection of hepatitis C virus (HCV)-infected blood donors by a multiple-antigen HCV enzyme immunoassay," Transfusion, 32(9):805-813 (1992).
Kohler et al., "Continuous cultures of fused cells secreting antibody of predefined specificity," Nature, 256 (5517):495-497 (1975).
U.S. Appl. No. 14/851,471, filed Sep. 11, 2015, Dawson et al.
Altschul, S.F. et al., "Gapped BLAST and PSI-BLAST: a new generation of protein database search programs," Nucleic Acids Res. (1997) 25:3389-3402.
Beckett et al., "A minimal peptide substrate in biotin holoenzyme synthetase-catalyzed biotinylation," Protein Sci. (1999) 8(4):921-929.
Bodor, G.S. et al., "Development of monoclonal antibodies for an assay of cardiac Troponin-I and preliminary results in suspected cases of myocardial infarction," Clinical Chem. (1992) 38:2203-2214.
Boder, E.T. et al., "Yeast surface display for screening combinatorial polypeptide libraries," Nature Biotech. (1997) 15:553-557.
Buchwald, H. et al., "Long-term, continuous intravenous heparin administration by an implantable infusion pump in ambulatory patients with recurrent venous thrombosis," Surgery (1980) 88:507-516.
Chothia, C. et al., "Structural repertoire of the human VH segments," J. Mol. Biol. (1992) 227:799-817.
Cleek et al., "Biodegradable polymeric carriers for a bFGF antibody for cardiovascular application," Pro. Int. Symp. Control. Rel. Bioact. Mater. (1997) 24:853-854.
Co, M.S. et al., "Genetically engineered deglycosylation of the variable domain increases the affinity of an anti-CD33 monoclonal antibody," Mol. Immunol (1993) 30:1361-1367.
Colman, P.M., "Effects of amino acid sequence changes on antibody-antigen interactions," Research in Immunology (1994) 145:33-36.

Cummins, B. et al., "Cardiac-specific troponin radioimmunoassay in the diagnosis of acute myocardial infarction," Am. Heart Journal (1987) 113:1333-1344.
Dijkema et al., "Cloning and expression of the chromosomal immune interferon gene of the rat," EMBO J. (1985) 4(3):761-767.
During et al., "Controlled release of dopamine from a polymeric brain implant: in vivo characterization," Ann. Neurol. (1989) 25:351-356.
Erikkson, S. et al., "Comparison of cardiac troponin. Immunoassays variably affected by circulating autoantibodies," Clin. Chem. (2005) 51(5):848-855.
Filatov, V.L. et al., "Epitope mapping of anti-troponin I monoclonal antibodies," Biochem. Mol. Biol. Int. (1998) 45(6):1179-1187.
Foote, J. et al., "Antibody frame work residues affecting the confirmation of the hypervariable loops," J. Mol. Biol. (1992) 224:487-499.
Giege, R. et al., "An introduction to the crystalligenesis of biological macromolecules," Crystallization of Nucleic Acids and Proteins, a Practical Approach, 2nd Edition, Oxford University Press, New York (1999) 20 1-16.
Gillies et al., "High-level expression of chimeric antibodies using adapted cDNA variable region cassettes," J. Immunol. Methods (1989) 125:191-202.
Goodson, J.M. et al., Medical Applications of Controlled Release, Chapter 6, Dental Applications (1984) 2:115-138.
Gorman et al., "The Rous sarcoma virus long terminal repeat is a strong promoter when introduced into a variety of eukaryotic cells by DNA-mediated transfection," Proc. Natl. Acad. Sci. USA (1982) 79(22):6777-6781.
Gu et al., "Three conformational snapshots of the hepatitis C virus NS3 helicase reveal a ratchet translocation mechanism," Proc. Natl. Acad. Sci. USA (2010) 107(2):521-528.
Higgins et al., "Fast and sensitive multiple sequence alignments on a micro computer," CABIOS (1989) 5(2):151-153.
Howard, M.A. et al., "Intracerebral drug delivery in rats with lesion-induced memory deficits," J. Neurosurg. (1989) 71:105-112.
Hytest 1999 Product Catalog, 3 pages.
Hytest 2000 General Product Catalog, 3 pages.
Hytest 2001-2002 General Product Catalog, 3 pages.
Hytest 2001 Cardiac Markers Panel, 4 pages.
Hytest 2003 General Product Catalog, 3 pages.
Hytest 2004-2005 General Product Catalog, 3 pages.
Hytest 2004 Cardiac Markers Panel, 4 pages.
Hytest 2005-2006 General Product Catalog, 3 pages.
Hytest 2005 Markers of Cardiovascular Diseases Catalog, 4 pages.
Hytest 2006-2007—General Product Catalog, 3 pages.
Hytest 2007-2008 General Product Catalog, 3 pages.
Hytest 2007 markers of Cardiovascular Diseases Catalog, 4 pages.
Hytest 2008-2009 General Product Catalog, 3 pages.
Hytest 2008 Markers of Cardiovascular Diseases and Metabolis Syndrome, 4 pages.
International Search Report and Written Opinion for Application No. PCT/US2013/077487 dated Apr. 22, 2014 (23 pages).
International Search Report and Written Opinion for Application No. PCT/US2010/024979 dated May 6, 2010 (16 pages).
International Search Report and Written Opinion for Application No. PCT/US2013/077504 dated Jul. 1, 2014 (14 pages).
Jay et al., "Chemical synthesis of a biologically active gene for human immune interferon-gamma Prospect for site-specific mutagenesis and structure-function studies," J. Biol. Chem. (1984) 259(10):6311-6317.
Jayaraman et al., "Polymerase chain reaction-mediated gene synthesis: synthesis of a gene coding for isozyme C of horseradish peroxidase," Proc. Natl. Acad. Sci. USA (1991) 88(10):4084-4088.
Jefferis, R. et al., "Glycosylation of recombinant antibody therapeutics," Biotechnol. Prog. (2005) 21:11-16.
Kabat et al, Sequences of Proteins of Immunological Interest, National Institutes of Health, Bethesda, Maryland (1987) and (1991), 4th Edition, 4 pages.
Kabat et al., Sequences of Proteins of Immunological Interest, 5th Edition, Department of Health and Human Services, NIH Publication No. 91-3242 (1991), 11 pages.
Katrukha et al., "Degradation of cardiac troponin: implication for reliable immunodetection," Clin. Chem. (1998) 44(12):2433-2440.

(56) References Cited

OTHER PUBLICATIONS

Katrukha, "Troponin. Measurement: the concept of a precise immunoassay," Clin. Lab. Internat. (2006) 30(5): 14-16.
Katrukha, "New approach to standardization of human cardiac Troponin I (cTnI)," Scand. J. Clin. Lab. Invest. (1999) 59(Suppl 230):124-127.
Katrukha, "Biochemical factors influencing measurement of cardiac troponin I in serum," Clin. Chem. Lab Med. (1999) 37(11/12):1091-1095.
Katrukha, "Antibody selection strategies in cardiac troponin assays," Cardiac Markers, Second Edition 173-185.
Kaufman, R.J. et al., "Amplification and expression of sequences cotransfected with a modular dihydrofolate reductase complementary DNA gene," Mol. Biol. (1982) 159:601-621.
Kim et al., "Mutational analysis of the hepatitis C virus RNA helicase," J. Virology (1997) 71(12):9400-9409.
Kim et al., "Template requirements for De Novo RNA synthesis by hepatitis C virus nonstructural protein 5B polymerase on the viral X RNA," J. Virology (2002) 76(14):6944-6956.
Kim, D. et al., "Mutational analysis of the hepatitis C virus RNA helicase," J. Virology (1997) 71(12):9400-9409.
Kim, M. et al., "Template requirements for De Novo RNA synthesis by Hepatitus C virus nonstructural protein 5B polymerase on the viral X RNA," J. Virol. (2002) 76(14):6944-6945.
Kipriyanov, S.M. et al., "Single-chain antibody streptavidin fusions: tetrameric bifunctional ScFv-complexes with biotin binding activity and enhanced affinity to antigen," Human Antibodies and Hybridomas (1995) 6:93-101.
Kipriyanov, S.M. et al., "Recombinant single-chain Fv fragments carrying c-terminal cysteine residues: production of bivalent and biotinylated miniantibodies," Mol. Immunol. (1994) 31:1047-1058.
Kontermann, Antibody Engineering, p. 790, Springer-Verlag, New York (2001).
Lam et al., "Microencapsulation of recombinant humanized monoclonal antibody for local delivery," Proc. Int'l Symp. Control Rel. Bioact. Mater. (1997) 24:759-760.
Langer et al., "Chemical physical structure of polymers as carriers for controlled release of bioactive agents: a review," J. Macromol. Sci. Rev. Macromol. Chem. (1983) 23:61-126.
Langer et al., "New methods of drug delivery," Science (1990) 249:1527-1533.
Levy, R.J. et al , "Inhibition of calcification of bioprosthetic heart valves by local controlled-release diphosphonate," Science (1985) 228:190-192.
Medical Applicants of Controlled Release, Langer and Wise (eds), CRC Press, Boca Raton, Florida (1974).
Mizushima et al., "pEF-BOS, a powerful mammalian expression vector," Nucleic Acids Research (1990) 18:5322-5323.
Morrison et al., "Numeric human antibody molecules: mouse antigen-binding domains with human constant region domains," Proc. Natl. Acad. Sci. (1984) 81:6851-6855.
Needleman et al., J. Mol. Biol. (1970) 48:443.
Neuberger et al., "Recombinant antibodies possessing novel effector functions," Nature (1984) 312:604-608.
Ning et al., "Intratumoral radioimmunotherapy of a human colon cancer xenograft using a sustained-released gel," Radiotherapy and Oncology (1996) 39:179-189.
Ogata et al., "Nucleide sequence and mutation rate of the H strain of hepatitis C virus," Proc. Natl. Acad. Sci. USA (1991) 88(8):3392-3396.
Paul, Fundamental Immunology, 3rd Edition (1993) pp. 292-295, under the heading "FV Structure and Diversity in Three Dimensions".
Pearson et al., "Improved tools for biological sequence comparison," Proc. Natl. Acad. Sci. (1988) 85:2444-2448.
Peronnet et al., "Isoelectric point determination of cardiac troponin I forms present in plasma from patients with myocardial infarction," (2007) 377(1-2):243-247.
Queen et al., "A humanized antibody that binds to the interleukin 2 receptor," Proc. Natl. Acad. Sci. USA (1989) 86(24):10029-10033.
Quinn, F. et al., "36 Bulk Reagent Random-access analyzer: Architect; 2000," The Immunoassay Handbook, 2nd Edition (2001) 363-367.
Rama, D. et al., "Epitope localization of monoclonal antibodies used in human troponin I immunoenzymometric assay," Hybridoma (1997) 16(2):153-157.
Reverse Translate a Protein (1998) (www.vivo.colostae.edu/molkit/translate/index.html), 1 page.
Rudikoff et al., "Single amino acid substitution altering antigen-binding specificity," Proc. Natl. Acad. Sci USA (1982) 79(6):1979-1983.
Sallberg et al., "Immunogenicity and antigenicity of the ATPase/helicase domain of the hepatitis C virus non-structural 3 protein," J. Gen. Virol. (1996) 77(Pt 11):2721-2728.
Sambrook et al., A Laboratory Manual, Molecular Cloning, 2nd Edition, Cold Spring Harbor Laboratory Press, Cold Spring Harbor, New York (1989) 30 pages.
Saudek et al., "A preliminary trial of the programmable implantable medication system for insulin delivery," N. Engl. J. Med. (1989) 321:574-579.
Schiestl et al., "High efficiency transformation of intact yeast cells using single stranded nucleic acids as a carrier," Current Genetics (1989) 16(5-6):339-346.
Shah et al., "Combination HCV core antigen and antibody assay on a fully automated chemiluminescence analyzer," Transfusion (2003) 43:1067-1074.
Shields, R.L. et al., "Lack of fucose on human IgG1 N-linked oligosaccharide improves binding to human FcγRIII and antibody dependent cellular toxicity," J. Biol. Chem. (2002) 277:26733-26740.
Smith et al., "Comparison of biosequences," Appl. Math (1981) 2:482-489.
Song et al., "Antibody mediated lung targeting of long-circulating emulsions," PDA Journal of Pharmaceutical Science and Technology (1995) 50:372-377.
Table Showing Codon-amino acid Abbreviations (www.hgmd.cf.ac.uk/docs/cd_amino.html), printed Jan. 23, 2013, 3 pages.
Tai et al., "Structural-based mutational analysis of the hepatitis C Virus NS3 helicase," J. Virology (2001) 74(17):8289-8207.
Takeda et al., "Constsruction of chimaeric processed immunoglobulin genes containing mouse variable and human constant region sequences," Nature (1985) 314:452-454.
Umana et al., "Engineered glycoforms of an antineuro-blastoma IgG1 with optimized antibody-dependent cellular cytotoxic activity," Nat. Biotech. (1999) 17:176-181.
Urlaub et al., "Isolation of Chinese hamster cell mutants deficient in dehydrofolate reductase activity," Proc. Natl. Acad. Sci. (1980) 77:4216-4220.
Wallick, S.C. et al., "Glycosylation of a VH residue of a monoclonal antibody against alpha(1-6) dextran increases its affinity for antigens," Exp. Med. (1988) 168:1099-1109.
Winnaker et al., From Genes to Cones, Verlagsgesellschaft, Weinheim, Germany (1987).
Wright, A. et al., "Antibody variable region glycosylation: position effects on antigen binding and carbohydrate structure," EMBO J. (1991) 10:2717-2723.
Wu et al, "Receptor-mediated in vitro gene transformation by a soluble DNA carrier system," J. Biol. Chem. (1987) 262:4429-4432.
Ylikotila et al., "Utilization of recombinant fab fragments in a cTnI immunoassay conducted in spot wells," Clinc. Biochem. (2006) 39:843-850.
United States Patent Office Action for U.S. Appl. No. 14/139,053 dated Oct. 6, 2015 (15 pages).
United States Patent Office Action for U.S. Appl. No. 14/139,108 dated Jan. 21, 2015 (11 pages).
United States Patent Office Notice of Allowance for U.S. Appl. No. 14/139,108 dated Jul. 17, 2015 (5 pages).
United States Patent Office Action for U.S. Appl. No. 12/391,937 dated Feb. 24, 2011 (15 pages).
United States Patent Office Notice of Allowance for U.S. Appl. No. 12/391,937 dated Aug. 5, 2011 (13 pages).
United States Patent Office Notice of Allowance for U.S. Appl. No. 14/035,420 dated Feb. 27, 2015 (8 pages).

(56) References Cited

OTHER PUBLICATIONS

United States Patent Office Action for U.S. Appl. No. 14/035,420 dated Mar. 18, 2014 (9 pages).
United States Patent Office Action for U.S. Appl. No. 90/012,377 dated Feb. 6, 2013 (15 pages).
United States Patent Office Action for U.S. Appl. No. 14/461,082 dated Apr. 15, 2016 (7 pages).

* cited by examiner

Figure 1a: Anti-Core134-171 heavy chain variable domain sequences

Figure 1b: Anti-Core134-171 light chain variable domain sequences

SEQUENCE LISTING

<160> NUMBER OF SEQ ID NOS: 581

<210> SEQ ID NO 1
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggtccagc tgcaacagtc tggacctgag ttggtgaagc ctggggcctc agtgaagata      60
tcttgcaaga cttctggata cactttcact gaatacgcca tgcactggat gaagcagagc     120
catggaaaga gccttgagtg gattggaggt atcaatccta ctaatggtga tacaatctac     180
aaccagaagt tcaaggacaa ggccaaattg actgtagaca ggtcctccag cacagcctac     240
atggagctcc gcagcctgac atctgacgat tctgcattat tttattgtgc aagacgggaa     300
ctggactact ttgcctcctg gggccaaggc accactctca cagtctcctc a              351

<210> SEQ ID NO 2
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ala Met His Trp Met Lys Gln Ser His Gly Lys Ser Leu Glu Trp Ile
        35                  40                  45

Gly Gly Ile Asn Pro Thr Asn Gly Asp Thr Ile Tyr Asn Gln Lys Phe
    50                  55                  60

Lys Asp Lys Ala Lys Leu Thr Val Asp Arg Ser Ser Ser Thr Ala Tyr
65                  70                  75                  80

Met Glu Leu Arg Ser Leu Thr Ser Asp Asp Ser Ala Leu Phe Tyr Cys
                85                  90                  95

Ala Arg Arg Glu Leu Asp Tyr Phe Ala Ser Trp Gly Gln Gly Thr Thr
            100                 105                 110

Leu Thr Val Ser Ser
        115

<210> SEQ ID NO 3
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gaggtccagc tgcaacagtc tggacctgag ctggtgaagc ctggggcctc agtgaagata      60
tcttgcaaga cttctggata cactttcact gaatacgcca tgcactggat gaagcagagc     120
catggaaaga gccttgagtg gattggcggt atcaatccta ctaatggtga tacaatctac     180
aaccagaggt tcaaggacaa ggccaaattg actgtagaca ggtcctccag cacagcctac     240

-continued

```
atggagctcc gcagcctgac atctgacgat tctgcattat tttattgtgc aagacgggaa    300
ctggactact ttgcctcctg gggccaaggc accactctca cagtctcctc a              351
```

<210> SEQ ID NO 4
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ala Met His Trp Met Lys Gln Ser His Gly Lys Ser Leu Glu Trp Ile
        35                  40                  45

Gly Gly Ile Asn Pro Thr Asn Gly Asp Thr Ile Tyr Asn Gln Arg Phe
    50                  55                  60

Lys Asp Lys Ala Lys Leu Thr Val Asp Arg Ser Ser Thr Ala Tyr
65                  70                  75                  80

Met Glu Leu Arg Ser Leu Thr Ser Asp Asp Ser Ala Leu Phe Tyr Cys
                85                  90                  95

Ala Arg Arg Glu Leu Asp Tyr Phe Ala Ser Trp Gly Gln Gly Thr Thr
            100                 105                 110

Leu Thr Val Ser Ser
        115

<210> SEQ ID NO 5
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gaggtccagc tgcaacagtc tggacctgaa ctggtgaagc ctggggcctc agtgaagata    60
tcctgtaagg cttcgggatt cactttcact gaatacgcca tgcactggat gaaacagagc    120
catggaaaga gccttgagtg gattggaggt atcaatccta ctaacggtga tgcaatctac    180
aaccagaagt tcaaggacaa ggccaagttg actgtagaca ggtcctccag cacagcctac    240
atggagctcc gcagcctgac atctgacgat tctgcattat tttattgtgc aagacgggaa    300
ctggactact tccctcctg gggccaaggc accactctca cagtctcctc a              351
```

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Gln Gln Ser Gly Pro Glu Leu Val Lys Pro Gly Ala
1               5                   10                  15

Ser Val Lys Ile Ser Cys Lys Ala Ser Gly Phe Thr Phe Thr Glu Tyr
            20                  25                  30

Ala Met His Trp Met Lys Gln Ser His Gly Lys Ser Leu Glu Trp Ile
            35                  40                  45

Gly Gly Ile Asn Pro Thr Asn Gly Asp Ala Ile Tyr Asn Gln Lys Phe
 50                  55                  60

Lys Asp Lys Ala Lys Leu Thr Val Asp Arg Ser Ser Thr Ala Tyr
 65                  70                  75                  80

Met Glu Leu Arg Ser Leu Thr Ser Asp Ser Ala Leu Phe Tyr Cys
                 85                  90                  95

Ala Arg Arg Glu Leu Asp Tyr Phe Pro Ser Trp Gly Gln Gly Thr Thr
                100                 105                 110

Leu Thr Val Ser Ser
        115

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaggtccagc tgcaacagtc tggacctgaa ctggaaaagc ctggggcttc agtgaggata      60
tcctgcaaga cttctggata cacattcact gaatacgcca tgcactgggt gaagcagagc     120
catggaaaga gccttgagtg gattggaggt attaatccta caaatggcaa tgctatctac     180
aaccagatat tcaaggacaa ggccacactg actgtggaca ggtcctccag cacagcctac     240
atgggcctcc gcagcctgac attcggggat tctgagtct acttctgtgt aagacgacaa      300
ctggactact ttgactattg gggccagggc gcctctctca cagtctcctc a               351

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Gln Gln Ser Gly Pro Glu Leu Glu Lys Pro Gly Ala
 1               5                  10                  15

Ser Val Arg Ile Ser Cys Lys Thr Ser Gly Tyr Thr Phe Thr Glu Tyr
             20                  25                  30

Ala Met His Trp Val Lys Gln Ser His Gly Lys Ser Leu Glu Trp Ile
            35                  40                  45

Gly Gly Ile Asn Pro Asn Asn Gly Asn Ala Ile Tyr Asn Gln Ile Phe
 50                  55                  60

Lys Asp Lys Ala Thr Leu Thr Val Asp Arg Ser Ser Thr Ala Tyr
 65                  70                  75                  80

Met Gly Leu Arg Ser Leu Thr Phe Gly Asp Ser Gly Val Tyr Phe Cys
                 85                  90                  95

Val Arg Arg Gln Leu Asp Tyr Phe Asp Tyr Trp Gly Gln Gly Ala Ser
                100                 105                 110

Leu Thr Val Ser Ser
        115

<210> SEQ ID NO 9
<211> LENGTH: 351

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gaggtccagc tgcaacagtc tggacctgag ctggaaaagc ctggggcttc agtgaagata     60
tcctgcaaga cttctggata cacattcact gaatacgcca tacactgggt gaagcagagc    120
catggaatga gccttgagtg gattggaggt attaatccta gcaatggcaa tgctatctac    180
aaccaaatat tcaaggacaa ggccacactg actgtggaca ggtcctccag cacagcctac    240
atgggcctcc gcagcctgac atttggggat tctggagtct acttctgtgt aagacgacaa    300
ctggacttct ttgactattg gggccagggc gcctctctca cagtctcctc a             351
```

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Val Gln Leu Gln Gln Ser Gly Pro Glu Leu Glu Lys Pro Gly Ala
1               5                   10                  15

Ser Val Lys Ile Ser Cys Lys Thr Ser Gly Tyr Thr Phe Thr Glu Tyr
                20                  25                  30

Ala Ile His Trp Val Lys Gln Ser His Gly Met Ser Leu Glu Trp Ile
            35                  40                  45

Gly Gly Ile Asn Pro Ser Asn Gly Asn Ala Ile Tyr Asn Gln Ile Phe
        50                  55                  60

Lys Asp Lys Ala Thr Leu Thr Val Asp Arg Ser Ser Thr Ala Tyr
65                  70                  75                  80

Met Gly Leu Arg Ser Leu Thr Phe Gly Asp Ser Gly Val Tyr Phe Cys
                85                  90                  95

Val Arg Arg Gln Leu Asp Phe Phe Asp Tyr Trp Gly Gln Gly Ala Ser
                100                 105                 110

Leu Thr Val Ser Ser
        115
```

<210> SEQ ID NO 11
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gaggtccagc tgcaacagtc tggacctgag ctggaaaagc ctggggcttc agtgaagata     60
tcctgcaaga cttctggata cacattcact gaatacgcca tgcactgggt gaagcagagc    120
catggaatga gccttgagtg gattggaggt attaatccta gcaatggcaa tgctatctac    180
aaccagatat tcaaggacaa ggccacactg actgtggaca ggtcctccag cacagcctac    240
atgggcctcc gcagcctgac atttggggat tctggagtct acttctgtgt aagacgacaa    300
ctggacttct ttgactattg gggccagggc gcctctctca cagtctcctc a             351
```

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Pro Glu Leu Glu Lys Pro Gly Ala
1               5                   10                  15

Ser Val Lys Ile Ser Cys Lys Thr Ser Gly Tyr Thr Phe Thr Glu Tyr
                20                  25                  30

Ala Met His Trp Val Lys Gln Ser His Gly Met Ser Leu Glu Trp Ile
            35                  40                  45

Gly Gly Ile Asn Pro Ser Asn Gly Asn Ala Ile Tyr Asn Gln Ile Phe
        50                  55                  60

Lys Asp Lys Ala Thr Leu Thr Val Asp Arg Ser Ser Thr Ala Tyr
65                  70                  75                  80

Met Gly Leu Arg Ser Leu Thr Phe Gly Asp Ser Gly Val Tyr Phe Cys
                85                  90                  95

Val Arg Arg Gln Leu Asp Phe Phe Asp Tyr Trp Gly Gln Gly Ala Ser
                100                 105                 110

Leu Thr Val Ser Ser
        115

<210> SEQ ID NO 13
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaggtccggc tgcagcagcc tggacctgag gtggaaaagc ctggggcttc agtgaagata      60
tcctgcaaga cttctggata cacattcact gaatacgcca tccactgggt gaaacagagc     120
catggagaga gccttgagtg gattggaggt attaatccta gcaatggcga tcctatctat     180
aaccagatat tcaaggacaa ggccacactg actgtggaca ggtcctccaa cacagcctac     240
atgggcctcc gcagcctgac agttggggat tctggagtct acttctgtgt tagacgacaa     300
ctggactact ttgactttgg gggccagggc gcctctctca cagtctcctc a              351

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Arg Leu Gln Gln Pro Gly Pro Glu Val Glu Lys Pro Gly Ala
1               5                   10                  15

Ser Val Lys Ile Ser Cys Lys Thr Ser Gly Tyr Thr Phe Thr Glu Tyr
                20                  25                  30

Ala Ile His Trp Val Lys Gln Ser His Gly Glu Ser Leu Glu Trp Ile
            35                  40                  45

Gly Gly Ile Asn Pro Ser Asn Gly Asp Pro Ile Tyr Asn Gln Ile Phe
        50                  55                  60

```
Lys Asp Lys Ala Thr Leu Thr Val Asp Arg Ser Ser Asn Thr Ala Tyr
 65                  70                  75                  80

Met Gly Leu Arg Ser Leu Thr Val Gly Asp Ser Gly Val Tyr Phe Cys
                 85                  90                  95

Val Arg Arg Gln Leu Asp Tyr Phe Asp Phe Trp Gly Gln Gly Ala Ser
            100                 105                 110

Leu Thr Val Ser Ser
        115

<210> SEQ ID NO 15
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
cagggtcaga tgcagcagtc tggagctgaa ctggcgaagc ctggggcttc agtgaagctg      60
tcctgcaaga cttctggctt caccttcagc agtagttata taagttggtt gaagcaaaag     120
cctggacaga gtcttgagtg gattgcatgg atttatgctg gaactggtaa tactaactat     180
aatcagaagt tcacagacaa ggcccaactg actgtagaca catcctccag tacagcctac     240
atgcaactca gcagcctgac aactgaggac tctgccatct attactgtgc gataagtggg     300
acgggattta cttactgggg ccaagggact ctggtcactg tctctgcaac a              351

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Gly Gln Met Gln Gln Ser Gly Ala Glu Leu Ala Lys Pro Gly Ala
 1               5                  10                  15

Ser Val Lys Leu Ser Cys Lys Thr Ser Gly Phe Thr Phe Ser Ser Ser
                20                  25                  30

Tyr Ile Ser Trp Leu Lys Gln Lys Pro Gly Gln Ser Leu Glu Trp Ile
            35                  40                  45

Ala Trp Ile Tyr Ala Gly Thr Gly Asn Thr Asn Tyr Asn Gln Lys Phe
 50                  55                  60

Thr Asp Lys Ala Gln Leu Thr Val Asp Thr Ser Ser Ser Thr Ala Tyr
 65                  70                  75                  80

Met Gln Leu Ser Ser Leu Thr Thr Glu Asp Ser Ala Ile Tyr Tyr Cys
                 85                  90                  95

Ala Ile Ser Gly Thr Gly Phe Thr Tyr Trp Gly Gln Gly Thr Leu Val
            100                 105                 110

Thr Val Ser Ala
        115

<210> SEQ ID NO 17
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 17

```
cagggtcaga tgcagcagtc tggagctgaa ctggtgaagc ctggggcttc agtgaagctg      60
tcctgcaaga cttctggctt caccttcagc agtagttata taagttggtt gaagcaaaag     120
cctggacaga gtcttgagtg gattgcatgg atttatgctg aactggtaa tactaactat      180 aatcagaagt tcacagacaa ggcccaactg actgtagaca catcctccag tacagcctac     240
atgcaactca gcagcctgac aactgaggac tctgccatct attactgtgc gataagtggg     300
acgggattta cttactgggg ccaagggact ctggtcactg tctctgcaac a              351
```

<210> SEQ ID NO 18
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Gln Gly Gln Met Gln Gln Ser Gly Ala Glu Leu Ala Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Phe Ala Gly Thr Gly Asn Thr Asn Tyr Asn Gln Lys Phe
    50                  55                  60

Thr Asp Lys Ala Gln Leu Thr Val Asp Thr Ser Ser Ser Thr Ala Tyr
65                  70                  75                  80

Met Gln Leu Ser Ser Leu Thr Thr Glu Asp Ser Ala Ile Tyr Tyr Cys
                85                  90                  95

Ala Ile Ser Gly Thr Gly Phe Thr Tyr Trp Gly Gln Gly Thr Leu Val
            100                 105                 110

Thr Val Ser Ala
        115
```

<210> SEQ ID NO 19
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
cagggtcaga tgcagcagtc tggagctgag ctggcgaagc ctggggcttc agtgaaactg      60
tcctgcaaga cttctggctt caccttcagc agtagttata taagttggtt gaagcaaaag     120
cctggacaga gtcttgagtg gattgcatgg atttttgctg aactggtaa tactaattat      180 aatcagaagt tcacagacaa ggcccaactg actgtagaca catcctccag tacagcctac     240
atgcaactca gcagcctgac aactgaggac tctgccatct attactgtgc gataagtggg     300
acgggattta cttactgggg ccaagggact ctggtcactg tctctgca                  348
```

<210> SEQ ID NO 20
<211> LENGTH: 116
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 20

```
Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Asn Thr Asn Tyr Asn Gln Lys Phe
    50                  55                  60

Thr Asp Lys Ala Gln Leu Thr Val Asp Thr Ser Ser Ser Thr Ala Tyr
65                  70                  75                  80

Met Gln Leu Ser Ser Leu Thr Thr Glu Asp Ser Ala Ile Tyr Tyr Cys
                85                  90                  95

Ala Ile Ser Gly Thr Gly Phe Thr Tyr Trp Gly Gln Gly Thr Leu Val
            100                 105                 110

Thr Val Ser Ala
        115
```

<210> SEQ ID NO 21
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21

```
cagggtcaga tgcagcagtc tggagctgag ctggtgaagc ctggggcttc agtgaagctg     60
tcctgcaaga cttctggctt caccttcagc agtagtttta agttggtt gaagcaaaag      120
cctggacaga gtcttgagtg gattgcatgg atttatgctg gaactggaaa tactaactat    180
aatcagaagt tcacagacaa ggcccaactg actgtagaca catcctccag cacagcctac    240
atgcaattca gcagcctgac gactgaggac tctgccatct attactgtgc gataagtggg    300
acggggttta cttactgggg ccaagggact ctggtcactg tctctgca                 348
```

<210> SEQ ID NO 22
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

```
Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Phe Ile Ser Trp Leu Lys Gln Lys Pro Gly Gln Ser Leu Glu Trp Ile
        35                  40                  45

Ala Trp Ile Tyr Ala Gly Thr Gly Asn Thr Asn Tyr Asn Gln Lys Phe
    50                  55                  60

Thr Asp Lys Ala Gln Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
```

```
                    85                  90                  95
Ala Ile Ser Gly Thr Gly Phe Thr Tyr Trp Gly Gln Gly Thr Leu Val
            100                 105                 110

Thr Val Ser Ala
        115

<210> SEQ ID NO 23
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
cagggtcaga tgcagcagtc tggagctgag ctggtgaagc ctggggcttc agtgaagctg      60
tcctgcaaga cttctggctt caccttcagc agtagttatt ttagttggtt gaagcaaaag    120
cctggacaga gtcttgagtg gattgcatgg atttatgctg gaactggtaa tactatctat    180
aatcagaagt tcacagacaa ggcccaactg actgtagaca cagcctccag cacagccttc    240
atgcaactca gcagcctgac aattgaggac tctgccatct actactgtgc gataagtggg    300
acggggttta cttactgggg ccaagggact ctggtcactg tctctgcaac a              351

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Phe Ser Trp Leu Lys Gln Lys Pro Gly Gln Ser Leu Glu Trp Ile
        35                  40                  45

Ala Trp Ile Tyr Ala Gly Thr Gly Asn Thr Ile Tyr Asn Gln Lys Phe
    50                  55                  60

Thr Asp Lys Ala Gln Leu Thr Val Asp Thr Ala Ser Ser Thr Ala Phe
65                  70                  75                  80

Met Gln Leu Ser Ser Leu Thr Ile Glu Asp Ser Ala Ile Tyr Tyr Cys
                85                  90                  95

Ala Ile Ser Gly Thr Gly Phe Thr Tyr Trp Gly Gln Gly Thr Leu Val
            100                 105                 110

Thr Val Ser Ala
        115

<210> SEQ ID NO 25
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
cagggtcagc tgcagcagtc tggagctgag ctggtgaagc ctggggcttc agtgaagctg      60
```

```
tcctgcaaga cttctggctt caccttcagc agtagttata taagttggtt gaagcaaagg    120
cctggacaga gtcttgagtg gattgcatgg atttatgctg gaactggtgg tactaactat    180
aatcagaagt tcacagacaa ggcccaactg actgtagaca catcctccag cacagcctac    240
atgcaattca gcagcctgac aactgaggac tctgccatct attactgtgc gataagtggg    300
acggggttta tttactgggg ccaagggact ctggtcactg tctctgca                348
```

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gln Gly Gln Leu Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Leu Lys Gln Arg Pro Gly Gln Ser Leu Glu Trp Ile
        35                  40                  45

Ala Trp Ile Tyr Ala Gly Thr Gly Gly Thr Asn Tyr Asn Gln Lys Phe
    50                  55                  60

Thr Asp Lys Ala Gln Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Ile Ser Gly Thr Gly Phe Ile Tyr Trp Gly Gln Gly Thr Leu Val
            100                 105                 110

Thr Val Ser Ala
        115
```

<210> SEQ ID NO 27
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
cagggtcagt tgcagcagtc tggaccagta ctggtgaagc ctggggcttc agaaatacta     60
tactgcaaga cttctggctt caccttcagc agtacctata taagttggtt gaagcaaaag    120
cctggacaga gtcttgagtg gattgcgtgg atttatgctg gaactggtgc tactaattat    180
aatcagaagt tcacaggcaa ggcccaactg actgtagacg cttcctccaa cacagcctac    240
atgcacttca gcggcctgac acctgaggac tctgccatct attactgtgc aatttctggg    300 gcggggttt actggggcca agggactctg gtcactgtct ctgca                     345
```

<210> SEQ ID NO 28
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Gly Gln Leu Gln Gln Ser Gly Pro Val Leu Val Lys Pro Gly Ala
1               5                   10                  15

Ser Glu Ile Leu Tyr Cys Lys Thr Ser Gly Phe Thr Phe Ser Ser Thr
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Ala Thr Asn Tyr Asn Gln Lys Phe
50                  55                  60

Thr Gly Lys Ala Gln Leu Thr Val Asp Ala Ser Asn Thr Ala Tyr
65                  70                  75                  80

Met His Phe Ser Gly Leu Thr Pro Glu Asp Ser Ala Ile Tyr Tyr Cys
            85                  90                  95

Ala Ile Ser Gly Ala Gly Val Tyr Trp Gly Gln Gly Thr Leu Val Thr
            100                 105                 110

Val Ser Ala
115

<210> SEQ ID NO 29
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
cagggccaac tgcagcagcc tggggctgag tttgtgaagc ctggggcttc actgaagctg     60
tcctgcaggg cttctggcta caccttcacc agctactgga tacactgggt gaagcagagg    120
cctggacaag gccttgagtg gattggagaa attgatcctt ctgacagtta tattaaccag    180
aatcaaaagt tcaggggcaa ggccacattg actgtgacaa atcctccag cacagcctac     240 atggaactca gcggcctgac atctgaagac tctgcggtct attactgtgc aagacattac    300
tacggtgttc ttgactcctg gggccaaggt accactctca cagtctcctc aaca          354

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Gly Gln Leu Gln Gln Pro Gly Ala Glu Phe Val Lys Pro Gly Ala
1               5                   10                  15

Ser Leu Lys Leu Ser Cys Arg Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Ile Asn Gln Asn Gln Lys Phe
50                  55                  60

Arg Gly Lys Ala Thr Leu Thr Val Asp Lys Ser Ser Ser Thr Ala Tyr
65                  70                  75                  80

Met Glu Leu Ser Gly Leu Thr Ser Glu Asp Ser Ala Val Tyr Tyr Cys
            85                  90                  95

Ala Arg His Tyr Tyr Gly Val Leu Asp Ser Trp Gly Gln Gly Thr Thr
            100                 105                 110

Leu Thr Val Ser Ser
        115

<210> SEQ ID NO 31
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cagggccaac tgcagcagcc tggggctgag tttgtgaagc ctggggcttc actgaagctg      60
tcctgcaggg cttctggcta caccttcacc agctactgga ttcactgggt gaagcagagg     120
cctggacaag ccttgagtg gatcggagaa gttgatcctt ctgacagtta tattaaccag      180
aatgaaaagt tcaggggcaa ggccacattg actgtggaca aatcctccag cacagcctac    240
atgcagctcg gcagcctgac atctgaagac tctgcggtct attactgtgc aagacattac    300
tacggtgttc ttgactcctg gggccaaggc accgctctca cagtctcctc a             351

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Gly Gln Leu Gln Gln Pro Gly Ala Glu Phe Val Lys Pro Gly Ala
1               5                   10                  15

Ser Leu Lys Leu Ser Cys Arg Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Val Asp Pro Ser Asp Ser Tyr Ile Asn Gln Asn Glu Lys Phe
    50                  55                  60

Arg Gly Lys Ala Thr Leu Thr Val Asp Lys Ser Ser Thr Ala Tyr
65                  70                  75                  80

Met Gln Leu Gly Ser Leu Thr Ser Glu Asp Ser Ala Val Tyr Tyr Cys
                85                  90                  95

Ala Arg His Tyr Tyr Gly Val Leu Asp Ser Trp Gly Gln Gly Thr Ala
            100                 105                 110

Leu Thr Val Ser Ser
        115

<210> SEQ ID NO 33
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
caggtccaac tgcagcagcc tggggctgaa cttgtgaagc ctggggcttc actgaagctg      60
tcctgcaggg cctctggcta caccttcacc agctactgga ttcactgggt gaagcagagg     120
cctggacaag ccttgagtg gatcggagag attgatcctt ctgatagtta tactaactac      180
aatcaaaagt tcaagggcaa ggccacattg actgtagaca aatcctccag gcagcctac     240

```
atgcagctca gcagcctgac atctgaggac tctgcggtct attactgtgc aagacattac    300
tacggtgtct tgactcctg gggccaaggc accaaactca cagtctcctc a              351
```

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Gln Gln Pro Gly Ala Glu Leu Val Lys Pro Gly Ala
1               5                   10                  15

Ser Leu Lys Leu Ser Cys Arg Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Arg Ala Ala Tyr
65                  70                  75                  80

Met Gln Leu Ser Ser Leu Thr Ser Glu Asp Ser Ala Val Tyr Tyr Cys
                85                  90                  95

Ala Arg His Tyr Tyr Gly Val Phe Asp Ser Trp Gly Gln Gly Thr Lys
            100                 105                 110

Leu Thr Val Ser Ser
        115
```

<210> SEQ ID NO 35
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
caggtccaac tgcagcagcc tggggctgag cttgtgaagc ctggggcttc agtgaagctg    60
tcctgcaagg cttctggcta caccctcagt agctattgga tgcactgggt gaagcagagg   120
cctggacaag gccttgagtg gatcggagag attcatcctt ctgatagtta tactagctac   180
aatcaaaagt tcaaggacaa ggccacattg actgtagaca atcctccag cacagcctac    240 atgcagctca gcagcctgac atctgaggac tctgcagtct attactgtgc aagggggggc   300
tactataggt acgacgagtt tgcttactgg ggccaaggga ctctggtcac tgtctctgca   360
```

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Leu Ser Ser Tyr
            20                  25                  30
```

```
Trp Met His Trp Val Lys Gln Arg Pro Gly Gln Gly Leu Glu Trp Ile
        35                  40                  45

Gly Glu Ile His Pro Ser Asp Ser Tyr Thr Ser Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Tyr Arg Tyr Asp Glu Phe Ala Tyr Trp Gly Gln
            100                 105                 110

Gly Thr Leu Val Thr Val Ser Ala
            115                 120

<210> SEQ ID NO 37
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
caggtccatc tgcagcagcc tggggctgag ctggtgaggc ctggggtttc agtgaagctg      60
tcctgcaagg cttctggcta caccttcacc acctactcga taaactggat gaagcagagg     120
cctggacaag gccttgagtg gatcggaaat atttatcctt ctaccagtca tactaactac     180
aatcaaaagt tcagggacaa ggccacaatg actgtagaca atcctccag cacagcctac      240 atgcagctca gcagcccgac atctgaggac tctgcggtct attattgtac aataaatgcc     300
tattctatgg actactgggg tcaaggaacc tcagtcaccg tctcctca                  348

<210> SEQ ID NO 38
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val His Leu Gln Gln Pro Gly Ala Glu Leu Val Arg Pro Gly Val
1               5                   10                  15

Ser Val Lys Leu Ser Cys Lys Ala Ser Gly Tyr Thr Phe Thr Thr Tyr
            20                  25                  30

Ser Ile Asn Trp Met Lys Gln Arg Pro Gly Gln Gly Leu Glu Trp Ile
        35                  40                  45

Gly Asn Ile Tyr Pro Ser Thr Ser His Thr Asn Tyr Asn Gln Lys Phe
    50                  55                  60

Arg Asp Lys Ala Thr Met Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Ile Asn Ala Tyr Ser Met Asp Tyr Trp Gly Gln Gly Thr Ser Val
            100                 105                 110

Thr Val Ser Ser
        115

<210> SEQ ID NO 39
```

<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caggtccagc ttcagcagtc tggggctgga ctggcaaaac ctggggcctc agtgaagatg      60
tcctgcaagg cttctggcta cacctttact gccaacaaga tgcactgggc aaaacagcgg     120
cctggacagg gtctggaatg gattggatac attgatccta gctctggtta tactgaatac     180
aatcataaga tccagtacaa ggccactttg actgcagaca catcctccag cacagcctac     240
atgcaactga gcaccctaac atttgaagac tctgcagtct attactgtac aaattttgct     300
tactggggcc aagggactct ggtcactgtc tcagcaaca                            339

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Gln Ser Gly Ala Gly Leu Ala Lys Pro Gly Ala
1               5                   10                  15

Ser Val Lys Met Ser Cys Lys Ala Ser Gly Tyr Thr Phe Thr Ala Asn
            20                  25                  30

Lys Met His Trp Ala Lys Gln Arg Pro Gly Gln Gly Leu Glu Trp Ile
        35                  40                  45

Gly Tyr Ile Asp Pro Ser Ser Gly Tyr Thr Glu Tyr Asn His Lys Ile
    50                  55                  60

Gln Tyr Lys Ala Thr Leu Thr Ala Asp Thr Ser Ser Ser Thr Ala Tyr
65                  70                  75                  80

Met Gln Leu Ser Thr Leu Thr Phe Glu Asp Ser Ala Val Tyr Tyr Cys
                85                  90                  95

Thr Asn Phe Ala Tyr Trp Gly Gln Gly Thr Leu Val Thr Val Ser Ala
            100                 105                 110

<210> SEQ ID NO 41
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtccagc ttcagcagtc tggggctgga ctggcaaaac ctggggcctc agtgaagatg      60
tcctgcaagg cttctggcta cacctttact gccaacaaga tgcactgggc aaaacagcgg     120
cctggacagg gtctggaatg gattggatac attgatccta gctctggtta tactgaatac     180
aatcataaga tccaggacaa ggccacattg actgcagaca catcctccag cacagcctac     240
atgcaactga gcagcctaac atttgaagac tctgcagtct attactgtac aaattttgct     300
tactggggcc aagggactct ggtcactgtc tcagca                               336

<210> SEQ ID NO 42
<211> LENGTH: 112

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Ser Gly Ala Gly Leu Ala Lys Pro Gly Ala
1               5                   10                  15

Ser Val Lys Met Ser Cys Lys Ala Ser Gly Tyr Thr Phe Thr Ala Asn
            20                  25                  30

Lys Met His Trp Ala Lys Gln Arg Pro Gly Gln Gly Leu Glu Trp Ile
        35                  40                  45

Gly Tyr Ile Asp Pro Ser Ser Gly Tyr Thr Glu Tyr Asn His Lys Ile
    50                  55                  60

Gln Asp Lys Ala Thr Leu Thr Ala Asp Thr Ser Ser Thr Ala Tyr
65                  70                  75                  80

Met Gln Leu Ser Ser Leu Thr Phe Glu Asp Ser Ala Val Tyr Tyr Cys
                85                  90                  95

Thr Asn Phe Ala Tyr Trp Gly Gln Gly Thr Leu Val Thr Val Ser Ala
            100                 105                 110

<210> SEQ ID NO 43
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caggtccagc ttcagcagtc tggggctgga ctggcaaaac ctggggcctc agtgaagatg      60
tcctgcaagg cttctggcta cccttttact gccaacaaga tgcactggac aaaacagcgg     120
cctggacagg gtctggaatg gattggatac attgatccta gctctggtta tactcaatac     180
aatcataaga tccaggacaa ggccacattg actgcagaca catcctccag cacagcctac     240
atgcaactga gcagcctaac atttgaagac tctgcagtct attactgtac aaatttttgct   300
tactggggcc aagggactct ggtcactgtc tcagca                                336

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Gln Gln Ser Gly Ala Gly Leu Ala Lys Pro Gly Ala
1               5                   10                  15

Ser Val Lys Met Ser Cys Lys Ala Ser Gly Tyr Thr Phe Thr Ala Asn
            20                  25                  30

Lys Met His Trp Thr Lys Gln Arg Pro Gly Gln Gly Leu Glu Trp Ile
        35                  40                  45

Gly Tyr Ile Asp Pro Ser Ser Gly Tyr Thr Gln Tyr Asn His Lys Ile
    50                  55                  60

Gln Asp Lys Ala Thr Leu Thr Ala Asp Thr Ser Ser Thr Ala Tyr
65                  70                  75                  80

Met Gln Leu Ser Ser Leu Thr Phe Glu Asp Ser Ala Val Tyr Tyr Cys

```
                                85                  90                  95
Thr Asn Phe Ala Tyr Trp Gly Gln Gly Thr Leu Val Thr Val Ser Ala
                100                 105                 110
```

<210> SEQ ID NO 45
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
caggtccacc ttcagcagtc tggggctgaa ctggccaaac ctggggcctc agtgcagatg     60
tcctgcaagg cttctggcta cacctttact gccaacaaga tgcactgggc aagacagcgg    120
cctagacagg gtctggaatg gattggatac attgatcctg cctctggcta tactgaatac    180
aatcagaaga tcaaggacag ggccacattg actgcagaca atcctccag cacagcctac     240 atgcaactga gcagcctgac atctgaggac tctgcagtct attactgtac aaattttgct    300
tactggggcc aagggactct ggtcactgtc tctacaaca                           339
```

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gln Val His Leu Gln Gln Ser Gly Ala Glu Leu Ala Lys Pro Gly Ala
1               5                   10                  15
Ser Val Gln Met Ser Cys Lys Ala Ser Gly Tyr Thr Phe Thr Ala Asn
                20                  25                  30
Lys Met His Trp Ala Arg Gln Arg Pro Arg Gln Gly Leu Glu Trp Ile
            35                  40                  45
Gly Tyr Ile Asp Pro Ala Ser Gly Tyr Thr Glu Tyr Asn Gln Lys Ile
        50                  55                  60
Lys Asp Arg Ala Thr Leu Thr Ala Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Thr Asn Phe Ala Tyr Trp Gly Gln Gly Thr Leu Val Thr Val Ser Thr
                100                 105                 110
```

<210> SEQ ID NO 47
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
caggtccagc ttcagcagtc tggggctgaa ctggcaaaac ctggggcctc agtgaagatg     60
tcctgcaagg cttctggcta cacctttact agcaacaaga tgcactgggc aaaacagcgg    120
cctggacagg gtctggaatg gattggatac attgatccta gctctggtta tactgaatac    180
aatcagaaga tcaaggacaa ggccacattg actgcagaca atcctccag cacagcctac     240
```

```
atgcaactga gcagcctgac atctgaggac tctgcagtct attactgtac aaatttgct      300 tactggggcc aagggactct ggtcactgtc tctgcaaca                             339
```

<210> SEQ ID NO 48
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Asn
            20                  25                  30

Lys Met His Trp Ala Lys Gln Arg Pro Gly Gln Gly Leu Glu Trp Ile
        35                  40                  45

Gly Tyr Ile Asp Pro Ser Ser Gly Tyr Thr Gly Tyr Asn Gln Lys Ile
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Asn Phe Ala Tyr Trp Gly Gln Gly Thr Leu Val Thr Val Ser Ala
            100                 105                 110
```

<210> SEQ ID NO 49
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
caggtccagt tgcagcagtc tggacctgag ttggtgaagc ctggggcttc aatgaggata      60
tcctgcaagg cttctggcta caccttcaca agctactatg tacactggat aaagcagagg     120
cctggacagg gacttgagtg gattggatgt atttatcctg agatgttaa tactgactat      180 aatgagaagt tcaagggcaa ggccacgctg actgcagaca atcctccag cacagcctac      240 atgcaggtca gcaccctgac ctctgaggac tctgcgatct atttctgtgt cctttattac     300
tacggtagtt ttgcttactg gggccaaggg actctggtca ctgtctctgc a              351
```

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Val Gln Leu Gln Gln Ser Gly Pro Glu Leu Val Lys Pro Gly Ala
1               5                   10                  15

Ser Met Arg Ile Ser Cys Lys Ala Ser Gly Tyr Thr Phe Thr Ser Tyr
            20                  25                  30

Tyr Val His Trp Ile Lys Gln Arg Pro Gly Gln Gly Leu Glu Trp Ile
        35                  40                  45
```

```
Gly Cys Ile Tyr Pro Gly Asp Val Asn Thr Asp Tyr Asn Glu Lys Phe
    50                  55                  60
Lys Gly Lys Ala Thr Leu Thr Ala Asp Lys Ser Ser Thr Ala Tyr
 65                  70                  75                  80
Met Gln Val Ser Thr Leu Thr Ser Glu Asp Ser Ala Ile Tyr Phe Cys
                 85                  90                  95
Val Leu Tyr Tyr Tyr Gly Ser Phe Ala Tyr Trp Gly Gln Gly Thr Leu
                100                 105                 110
Val Thr Val Ser Ala
        115
```

<210> SEQ ID NO 51
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
gatgtacagc ttcaggagtc aggacctggc ctcgtgaatc cttctcagtc tctgtctctc     60
acctgctctg tcactggcta ctccatcacc agtggttatt actggatctg gatccagcag    120
tctccaggaa acaaactgga atggatgggc tacataaagt acgacggtgg caataactac    180
agcccatctc tcaaaaatcg aatctccatc gctcgtgaca catctaagaa ccagtgtttc    240
ctgaagttga attctgtgac tattgaggac acagctacat attactgtac aagagggtcg    300
gactcctttg actactgggg ccaaggcacc actctcacag tctcctca                 348
```

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Val Gln Leu Gln Glu Ser Gly Pro Gly Leu Val Asn Pro Ser Gln
  1               5                  10                  15
Ser Leu Ser Leu Thr Cys Ser Val Thr Gly Tyr Ser Ile Thr Ser Gly
                 20                  25                  30
Tyr Tyr Trp Ile Trp Ile Gln Gln Ser Pro Gly Asn Lys Leu Glu Trp
             35                  40                  45
Met Gly Tyr Ile Lys Tyr Asp Gly Gly Asn Asn Tyr Ser Pro Ser Leu
 50                  55                  60
Lys Asn Arg Ile Ser Ile Ala Arg Asp Thr Ser Lys Asn Gln Cys Phe
 65                  70                  75                  80
Leu Lys Leu Asn Ser Val Thr Ile Glu Asp Thr Ala Thr Tyr Tyr Cys
                 85                  90                  95
Thr Arg Gly Ser Asp Ser Phe Asp Tyr Trp Gly Gln Gly Thr Thr Leu
                100                 105                 110
Thr Val Ser Ser
        115
```

<210> SEQ ID NO 53
<211> LENGTH: 348
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 53

```
gatgtacagc ttcaggagtc aggacctggc ctcgtgaatc cttctcagtc tctgtctctc    60
acctgctctg tcactggcta ctccatcacc agtggttatt actggatctg gatccggcag   120
tttccaggaa acaaactgga atggatgggc tacataaagt acgacggtgg caataactac   180
agcccatctc tcaaaaatcg aatctccatc gctcgtgaca catctaagaa ccagttttc    240
ctgaagttga attctgtgac tattgaggac acagctacat attactgtac aagagggtcg   300
gactcctttg actactgggg ccaaggcacc actctcacag tctcctca                348
```

<210> SEQ ID NO 54
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Val Gln Leu Gln Glu Ser Gly Pro Gly Leu Val Asn Pro Ser Gln
1               5                   10                  15
Ser Leu Ser Leu Thr Cys Ser Val Thr Gly Tyr Ser Ile Thr Ser Gly
            20                  25                  30
Tyr Tyr Trp Ile Trp Ile Arg Gln Phe Pro Gly Asn Lys Leu Glu Trp
        35                  40                  45
Met Gly Tyr Ile Lys Tyr Asp Gly Gly Asn Asn Tyr Ser Pro Ser Leu
    50                  55                  60
Lys Asn Arg Ile Ser Ile Ala Arg Asp Thr Ser Lys Asn Gln Phe Phe
65                  70                  75                  80
Leu Lys Leu Asn Ser Val Thr Ile Glu Asp Thr Ala Thr Tyr Tyr Cys
                85                  90                  95
Thr Arg Gly Ser Asp Ser Phe Asp Tyr Trp Gly Gln Gly Thr Thr Leu
            100                 105                 110
Thr Val Ser Ser
        115
```

<210> SEQ ID NO 55
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gatgtgcagc ttcaggagtc gggacctggc ctggtgaaac cttctcagtc tctgtccctc    60
acctgcactg tcactggcta ctcaatcacc agtgattatg cctggaactg gatccggcag   120
tttcctggaa acaaactgga gtggatgggc tacataagct acagtggtac cactgtctac   180
agcccatctc tcaaaagtcg aatctccatc actcgggaca catccaaaaa ccagttcttc   240
ctgcaattga attctgtgac tattgaggac tcagccacgt attattgtgg gggtaattac   300
tggggccaag ggactctggt cactgtctct gca                                333
```

<210> SEQ ID NO 56
<211> LENGTH: 111
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 56

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Thr Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Ser Ala Thr Tyr Tyr Cys
            85                  90                  95

Gly Gly Asn Tyr Trp Gly Gln Gly Thr Leu Val Thr Val Ser Ala
        100                 105                 110
```

<210> SEQ ID NO 57
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
caggtgcagc tggaggagtc aggacctggc ctggtggcgc cctcacagag cctgtccatc      60
acttgcactg tctctggatt ttcattaacc agctatggtg tacactgggt tcgccagcct     120
ccaggaaagg gtctggagtg gctgggagta atatgggctg ttggaagtat aaattataat     180
tcggctctca tgtccagact gagcatcagc aaagacaact ccaagagcca gttttcttta     240
aaaatgaaca gtctacgaac tgatgacaca gccatgtact actgtgccag agatcggact     300
acggctaccc ccttctttga ctactggggc caaggcacca ctctcacagt ctcctcatcc     360
aaaaca                                                                366
```

<210> SEQ ID NO 58
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Gln Val Gln Leu Glu Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Val Gly Ser Ile Asn Tyr Asn Ser Ala Leu Met
    50                  55                  60

Ser Arg Leu Ser Ile Ser Lys Asp Asn Ser Lys Ser Gln Val Phe Leu
65                  70                  75                  80
```

```
Lys Met Asn Ser Leu Arg Thr Asp Asp Thr Ala Met Tyr Tyr Cys Ala
            85                  90                  95

Arg Asp Arg Thr Thr Ala Thr Pro Phe Phe Asp Tyr Trp Gly Gln Gly
            100                 105                 110

Thr Thr Leu Thr Val Ser Ser
            115
```

<210> SEQ ID NO 59
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
caggtgcagc tgaagcagtc aggacctggc ctagtgcagc cctcacagag cctgtccatc    60
acctgcacag tctctggttt ctcattaatt acccatggtg tacactgggt tcgccagtct   120
ccaggaaagg gtctggagtg gctgggagtg atatggagtg gtggaagcac agactataat   180
gcagctttca tatccagact gagcatcagc aaggacacct ccaagagcca agttttcctt   240
aaaatgagca gtctgcaagc tgatgacaca gccatatact actgtgccag aaatgggggg   300
gctacggcct ttgactactg gggccaaggc accactctca cagtctcctc a            351
```

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Thr His
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Thr Ser Lys Ser Gln Val Phe Leu
65                  70                  75                  80

Lys Met Ser Ser Leu Gln Ala Asp Asp Thr Ala Ile Tyr Tyr Cys Ala
            85                  90                  95

Arg Asn Gly Gly Ala Thr Ala Phe Asp Tyr Trp Gly Gln Gly Thr Thr
            100                 105                 110

Leu Thr Val Ser Ser
        115
```

<210> SEQ ID NO 61
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
caggtacagc tgaagcagtc aggacctggc ctagtgcagc cctcacagag cctgtccatc    60
```

```
acctgcacag tctctggttt ctcattaatt acctatggtg tacactgggt tcgccagtct    120
ccaggaaagg gtctggagtg gctgggagtg atatggggtg gtggaagcac aggctataat    180
gcagctttcg tatccagact gaacatcacc aaggacaact ccaagagcca agttttcttt    240
aaaatgaaca gtctgcaacc tgatgacaca gccatatact actgtgccag aaatggaggg    300
gctacggtct ttgactactg gggccaaggc accactctca cagtctcctc a             351
```

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Thr Tyr
            20                  25                  30

Gly Val His Trp Val Arg Gln Ser Pro Gly Lys Gly Leu Glu Trp Leu
        35                  40                  45

Gly Val Ile Trp Gly Gly Gly Ser Thr Gly Tyr Asn Ala Ala Phe Val
    50                  55                  60

Ser Arg Leu Asn Ile Thr Lys Asp Asn Ser Lys Ser Gln Val Phe Phe
65                  70                  75                  80

Lys Met Asn Ser Leu Gln Pro Asp Asp Thr Ala Ile Tyr Tyr Cys Ala
                85                  90                  95

Arg Asn Gly Gly Ala Thr Val Phe Asp Tyr Trp Gly Gln Gly Thr Thr
            100                 105                 110

Leu Thr Val Ser Ser
        115
```

<210> SEQ ID NO 63
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gaggtgcagc tggtggagtc tgggggagac ttagtgaagc ctggagggtc cctgaaactc     60
tcctgtgcag cctctggatt cactttcagt aactatggca tgtcttgggt tcgccagact    120
ccagacaaga ggctggagtg ggtcgcaacc attagtagtg gtggtagtta tagctactat    180
ccagacagtg taaaggggcg gttcaccatc tccagagaca atgccaagaa catcctgtac    240
ctgcaaatga gcagtctgaa gtctgaggac acagccatgt attactgtgc aagtctctac    300
tacggctacg gggactactg gggccaaggc accgctttca cagtctcctc a             351
```

<210> SEQ ID NO 64
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
                20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Ser Tyr Pro Asp Ser Val
        50                  55                  60

Lys Gly Arg Phe Thr Ile Ser Arg Asp Asn Ala Lys Asn Ile Leu Tyr
65                  70                  75                  80

Leu Gln Met Ser Ser Leu Lys Ser Glu Asp Thr Ala Met Tyr Tyr Cys
                85                  90                  95

Ala Ser Leu Tyr Tyr Gly Tyr Gly Asp Tyr Trp Gly Gln Gly Thr Ala
            100                 105                 110

Phe Thr Val Ser Ser
            115

<210> SEQ ID NO 65
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gaagtgcagc tggtggagtc tgggggaggc ttggtgaagc ctggagggtc cctgaaactc      60
tcctgtgcag cctctggatt cactttcagt gactcttata tgtattgggt tcgccagact     120
ccggaccaga ggctggagtg ggtcgcaacc attagtgatg gtggtagtta caccttctat     180
ccagacagtg tgaagggacg attcaccatc tccagagaca atgcccagaa caacctgtac     240
ctgcaaatga gcagtctgaa gtctgaggac acagccatgt attactgtgc atccccccat     300
gctggctact cggctggttt gcttactggg ggccgaggga ctctggtcac tgtctctgca     360

<210> SEQ ID NO 66
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Ser
                20                  25                  30

Tyr Met Tyr Trp Val Arg Gln Thr Pro Asp Gln Arg Leu Glu Trp Val
            35                  40                  45

Ala Thr Ile Ser Asp Gly Gly Ser Tyr Thr Phe Tyr Pro Asp Ser Val
        50                  55                  60

Lys Gly Arg Phe Thr Ile Ser Arg Asp Asn Ala Gln Asn Asn Leu Tyr
65                  70                  75                  80

Leu Gln Met Ser Ser Leu Lys Ser Glu Asp Thr Ala Met Tyr Tyr Cys
                85                  90                  95

Ala Ser Pro His Ala Gly Tyr Phe Gly Trp Phe Ala Tyr Trp Gly Arg
            100                 105                 110

```
Gly Thr Leu Val Thr Val Ser Ala
        115                 120
```

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gaggtgcagc tggtggagtc tgggggagac ttagtgaagc ctggagggtc cctgaaactc      60
tcctgtgcag cctctggatt cactttcaat cactatggca tgtcttgggt tcgccagcct     120
ccagacaaga gactggagtg ggtcgcaacc attagtagtg gtggtggtta cacctactat     180
ccagacagtg tgaaggggcg cttcaccatc tccagagaca atgccaagga caccctgtcc     240
ctgcaaatga gcagtctgag gtctggggac acagccgtgt attactgtgc aagcctatac     300
ggtagcctgt ttgcttactg gggccaaggg actctggtca ctgtctctgc a              351
```

<210> SEQ ID NO 68
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn His Tyr
            20                  25                  30

Gly Met Ser Trp Val Arg Gln Pro Pro Asp Lys Arg Leu Glu Trp Val
        35                  40                  45

Ala Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asp Thr Leu Ser
65                  70                  75                  80

Leu Gln Met Ser Ser Leu Arg Ser Gly Asp Thr Ala Val Tyr Tyr Cys
                85                  90                  95

Ala Ser Leu Tyr Gly Ser Leu Phe Ala Tyr Trp Gly Gln Gly Thr Leu
            100                 105                 110

Val Thr Val Ser Ala
        115
```

<210> SEQ ID NO 69
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gacgtgaagc tcgtggagtc tgggggaggc ttagtgaagc ttggagggtc cctgaaactc      60
tcctgtgcag cctctggatt cactttcagt agctattaca tgtcttgggt tcgccagact     120
ccagagaaga ggctggagtt ggtcgcagcc attaatagta atggtggtag cacctactat     180
```

```
ccagacactg tgaagggccg attcaccatc tccagagaca atgccaagaa caccctgtac    240
ctgcaaatga gcagtctgaa gtctgaggac acagccttgt attactgtgc aagacatggg    300
ggactgggac gtagggactg gtacttcgat gtctggggcg cagggaccac ggtcaccgtc    360
tcctca                                                               366
```

<210> SEQ ID NO 70
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg His Gly Gly Leu Gly Arg Arg Asp Trp Tyr Phe Asp Val Trp
            100                 105                 110

Gly Ala Gly Thr Thr Val Thr Val Ser Ser
        115                 120
```

<210> SEQ ID NO 71
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
gaagtgaaac tggtggagtc tgggggaagt ttagtgcagc ctggagggtc cctgaaactc    60
tcctgcgcag cctctggatt caatttcaat acctatgcca tgtcttgggt tcgccagact    120
ccagagaaga ggctggagtg ggtcgcatac attagtaatg gtggtggtaa cacctactat    180
gtagacactg taaagggccg attcaccatc tccagagaca atgccaagaa caccctgtac    240
ctgcgaatga gcagtctgaa gtctgaggac acggccatgt attactgtgc aagacatggg    300
ctctactggg gctattctat ggactactgg ggtcaaggaa cctcagtcac cgtctcctca    360
```

<210> SEQ ID NO 72
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Glu Val Lys Leu Val Glu Ser Gly Gly Ser Leu Val Gln Pro Gly Gly
1               5                   10                  15
```

```
Ser Leu Lys Leu Ser Cys Ala Ala Ser Gly Phe Asn Phe Asn Thr Tyr
            20                  25                  30

Ala Met Ser Trp Val Arg Gln Thr Pro Glu Lys Arg Leu Glu Trp Val
        35                  40                  45

Ala Tyr Ile Ser Asn Gly Gly Asn Thr Tyr Tyr Val Asp Thr Val
    50                  55                  60

Lys Gly Arg Phe Thr Ile Ser Arg Asp Asn Ala Lys Asn Thr Leu Tyr
65                  70                  75                  80

Leu Arg Met Ser Ser Leu Lys Ser Glu Asp Thr Ala Met Tyr Tyr Cys
                85                  90                  95

Ala Arg His Gly Leu Tyr Trp Gly Tyr Ser Met Asp Tyr Trp Gly Gln
            100                 105                 110

Gly Thr Ser Val Thr Val Ser Ser
        115                 120

<210> SEQ ID NO 73
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gaagtgaagc tggtggagtc tgggggaggt ttagtgcagc caggagggtc cctgaaactc      60
tcctgtgcag cctctggatt cactttcagt agctatgcca tgtcttgggt tcgccagact     120
ccagagagga ggctggagtg ggtcacatac attagtaatg gtggtggtag cacctactat     180
tcagacactg taaagggccg attcaccttc tccagagaca atgccaagaa cacactgtac     240
ctgcaaatga gcagtctgaa gtctgaggac acggccatgt attactgtgc aagacatgga     300
ctgggaagga cagggtttgc ttcctggggc caagggactc tggtcactgt ctctgca      357

<210> SEQ ID NO 74
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Arg Arg Leu Glu Trp Val
        35                  40                  45

Thr Tyr Ile Ser Asn Gly Gly Gly Ser Thr Tyr Tyr Ser Asp Thr Val
    50                  55                  60

Lys Gly Arg Phe Thr Phe Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Leu Gly Arg Thr Gly Phe Ala Ser Trp Gly Gln Gly
            100                 105                 110

Thr Leu Val Thr Val Ser Ala
        115
```

<210> SEQ ID NO 75
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
gatgtgcagc tggtggagtc tgggggaggc ctagtgcagg ctggagggtc ccggaaactc      60
tcctgtgcag cctctggatt ccctttcagt tcctttggaa tgcactgggt tcgtcaggct     120
ccagagaagg ggctggagtg ggtcgcctcc attagtagtc gcactagtaa gatctactat     180
gcagacaacc tgaagggccg attcaccatc tccagagaca atcccaagaa caccctgttc     240
ctgcaaatga ccagtcttgg atctgaggac acggccatgt attactgtgt aagatccgtc     300
tttggtaatt cttactggtt tttcgatgtc tggggcgcag ggaccacggt caccgtctcc     360
tca                                                                   363
```

<210> SEQ ID NO 76
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Val Gln Leu Val Glu Ser Gly Gly Gly Leu Val Gln Ala Gly Gly
1               5                   10                  15

Ser Arg Lys Leu Ser Cys Ala Ala Ser Gly Phe Pro Phe Ser Ser Phe
            20                  25                  30

Gly Met His Trp Val Arg Gln Ala Pro Glu Lys Gly Leu Glu Trp Val
        35                  40                  45

Ala Ser Ile Ser Ser Arg Thr Ser Lys Ile Tyr Tyr Ala Asp Asn Leu
    50                  55                  60

Lys Gly Arg Phe Thr Ile Ser Arg Asp Asn Pro Lys Asn Thr Leu Phe
65                  70                  75                  80

Leu Gln Met Thr Ser Leu Gly Ser Glu Asp Thr Ala Met Tyr Tyr Cys
                85                  90                  95

Val Arg Ser Val Phe Gly Asn Ser Tyr Trp Phe Phe Asp Val Trp Gly
            100                 105                 110

Ala Gly Thr Thr Val Thr Val Ser Ser
        115                 120

<210> SEQ ID NO 77
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
gaagtgaagc ttgaggagtc tgaggaggc ttggtacaac ctgggggatc catgaaactc       60
tcctgtgtag cctctggatt ttctttcagt agctactgga tgtcttgggt ccgccagtct     120
ccagagaagg ggcttgactg ggttgctgaa attagattga gatctgataa ttatgcaacc     180
cattatgcgg agtctgtgaa agggaggttc accatctcaa gagatgattc cataagtcgt     240
```

```
ctctacctgc aaatgaacac cttaagagct gaagacactg gaatttatta ctgtacatgg    300
atgacgtact ggggccaagg gactctggtc actgtctctg caaca                   345
```

<210> SEQ ID NO 78
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ser Phe Ser Ser Tyr
            20                  25                  30

Trp Met Ser Trp Val Arg Gln Ser Pro Glu Lys Gly Leu Asp Trp Val
        35                  40                  45

Ala Glu Ile Arg Leu Arg Ser Asp Asn Tyr Ala Thr His Tyr Ala Glu
    50                  55                  60

Ser Val Lys Gly Arg Phe Thr Ile Ser Arg Asp Asp Ser Ile Ser Arg
65                  70                  75                  80

Leu Tyr Leu Gln Met Asn Thr Leu Arg Ala Glu Asp Thr Gly Ile Tyr
                85                  90                  95

Tyr Cys Thr Trp Met Thr Tyr Trp Gly Gln Gly Thr Leu Val Thr Val
            100                 105                 110

Ser Ala
```

<210> SEQ ID NO 79
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
gaggtgaagc tggtggagtc tggaggaggc ttggtacagc ctgggggttc tctgagactc    60
tcctgtgcaa gttctgggtt caccttcact gattactaca tgagctgggt ccgccagcct   120
ccaggaaagg cacttgagtg gttgggtttt attagaaaca agcttatgg ttacacgacc    180 gagttcagtg catctgtgaa cggtcggttc accatctcca gagatgattc ccaaagcgtc   240
ccctatcttc aaatgaacac cctgagagct gaggacagtg ccacttatta ctgtgcgaga   300
gtcctctact atgattacgg gggatttgct tactggggcc aagggactct ggtcactgtc   360
tctaca                                                              366
```

<210> SEQ ID NO 80
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Glu Val Lys Leu Val Glu Ser Gly Gly Gly Leu Val Gln Pro Gly Gly
1               5                   10                  15

Ser Leu Arg Leu Ser Cys Ala Ser Ser Gly Phe Thr Phe Thr Asp Tyr
```

```
                    20                  25                  30
Tyr Met Ser Trp Val Arg Gln Pro Pro Gly Lys Ala Leu Glu Trp Leu
            35                  40                  45

Gly Phe Ile Arg Asn Lys Ala Tyr Gly Tyr Thr Thr Glu Phe Ser Ala
        50                  55                  60

Ser Val Asn Gly Arg Phe Thr Ile Ser Arg Asp Asp Ser Gln Ser Val
65                  70                  75                  80

Pro Tyr Leu Gln Met Asn Thr Leu Arg Ala Glu Asp Ser Ala Thr Tyr
                85                  90                  95

Tyr Cys Ala Arg Val Leu Tyr Tyr Asp Tyr Gly Gly Phe Ala Tyr Trp
            100                 105                 110

Gly Gln Gly Thr Leu Val Thr Val Ser Thr
            115                 120

<210> SEQ ID NO 81
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtccagc tgcagcagtc tggacctgag ctggtaaagc ctggggcttc agtgaagatg      60
tcctgtaagg cttccggata cagattcact agctatgtta tgcactgggt gaggcagaag     120
cctggacagg gccttgagtg gattggatat attgatcctc acaatgatga tacaaaatac     180
agtgagaagt tcagaggtaa ggccacactg acttcagaca gtcctccac cacagcctac      240 atggagctca gcagcctgac ctctgaggac tctgcggtct attactgtgt gagatattct     300
tacgacaggg attacagtcc tatggactac tggggtcaag aacctcagt caccgtctcc      360 tca                                                                    363

<210> SEQ ID NO 82
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Arg Phe Thr Ser Tyr
            20                  25                  30

Val Met His Trp Val Arg Gln Lys Pro Gly Gln Gly Leu Glu Trp Ile
        35                  40                  45

Gly Tyr Ile Asp Pro His Asn Asp Asp Thr Lys Tyr Ser Glu Lys Phe
    50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Val Arg Tyr Ser Tyr Asp Arg Asp Tyr Ser Pro Met Asp Tyr Trp Gly
            100                 105                 110

Gln Gly Thr Ser Val Thr Val Ser Ser
            115                 120
```

<210> SEQ ID NO 83
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
cagctgcaac agtctggacc tgagctggtg aagcctgggg cttcagtgaa aatttcctgc      60
aagacttctg gatacacatt cactgaaaac gccatgcact gggtgaagca gagccgtgga     120
aagagccttg agtggattgg aggtgttaat cctaacaatg gtgatactgt ctacacccag     180
aagttcaagg gcaaggccac attgactgta gccaagtctt ccagcacagc ctacatggag     240
ctccgcacca tgacatgtga ggaatctaca gtgtattact gtgcaagccg ggaaccggac     300
ttctttgact actggggcca aggctcctct gtcacagtct cctca                    345

<210> SEQ ID NO 84
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Leu Gln Gln Ser Gly Pro Glu Leu Val Lys Pro Gly Ala Ser Val
1               5                   10                  15

Lys Ile Ser Cys Lys Thr Ser Gly Tyr Thr Phe Thr Glu Asn Ala Met
            20                  25                  30

His Trp Val Lys Gln Ser Arg Gly Lys Ser Leu Glu Trp Ile Gly Gly
        35                  40                  45

Val Asn Pro Asn Asn Gly Asp Thr Val Tyr Thr Gln Lys Phe Lys Gly
    50                  55                  60

Lys Ala Thr Leu Thr Val Ala Lys Ser Ser Ser Thr Ala Tyr Met Glu
65                  70                  75                  80

Leu Arg Thr Met Thr Cys Glu Glu Ser Thr Val Tyr Tyr Cys Ala Ser
                85                  90                  95

Arg Glu Pro Asp Phe Phe Asp Tyr Trp Gly Gln Gly Ser Ser Val Thr
            100                 105                 110

Val Ser Ser
        115

<210> SEQ ID NO 85
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
cagctgcaac agtctggacc tgtactggtg aagcctgggg cttcagtgaa aatttcctgc      60
aagacttctg gatacacatt cactgaaaac gccatgcact gggtgaagca gagccatgga     120
aagagccttg agtggattgg aggtgttaat cctaacaatg gtgatactat ctacaaccag     180
aagttcaagg gcaaggccac attgactgta gacaagtcct ccagcacagc cttcatggag     240
ctccgcagcc tgacatctga agaatcccca gtctatttct gtgtaagacg ggaactggac     300

```
ttctttgact actggggcca aggcacctct gtcacagtct cctca              345
```

<210> SEQ ID NO 86
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Gln Leu Gln Gln Ser Gly Pro Val Leu Val Lys Pro Gly Ala Ser Val
1               5                   10                  15

Lys Ile Ser Cys Lys Thr Ser Gly Tyr Thr Phe Thr Glu Asn Ala Met
            20                  25                  30

His Trp Val Lys Gln Ser His Gly Lys Ser Leu Glu Trp Ile Gly Gly
        35                  40                  45

Val Asn Pro Asn Asn Gly Asp Thr Ile Tyr Asn Gln Lys Phe Lys Gly
    50                  55                  60

Lys Ala Thr Leu Thr Val Asp Lys Ser Ser Thr Ala Phe Met Glu
65                  70                  75                  80

Leu Arg Ser Leu Thr Ser Glu Glu Ser Pro Val Tyr Phe Cys Val Arg
                85                  90                  95

Arg Glu Leu Asp Phe Phe Asp Tyr Trp Gly Gln Gly Thr Ser Val Thr
            100                 105                 110

Val Ser Ser
        115
```

<210> SEQ ID NO 87
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
cagctgcaac agtctggccc tgtcctggtg aagtctggga cttcagttaa aatttcctgc     60
aagacttctg gatacacatt cactgaaaac gccatgcact gggtgaaaca gagccatgga    120
cagagccttg agtggattgg aggtgttaat cctaacaatg gtgatactat cttcaaccag    180
aagttcaagg gcaaggccac attgactgta gacaagtcct ccagcacagc cttcatggag    240
ctccgcagcc tgacatctga gaatccacag tctattact gtgtaagacg ggaactggac    300
ttctttgact actggggtca aggcacctct gtcacagtct cctca                    345
```

<210> SEQ ID NO 88
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Gln Leu Gln Gln Ser Gly Pro Val Leu Val Lys Ser Gly Thr Ser Val
1               5                   10                  15

Lys Ile Ser Cys Lys Thr Ser Gly Tyr Thr Phe Thr Glu Asn Ala Met
            20                  25                  30

His Trp Val Lys Gln Ser His Gly Gln Ser Leu Glu Trp Ile Gly Gly
```

```
                35                  40                  45
Val Asn Pro Asn Asn Gly Asp Thr Ile Phe Asn Gln Lys Phe Lys Gly
 50                  55                  60

Lys Ala Thr Leu Thr Val Asp Lys Ser Ser Thr Ala Phe Met Glu
 65                  70                  75                  80

Leu Arg Ser Leu Thr Ser Glu Glu Ser Thr Val Tyr Tyr Cys Val Arg
                 85                  90                  95

Arg Glu Leu Asp Phe Phe Asp Tyr Trp Gly Gln Gly Thr Ser Val Thr
                100                 105                 110

Val Ser Ser
        115

<210> SEQ ID NO 89
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
cagctgcaac agtctggccc tgtcctggtg aagcctggga cttcagtgaa aatttcctgc      60
aagacttctg gatacacatt cactgaaaac gccatgcact gggtgaaaca gagccatgga     120
aagagccttg agtggattgg aggtgttaat cctaacaatg gtgatactat cttcaaccag     180
aagttcaagg gcaaggccac attgactgta gacaagtcct ccagcacagc cttcatggag     240
ctccgcagcc tgacatctga gaatccacag tctattact gtgtaagacg ggaactggac      300
ttctttgact actggggcca aggcacctct gtcacagtct cctca                     345

<210> SEQ ID NO 90
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Leu Gln Gln Ser Gly Pro Val Leu Val Lys Pro Gly Thr Ser Val
  1               5                  10                  15

Lys Ile Ser Cys Lys Thr Ser Gly Tyr Thr Phe Thr Glu Asn Ala Met
                 20                  25                  30

His Trp Val Lys Gln Ser His Gly Lys Ser Leu Glu Trp Ile Gly Gly
             35                  40                  45

Val Asn Pro Asn Asn Gly Asp Thr Ile Phe Asn Gln Lys Phe Lys Gly
 50                  55                  60

Lys Ala Thr Leu Thr Val Asp Lys Ser Ser Thr Ala Phe Met Glu
 65                  70                  75                  80

Leu Arg Ser Leu Thr Ser Glu Glu Ser Thr Val Tyr Tyr Cys Val Arg
                 85                  90                  95

Arg Glu Leu Asp Phe Phe Asp Tyr Trp Gly Gln Gly Thr Ser Val Thr
                100                 105                 110

Val Ser Ser
        115

<210> SEQ ID NO 91
<211> LENGTH: 345
<212> TYPE: DNA
```

<210> ORGANISM: Artificial Sequence
<220> FEATURE:
<223> OTHER INFORMATION: Description of Artificial Sequence: Synthetic polynucleotide

<400> SEQUENCE: 91

```
cagctgcaac agtctggacc tgcccaggtg aagcctgggg cttcagtgat gatttcctgc      60
aagacttctg gatacacatt cactgaaaac gccatgcact gggtgaaaca gagccatgga     120
aagagccttg agtggattgg aggtgttaat cctaacaatg gtgatactat tttcaaccag     180
aagttcaagg acaaggccgc attgactgta gacaagtcct ccagcacagc cttcatggag     240
ctccgcagcc tgacatctga ggagtccaca gtctattact gtgtaagacg ggaattggac     300
ttcttttgact actggggcca aggcacctct gtcacagtct cctca                     345
```

<210> SEQ ID NO 92
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Gln Leu Gln Gln Ser Gly Pro Ala Gln Val Lys Pro Gly Ala Ser Val
1               5                   10                  15
Met Ile Ser Cys Lys Thr Ser Gly Tyr Thr Phe Thr Glu Asn Ala Met
            20                  25                  30
His Trp Val Lys Gln Ser His Gly Lys Ser Leu Glu Trp Ile Gly Gly
        35                  40                  45
Val Asn Pro Asn Asn Gly Asp Thr Ile Phe Asn Gln Lys Phe Lys Asp
    50                  55                  60
Lys Ala Ala Leu Thr Val Asp Lys Ser Ser Ser Thr Ala Phe Met Glu
65                  70                  75                  80
Leu Arg Ser Leu Thr Ser Glu Glu Ser Thr Val Tyr Tyr Cys Val Arg
                85                  90                  95
Arg Glu Leu Asp Phe Phe Asp Tyr Trp Gly Gln Gly Thr Ser Val Thr
            100                 105                 110
Val Ser Ser
        115
```

<210> SEQ ID NO 93
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
cagctgcaac agtctggacc tgtcctggtg aagcctgggg cttcagtgat gatttcctgc      60
aagacttctg gatacacatt cactgaaaac gccatgcact gggtgaaaca gagccatgga     120
aagagccttg agtggattgg aggtgttaat cctaacaatg gtgatactat tttcaaccag     180
aagttcaagg gcaaggccac attgactgta gacaagtcct ccaacacagc cttcacggag     240
ctccgcagcc tgccatctga agaatccaca gtctattact gtgttagacg gggattggac     300
ttcttttgact actggggcca aggcacctct gtcacagtct cctca                     345
```

<210> SEQ ID NO 94

```
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Leu Gln Gln Ser Gly Pro Val Leu Val Lys Pro Gly Ala Ser Val
1               5                   10                  15

Met Ile Ser Cys Lys Thr Ser Gly Tyr Thr Phe Thr Glu Asn Ala Met
            20                  25                  30

His Trp Val Lys Gln Ser His Gly Lys Ser Leu Glu Trp Ile Gly Gly
        35                  40                  45

Val Asn Pro Asn Asn Gly Asp Thr Ile Phe Asn Gln Lys Phe Lys Gly
    50                  55                  60

Lys Ala Thr Leu Thr Val Asp Lys Ser Ser Asn Thr Ala Phe Thr Glu
65                  70                  75                  80

Leu Arg Ser Leu Pro Ser Glu Glu Ser Thr Val Tyr Tyr Cys Val Arg
                85                  90                  95

Arg Gly Leu Asp Phe Phe Asp Tyr Trp Gly Gln Gly Thr Ser Val Thr
            100                 105                 110

Val Ser Ser
        115

<210> SEQ ID NO 95
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
cagctgcaac agtctggccc tgtcctggtg gggcctgggg cttcagtgat gatttcctgc      60
aagacttctg gatacacatt cactgaaaac gccatgcact gggtggaaca gagccatgga     120
aagagccttg agtggattgg aggtgttaat cctaacaatg gtgatactat tttcaaccag     180
aagttcaagg gcaaggccac attgactgta gacaagtcct ccagcacagc cttcatggag     240
ttccgcagcc tgacatctga gaatccacac gtctattact gtgtaagacg ggaattggac     300
ttctttgact actggggcca aggcacctct gtcacagtct cctca                     345

<210> SEQ ID NO 96
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Leu Gln Gln Ser Gly Pro Val Leu Val Gly Pro Gly Ala Ser Val
1               5                   10                  15

Met Ile Ser Cys Lys Thr Ser Gly Tyr Thr Phe Thr Glu Asn Ala Met
            20                  25                  30

His Trp Val Glu Gln Ser His Gly Lys Ser Leu Glu Trp Ile Gly Gly
        35                  40                  45

Val Asn Pro Asn Asn Gly Asp Thr Ile Phe Asn Gln Lys Phe Lys Gly
    50                  55                  60
```

```
Lys Ala Thr Leu Thr Val Asp Lys Ser Ser Ser Thr Ala Phe Met Glu
 65                 70                  75                  80

Phe Arg Ser Leu Thr Ser Glu Glu Ser Thr Val Tyr Tyr Cys Val Arg
                 85                  90                  95

Arg Glu Leu Asp Phe Phe Asp Tyr Trp Gly Gln Gly Thr Ser Val Thr
            100                 105                 110

Val Ser Ser
        115

<210> SEQ ID NO 97
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
cagctgcaac agtctggacc tgtcctggtg aagcctgggg cttcagtgat gatttcctgc      60
aagacttctg gatacacatt cactgaaaac gccatgcact gggtgaaaca gagccatgga     120
aagagccttg agtggattgg aggtgttaat cctaacaatg gtgatactat tttcaaccag     180
aagttcaagg gcaaggccac attgactgta gacaagtcct ccagcacagc cttcatggag     240
ttccgcagcc tgacatctga gaatccacag gtctattact gtgtaagacg ggaattggac     300
ttctttgact actggggcca aggcacctct gtcacagtct cctcaaca                  348

<210> SEQ ID NO 98
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Leu Gln Gln Ser Gly Pro Val Leu Val Lys Pro Gly Ala Ser Val
  1               5                  10                  15

Met Ile Ser Cys Lys Thr Ser Gly Tyr Thr Phe Thr Glu Asn Ala Met
                 20                  25                  30

His Trp Val Lys Gln Ser His Gly Lys Ser Leu Glu Trp Ile Gly Gly
             35                  40                  45

Val Asn Pro Asn Asn Gly Asp Thr Ile Phe Asn Gln Lys Phe Lys Gly
         50                  55                  60

Lys Ala Thr Leu Thr Val Asp Lys Ser Ser Ser Thr Ala Phe Met Glu
 65                 70                  75                  80

Phe Arg Ser Leu Thr Ser Glu Glu Ser Thr Val Tyr Tyr Cys Val Arg
                 85                  90                  95

Arg Glu Leu Asp Phe Phe Asp Tyr Trp Gly Gln Gly Thr Ser Val Thr
            100                 105                 110

Val Ser Ser
        115

<210> SEQ ID NO 99
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 99

```
cagctgcaac agtctggacc tgtcctggtg aagcctgggg cttcagtgat gatttcctgc    60
aagacttctg gatacacatt cactgaaaac gccatgcact gggtgaaaca gagccatgga   120
aagagccttg agtggattgg aggtgttaat cctaacaatg gtgatactat tttcaaccag   180
aagttcaagg gcaaggccac attgactgta gacaagtcct ccagcacagc cttcatggag   240
ctccgcagcc tgacatctga agaatccaca gtctattact gtgtaagacg ggaattggac   300
ttctttgact actggggcca aggcacctct gtcacagtct cctca                   345
```

<210> SEQ ID NO 100
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gln Leu Gln Gln Ser Gly Pro Val Leu Val Lys Pro Gly Ala Ser Val
1               5                   10                  15

Met Ile Ser Cys Lys Thr Ser Gly Tyr Thr Phe Thr Glu Asn Ala Met
            20                  25                  30

His Trp Val Lys Gln Ser His Gly Lys Ser Leu Glu Trp Ile Gly Gly
        35                  40                  45

Val Asn Pro Asn Asn Gly Asp Thr Ile Phe Asn Gln Lys Phe Lys Gly
    50                  55                  60

Lys Ala Thr Leu Thr Val Asp Lys Ser Ser Ser Thr Ala Phe Met Glu
65                  70                  75                  80

Leu Arg Ser Leu Thr Ser Glu Glu Ser Thr Val Tyr Tyr Cys Val Arg
                85                  90                  95

Arg Glu Leu Asp Phe Phe Asp Tyr Trp Gly Gln Gly Thr Ser Val Thr
            100                 105                 110

Val Ser Ser
        115
```

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101

```
gaatacgcca tgcac                                                     15
```

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Glu Tyr Ala Met His
1               5
```

<210> SEQ ID NO 103
<211> LENGTH: 15

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gaatacgcca tacac                                                     15

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Tyr Ala Ile His
1               5

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
agtagttata taagt                                                     15

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ser Tyr Ile Ser
1               5

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agtagtttta taagt                                                     15

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ser Phe Ile Ser
1               5
```

```
<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
agtagttatt ttagt                                                          15

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Ser Tyr Phe Ser
1               5

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
agcagtacct atataagt                                                       18

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Thr Tyr Ile Ser
1               5

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
agctactgga tacac                                                          15

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Tyr Trp Ile His
1               5
```

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
agctattgga tgcac                                              15

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Tyr Trp Met His
1               5

<210> SEQ ID NO 117
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cctactcgat aaac                                               14

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Tyr Ser Ile Asn
1               5

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gccaacaaga tgcac                                              15

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Asn Lys Met His
1               5

<210> SEQ ID NO 121
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
agcaacaaga tgcac                                                     15

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Asn Lys Met His
1               5

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
agctactatg tacac                                                     15

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Tyr Tyr Val His
1               5

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
agtggttatt actggatc                                                  18

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 126

Ser Gly Tyr Tyr Trp Ile
1               5

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
agtgattatg cctggaac                                                 18

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Asp Tyr Ala Trp Asn
1               5

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agctatggtg tacac                                                    15

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Tyr Gly Val His
1               5

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
acccatggtg tacac                                                    15

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 132

Thr His Gly Val His
1               5

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
acctatggtg tacac                                                      15

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Tyr Gly Val His
1               5

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aactatggca tgtct                                                      15

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Tyr Gly Met Ser
1               5

<210> SEQ ID NO 137
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gactcttata tgtat                                                      15

<210> SEQ ID NO 138
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 138

Asp Ser Tyr Met Tyr
1               5

<210> SEQ ID NO 139
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cactatggca tgtct                                                    15

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

His Tyr Gly Met Ser
1               5

<210> SEQ ID NO 141
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agctattaca tgtct                                                    15

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Tyr Tyr Met Ser
1               5

<210> SEQ ID NO 143
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
acctatgcca tgtct                                                    15

<210> SEQ ID NO 144
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Thr Tyr Ala Met Ser
1               5

<210> SEQ ID NO 145
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
agctatgcca tgtct                                                      15

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Tyr Ala Met Ser
1               5

<210> SEQ ID NO 147
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tcctttggaa tgcac                                                      15

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Phe Gly Met His
1               5

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
agctactgga tgtct                                                      15
```

```
<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Tyr Trp Met Ser
1               5

<210> SEQ ID NO 151
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gattactaca tgagc                                                    15

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Tyr Tyr Met Ser
1               5

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
agctatgtta tgcac                                                    15

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Tyr Val Met His
1               5

<210> SEQ ID NO 155
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gaaaacgcca tgcac                                                    15
```

```
<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Asn Ala Met His
1               5

<210> SEQ ID NO 157
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggtatcaatc ctactaatgg tgatacaatc tacaaccaga agttcaagga c            51

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ile Asn Pro Thr Asn Gly Asp Thr Ile Tyr Asn Gln Lys Phe Lys
1               5                   10                  15

Asp

<210> SEQ ID NO 159
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ggtatcaatc ctactaatgg tgatacaatc tacaaccaga ggttcaagga c            51

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Ile Asn Pro Thr Asn Gly Asp Thr Ile Tyr Asn Gln Arg Phe Lys
1               5                   10                  15

Asp

<210> SEQ ID NO 161
<211> LENGTH: 51
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 161
ggtattaatc ctaacaatgg caatgctatc tacaaccaga tattcaagga c          51

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Ile Asn Pro Asn Asn Gly Asn Ala Ile Tyr Asn Gln Ile Phe Lys
1               5                   10                  15
Asp

<210> SEQ ID NO 163
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggtattaatc ctagcaatgg caatgctatc tacaaccaaa tattcaagga c          51

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Ile Asn Pro Ser Asn Gly Asn Ala Ile Tyr Asn Gln Ile Phe Lys
1               5                   10                  15
Asp

<210> SEQ ID NO 165
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggtattaatc ctagcaatgg cgatcctatc tataaccaga tattcaagga c          51

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Ile Asn Pro Ser Asn Gly Asp Pro Ile Tyr Asn Gln Ile Phe Lys
1               5                   10                  15

Asp

<210> SEQ ID NO 167
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tggatttatg ctggaactgg taatactaac tataatcaga agttcacaga c          51

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Trp Ile Tyr Ala Gly Thr Gly Asn Thr Asn Tyr Asn Gln Lys Phe Thr
1               5                   10                  15
Asp

<210> SEQ ID NO 169
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tggatttttg ctggaactgg taatactaat tataatcaga agttcacaga c          51

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Trp Ile Phe Ala Gly Thr Gly Asn Thr Asn Tyr Asn Gln Lys Phe Thr
1               5                   10                  15
Asp

<210> SEQ ID NO 171
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tggatttatg ctggaactgg taatactatc tataatcaga agttcacaga c          51

<210> SEQ ID NO 172
<211> LENGTH: 17
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 172

Trp Ile Tyr Ala Gly Thr Gly Asn Thr Ile Tyr Asn Gln Lys Phe Thr
1               5                   10                  15
Asp

<210> SEQ ID NO 173
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
tggatttatg ctggaactgg tggtactaac tataatcaga agttcacaga c         51

<210> SEQ ID NO 174
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Trp Ile Tyr Ala Gly Thr Gly Gly Thr Asn Tyr Asn Gln Lys Phe Thr
1               5                   10                  15
Asp

<210> SEQ ID NO 175
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
tggatttatg ctggaactgg tgctactaat tataatcaga agttcacagg c         51

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 176

Trp Ile Tyr Ala Gly Thr Gly Ala Thr Asn Tyr Asn Gln Lys Phe Thr
1               5                   10                  15
Gly

<210> SEQ ID NO 177
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
gaaattgatc cttctgacag ttatattaac cagaatcaaa agttcagggg c          51

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Glu Ile Asp Pro Ser Asp Ser Tyr Ile Asn Gln Asn Gln Lys Phe Arg
1               5                   10                  15

Gly

<210> SEQ ID NO 179
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gaagttgatc cttctgacag ttatattaac cagaatgaaa agttcagggg c          51

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Glu Val Asp Pro Ser Asp Ser Tyr Ile Asn Gln Asn Glu Lys Phe Arg
1               5                   10                  15

Gly

<210> SEQ ID NO 181
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gagattgatc cttctgatag ttatactaac tacaatcaaa agttcaaggg c          51

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Glu Ile Asp Pro Ser Asp Ser Tyr Thr Asn Tyr Asn Gln Lys Phe Lys
1               5                   10                  15

Gly

<210> SEQ ID NO 183
<211> LENGTH: 51

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gagattcatc cttctgatag ttatactagc tacaatcaaa agttcaagga c            51

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Ile His Pro Ser Asp Ser Tyr Thr Ser Tyr Asn Gln Lys Phe Lys
1               5                   10                  15
Asp

<210> SEQ ID NO 185
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aatatttatc cttctaccag tcatactaac tacaatcaaa agttcaggga c            51

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asn Ile Tyr Pro Ser Thr Ser His Thr Asn Tyr Asn Gln Lys Phe Arg
1               5                   10                  15
Asp

<210> SEQ ID NO 187
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tacattgatc ctagctctgg ttatactgaa tacaatcata agatccagta c            51

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188
```

Tyr Ile Asp Pro Ser Ser Gly Tyr Thr Glu Tyr Asn His Lys Ile Gln
1               5                   10                  15

Tyr

<210> SEQ ID NO 189
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tacattgatc ctagctctgg ttatactgaa tacaatcata agatccagga c        51

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Ile Asp Pro Ser Ser Gly Tyr Thr Glu Tyr Asn His Lys Ile Gln
1               5                   10                  15

Asp

<210> SEQ ID NO 191
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tacattgatc ctagctctgg ttatactcaa tacaatcata agatccagga c        51

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Ile Asp Pro Ser Ser Gly Tyr Thr Gln Tyr Asn His Lys Ile Gln
1               5                   10                  15

Asp

<210> SEQ ID NO 193
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tacattgatc ctgcctctgg ctatactgaa tacaatcaga agatcaagga c        51

<210> SEQ ID NO 194
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Tyr Ile Asp Pro Ala Ser Gly Tyr Thr Glu Tyr Asn Gln Lys Ile Lys
1               5                   10                  15
Asp

<210> SEQ ID NO 195
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tacattgatc ctagctctgg ttatactgaa tacaatcaga agatcaagga c           51

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Tyr Ile Asp Pro Ser Ser Gly Tyr Thr Glu Tyr Asn Gln Lys Ile Lys
1               5                   10                  15
Asp

<210> SEQ ID NO 197
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tgtatttatc ctggagatgt taatactgac tataatgaga gttcaaggg c            51

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Cys Ile Tyr Pro Gly Asp Val Asn Thr Asp Tyr Asn Glu Lys Phe Lys
1               5                   10                  15
Gly

<210> SEQ ID NO 199
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 199
tacataaagt acgacggtgg caataactac agcccatctc tcaaaaat            48

<210> SEQ ID NO 200
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Tyr Ile Lys Tyr Asp Gly Gly Asn Asn Tyr Ser Pro Ser Leu Lys Asn
1               5                   10                  15

<210> SEQ ID NO 201
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tacataagct acagtggtac cactgtctac agcccatctc tcaaaagt            48

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Tyr Ile Ser Tyr Ser Gly Thr Thr Val Tyr Ser Pro Ser Leu Lys Ser
1               5                   10                  15

<210> SEQ ID NO 203
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gtaatatggg ctgttggaag tataaattat aattcggctc tcatgtcc            48

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Val Ile Trp Ala Val Gly Ser Ile Asn Tyr Asn Ser Ala Leu Met Ser
1               5                   10                  15

<210> SEQ ID NO 205
<211> LENGTH: 48
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 205
gtgatatgga gtggtggaag cacagactat aatgcagctt tcatatcc                 48

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Val Ile Trp Ser Gly Gly Ser Thr Asp Tyr Asn Ala Ala Phe Ile Ser
1               5                   10                  15

<210> SEQ ID NO 207
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gtgatatggg gtggtggaag cacaggctat aatgcagctt tcgtatcc                 48

<210> SEQ ID NO 208
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Val Ile Trp Gly Gly Gly Ser Thr Gly Tyr Asn Ala Ala Phe Val Ser
1               5                   10                  15

<210> SEQ ID NO 209
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
accattagta gtggtggtag ttatagctac tatccagaca gtgtaaaggg g             51

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Ile Ser Ser Gly Gly Ser Tyr Ser Tyr Tyr Pro Asp Ser Val Lys
1               5                   10                  15
Gly

<210> SEQ ID NO 211
```

<210> SEQ ID NO 211
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
accattagtg atggtggtag ttacaccttc tatccagaca gtgtgaaggg a           51

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Thr Ile Ser Asp Gly Gly Ser Tyr Thr Phe Tyr Pro Asp Ser Val Lys
1               5                   10                  15
Gly

<210> SEQ ID NO 213
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
accattagta gtggtggtgg ttacacctac tatccagaca gtgtgaaggg g           51

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Ile Ser Ser Gly Gly Gly Tyr Thr Tyr Tyr Pro Asp Ser Val Lys
1               5                   10                  15
Gly

<210> SEQ ID NO 215
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gccattaata gtaatggtgg tagcacctac tatccagaca ctgtgaaggg c           51

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Ala Ile Asn Ser Asn Gly Gly Ser Thr Tyr Tyr Pro Asp Thr Val Lys
1               5                   10                  15

Gly

<210> SEQ ID NO 217
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tacattagta atggtggtgg taacacctac tatgtagaca ctgtaaaggg c         51

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Tyr Ile Ser Asn Gly Gly Asn Thr Tyr Tyr Val Asp Thr Val Lys
1               5                   10                  15

Gly

<210> SEQ ID NO 219
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tacattagta atggtggtgg tagcacctac tattcagaca ctgtaaaggg c         51

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Tyr Ile Ser Asn Gly Gly Gly Ser Thr Tyr Tyr Ser Asp Thr Val Lys
1               5                   10                  15

Gly

<210> SEQ ID NO 221
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tccattagta gtcgcactag taagatctac tatgcagaca acctgaaggg c         51

<210> SEQ ID NO 222
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Ile Ser Ser Arg Thr Ser Lys Ile Tyr Tyr Ala Asp Asn Leu Lys
1               5                   10                  15

Gly

<210> SEQ ID NO 223
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gaaattagat tgagatctga taattatgca acccattatg cggagtctgt gaaaggg      57

<210> SEQ ID NO 224
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Glu Ile Arg Leu Arg Ser Asp Asn Tyr Ala Thr His Tyr Ala Glu Ser
1               5                   10                  15

Val Lys Gly

<210> SEQ ID NO 225
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tttattagaa acaaagctta tggttacacg accgagttca gtgcatctgt gaacggt      57

<210> SEQ ID NO 226
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Phe Ile Arg Asn Lys Ala Tyr Gly Tyr Thr Thr Glu Phe Ser Ala Ser
1               5                   10                  15

Val Asn Gly

<210> SEQ ID NO 227
<211> LENGTH: 51
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 227
tatattgatc ctcacaatga tgatacaaaa tacagtgaga agttcagagg t    51

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Ile Asp Pro His Asn Asp Asp Thr Lys Tyr Ser Glu Lys Phe Arg
1               5                   10                  15

Gly

<210> SEQ ID NO 229
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ggtgttaatc ctaacaatgg tgatactgtc tacacccaga agttcaaggg c    51

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Val Asn Pro Asn Asn Gly Asp Thr Val Tyr Thr Gln Lys Phe Lys
1               5                   10                  15

Gly

<210> SEQ ID NO 231
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggtgttaatc ctaacaatgg tgatactatc tacaaccaga agttcaaggg c    51

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Val Asn Pro Asn Asn Gly Asp Thr Ile Tyr Asn Gln Lys Phe Lys
1               5                   10                  15

Gly

<210> SEQ ID NO 233
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ggtgttaatc ctaacaatgg tgatactatc ttcaaccaga agttcaaggg c            51

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Val Asn Pro Asn Asn Gly Asp Thr Ile Phe Asn Gln Lys Phe Lys
1               5                   10                  15

Gly

<210> SEQ ID NO 235
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ggtgttaatc ctaacaatgg tgatactatt ttcaaccaga agttcaagga c            51

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Val Asn Pro Asn Asn Gly Asp Thr Ile Phe Asn Gln Lys Phe Lys
1               5                   10                  15

Asp

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
cgggaactgg actactttgc ctcc                                          24

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Arg Glu Leu Asp Tyr Phe Ala Ser
1               5

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
cgggaactgg actactttcc ctcc                                           24

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Arg Glu Leu Asp Tyr Phe Pro Ser
1               5

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cgacaactgg actactttga ctat                                           24

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Arg Gln Leu Asp Tyr Phe Asp Tyr
1               5

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cgacaactgg acttctttga ctat                                           24

<210> SEQ ID NO 244
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 244

Arg Gln Leu Asp Phe Phe Asp Tyr
1               5

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cgacaactgg actactttga cttt                                          24

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Arg Gln Leu Asp Tyr Phe Asp Phe
1               5

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
agtgggacgg ggtttactta c                                             21

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Gly Thr Gly Phe Thr Tyr
1               5

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
agtgggacgg ggtttattta c                                             21

<210> SEQ ID NO 250
<211> LENGTH: 7
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Gly Thr Gly Phe Ile Tyr
1               5

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tctggggcgg gggtttac                                                     18

<210> SEQ ID NO 252
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ser Gly Ala Gly Val Tyr
1               5

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cattactacg gtgttcttga ctcc                                              24

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

His Tyr Tyr Gly Val Leu Asp Ser
1               5

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
cattactacg gtgtctttga ctcc                                              24

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

His Tyr Tyr Gly Val Phe Asp Ser
1               5

<210> SEQ ID NO 257
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gggggctact ataggtacga cgagtttgct tac                                    33

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Gly Tyr Tyr Arg Tyr Asp Glu Phe Ala Tyr
1               5                   10

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aatgcctatt ctatggacta c                                                 21

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Asn Ala Tyr Ser Met Asp Tyr
1               5

<210> SEQ ID NO 261
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261 tttgcttac                                                                9

<210> SEQ ID NO 262
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Phe Ala Tyr
1

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tattactacg gtagttttgc ttac                                          24

<210> SEQ ID NO 264
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Tyr Tyr Tyr Gly Ser Phe Ala Tyr
1               5

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gggtcggact cctttgacta c                                             21

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Ser Asp Ser Phe Asp Tyr
1               5

<210> SEQ ID NO 267
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267 aattac                                                                6

<210> SEQ ID NO 268
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asn Tyr
1

<210> SEQ ID NO 269
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gatcggacta cggctacccc cttctttgac tac                                  33

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asp Arg Thr Thr Ala Thr Pro Phe Phe Asp Tyr
1               5                   10

<210> SEQ ID NO 271
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
aatggggggg ctacggcctt tgactac                                         27

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asn Gly Gly Ala Thr Ala Phe Asp Tyr
1               5

<210> SEQ ID NO 273
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aatggagggg ctacggtctt tgactac                              27

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Asn Gly Gly Ala Thr Val Phe Asp Tyr
1               5

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ctctactacg gctacgggga ctac                                 24

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Leu Tyr Tyr Gly Tyr Gly Asp Tyr
1               5

<210> SEQ ID NO 277
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ccccatgctg gctacttcgg ctggtttgct tac                       33

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Pro His Ala Gly Tyr Phe Gly Trp Phe Ala Tyr
1               5                   10

<210> SEQ ID NO 279
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 279
ctatacggta gcctgtttgc ttac                                              24

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Leu Tyr Gly Ser Leu Phe Ala Tyr
1               5

<210> SEQ ID NO 281
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
catgggggac tgggacgtag ggactggtac ttcgatgtc                              39

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

His Gly Gly Leu Gly Arg Arg Asp Trp Tyr Phe Asp Val
1               5                   10

<210> SEQ ID NO 283
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
catgggctct actggggcta ttctatggac tac                                    33

<210> SEQ ID NO 284
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

His Gly Leu Tyr Trp Gly Tyr Ser Met Asp Tyr
1               5                   10

<210> SEQ ID NO 285
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 285
catggactgg gaaggacagg gtttgcttcc                                             30

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

His Gly Leu Gly Arg Thr Gly Phe Ala Ser
1               5                   10

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tccgtctttg gtaattctta c                                                      21

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Val Phe Gly Asn Ser Tyr Trp Phe Phe Asp Val
1               5                   10

<210> SEQ ID NO 289
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289 atgacgtac                                                                     9

<210> SEQ ID NO 290
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Met Thr Tyr
1

<210> SEQ ID NO 291
```

<210> SEQ ID NO 291
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 291
gtcctctact atgattacgg gggatttgct tac                33

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 292

Val Leu Tyr Tyr Asp Tyr Gly Gly Phe Ala Tyr
1               5                   10

<210> SEQ ID NO 293
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 293
tattcttacg acagggatta cagtcctatg gactac                36

<210> SEQ ID NO 294
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Tyr Ser Tyr Asp Arg Asp Tyr Ser Pro Met Asp Tyr
1               5                   10

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 295
cgggaaccgg acttctttga ctac                24

<210> SEQ ID NO 296
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Arg Glu Pro Asp Phe Phe Asp Tyr
1               5

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
cgggaattgg acttctttga ctac           24

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Arg Glu Leu Asp Phe Phe Asp Tyr
1               5

<210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 299
cggggattgg acttctttga ctac           24

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Arg Gly Leu Asp Phe Phe Asp Tyr
1               5

<210> SEQ ID NO 301
<211> LENGTH: 347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 301
gacattgtgc tgacacagtc tcctgcttcc ttaattgttt ctctggggca gacggccacc      60
atctcatgca gggccagcca agtgtcagt acatctaggt ttagttatct gcactggatc     120
caacagaaac cagggcagcc acccaaactc ctcatcaagt atgcatccaa ccttgaatct    180
ggggtccctg tcaggttcag tggcagtggg tctgggacag acttcaccct caacatccat    240
cctgtggagg aggaggatac tgcaacatat ttctgtcagc acagttggga gtttccattc    300
acgttcggct cggggacaaa gttgaaaata aaacgggctg atgctgc                  347

<210> SEQ ID NO 302

<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Asp Ile Val Leu Thr Gln Ser Pro Ala Ser Leu Ile Val Ser Leu Gly
1               5                   10                  15

Gln Thr Ala Thr Ile Ser Cys Arg Ala Ser Gln Ser Val Ser Thr Ser
            20                  25                  30

Arg Phe Ser Tyr Leu His Trp Ile Gln Gln Lys Pro Gly Gln Pro Pro
        35                  40                  45

Lys Leu Leu Ile Lys Tyr Ala Ser Asn Leu Glu Ser Gly Val Pro Val
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Phe Cys Gln His Ser Trp
                85                  90                  95

Glu Phe Pro Phe Thr Phe Gly Ser Gly Thr Lys Leu Lys Ile Lys Arg
            100                 105                 110

<210> SEQ ID NO 303
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303
gacattgtgc tgacacagtc tcctgcttcc ttaattgttt ctctggggca gacggccacc      60
atctcatgca gggccagcca agtctcagt  acatctaggt ttagctatgt gcactggatc     120
caacagaaac cagggcagcc acccaaactc ctcatcaagt atgcatccaa ccttgaatct     180
ggggtccctg tcaggttcag tggcagtggg tctgggacag acttcaccct caacatccat     240
cctgtggagg aggaggatac tgcaacatat ttctgtcagc acagtggga gtttccattc      300 acgttcggct cggggacaaa gttgaaaata aaacgggctg atgctgc                   347

<210> SEQ ID NO 304
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Ile Val Leu Thr Gln Ser Pro Ala Ser Leu Ile Val Ser Leu Gly
1               5                   10                  15

Gln Thr Ala Thr Ile Ser Cys Arg Ala Ser Gln Ser Leu Ser Thr Ser
            20                  25                  30

Arg Phe Ser Tyr Val His Trp Ile Gln Gln Lys Pro Gly Gln Pro Pro
        35                  40                  45

Lys Leu Leu Ile Lys Tyr Ala Ser Asn Leu Glu Ser Gly Val Pro Val
    50                  55                  60

Arg Phe Ser Gly Ser Gly Ser Gly Thr Asp Phe Thr Leu Asn Ile His
65                  70                  75                  80

```
Pro Val Glu Glu Glu Asp Thr Ala Thr Tyr Phe Cys Gln His Ser Trp
                85                  90                  95
Glu Phe Pro Phe Thr Phe Gly Ser Gly Thr Lys Leu Lys Ile Lys Arg
            100                 105                 110

<210> SEQ ID NO 305
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 305
gacattgtgc tgacacagtc tcctgcttcc ttaattgtat ctctggggca gagggccacc    60
atctcatgta gggccagcca aagtgtcagt acatccaggt ttagttatgt gcactggatc   120
caacagaaac cagggcagcc acccaaactc ctcatcaagt atgcatccaa ccttgaatct   180
ggggtccctg tcaggttcag tggcagtggg tctgggacag acttcatcct caacatccat   240
cctgtggagg aggaggatac tgcaacatat ttctgtcagc acagttggga gtttccattc   300
acgttcggct cggggacaaa gttggaaata aaacgggctg atgctgc                 347

<210> SEQ ID NO 306
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Asp Ile Val Leu Thr Gln Ser Pro Ala Ser Leu Ile Val Ser Leu Gly
1               5                   10                  15
Gln Arg Ala Thr Ile Ser Cys Arg Ala Ser Gln Ser Val Ser Thr Ser
            20                  25                  30
Arg Phe Ser Tyr Val His Trp Ile Gln Gln Lys Pro Gly Gln Pro Pro
        35                  40                  45
Lys Leu Leu Ile Lys Tyr Ala Ser Asn Leu Glu Ser Gly Val Pro Val
    50                  55                  60
Arg Phe Ser Gly Ser Gly Ser Gly Thr Asp Phe Ile Leu Asn Ile His
65                  70                  75                  80
Pro Val Glu Glu Glu Asp Thr Ala Thr Tyr Phe Cys Gln His Ser Trp
                85                  90                  95
Glu Phe Pro Phe Thr Phe Gly Ser Gly Thr Lys Leu Glu Ile Lys Arg
            100                 105                 110

<210> SEQ ID NO 307
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307
gaagttttga tgacccaaag tccactctcc ctgcctgtca gtcttggaga tcaggcctcc    60
atctcttgca gatctagtca gagccttgaa catactaatg gaaacaccta tttagagtgg   120
ttcctgcaga gaccaggcca gcctccaaag ctcctgatct acaaagtttc cagccgattt   180
tctggggtcc cagacaggtt cagtggcagt ggatcaggga cagatttcac actcaagatc   240
```

```
agcagagtgg aggctgagga tctgggagtt tattactgtt ttcaaggttc acatgttcca    300
ttcacgttcg gctcgggac aaagttggca ataaaacggg ctgatgctgc              350
```

<210> SEQ ID NO 308
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

```
Glu Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Leu Glu His Thr
            20                  25                  30

Asn Gly Asn Thr Tyr Leu Glu Trp Phe Leu Gln Arg Pro Gly Gln Pro
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Ala Ile Lys
            100                 105                 110

Arg
```

<210> SEQ ID NO 309
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 309

```
gaagttttga tgacccaaag tccactctcc ctgcctgtca gtcttggaga tcaggcctcc    60
atctcttgca gatctagtca gagccttgaa catagtaatg aaacaccta tttagagtgg    120 ttcctgcaga gaccaggcca gcctccaaag ctcctgatct acaaagtttc agccgatttt    180
tctggggtcc cagacaggtt cagtggcagt ggatcaggga cagatttcac actcaagatc    240
agcagagtgg aggctgagga tctgggagtt tattactgtt ttcaaggttc acatgttcca    300
ttcacgttcg gctcgggac aaagttggca ataaaacggg ctgatgctgc              350
```

<210> SEQ ID NO 310
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

```
Glu Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Leu Glu His Ser
            20                  25                  30
```

```
Asn Gly Asn Thr Tyr Leu Glu Trp Phe Leu Gln Arg Pro Gly Gln Pro
            35                  40                  45

Pro Lys Leu Leu Ile Tyr Lys Val Ser Ser Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Ala Ile Lys
                100                 105                 110

Arg

<210> SEQ ID NO 311
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311
gatgttttga tggcccaaac tccactctcc ctgcctgtca cccttggaga tcaagcctcc      60
atctcttgca gatctagtca gagccttgta catagtaatg aaacacccta tttagagtgg     120
ttcctgcaga aaccaggcca gtctccaaag ctcctgatct acaacgtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcca     300
ctcacgttcg gctcggggac aaagttggaa ataaaacggg ctgatgctgc                350

<210> SEQ ID NO 312
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Asp Val Leu Met Ala Gln Thr Pro Leu Ser Leu Pro Val Thr Leu Gly
  1               5                  10                  15

Asp Gln Ala Ser Ile Ser Cys Arg Ser Ser Gln Ser Leu Val His Ser
                 20                  25                  30

Asn Gly Asn Thr Tyr Leu Glu Trp Phe Leu Gln Lys Pro Gly Gln Ser
            35                  40                  45

Pro Lys Leu Leu Ile Tyr Asn Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ser Gly Thr Lys Leu Glu Ile Lys
                100                 105                 110

Arg

<210> SEQ ID NO 313
<211> LENGTH: 350
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 313

```
gatgttttga tgacccaaac tccactctcc ctgcctgtca atcttggaga tcaggcctcc    60
atctcttgca gatctagtca gagccttcta catagtaatg gaaacaccta tttagagtgg   120
ttcctgcaga aaccaggcca gtctccaaag ctcctgatct acaatgtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcca   300
ttcacgttcg gctcggggac aaagttggca ataaaacggg ctgatgctgc               350
```

<210> SEQ ID NO 314
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

```
Asp Val Leu Met Thr Gln Thr Pro Leu Ser Leu Pro Val Asn Leu Gly
1               5                   10                  15
Asp Gln Ala Ser Ile Ser Cys Arg Ser Ser Gln Ser Leu Leu His Ser
            20                  25                  30
Asn Gly Asn Thr Tyr Leu Glu Trp Phe Leu Gln Lys Pro Gly Gln Ser
        35                  40                  45
Pro Lys Leu Leu Ile Tyr Asn Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Phe Thr Phe Gly Ser Gly Thr Lys Leu Ala Ile Lys
            100                 105                 110
Arg
```

<210> SEQ ID NO 315
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 315

```
gatgttttga tgacccaaac tccactctcc ctgcctgtca gtcttggaga tcaagcctcc    60
atctcttgca gatctagtca gagccttgta cataataatg gaaacaccta tttagaatgg   120
ttcctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcca   300
ttcacgttcg gctcggggac aaagttggaa ataaaacggg ctgatgctgc               350
```

<210> SEQ ID NO 316
<211> LENGTH: 113
<212> TYPE: PRT

<213> ORGANISM: Artificial Sequence
<220> FEATURE:
<223> OTHER INFORMATION: Description of Artificial Sequence: Synthetic
    polypeptide

<400> SEQUENCE: 316

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg

<210> SEQ ID NO 317
<211> LENGTH: 350
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 317
gatgttttga tgacccaaac tccactctcc ctgcctgtca gtcttggaga tcaagcctcc      60
atctcttgca gatctagtca gagcattgta cacagtaatg aaacacccta tttagagtgg     120
tacctgcaga aactaggcca gtctccaaag ctcctgatct acagagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tggacgttcg gtggaggcac caagctggaa atcaaacggg ctgatgctgc                350

<210> SEQ ID NO 318
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 318

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Leu Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Trp Thr Phe Gly Gly Gly Thr Lys Leu Glu Ile Lys
            100                 105                 110

Arg

<210> SEQ ID NO 319
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 319
gatgttgtga tgacccaaac tccactctcc ctgcctgtca gtcttggaga tcaagcctcc      60
atctcttgca gatctagtca gagccttcta catagtaatg aaacaccta tttagaatgg     120 tacctgcaga aacctggcca gtctccaaac ctcctgatct acaatgtttc caaccgattt    180
tctggggtcc cagacaggtt cagtggcagt ggatcaggga cagatttcgc actcaagatc    240
agcagagtgg gggctgagga tctgggagtt tattactgct ttcaaggttc acatgttccg    300
ctcacgttcg gtgctgggac caagctggag ctgaaacggg ctgatgctgc                350

<210> SEQ ID NO 320
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Asn Val Ser Asn Arg Phe Ser Gly Val Pro
    50                  55                  60

Asp Arg Phe Ser Gly Ser Gly Ser Gly Thr Asp Phe Ala Leu Lys Ile
65                  70                  75                  80

Ser Arg Val Gly Ala Glu Asp Leu Gly Val Tyr Tyr Cys Phe Gln Gly
            85                  90                  95

Ser His Val Pro Leu Thr Phe Gly Ala Gly Thr Lys Leu Glu Leu Lys
            100                 105                 110

Arg

<210> SEQ ID NO 321
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
gatgttgtgc tgacccaaac tccactctcc ctgcctctca gtcttggaga tcaggcctcc      60
atctcttgca gatctagtca gaccttcta cacagtgatg gagacaccta tttacattgg     120

```
tacctgcaga agccaggcca gtctccaaag ctcctgatct acaaactttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
tacacgttcg gaggggggac caagctggaa ataaaacggg ctgatgctgc                350
```

<210> SEQ ID NO 322
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

```
Asp Val Val Leu Thr Gln Thr Pro Leu Ser Leu Pro Phe Ser Phe Gly
1               5                   10                  15

Asn Lys Ala Ser Ile Phe Cys Lys Phe Ser Gln Thr Leu Leu His Arg
            20                  25                  30

Asp Gly Asn Pro Phe Leu Leu Trp Tyr Leu Gln Lys Pro Gly Gln Ser
        35                  40                  45

Pro Lys Leu Leu Ile Tyr Lys Leu Ser Asn Arg Phe Phe Gly Val Pro
    50                  55                  60

Lys Arg Phe Arg Gly Arg Gly Ser Gly Thr Asn Phe Pro Leu Lys Ile
65                  70                  75                  80

Ser Lys Gly Glu Ala Glu Asp Leu Gly Val Phe Phe Cys Ser Gln Ser
                85                  90                  95

Thr His Val Pro Tyr Thr Phe Gly Gly Gly Thr Lys Leu Glu Ile Lys
            100                 105                 110

Arg
```

<210> SEQ ID NO 323
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 323

```
gatattgtga tgacccagac tccactcact ttgtcggtta ccattggaca accagcttcc     60
atctcttgca gtcaagtca gagcctctta tttactaatg aaaaaccta tttaaattgg    120 tttttacaga ggccaggcca gtctccaaaa cgcctaatct atctgctgtc taaattggac    180
tctggagtcc ctgacaggtt cagtggcagt ggatcaggga cagatttcac actgaaaatc    240
agcagagtgg aggctgagga tttgggagtt tattactgct tgcagagtac atattttcct    300
ctcacgttcg gtgctgggac caagctggag ctgaaacggg ctgatgctgc                350
```

<210> SEQ ID NO 324
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

```
Asp Ile Val Met Thr Gln Thr Pro Leu Thr Leu Ser Val Thr Ile Gly
1               5                   10                  15
```

```
Gln Pro Ala Ser Ile Ser Cys Lys Ser Ser Gln Ser Leu Leu Phe Thr
            20                  25                  30

Asn Gly Lys Thr Tyr Leu Asn Trp Phe Leu Gln Arg Pro Gly Gln Ser
        35                  40                  45

Pro Lys Arg Leu Ile Tyr Leu Leu Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Thr Tyr Phe Pro Leu Thr Phe Gly Ala Gly Thr Lys Leu Glu Leu Lys
            100                 105                 110

Arg

<210> SEQ ID NO 325
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325
gatgttgtga tgacccagac tccactcact ttgtcggtta ccattggaca accagcttcc      60
atctcttgca agtcaagtca gagcctctta tatactaatg aaagaccta tttgaattgg     120 ttattacaga ggccaggcca gtctccaaaa cgcctaatct atctggtgtc aaaattggac    180
tctggagtcc ctgacaggtt cagtggcagt ggatcaggga cagatttcac actgaaaatc    240
agcagagtgg aggctgagga tttgggagtt tattactgct tgcagagtat acattttccg    300
tacacgttcg gaggggggac caagctggac ataaaacggg ctgatgctgc                350

<210> SEQ ID NO 326
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Ile His Phe Pro Tyr Thr Phe Gly Gly Gly Thr Lys Leu Asp Ile Lys
            100                 105                 110

Arg
```

<210> SEQ ID NO 327
<211> LENGTH: 350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 327

```
gatattgtga tgacgcaggc tgcattctcc aatccagtca ctcctggaac atcagtttcc    60
atctcctgca ggtctagtaa gagtctccta catagtaatg gcatcactta tttgtattgg   120
tatctgcaga agccaggcca gtctcctcag ctcctgattt atcagatgtc caagattgcc   180
tcaggagtcc cagacaggtt caggagcagt gggtcaggaa ctgatttcac actgagaatc   240
agcagagtgg aggctgcgga tgtgggtgtt tattactgtg ctcaaaatct agaacttccg   300
tggacgttcg gtggaggcac caagctggaa atcaaacggg ctgatgctgc              350
```

<210> SEQ ID NO 328
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 328

```
Asp Ile Val Met Thr Gln Ala Ala Phe Ser Asn Pro Val Thr Pro Gly
1               5                  10                  15
Thr Ser Val Ser Ile Ser Cys Arg Ser Ser Lys Ser Leu Leu His Ser
            20                  25                  30
Asn Gly Ile Thr Tyr Leu Tyr Trp Tyr Leu Gln Lys Pro Gly Gln Ser
        35                  40                  45
Pro Gln Leu Leu Ile Tyr Gln Met Ser Lys Ile Ala Ser Gly Val Pro
    50                  55                  60
Asp Arg Phe Arg Ser Ser Gly Ser Gly Thr Asp Phe Thr Leu Arg Ile
65                  70                  75                  80
Ser Arg Val Glu Ala Ala Asp Val Gly Val Tyr Tyr Cys Ala Gln Asn
                85                  90                  95
Leu Glu Leu Pro Trp Thr Phe Gly Gly Gly Thr Lys Leu Glu Ile Lys
            100                 105                 110
Arg
```

<210> SEQ ID NO 329
<211> LENGTH: 335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 329

```
gacattgtga tgacccagtc tcacaaattc atgtccacat caataggaga cagggtcagc    60
atcacctgca aggccagtca gaatgtgagt cctgctgtag cctggtatca acagaaacca   120
ggacaatctc ctaaactact gatttactcg gcatcctccc gatacactgg agtccctgat   180
cgcttcactg gcagtggatc tgggacggct ttcactttca ccatcagcag tgtgcaggct   240
gaagacctgg cagtttattt ctgtcagcaa cattttagta ctccgtggac gttcggtgga   300
ggcaccatgc tggaaatcaa acgggctgat gctgc                              335
```

<210> SEQ ID NO 330
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Asp Ile Val Met Thr Gln Ser His Lys Phe Met Ser Thr Ser Ile Gly
1               5                   10                  15

Asp Arg Val Ser Ile Thr Cys Lys Ala Ser Gln Asn Val Ser Pro Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Asp Arg Phe Thr Gly
50                  55                  60

Ser Gly Ser Gly Thr Ala Phe Thr Phe Thr Ile Ser Ser Val Gln Ala
65                  70                  75                  80

Glu Asp Leu Ala Val Tyr Phe Cys Gln Gln His Phe Ser Thr Pro Trp
                85                  90                  95

Thr Phe Gly Gly Gly Thr Met Leu Glu Ile Lys Arg
            100                 105

<210> SEQ ID NO 331
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 331
gacattgtga tgacccagtc tcaaaaattc atgtccacaa cagttgggga cagggtcaga      60
gtcacctgca aggccagtca gaatgtgggt actgctgtag cctggtatca acagaaacca     120
ggacaatctc ctaaactact gatttactca gcatccaatc ggtacactgg agtccctgat     180
cgcttcacag gcagtggatc tgggacagat ttcactctca ccattaccaa tatgcagtct     240
gaagacctgg cagattattt ctgtcagcaa tatagcacct atcctctcac gttcggctcg     300
ggggcaaagt tggaaataaa acgggctgat gctgc                                335

<210> SEQ ID NO 332
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Asp Ile Val Met Thr Gln Ser Gln Lys Phe Met Ser Thr Thr Val Gly
1               5                   10                  15

Asp Arg Val Arg Val Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
50                  55                  60

Ser Gly Ser Gly Thr Asp Phe Thr Leu Thr Ile Thr Asn Met Gln Ser

```
                65                  70                  75                  80
Glu Asp Leu Ala Asp Tyr Phe Cys Gln Gln Tyr Ser Thr Tyr Pro Leu
                        85                  90                  95

Thr Phe Gly Ser Gly Ala Lys Leu Glu Ile Lys Arg
                100                 105
```

<210> SEQ ID NO 333
<211> LENGTH: 332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 333

```
gacattgtga tgacccagtc tcacaaattc atgtccacat cagtaggaga cagggtcagc    60
atcacctgca aggccagtca ggatgtgggt actgctgtag cctggtatca acagaaacca   120
ggacaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcaact atctcacgtt cggtgctggg   300
accaagctgg aggtgaaacg ggctgatgct gc                                 332
```

<210> SEQ ID NO 334
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Asn Tyr Leu Thr
                85                  90                  95

Phe Gly Ala Gly Thr Lys Leu Glu Val Lys Arg
                100                 105
```

<210> SEQ ID NO 335
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 335

```
gacatccaga tgacccagtc tccatcctcc ttatctgcct ctctgggcga aagagtcagt    60
ctcacttgtc gggcaagtca ggacattggt ggtagcataa actggcttca gcaggaacca   120
gatggaacta ttaaacgcct gatctacgcc acatccagtt tagattctgg tgtccccaaa   180
```

```
aggttcagtg gcagtaggtc tgggtcagat tattctctca ccatcagcag ccttgagtct    240 gaagatttg tagactatta ctgtctacaa tatgctagtt ctcctccgac gttcggtgga    300
ggcaccaaac tggaaatcaa acgggctgat gctgc                              335
```

<210> SEQ ID NO 336
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Gly Ser
            20                  25                  30

Ile Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Pro
                85                  90                  95

Thr Phe Gly Gly Gly Thr Lys Leu Glu Ile Lys Arg
            100                 105
```

<210> SEQ ID NO 337
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 337

```
gacatccaga tgactcagtc tccagcctcc ctatctgcat ctgtgggaga aactgtcacc    60
atcacatgtc gagcaagtgg gaatattcac acttatttag catggtatca gcagaaacag    120
ggaaaatctc ctcagctcct ggtctacaat gcaaacacct tggcagatgg tgtgccatca    180
aggttcagtg gcagtggatc aggaacacaa ttttctctca agatcaacag tctgcagcct    240
gacgattttg ggagttatta ctgtcaacat ttttggagtg ctccgtggac gttcggtgga    300
ggcacccagc tggaaatcaa acgggctgat gctgc                              335
```

<210> SEQ ID NO 338
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Thr Tyr
            20                  25                  30
```

```
Leu Ala Trp Tyr Gln Gln Lys Gln Gly Lys Ser Pro Gln Leu Leu Val
         35                  40                  45

Tyr Asn Ala Asn Thr Leu Ala Asp Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Asp Asp Phe Gly Ser Tyr Tyr Cys Gln His Phe Trp Ser Ala Pro Trp
                 85                  90                  95

Thr Phe Gly Gly Gly Thr Gln Leu Glu Ile Lys Arg
            100                 105

<210> SEQ ID NO 339
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 339
gatattgtgt taactcagtc tccagccacc ctgtctgtga ctccaggaga tagagtcagt      60
ctttcctgca gggccagtca agaatttac aactacctac actggtatca acaaaaatca     120
catgagtctc caaggcttct caccaagtat gcttcccagt ccatctctgg atcccctcc     180 aggttcagtg gcagtggctc aggacagat ttcattctca ctatcaacag tgtggagact     240
gaagattttg gaatgtattt ctgtcaacag agtaacagct ggcctctcac gttcggtgct     300
gggaccaagc tggagctgag acgggctgat gctgc                                335

<210> SEQ ID NO 340
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Asp Ile Val Leu Thr Gln Ser Pro Ala Thr Leu Ser Val Thr Pro Gly
 1               5                  10                  15

Asp Arg Val Ser Leu Ser Cys Arg Ala Ser Gln Arg Ile Tyr Asn Tyr
                 20                  25                  30

Leu His Trp Tyr Gln Gln Lys Ser His Glu Ser Pro Arg Leu Leu Thr
         35                  40                  45

Lys Tyr Ala Ser Gln Ser Ile Ser Gly Ile Pro Ser Arg Phe Ser Gly
 50                  55                  60

Ser Gly Ser Gly Thr Asp Phe Ile Leu Thr Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Arg Arg
            100                 105

<210> SEQ ID NO 341
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 341

```
gatattgtgt taactcagtc tccagccacc ctgtctgtga ctccaggaga tagagtcagt    60
ctttcctgca gggccagtca agaatttac aactacctac actggtatca acaaaaatca   120
catgagtctc caaggcttct catcaagtat gcttcccagt ccatctctgg atcccctcc   180 aggttcagtg gcagtggctc agggacagat tcattctca ctatcaacag tgtggagact   240
gaagattttg gaatgtattt ctgtcaacag agtaacagct ggcctctcac gttcggtgct   300
gggaccaagc tggagctgag acgggctgat gctgc                             335
```

<210> SEQ ID NO 342
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

```
Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Arg Ile Tyr Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Ile Leu Thr Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Arg Arg
            100                 105
```

<210> SEQ ID NO 343
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 343

```
gacattgtga tgactcagtc tccagccacc ctgtctgtga ctccaggaga tagagtctct    60
ctttcctgca gggccagcca gagtattagc gactacttac actggtatca acaaaaatca   120
catgagtctc caaggcttct catcaaatat gcttcccaat ccatctctgg atcccctcc   180 aggttccgtg gcagtggatc agggtcacat ttcactctca gtatcaacag tgtggaacct   240
gaagatgttg gagtgtatta ctgtcaaaat ggtcacagtt ttccgtggac gttcggtgga   300
ggcaccaagc tggaaatcaa acgggctgat gctgc                             335
```

<210> SEQ ID NO 344
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Arg Gly
    50                  55                  60

Ser Gly Ser Gly Ser His Phe Thr Leu Ser Ile Asn Ser Val Glu Pro
65                  70                  75                  80

Glu Asp Val Gly Val Tyr Tyr Cys Gln Asn Gly His Ser Phe Pro Trp
                85                  90                  95

Thr Phe Gly Gly Gly Thr Lys Leu Glu Ile Lys Arg
            100                 105

<210> SEQ ID NO 345
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 345
gacattgtga tgactcagtc tccagccacc ctgtctgtga ctccaggaga tagagtctct    60
ctttcctgca gggccagcca gactattagc gactacttac actggtatca acaaaaatcg   120
catgagtctc caaggcttct catcaaatat gcttcccaat ccatctctgg atcccctcc    180 aggttcagtg gcagtggatc agggtcacat ttcactctca gtatcaacag tgtggaacct   240
gaagatgttg gagtgtatta ctgtcaaaat ggtcacagtt ttccgtggac gttcggtgga   300
ggcaccaagc tggaaatcaa acgggctgat gctgc                              335

<210> SEQ ID NO 346
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser His Phe Thr Leu Ser Ile Asn Ser Val Glu Pro
65                  70                  75                  80

Glu Asp Val Gly Val Tyr Tyr Cys Gln Asn Gly His Ser Phe Pro Trp
                85                  90                  95

Thr Phe Gly Gly Gly Thr Lys Leu Glu Ile Lys Arg
            100                 105

<210> SEQ ID NO 347

<211> LENGTH: 329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 347

```
gagattgtgc tcactcagtc tccagccatc acagctgcat ctctggggca aaacgtcacc      60
atcacctgca gagccagctc aagtgtaagt tacatgcatt ggtaccggca agagtccggc     120
acctccccc aactatggat ttatgagata ccagacgggg cttctggagt cccagctcgc      180
ttccgtgcca gtgggtctgg gacctcttat tctctcacaa tcagcagcat ggaggctgaa     240
gatgctgcca tttattactg ccagcagtgg aattatcctc tcacgttcgg tgctgggacc     300
aagctggagg tgaaacgggc tgatgctgc                                        329
```

<210> SEQ ID NO 348
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 348

Glu Ile Val Leu Thr Gln Ser Pro Ala Ile Thr Ala Ala Ser Leu Gly
1               5                   10                  15
Gln Asn Val Thr Ile Thr Cys Arg Ala Ser Ser Ser Val Ser Tyr Met
            20                  25                  30
His Trp Tyr Arg Gln Lys Ser Gly Thr Ser Pro Gln Leu Trp Ile Tyr
        35                  40                  45
Glu Ile Ser Arg Arg Ala Ser Gly Val Pro Ala Arg Phe Arg Ala Ser
    50                  55                  60
Gly Ser Gly Thr Ser Tyr Ser Leu Thr Ile Ser Ser Met Glu Ala Glu
65                  70                  75                  80
Asp Ala Ala Ile Tyr Tyr Cys Gln Gln Trp Asn Tyr Pro Leu Thr Phe
                85                  90                  95
Gly Ala Gly Thr Lys Leu Glu Val Lys Arg
            100                 105

<210> SEQ ID NO 349
<211> LENGTH: 329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 349

```
gaagttgtgc tcactcagtc tccagccatc acagctgcat ctctggggca aaaggtcacc      60
atcacctgca gagccagctc aagtgtaagt tacatgcact ggtaccggca agagtcaggc     120
acctccccc agccatggat ttatgaaata ccacactgg cttctggagt cccaactcgc       180
ttccgtgcca gtgggtctgg gacctcttat tctctcacaa tcagcagcat ggaggctgaa     240
gatgctgcca tttattactg ccagcagtgg aattatcctc tcacgttcgg tgctgggacc     300
aagctggaac tgaaacgggc tgatgctgc                                        329
```

<210> SEQ ID NO 350
<211> LENGTH: 106

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Glu Val Val Leu Thr Gln Ser Pro Ala Ile Thr Ala Ala Ser Leu Gly
1               5                   10                  15

Gln Lys Val Thr Ile Thr Cys Arg Ala Ser Ser Val Ser Tyr Met
            20                  25                  30

His Trp Tyr Arg Gln Lys Ser Gly Thr Ser Pro Gln Pro Trp Ile Tyr
        35                  40                  45

Glu Ile Ser Thr Leu Ala Ser Gly Val Pro Thr Arg Phe Arg Ala Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Thr Phe
                85                  90                  95

Gly Ala Gly Thr Lys Leu Glu Leu Lys Arg
            100                 105

<210> SEQ ID NO 351
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351
caaattgttc tcacccagtc tccaacaatc atgtctgcat ctctagggga acgggtcacc      60
atgacctgca ctgccagctc aagtgtgagt tccagttact tgcactggtt ccagcagaag     120
ccaggatcct cccccaaact ctggatttat agcacatcca acctggcttc tggagtccca     180
cctcgcttca gtggcagtgg gtctgggacc tcttactctc tctcaatcag cagcgtggag     240
gctgaagatg ttgccactta ttactgcctc cagtttcatc gttccccgtg acgttcggt      300
ggaggcgcca agttggaaat caaacgggct gatgctgc                             338

<210> SEQ ID NO 352
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Gln Ile Val Leu Thr Gln Ser Pro Thr Ile Met Ser Ala Ser Leu Gly
1               5                   10                  15

Glu Arg Val Thr Met Thr Cys Thr Ala Ser Ser Val Ser Ser Ser
            20                  25                  30

Tyr Leu His Trp Phe Gln Gln Lys Pro Gly Ser Ser Pro Lys Leu Trp
        35                  40                  45

Ile Tyr Ser Thr Ser Asn Leu Ala Ser Gly Val Pro Pro Arg Phe Ser
    50                  55                  60

Gly Ser Gly Ser Gly Thr Ser Tyr Ser Leu Ser Ile Ser Ser Val Glu
65                  70                  75                  80

Ala Glu Asp Val Ala Thr Tyr Tyr Cys Leu Gln Phe His Arg Ser Pro

```
                    85                  90                  95

Trp Thr Phe Gly Gly Gly Ala Lys Leu Glu Ile Lys Arg
            100                 105

<210> SEQ ID NO 353
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 353
caaattgttt tcacccagta tccagcaata atgtctgcat ctctagggga acgggtcacc        60
atgacctgca cagccagctc aagtgtaact tccagttact tgcactggtt ccagcagaag      120
ccaggatcct cccccaaact ctggatttat agcacgtcca acccgggttc tggagtccca      180
gctcgcttca gtggcagagg atctgggacc tcttactctc tctcaatcag cagcatggag      240
gctgaagatg ctgccactta ttactgcctc cagtttcatc gttccccgtg gacgttcggt      300
ggaggcacca agctggaaat cagacgggct gatgctgc                              338

<210> SEQ ID NO 354
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Gln Ile Val Phe Thr Gln Tyr Pro Ala Ile Met Ser Ala Ser Leu Gly
1               5                   10                  15

Glu Arg Val Thr Met Thr Cys Thr Ala Ser Ser Ser Val Thr Ser Ser
            20                  25                  30

Tyr Leu His Trp Phe Gln Gln Lys Pro Gly Ser Ser Pro Lys Leu Trp
        35                  40                  45

Ile Tyr Ser Thr Ser Asn Pro Gly Ser Gly Val Pro Ala Arg Phe Ser
    50                  55                  60

Gly Arg Gly Ser Gly Thr Ser Tyr Ser Leu Ser Ile Ser Ser Met Glu
65                  70                  75                  80

Ala Glu Asp Ala Ala Thr Tyr Tyr Cys Leu Gln Phe His Arg Ser Pro
                85                  90                  95

Trp Thr Phe Gly Gly Gly Thr Lys Leu Glu Ile Arg Arg
            100                 105

<210> SEQ ID NO 355
<211> LENGTH: 332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355
caaattgttc tcacccagtc tccagcaatc atgtctgtat ctccagggga aaggtctcc        60 atgacctgca gtgccagctc aagtgtcact tacatgcact ggtatcagca gaagtcaggc      120
acctccccca aaagatggat ttatgacaca tccgagctgg cttctggagt ccctgctcgc      180
ttcagtggca gtgggtctgg gaccacttac tctctcacaa tcagcagcat ggaggctgaa      240
```

```
gatgctgcca cttattactg ccagcagtgg agtaataaac cgctcacgtt cggtgctggg    300
accaagctgg agctgaaacg ggctgatgct gc                                   332
```

<210> SEQ ID NO 356
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

```
Gln Ile Val Leu Thr Gln Ser Pro Ala Ile Met Ser Val Ser Pro Gly
1               5                   10                  15

Glu Lys Val Ser Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Glu Leu Ala Ser Gly Val Pro Ala Arg Phe Ser Gly Ser
    50                  55                  60

Gly Ser Gly Thr Thr Tyr Ser Leu Thr Ile Ser Ser Met Glu Ala Glu
65                  70                  75                  80

Asp Ala Ala Thr Tyr Tyr Cys Gln Gln Trp Ser Asn Lys Pro Leu Thr
                85                  90                  95

Phe Gly Ala Gly Thr Lys Leu Glu Leu Lys Arg
            100                 105
```

<210> SEQ ID NO 357
<211> LENGTH: 332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 357

```
caaaatgttc tcacccagtc tccagcaatc atgtctgcat ctccagggga gaaggtcacc    60
atgtcctgca gtgccagctc aagtgtcact tacatgttct ggtaccagct gaagccagaa   120
tcctccccca gactcctgat ttatgacaca tccaatttgg cttctggcgt ccctgttcgc   180
ttcagtggca gtgggtctgg gacctcttac tctctcacaa tcagccgtat ggaggctgaa   240
gatgctgcca cttattactg ccaggagtgg agtagttacc cactcacgtt cggtgctggg   300
accaagctgg acctgaaacg ggctgatgct gc                                  332
```

<210> SEQ ID NO 358
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

```
Gln Asn Val Leu Thr Gln Ser Pro Ala Ile Met Ser Ala Ser Pro Gly
1               5                   10                  15

Glu Lys Val Thr Met Ser Cys Ser Ala Ser Ser Ser Val Thr Tyr Met
            20                  25                  30

Phe Trp Tyr Gln Leu Lys Pro Glu Ser Ser Pro Arg Leu Leu Ile Tyr
        35                  40                  45
```

```
Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Glu Trp Ser Ser Tyr Pro Leu Thr
                85                  90                  95

Phe Gly Ala Gly Thr Lys Leu Asp Leu Lys Arg
            100                 105
```

<210> SEQ ID NO 359
<211> LENGTH: 332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 359

```
caaattgttc tcacccagtc tccaacactc atgtctgcat cgccaggaga aaaggtcacc      60
atgacctgca gtgccagctc aactgtgact tacatttact ggtaccaaca gaagcccggc     120
tcctccccca gactctggat gtatgacaca ttcaacctgg tttctggagt ccctgctcgc     180
ttcagtggca gtaggtctgg gacctcttat tttctcacaa tcagtagcat ggagggtgaa     240
gatgctgcca cttattactg ccaacagtac agtgattccc cgtacacgtt cggagggggg     300
accaagctgg agataaaacg ggctgatgct gc                                   332
```

<210> SEQ ID NO 360
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 360

```
Gln Ile Val Leu Thr Gln Ser Pro Thr Leu Met Ser Ala Ser Pro Gly
1               5                   10                  15

Glu Lys Val Thr Met Thr Cys Ser Ala Ser Ser Thr Val Thr Tyr Ile
                20                  25                  30

Tyr Trp Tyr Gln Gln Lys Pro Gly Ser Ser Pro Arg Leu Trp Met Tyr
            35                  40                  45

Asp Thr Phe Asn Leu Val Ser Gly Val Pro Ala Arg Phe Ser Gly Ser
    50                  55                  60

Arg Ser Gly Thr Ser Tyr Phe Leu Thr Ile Ser Ser Met Glu Gly Glu
65                  70                  75                  80

Asp Ala Ala Thr Tyr Tyr Cys Gln Gln Tyr Ser Asp Ser Pro Tyr Thr
                85                  90                  95

Phe Gly Gly Gly Thr Lys Leu Glu Ile Lys Arg
            100                 105
```

<210> SEQ ID NO 361
<211> LENGTH: 332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 361

```
caaattgttc tcacccagtc tccagagatc atgtctgcat ctccagggga aaaggtcacc      60
```

```
ataacctgca gtgccagctc aagtgtaagt ttcatgtatt ggttccagca gaagccaggc    120
acttctccca aactctggat ttatatcaca tccaacctgg cttctggagt ccctactcgc    180
ttcagtggca gtggatctgg gacctcttac tctctcacaa tcagccgaat ggaggctgaa    240
gatgctgcca cttattactg ccagcaaagg agtagtttcc cgtacacgtt cggagggggg    300
accaaactgg aaatgaaacg ggctgatgct gc                                  332
```

<210> SEQ ID NO 362
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

```
Gln Ile Val Leu Thr Gln Ser Pro Glu Ile Met Ser Ala Ser Pro Gly
1               5                   10                  15

Glu Lys Val Thr Ile Thr Cys Ser Ala Ser Ser Val Ser Phe Met
            20                  25                  30

Tyr Trp Phe Gln Gln Lys Pro Gly Thr Ser Pro Lys Leu Trp Ile Tyr
        35                  40                  45

Ile Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Met Glu Ala Glu
65              70                  75                  80

Asp Ala Ala Thr Tyr Tyr Cys Gln Gln Arg Ser Ser Phe Pro Tyr Thr
                85                  90                  95

Phe Gly Gly Gly Thr Lys Leu Glu Met Lys Arg
            100                 105
```

<210> SEQ ID NO 363
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 363

```
gacattgtgc tgacccaatc tccagcttct ttggctgtgt ctctagggca gagggccatc    60
atctcctgca aggccagcca agtgtcagt tttgctggta ctaatttaat gcactggtac    120
caacagaaac caggacagca acccaaactc ctcatctatc gtgcatccaa cctagaaact    180
ggggttccta ccaggtttag tggcagtggg tctaggacag acttcaccct caatatccat    240
cctgtggagg aagatgatgc tgcaacctat tactgtcagc aaagtaggga atattacacg    300
ttcggagggg ggaccaagct ggaaataaaa cgggctgatg ctgc                     344
```

<210> SEQ ID NO 364
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

```
Asp Ile Val Leu Thr Gln Ser Pro Ala Ser Leu Ala Val Ser Leu Gly
1               5                   10                  15
```

Gln Arg Ala Ile Ile Ser Cys Lys Ala Ser Gln Ser Val Ser Phe Ala
            20                  25                  30

Gly Thr Asn Leu Met His Trp Tyr Gln Gln Lys Pro Gly Gln Gln Pro
        35                  40                  45

Lys Leu Leu Ile Tyr Arg Ala Ser Asn Leu Glu Thr Gly Val Pro Thr
    50                  55                  60

Arg Phe Ser Gly Ser Gly Ser Arg Thr Asp Phe Thr Leu Asn Ile His
65                  70                  75                  80

Pro Val Glu Glu Asp Asp Ala Ala Thr Tyr Tyr Cys Gln Gln Ser Arg
                85                  90                  95

Glu Tyr Tyr Thr Phe Gly Gly Thr Lys Leu Glu Ile Lys Arg
            100                 105                 110

<210> SEQ ID NO 365
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 365
gacattgtgc tgacccaatc tccagcttct ttggctgggt ctctagggaa aagggccccc      60
atctcctgca agccagcga agtgtcaat tttttggta ctaatttaat acactggtac       120
caacaaaaac caggacagcc ccccaaactc ctcatctatc atgcatccaa cctaaaaact      180
ggagtccctg ccaggttcag ggcaggggg tctaaaacaa acttccccct ccccattgat      240
cctgtggagg aaaatgatgt tgcaatctat tactgtctgc aaaataggaa aattcctctc      300
acgttcgggg ttgggaccaa gctggagctg aaacgggctg atgctgc                   347

<210> SEQ ID NO 366
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Asp Ile Val Leu Thr Gln Ser Pro Ala Ser Leu Ala Gly Ser Leu Gly
1               5                   10                  15

Lys Arg Ala Pro Ile Ser Cys Lys Ala Ser Glu Ser Val Asn Phe Phe
            20                  25                  30

Gly Thr Asn Leu Ile His Trp Tyr Gln Gln Lys Pro Gly Gln Pro Pro
        35                  40                  45

Lys Leu Leu Ile Tyr His Ala Ser Asn Leu Lys Thr Gly Val Pro Ala
    50                  55                  60

Arg Phe Arg Gly Arg Gly Ser Lys Thr Asn Phe Pro Leu Pro Ile Asp
65                  70                  75                  80

Pro Val Glu Glu Asn Asp Val Ala Ile Tyr Tyr Cys Leu Gln Asn Arg
                85                  90                  95

Lys Ile Pro Leu Thr Phe Gly Val Gly Thr Lys Leu Glu Leu Lys Arg
            100                 105                 110

<210> SEQ ID NO 367
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367
gacattgtgc tgacccaatc tccagcttct ttggctgtgt ctctagggca gagggccacc    60
atctcctgca gagccagcga aagtgttgat aattatggca ttagtttat gcactggtac   120 cagcagaaac caggacagcc acccaaactc ctcatctatc gtgcatccaa cctagaatct   180
gggatccctg ccaggttcag tggcagtggg tctaggacag acttcaccct caccattaat   240
cctgtggaga ctgatgatgt tgcaacctat tactgtcagc aaagtaataa ggatccattc   300
acgttcggct cggggcaaa gttggaaata aaacgggctg atgctgc                  347

<210> SEQ ID NO 368
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Phe Thr Phe Gly Ser Gly Ala Lys Leu Glu Ile Lys Arg
            100                 105                 110

<210> SEQ ID NO 369
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 369
gacattgtgg tgacacagtc tcctgcttcc ttagctgtat ctctggggca gagggccacc    60
atctcatgca gggccagcca aagtgtcagt acatctagat atagttatct gcactggtac   120
caacagaaac caggacaacc tcccaaactc ctcatcaagt atgcatccaa cctagaatct   180
ggggtccctg ccaggttcag tggcagtggg tctgggacag acttcaccct caatatccat   240
cctgtggggg aggaggatac tgcaacatat tactgtcagc acagttggga gtttccattc   300
acgttcggct cggggacaaa gttggaaata aaacgggctg atgctgc                 347

<210> SEQ ID NO 370
<211> LENGTH: 112
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 370

Asp Ile Val Val Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
                20                  25                  30

Arg Tyr Ser Tyr Leu His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Gly Glu Glu Asp Thr Ala Thr Tyr Tyr Cys Gln His Ser Trp
                85                  90                  95

Glu Phe Pro Phe Thr Phe Gly Ser Gly Thr Lys Leu Glu Ile Lys Arg
            100                 105                 110

<210> SEQ ID NO 371
<211> LENGTH: 347
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 371
gacattgtac tgacacagtc tcctgcttcc ttagctgtat ctctggggca gagggccacc      60
atctcatgca ggtccagcca agtgtcagt acatctagat atagttattt gcactggtac     120
caacagaaac caggacaacc tcccaaactc ctcatcaagt atgcatccaa cctagaatct     180
ggggtccctg ccaggttcag tggcagtggg tctgggacag acttcaccct caacatccat     240
cctgtggggg aggaggatcc tgcaacatat tactgtcagc acagttggga gtttccattc     300
acgttcggct cggggacaaa gttggaaata aaacgggctg atgctgc                   347

<210> SEQ ID NO 372
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 372

Asp Ile Val Leu Thr Gln Ser Pro Ala Ser Leu Ala Val Ser Leu Gly
1               5                   10                  15

Gln Arg Ala Thr Ile Ser Cys Arg Ser Ser Gln Ser Val Ser Thr Ser
                20                  25                  30

Arg Tyr Ser Tyr Leu His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Gly Glu Glu Asp Pro Ala Thr Tyr Tyr Cys Gln His Ser Trp
                85                  90                  95

Glu Phe Pro Phe Thr Phe Gly Ser Gly Thr Lys Leu Glu Ile Lys Arg

<210> SEQ ID NO 373
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 373

```
gacattgccc tgacacagtc tcctgcttcg ttagctgtat ctctggggca gagggccacc    60
atctcatgca gggccagcca agtgtcagt acatctaggt atagttatat gcactggtac   120
caacagaaac caggacaacc acccgaactc ctcatcaagt atgcatccaa cctagaatct   180
ggggtccctg ccaggttcag tggcagtggg tctgggacag acttcaccct caacatccat   240
cctgtggggg aggaggatac tgcaacatat tactgtcagc acagttggga ttttccattc   300
acgttcggct cggggacaaa gttggaaata aaacgggctg atgctgc                 347
```

<210> SEQ ID NO 374
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly Gln Pro Pro
        35                  40                  45

Glu Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Gly Glu Glu Asp Thr Ala Thr Tyr Tyr Cys Gln His Ser Trp
                85                  90                  95

Asp Phe Pro Phe Thr Phe Gly Ser Gly Thr Lys Leu Glu Ile Lys Arg
            100                 105                 110

<210> SEQ ID NO 375
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 375

```
gacattgtgc tgacacagtc tcctgcttcc ttagctgttt ctctggggca gagggccacc    60
atctcatgca gggccagcca agtgtcagt acatctaggt atagctacat gcactggtac   120
caacagaaac caggacagcc acccaaactc ctcatcaagt atgcatccaa cctagaatct   180
ggggtccctg ccaggttcag tggcagtggg tctgggacag acttcaccct caacatccat   240
cctgtggcgg aggaggatac tgcaacatat tactgtcagc acagttggga gtttccattc   300
acgttcggct cggggacaaa gttggaaata aaacgggctg atgctgc                 347
```

<210> SEQ ID NO 376
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 376

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Ala Glu Glu Asp Thr Ala Thr Tyr Tyr Cys Gln His Ser Trp
                85                  90                  95

Glu Phe Pro Phe Thr Phe Gly Ser Gly Thr Lys Leu Glu Ile Lys Arg
            100                 105                 110

<210> SEQ ID NO 377
<211> LENGTH: 347
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 377
gacattgtgc tgacacagtc tcttgcttcc ttagctgttt ctctggggca gagggccacc      60
atctcatgca gggccagcca agtgtcagt acatctaggt atagttatat gcactggtac     120
caacagaaac caggacagcc acccaaactc ctcatcaagt atgcatccaa ccttgaatgt     180
ggggtccgtg ccaggttcag tggcagtggg tgtgggacag acttcaccct caacatccat     240
cctgtggagg aggaggatac tgcagcatat tactgtcagc acagttggga gtttccattc     300
acgttcggct cggggacaaa attggaaata aaacgggctg atgctgc                    347

<210> SEQ ID NO 378
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 378

Asp Ile Val Leu Thr Gln Ser Leu Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Cys Gly Val Arg Ala
    50                  55                  60

```
Arg Phe Ser Gly Ser Gly Cys Gly Thr Asp Phe Thr Leu Asn Ile His
 65                  70                  75                  80

Pro Val Glu Glu Glu Asp Thr Ala Ala Tyr Tyr Cys Gln His Ser Trp
                 85                  90                  95

Glu Phe Pro Phe Thr Phe Gly Ser Gly Thr Lys Leu Glu Ile Lys Arg
            100                 105                 110
```

<210> SEQ ID NO 379
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 379

```
gacattgtac tgacacagtc tcctgcttcc ttagctgttt ctctgggca gagggccacc      60
atctcctgca gggccagcca agtgtcagt acatctaggt atagttatgt gcactggtat    120
caacagaaac caggacagcc acccaaactc ctcatcaagt atgcagccaa cctagaatct   180
ggggtccctg ccaggttcag tggcagtggg tctgggacag acttcaccct caacatccat   240
cctgtggcgg aggaggatgc tgcagcatat tactgtcagc acagtgggga gtttccattc   300
acgttcggct cggggacaaa gttggaaata aaacgggctg atgctgc                347
```

<210> SEQ ID NO 380
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Thr Ser
             20                  25                  30

Arg Tyr Ser Tyr Val His Trp Tyr Gln Gln Lys Pro Gly Gln Pro Pro
         35                  40                  45

Lys Leu Leu Ile Lys Tyr Ala Ala Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Ala Glu Glu Asp Ala Ala Ala Tyr Tyr Cys Gln His Ser Trp
                 85                  90                  95

Glu Phe Pro Phe Thr Phe Gly Ser Gly Thr Lys Leu Glu Ile Lys Arg
            100                 105                 110
```

<210> SEQ ID NO 381
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 381

```
gacattgtgc tgacacagtc tcctgcttcc ttagctgttt ctctgggca gaggaccacc      60
atctcatgcg gggccagcca agtgtcagt acatctaggt ttagttatat gcactggtac    120
```

-continued

```
caacagaaac caggacagcc acccaaactc ctcatcaagt atgcatccaa cctagaatct    180
ggggtccctg ccaggttcag tggcagtggg tctgggacag acttcaccct caacatccat    240
cctgtggcgg aggaggatac tgcagcatat tactgtcagc acagttggga gtttccattc    300
acgttcggct cggggacaaa gttggaaata aaacgggctg atgctgc                  347
```

<210> SEQ ID NO 382
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

```
Asp Ile Val Leu Thr Gln Ser Pro Ala Ser Leu Ala Val Ser Leu Gly
1               5                   10                  15

Gln Arg Thr Thr Ile Ser Cys Gly Ala Ser Gln Ser Val Ser Thr Ser
            20                  25                  30

Arg Phe Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Ala Glu Glu Asp Thr Ala Ala Tyr Tyr Cys Gln His Ser Trp
                85                  90                  95

Glu Phe Pro Phe Thr Phe Gly Ser Gly Thr Lys Leu Glu Ile Lys Arg
            100                 105                 110
```

<210> SEQ ID NO 383
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 383

```
gacattgtgc tgacacagtc tcctgcttcc ttagctgttt ctctggggca gagggccacc     60
atctcatgca gggccagcca aagtgtcagt acatctaggt atagttatat gcactggtac    120
caacagaaac caggacagcc acccaaactc ctcatcaagt atgcatccaa cctagaatct    180
ggggtccctg ccaggttcag tggcagtggg tctgggacag acttcaccct caacatccat    240
cctgtggcgg aggaggatac tgcagcatat tactgtcagc acagttgggg gtttccattc    300
acgttcggct cggggacaaa gttggaaata aagcgggctg atgctgc                  347
```

<210> SEQ ID NO 384
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30
```

Arg Tyr Ser Tyr Met His Trp Tyr Gln Gln Lys Pro Gly Gln Pro
            35                  40                  45

Lys Leu Leu Ile Lys Tyr Ala Ser Asn Leu Glu Ser Gly Val Pro Ala
     50                  55                  60

Arg Phe Ser Gly Ser Gly Ser Gly Thr Asp Phe Thr Leu Asn Ile His
65                  70                  75                  80

Pro Val Ala Glu Glu Asp Thr Ala Ala Tyr Tyr Cys Gln His Ser Trp
                85                  90                  95

Gly Phe Pro Phe Thr Phe Gly Ser Gly Thr Lys Leu Glu Ile Lys Arg
            100                 105                 110

<210> SEQ ID NO 385
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 385
gacattgtgc tgacacagtc tcctgcttcc ttagctgtat ctttgggaaa aaaggccacc      60
atctcatgca gggccagcca agtgtcagt acatctaggt atagttatat gcactggtac     120
caacagaaac caggacaccc acccaaactc ctcatcaaat atgcatccaa cctagaatct     180
ggggtccctg ccaggttcag tggcagtggg tctgggacag acttcaccct caacatccat     240
cctgtggcgg aggaggatac tgcagcatat tactgtcagc acagttggga gtttccattc     300
acgttcggct cggggacaaa gttggaaata aaacggctg atgctgc                    347

<210> SEQ ID NO 386
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Asp Ile Val Leu Thr Gln Ser Pro Ala Ser Leu Ala Val Ser Leu Gly
1               5                   10                  15

Lys Lys Ala Thr Ile Ser Cys Arg Ala Ser Gln Ser Val Ser Thr Ser
            20                  25                  30

Arg Tyr Ser Tyr Met His Trp Tyr Gln Gln Lys Pro Gly His Pro Pro
            35                  40                  45

Lys Leu Leu Ile Lys Tyr Ala Ser Asn Leu Glu Ser Gly Val Pro Ala
     50                  55                  60

Arg Phe Ser Gly Ser Gly Ser Gly Thr Asp Phe Thr Leu Asn Ile His
65                  70                  75                  80

Pro Val Ala Glu Glu Asp Thr Ala Ala Tyr Tyr Cys Gln His Ser Trp
                85                  90                  95

Glu Phe Pro Phe Thr Phe Gly Ser Gly Thr Lys Leu Glu Ile Lys Arg
            100                 105                 110

<210> SEQ ID NO 387
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 387

```
gacattgtgc tgacacagtc tcctgcttcc ttagctgttt ctctggggca gagggccacc      60
atctcatgca gggccagcca agtgtcagt acatctaggt atagttatat gcactggtac     120
caacagaaac caggacagcc acccaaactc ctcatcaagt atgcatccaa ccttgaatct     180
ggggtccctg ccaggttcag tggcagtggg tctgggacag acttcaccct caacatccat     240
cctgtggcgg aggaggatac tgcagcatat tactgtcagc acagtgggga gtttccattc     300
acgttcggct cggggacaaa attggaaata aaacgggctg atgctgc                   347
```

<210> SEQ ID NO 388
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 388

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Gln Ser Val Ser Thr Ser
            20                  25                  30
Arg Tyr Ser Tyr Met His Trp Tyr Gln Gln Lys Pro Gly Gln Pro Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Ala Glu Glu Asp Thr Ala Ala Tyr Tyr Cys Gln His Ser Trp
                85                  90                  95
Glu Phe Pro Phe Thr Phe Gly Ser Gly Thr Lys Leu Glu Ile Lys Arg
            100                 105                 110
```

<210> SEQ ID NO 389
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 389

```
agatctagtc agagccttga acatagtaat ggaaacacct atttagag                   48
```

<210> SEQ ID NO 390
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

```
Arg Ser Ser Gln Ser Leu Glu His Ser Asn Gly Asn Thr Tyr Leu Glu
1               5                   10                  15
```

<210> SEQ ID NO 391
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
agatctagtc agagccttgt acatagtaat ggaaacacct atttagag         48

<210> SEQ ID NO 392
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Arg Ser Ser Gln Ser Leu Val His Ser Asn Gly Asn Thr Tyr Leu Glu
1               5                   10                  15

<210> SEQ ID NO 393
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
agatctagtc agagccttgt acatagtaat ggaaacacct atttagag         48

<210> SEQ ID NO 394
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Arg Ser Ser Gln Ser Leu Leu His Ser Asn Gly Asn Thr Tyr Leu Glu
1               5                   10                  15

<210> SEQ ID NO 395
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
agatctagtc agagcattgt acacagtaat ggaaacacct atttagag         48

<210> SEQ ID NO 396
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Arg Ser Ser Gln Ser Ile Val His Ser Asn Gly Asn Thr Tyr Leu Glu
1               5                   10                  15

<210> SEQ ID NO 397
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
agatctagtc agagccttga acatactaat ggaaacacct atttagag                 48

<210> SEQ ID NO 398
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Arg Ser Ser Gln Ser Leu Glu His Thr Asn Gly Asn Thr Tyr Leu Glu
1               5                   10                  15

<210> SEQ ID NO 399
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
agatctagtc agagccttgt acataataat ggaaacacct atttagaa                 48

<210> SEQ ID NO 400
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Arg Ser Ser Gln Ser Leu Val His Asn Asn Gly Asn Thr Tyr Leu Glu
1               5                   10                  15

<210> SEQ ID NO 401
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
aggtctagta agagtctcct acatagtaat ggcatcactt atttgtat                 48

<210> SEQ ID NO 402
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Arg Ser Ser Lys Ser Leu Leu His Ser Asn Gly Ile Thr Tyr Leu Tyr
1               5                   10                  15
```

```
<210> SEQ ID NO 403
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
agatctagtc agaccttct acacagtgat ggagacacct atttacat              48

<210> SEQ ID NO 404
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Lys Phe Ser Gln Thr Leu Leu His Arg Asp Gly Asn Pro Phe Leu Leu
1               5                   10                  15

<210> SEQ ID NO 405
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
aagtcaagtc agagcctctt atttactaat ggaaaaacct atttaaat              48

<210> SEQ ID NO 406
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Lys Ser Ser Gln Ser Leu Leu Phe Thr Asn Gly Lys Thr Tyr Leu Asn
1               5                   10                  15

<210> SEQ ID NO 407
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
aagtcaagtc agagcctctt atatactaat ggaaagacct atttgaat              48

<210> SEQ ID NO 408
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Lys Ser Ser Gln Ser Leu Leu Tyr Thr Asn Gly Lys Thr Tyr Leu Asn
1               5                   10                  15
```

<210> SEQ ID NO 409
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
aaggccagtc agaatgtgag tcctgctgta gcc                                   33

<210> SEQ ID NO 410
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Lys Ala Ser Gln Asn Val Ser Pro Ala Val Ala
1               5                   10

<210> SEQ ID NO 411
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
aaggccagtc agaatgtggg tactgctgta gcc                                   33

<210> SEQ ID NO 412
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Lys Ala Ser Gln Asn Val Gly Thr Ala Val Ala
1               5                   10

<210> SEQ ID NO 413
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
aaggccagtc aggatgtggg tactgctgta gcc                                   33

<210> SEQ ID NO 414
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

-continued

Lys Ala Ser Gln Asp Val Gly Thr Ala Val Ala
1               5                   10

<210> SEQ ID NO 415
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
cgggcaagtc aggacattgg tggtagcata aac                                    33

<210> SEQ ID NO 416
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Arg Ala Ser Gln Asp Ile Gly Gly Ser Ile Asn
1               5                   10

<210> SEQ ID NO 417
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
cgagcaagtg ggaatattca cacttattta gca                                    33

<210> SEQ ID NO 418
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Arg Ala Ser Gly Asn Ile His Thr Tyr Leu Ala
1               5                   10

<210> SEQ ID NO 419
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
agggccagtc aaagaattta caactaccta cac                                    33

<210> SEQ ID NO 420
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 420

Arg Ala Ser Gln Arg Ile Tyr Asn Tyr Leu His
1               5                   10

<210> SEQ ID NO 421
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
agggccagcc agagtattag cgactactta cac                                    33

<210> SEQ ID NO 422
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Arg Ala Ser Gln Ser Ile Ser Asp Tyr Leu His
1               5                   10

<210> SEQ ID NO 423
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
agggccagcc agactattag cgactactta cac                                    33

<210> SEQ ID NO 424
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Arg Ala Ser Gln Thr Ile Ser Asp Tyr Leu His
1               5                   10

<210> SEQ ID NO 425
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
agagccagct caagtgtaag ttacatgcat                                        30

<210> SEQ ID NO 426
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                peptide

<400> SEQUENCE: 426

Arg Ala Ser Ser Ser Val Ser Tyr Met His
1               5                   10

<210> SEQ ID NO 427
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
agagccagct caagtgtaag ttacatgcat                                          30

<210> SEQ ID NO 428
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Arg Ala Ser Ser Ser Val Ser Tyr Met His
1               5                   10

<210> SEQ ID NO 429
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
actgccagct caagtgtgag ttccagttac ttgcac                                   36

<210> SEQ ID NO 430
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Thr Ala Ser Ser Ser Val Ser Ser Ser Tyr Leu His
1               5                   10

<210> SEQ ID NO 431
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
acagccagct caagtgtaac ttccagttac ttgcac                                   36

<210> SEQ ID NO 432
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 432

Thr Ala Ser Ser Ser Val Thr Ser Ser Tyr Leu His
1               5                   10

<210> SEQ ID NO 433
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
agtgccagct caagtgtcac ttacatgcac                                          30

<210> SEQ ID NO 434
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Ser Ala Ser Ser Ser Val Thr Tyr Met His
1               5                   10

<210> SEQ ID NO 435
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
agtgccagct caagtgtcac ttacatgttc                                          30

<210> SEQ ID NO 436
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Ser Ala Ser Ser Ser Val Thr Tyr Met Phe
1               5                   10

<210> SEQ ID NO 437
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
agtgccagct caactgtgac ttacatttac                                          30

<210> SEQ ID NO 438
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ser Ala Ser Ser Thr Val Thr Tyr Ile Tyr
1               5                   10

<210> SEQ ID NO 439
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
agtgccagct caagtgtaag tttcatgtat                                          30

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Ser Ala Ser Ser Ser Val Ser Phe Met Tyr
1               5                   10

<210> SEQ ID NO 441
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
aaggccagcc aaagtgtcag ttttgctggt actaatttaa tgcac                         45

<210> SEQ ID NO 442
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Lys Ala Ser Gln Ser Val Ser Phe Ala Gly Thr Asn Leu Met His
1               5                   10                  15

<210> SEQ ID NO 443
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
aaagccagcg aaagtgtcaa ttttttggt actaatttaa tacac                          45
```

```
<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Lys Ala Ser Glu Ser Val Asn Phe Phe Gly Thr Asn Leu Ile His
1               5                   10                  15

<210> SEQ ID NO 445
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
agagccagcg aaagtgttga taattatggc attagttttta tgcac              45

<210> SEQ ID NO 446
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Arg Ala Ser Glu Ser Val Asp Asn Tyr Gly Ile Ser Phe Met His
1               5                   10                  15

<210> SEQ ID NO 447
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
agggccagcc aaagtgtcag tacatctaga tatagttatc tgcac              45

<210> SEQ ID NO 448
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Arg Ala Ser Gln Ser Val Ser Thr Ser Arg Tyr Ser Tyr Leu His
1               5                   10                  15

<210> SEQ ID NO 449
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
agggccagcc aaagtgtcag tacatctagg tatagttata tgcac              45
```

<210> SEQ ID NO 450
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Arg Ala Ser Gln Ser Val Ser Thr Ser Arg Tyr Ser Tyr Met His
1               5                   10                  15

<210> SEQ ID NO 451
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ggggccagcc aaagtgtcag tacatctagg tttagttata tgcac            45

<210> SEQ ID NO 452
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Gly Ala Ser Gln Ser Val Ser Thr Ser Arg Phe Ser Tyr Met His
1               5                   10                  15

<210> SEQ ID NO 453
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
aggtccagcc aaagtgtcag tacatctaga tatagttatt tgcac            45

<210> SEQ ID NO 454
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Arg Ser Ser Gln Ser Val Ser Thr Ser Arg Tyr Ser Tyr Leu His
1               5                   10                  15

<210> SEQ ID NO 455
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
agggccagcc aaagtgtcag tacatctagg tttagttatc tgcac                      45

<210> SEQ ID NO 456
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Arg Ala Ser Gln Ser Val Ser Thr Ser Arg Phe Ser Tyr Leu His
1               5                   10                  15

<210> SEQ ID NO 457
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
agggccagcc aaagtgtcag tacatctagg tatagttatg tgcactgg                   48

<210> SEQ ID NO 458
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Arg Ala Ser Gln Ser Val Ser Thr Ser Arg Tyr Ser Tyr Val His
1               5                   10                  15

<210> SEQ ID NO 459
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
agggccagcc aaagtgtcag tacatccagg tttagttatg tgcac                      45

<210> SEQ ID NO 460
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Arg Ala Ser Gln Ser Val Ser Thr Ser Arg Phe Ser Tyr Val His
1               5                   10                  15

<210> SEQ ID NO 461
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 461
agggccagcc aaagtctcag tacatctagg tttagctatg tgcac                    45

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Arg Ala Ser Gln Ser Leu Ser Thr Ser Arg Phe Ser Tyr Val His
1               5                   10                  15

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
aaagtttcca gccgattttc t                                              21

<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Lys Val Ser Ser Arg Phe Ser
1               5

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
aaagtttcca accgattttc t                                              21

<210> SEQ ID NO 466
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Lys Val Ser Asn Arg Phe Ser
1               5

<210> SEQ ID NO 467
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 467
aaactttcca accgattttc t                                              21

<210> SEQ ID NO 468
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Lys Leu Ser Asn Arg Phe Phe
1               5

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
aatgtttcca accgattttc t                                              21

<210> SEQ ID NO 470
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Asn Val Ser Asn Arg Phe Ser
1               5

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
agagtttcca accgattttc t                                              21

<210> SEQ ID NO 472
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Arg Val Ser Asn Arg Phe Ser
1               5

<210> SEQ ID NO 473
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 473
cagatgtcca agattgcctc a                                              21

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Gln Met Ser Lys Ile Ala Ser
1               5

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
ctgctgtcta aattggactc t                                              21

<210> SEQ ID NO 476
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Leu Leu Ser Lys Leu Asp Ser
1               5

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ctggtgtcaa aattggactc t                                              21

<210> SEQ ID NO 478
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Leu Val Ser Lys Leu Asp Ser
1               5

<210> SEQ ID NO 479
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
tcggcatcct cccgatacac t                                              21

<210> SEQ ID NO 480
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Ser Ala Ser Ser Arg Tyr Thr
1               5

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
tcagcatcca atcggtacac t                                              21

<210> SEQ ID NO 482
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Ser Ala Ser Asn Arg Tyr Thr
1               5

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tgggcatcca cccggcacac t                                              21

<210> SEQ ID NO 484
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Trp Ala Ser Thr Arg His Thr
1               5
```

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
gccacatcca gtttagattc t                                              21

<210> SEQ ID NO 486
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Ala Thr Ser Ser Leu Asp Ser
1               5

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
aatgcaaaca ccttggcaga t                                              21

<210> SEQ ID NO 488
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Asn Ala Asn Thr Leu Ala Asp
1               5

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
gcttcccagt ccatctctgg g                                              21

<210> SEQ ID NO 490
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Ala Ser Gln Ser Ile Ser Gly

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tatgcttccc aatccatctc t                                           21

<210> SEQ ID NO 492
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Tyr Ala Ser Gln Ser Ile Ser
1               5

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gagatatcca gacgggcttc t                                           21

<210> SEQ ID NO 494
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Glu Ile Ser Arg Arg Ala Ser
1               5

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
gaaatatcca cactggcttc t                                           21

<210> SEQ ID NO 496
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Glu Ile Ser Thr Leu Ala Ser
1               5

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
agcacatcca acctggcttc t                                           21

<210> SEQ ID NO 498
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Ser Thr Ser Asn Leu Ala Ser
1               5

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
agcacgtcca acccgggttc t                                           21

<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Ser Thr Ser Asn Pro Gly Ser
1               5

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
gacacatccg agctggcttc t                                           21

<210> SEQ ID NO 502
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 502

Asp Thr Ser Glu Leu Ala Ser
1               5

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gacacatcca atttggcttc t                                              21

<210> SEQ ID NO 504
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Asp Thr Ser Asn Leu Ala Ser
1               5

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
gacacattca acctggtttc t                                              21

<210> SEQ ID NO 506
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Asp Thr Phe Asn Leu Val Ser
1               5

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
atcacatcca acctggcttc t                                              21

<210> SEQ ID NO 508
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 508

Ile Thr Ser Asn Leu Ala Ser
1               5

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
cgtgcatcca acctagaaac t                                              21

<210> SEQ ID NO 510
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Arg Ala Ser Asn Leu Glu Thr
1               5

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
catgcatcca acctaaaaac t                                              21

<210> SEQ ID NO 512
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

His Ala Ser Asn Leu Lys Thr
1               5

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
cgtgcatcca acctagaatc t                                              21

<210> SEQ ID NO 514
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 514

Arg Ala Ser Asn Leu Glu Ser
1               5

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
tatgcatcca acctagaatc t                                           21

<210> SEQ ID NO 516
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Tyr Ala Ser Asn Leu Glu Ser
1               5

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
tatgcatcca accttgaatg t                                           21

<210> SEQ ID NO 518
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Tyr Ala Ser Asn Leu Glu Cys
1               5

<210> SEQ ID NO 519
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
tttcaaggtt cacatgttcc attcacg                                     27

<210> SEQ ID NO 520
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Phe Gln Gly Ser His Val Pro Phe Thr
1               5

<210> SEQ ID NO 521
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
tttcaaggtt cacatgttcc actcacg                                        27

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Phe Gln Gly Ser His Val Pro Leu Thr
1               5

<210> SEQ ID NO 523
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
tttcaaggtt cacatgttcc gtggacg                                        27

<210> SEQ ID NO 524
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Phe Gln Gly Ser His Val Pro Trp Thr Phe
1               5                   10

<210> SEQ ID NO 525
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
gctcaaaatc tagaacttcc gtggacg                                        27
```

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Ala Gln Asn Leu Glu Leu Pro Trp Thr
1               5

<210> SEQ ID NO 527
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tctcaaagta cacatgttcc gtacacg                                         27

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ser Gln Ser Thr His Val Pro Tyr Thr
1               5

<210> SEQ ID NO 529
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
ttgcagagta catattttcc tctcacg                                         27

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Leu Gln Ser Thr Tyr Phe Pro Leu Thr
1               5

<210> SEQ ID NO 531
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531

```
ttgcagagta tacattttcc gtacacg                                              27
```

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Leu Gln Ser Ile His Phe Pro Tyr Thr
1               5

<210> SEQ ID NO 533
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533

```
ctacaatatg ctagttctcc tccgacg                                              27
```

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Leu Gln Tyr Ala Ser Ser Pro Pro Thr
1               5

<210> SEQ ID NO 535
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535

```
ctccagtttc atcgttcccc gtggacg                                              27
```

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Leu Gln Phe His Arg Ser Pro Trp Thr
1               5

<210> SEQ ID NO 537
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 537
ctgcaaaata ggaaaattcc tctcacg                                              27

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Leu Gln Asn Arg Lys Ile Pro Leu Thr
1               5

<210> SEQ ID NO 539
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
cagcaacatt ttagtactcc gtggacg                                              27

<210> SEQ ID NO 540
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gln Gln His Phe Ser Thr Pro Trp Thr
1               5

<210> SEQ ID NO 541
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
cagcaatata gcacctatcc tctcacg                                              27

<210> SEQ ID NO 542
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Gln Gln Tyr Ser Thr Tyr Pro Leu Thr
1               5

<210> SEQ ID NO 543
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 543
cagcaatata gcaactatct cacg                                          24

<210> SEQ ID NO 544
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Gln Gln Tyr Ser Asn Tyr Leu Thr
1               5

<210> SEQ ID NO 545
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
caacagagta acagctggcc tctcacg                                       27

<210> SEQ ID NO 546
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Gln Gln Ser Asn Ser Trp Pro Leu Thr
1               5

<210> SEQ ID NO 547
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
cagcagtgga attatcctct cacg                                          24

<210> SEQ ID NO 548
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gln Gln Trp Asn Tyr Pro Leu Thr
1               5

<210> SEQ ID NO 549
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 549
cagcagtgga gtaataaacc gctcacg                                          27

<210> SEQ ID NO 550
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Gln Gln Trp Ser Asn Lys Pro Leu Thr
1               5

<210> SEQ ID NO 551
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
caacagtaca gtgattcccc gtacacg                                          27

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Gln Gln Tyr Ser Asp Ser Pro Tyr Thr
1               5

<210> SEQ ID NO 553
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
cagcaaagga gtagtttccc gtacacg                                          27

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Gln Gln Arg Ser Ser Phe Pro Tyr Thr
1               5

<210> SEQ ID NO 555
<211> LENGTH: 24
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
cagcaaagta gggaatatta cacg                                              24

<210> SEQ ID NO 556
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gln Gln Ser Arg Glu Tyr Tyr Thr
1               5

<210> SEQ ID NO 557
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
cagcaaagta ataaggatcc attcacg                                           27

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gln Gln Ser Asn Lys Asp Pro Phe Thr
1               5

<210> SEQ ID NO 559
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
caaaatggtc acagttttcc gtggacg                                           27

<210> SEQ ID NO 560
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gln Asn Gly His Ser Phe Pro Trp Thr
1               5

```
<210> SEQ ID NO 561
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
caacattttt ggagtgctcc gtggacg                                              27

<210> SEQ ID NO 562
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Gln His Phe Trp Ser Ala Pro Trp Thr
1               5

<210> SEQ ID NO 563
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
caggagtgga gtagttaccc actcacg                                              27

<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gln Glu Trp Ser Ser Tyr Pro Leu Thr
1               5

<210> SEQ ID NO 565
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
cagcacagtt gggagtttcc attcacg                                              27

<210> SEQ ID NO 566
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Gln His Ser Trp Glu Phe Pro Phe Thr
1               5
```

<210> SEQ ID NO 567
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
cagcacagtt gggatttttcc attcacg                                              27

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gln His Ser Trp Asp Phe Pro Phe Thr
1               5

<210> SEQ ID NO 569
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
cagcacagtt gggatttttcc attcacg                                              27

<210> SEQ ID NO 570
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gln His Ser Trp Gly Phe Pro Phe Thr
1               5

<210> SEQ ID NO 571
<211> LENGTH: 507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 571
atgtctacca acccgaaacc gcagaaaaaa acaaacgta acaccaaccg tcgtccgcag             60
gacgttaaat tcccgggtgg tggtcagatc gttggtggtg tttacctgct gccgcgtcgt          120
ggtccgcgtc tgggtgttcg tgctacgcgt aaaacctctg aacgttctca gccgcgtggg          180
cgtcgtcagc cgatcccgaa agctcgtcgt ccggaaggtc gtacctgggc tcagccgggt          240
tacccgtggc cgctgtacgg taacgaaggt tgcggttggg ctggttggct gctgtctccg          300
cgtggatctc gtccgtcttg gggtccgacc gaccgcgtc gtcgttctcg taaccttggt           360
aaagttatcg ataccctgac ctgcggtttc gctgacctga tgggttacat accgctggtt          420

```
ggagctccgc tgggtggtgc tgctcgtgct ctggcgcatg gcgtgcgtgt tctggaagat    480
ggcgtcaact atgccaccgg taatctg                                        507
```

<210> SEQ ID NO 572
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu
                165
```

<210> SEQ ID NO 573
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

```
Met Gly Tyr Ile Pro Leu Val Gly Ala Pro Leu Gly Gly Ala Ala Arg
1               5                   10                  15

Ala Leu Ala His Gly
            20
```

<210> SEQ ID NO 574
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

```
Gly Ala Pro Leu Gly Gly Ala Ala Arg Ala Leu Ala His Gly Val Arg
1               5                   10                  15
```

```
Val Leu Glu Asp Gly
            20

<210> SEQ ID NO 575
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Leu Ala His Gly Val Arg Val Leu Glu Asp Gly Val Asn Tyr Ala Thr
1               5                   10                  15

Gly Asn Leu Pro Gly
            20

<210> SEQ ID NO 576
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly Cys
        35

<210> SEQ ID NO 577
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly Gln Tyr Ile Lys Ala Asn Ser Lys Phe Ile
        35                  40                  45

Gly Ile Thr Glu Leu
    50

<210> SEQ ID NO 578
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 578

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
```

-continued

```
                    20                  25                  30

Thr Gly Asn Leu Pro Gly
        35

<210> SEQ ID NO 579
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
            20                  25                  30

Thr Gly Asn Leu Pro Gly Gln Gln Lys Phe Gln Phe Gln Phe Glu Gln
        35                  40                  45

Gln

<210> SEQ ID NO 580
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 580

His His His His His His
1               5

<210> SEQ ID NO 581
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
aagcagtggt atcaacgcag agtaccccccc cccccccccc c              41
```

HCV CORE LIPID BINDING DOMAIN MONOCLONAL ANTIBODIES

The present application is filed as a U.S. non-provisional patent application claiming the benefit of priority of U.S. Provisional Patent Application No. 61/783,529, which was filed Mar. 14, 2013. The entire text of the aforementioned application is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 28, 2015, is named 11950USO1_SL.txt and is 262,730 bytes in size.

FIELD OF THE INVENTION

The present disclosure provides novel monoclonal antibodies to the HCV core protein, and methods and compositions for uses thereof for detection of HCV infection.

BACKGROUND OF THE INVENTION

According to WHO statistics, as many as 170 million people worldwide are infected by hepatitis C virus (HCV), a viral infection of the liver. 75 to 85% of persons infected with HCV progress to chronic infection, approximately 20% of these cases develop complications of chronic hepatitis C, including cirrhosis of the liver or hepatocellular carcinoma after 20 years of infection. The current recommended treatment for HCV infections is a combination of interferon and ribavirin drugs, however the treatment is not effective in all cases and the liver transplantation is indicated in hepatitis C-related end-stage liver disease. At present, there is no vaccine available to prevent HCV infection, therefore all precautions to avoid infection must be taken.

Thus, patient care, as well as the prevention of transmission of Hepatitis C Virus (HCV) by blood and blood products or by close personal contact requires extreme vigilance using sensitive detection assays. This creates a need for specific methods for screening and identifying carriers of HCV and HCV-contaminated blood or blood products. Serological determination of HCV exposure relies on the detection of HCV present in human blood plasma or sera. This can be accomplished by detection of distinct structural and non-structural proteins encoded by the virus.

The HCV virus is a (+) sense single-stranded enveloped RNA virus in the Hepacivirus genus of the Flaviviridae family. The viral genome is approximately 10 kb in length and encodes a 3011 amino acid polyprotein precursor. The HCV genome has a large single open reading frame (ORF) coding for a unique polyprotein. This polyprotein is co- and post-translationally processed by cellular and viral proteases into three structural proteins, i.e., core, E1 and E2 and at least six non-structural NS2, NS3, NS4A, NS4B, NS5A and NS5B proteins. (Choo et al., Science 244: 359-362 (1989)).

Following HCV exposure, the virus enters a susceptible hepatocyte and viral replication occurs. During an eclipse phase period of approximately 10 days, viral presence is not evident (i.e., viral RNA cannot be detected), serum transaminase levels are within normal limits, and no evidence exists of an immune response to HCV (Busch et al., Transfusion 40:143 (2000)). Typically, about 10 days following exposure, HCV RNA can be detected, often with viral loads between 100,000-120,000,000 HCV RNA copies per ml of serum. Typically several weeks later, an increase in ALT levels is observed, indicating inflammation of the liver; antibodies are detected an average of about 70 days after exposure.

Screening of blood for exposure to HCV, either by the detection of antibodies to HCV or by the detection of viral-specific molecules (e.g., HCV RNA or HCV core proteins) in serum/plasma is an integral and important part of patient care. Blood or blood products derived from individuals identified as having been exposed to HCV, by these tests, are removed from the blood supply and are not utilized for distribution to recipients of blood products (see, e.g., U.S. Pat. No. 6,172,189). These tests may also be utilized in the clinical setting to diagnose liver disease attributable to HCV infection.

Serologic antibody tests rely on the use of recombinant antigens or synthetic peptides, representing selected fragments of the viral polyprotein. The first generation anti-HCV screening tests were based on detection of antibodies directed against a recombinant protein (HCV genotype 1a) originating from sequences located in the nonstructural NS-4 protein (C100-3) (Choo et al., Science 244:359 (1989); Kuo et al., Science 244:362 (1989)). The first generation assays failed to detect antibodies in approximately 10% of individuals having chronic HCV infection and up to 10-30% of individuals presenting with acute HCV infection. The second generation anti-HCV assays have incorporated recombinant proteins from three different regions of the HCV genome (HCV genotype 1a), including amino acid sequences from the core, NS3, and NS4 protein (Mimms et al., Lancet 336:1590 (1990); Bresters et al., Vox Sang 62:213 (1992)), allowing a marked improvement over the first generation tests in identifying HCV infected blood donors (Aach et al., N Engl J Med 325:1325 (1991); Kleinman et al., Transfusion 32:805 (1992). The second-generation assays detect antibodies in close to 100% of chronic HCV cases (Hino K., Intervirology 37:77 (1994)) and in nearly 100% of the acute cases by 12 weeks post infection (Alter et al., N Engl J Med 327:1899 (1992); Bresters et al., Vox Sang 62:213 (1992)). The third generation test includes a recombinant protein expressing amino acid sequences from the NS5 region, as well as antigens from the core, NS3 and NS4. Some studies have indicated a slight improvement in sensitivity in comparing the third generation tests to second generation tests (Lee et al., Transfusion 35:845 (1995); Courouce et al. Transfusion 34:790-795 (1994)), but this improvement is largely attributed to changes in the NS3 protein rather than the inclusion of NS5 (Courouce et al., Lancet 343:853 (1994)).

In general, the second and third generation HCV antibody tests detect exposure to HCV about 70 days after exposure. Since HCV establishes persistent, and in many cases lifelong infection, the detection of antibodies to HCV represents a very efficient method for determining exposure to HCV. However, antibody testing alone will frequently fail to detect HCV infected individuals during the first 70 days after exposure.

It has been suggested that testing for HCV antigen detects exposure to HCV significantly earlier than antibody testing and represents an alternative to nucleic acid testing for detecting exposure to HCV during the pre-seroconversion period. The HCV antigen detection test is rapid, simple, may-not require sample extraction or other pretreatment, and is not as prone to handling errors (e.g., contamination) as may occur in the HCV RNA tests. Thus, HCV core antigen tests present a practical alternative to HCV RNA for screening blood donors or for monitoring antiviral therapy.

Existing HCV antigen tests rely on detecting the presence of the HCV core antigen in serum or plasma. HCV core protein is a structural protein of HCV comprising the first 191 amino acids of the polyprotein and that forms the internal viral coat encapsidating the genomic RNA. Two different types of serologic assays have been developed which permit detection of HCV core antigens in serum. One assay format detects HCV core antigens in subjects prior to seroconversion and is utilized in screening blood donors, while the other assay format detects core antigens only in hepatitis C patients, regardless of their HCV antibody status, and is utilized in clinical laboratories to diagnose exposure to HCV or to monitor antiviral therapy. The currently available core antigen detection assays all use antibodies against the DNA binding domain of HCV core which is located at amino acids 1-125 of the core protein. The core protein also contains a lipid binding domain that is located between amino acids 134-171. To date there have been no antigens described from that section of core protein and until now it has been assumed that core detection required antibodies against the DNA binding domain.

Thus, binding proteins that can readily detect HCV core antigen will markedly improve the available methods of detection of HCV exposure in a patient. Thus, there is a recognized need for new antibodies that can readily be employed in screening tests.

SUMMARY OF THE INVENTION

The present invention in general is directed to a monoclonal antibody that is specifically immunoreactive with the lipid binding domain of HCV core antigen. More particularly, the HCV core antigen is amino acid residues 134-171 of HCV. In more particular embodiments, the antibody specifically binds at least one epitope formed by amino acid sequence MGYIPLVGAPLGGAARALAHGVRV-LEDGVNYATGNLPG (SEQ ID NO: 578). In more specific embodiments, the antibody is immunoreactive with an epitope formed by amino acids 141-161, 134-154 and 151-171 of HCV core antigen.

Another aspect of the invention provides a monoclonal antibody that is specifically immunoreactive with the lipid binding domain of HCV core antigen, wherein said monoclonal antibody has a heavy chain variable domain selected from the group consisting of the antibodies listed in FIG. 1A, and a light chain variable domain selected from the group consisting of the antibodies listed in FIG. 1B.

It is contemplated that any of the antibodies described herein may be prepared as immunoassay reagents, more particularly, such reagents preferably are labeled with a detectable label.

In still other embodiments, immunoassay reagents of the invention comprise one or more of the antibodies disclosed herein being bound to a solid phase.

The immunoassay reagents comprising the antibodies of the invention may further comprise an additional antibody against an HCV antigen. For example, such an additional antibody is an additional anti-core antibody.

A further aspect of the invention is directed to an immunoassay for the detection of HCV in a test sample, said immunoassay comprising:

(i) contacting a test sample suspected of containing HCV with a first antibody directed against HCV core antigen to form a complex between said first antibody and antigen located within said test sample;

(ii) contacting said complex formed in step (i) with an antibody of any of claims 1-6, to form a complex between said antibody of any of claims 1-6 and antigen in the complex formed in step (i) wherein said antibody of any of claims 1-6 is detectably labeled and (iii) detecting the label of the complex formed in step (ii).

In more specific embodiments, the immunoassay may further be characterized in that the first antibody is directed to the DNA binding domain of HCV core antigen. In more particular embodiments the antibody employed in step (ii) is labeled with a fluorescent label. In exemplary embodiments, the label is acridinium.

In some embodiments, the immunoassay is one in which the antibody of step (i) is coated on solid phase. In specific preferred embodiments, the antibody of step (i) comprises an antibody that is distinct from the antibody of step (ii). Alternatively, the immunoassay is one in which the antibody of step (i) comprises an antibody that is the same as the antibody of step (ii).

Any of the immunoassays of the invention may be used on a test sample obtained from a patient and the method further comprises diagnosing, prognosticating, or assessing the efficacy of a therapeutic/prophylactic treatment of the patient, wherein, if the method further comprises assessing the efficacy of a therapeutic/prophylactic treatment of the patient, the method optionally further comprises modifying the therapeutic/prophylactic treatment of the patient as needed to improve efficacy.

As will be described in further detail herein, it will be understood by those skilled in the art that any of the immunoassays of the invention may be readily adapted for use in an automated system or a semi-automated system.

BRIEF DESCRIPTION OF SEVERAL VIEWS OF THE DRAWINGS

FIG. 1A shows the heavy chain variable domains of preferred antibodies of the present invention. FIG. 1A discloses SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 88, 90, 90, 92, 94, 96, 98, and 100, respectively, in order of appearance.

FIG. 1B shows the light chain variable domains of preferred antibodies of the present invention. FIG. 1B discloses SEQ ID NOS: 302, 304, 306, 308, 310, 312, 314, 316, 318, 320, 322, 324, 324, 326, 328, 330, 332, 334, 336, 338, 340, 340, 342, 344, 346, 348, 350, 352, 354, 356, 358, 360, 362, 364, 364, 366, 368, 370, 370, 370, 372, 374, 376, 376, 378, 380, 382, 384, 386, 388, 388, and 388, respectively, in order of appearance.

FIG. 2 shows two representations of a clustering diagram derived from the alignments of FIG. 1A.

DETAILED DESCRIPTION OF THE INVENTION

The present invention describes the development of monoclonal antibodies directed against the Hepatitis C Virus core antigen, specifically, the lipid binding domain of core antigen between amino acids 134-171. The immunogen used was a synthetic peptide and screening of hybridomas utilized both the immunogen peptide and a set of three overlapping smaller peptides within the 134-171 region. In addition, a recombinant core antigen representing amino acids 1-169 was used for screening to determine the efficacy of the identified monoclonal antibodies as reactive with HCV core protein. The antibodies are delineated by their reactivity to the antigen, the immunogen peptide, and smaller overlapping peptides comprising the immunogen. Binding kinetics of the antibodies to the immunogen peptide were determined by SPR (surface plasmon resonance) using a BIAcore 4000 instrument. Immunoreactivity to the recombinant core antigen was determined by standard ELISA.

In addition, to show that the monoclonal antibodies of the present invention were useful in analyzing the presence of core antigen, core antigen capture microtiter plate assays were performed by using monoclonal antibodies directed to epitopes within the DNA binding domain of HCV core (e.g. amino acids 1-125) as the capture reagent and the 134-171-directed antibodies of the present invention as detection reagents. These assays produced results to demonstrate the utility of the 134-171-directed antibodies of the invention for HCV core antigen detection immunoassays. This is the first demonstration of an antigen capture assay that independently targets two major domains of HCV core for capture and detection. Previously reported core antigen detection assays use antibodies that bind to epitopes within the DNA binding domain (e.g., amino acids 1-125).

To produce the antibodies of the present invention, mice were immunized with a synthetic peptide comprised of HCV core genotype 1 consensus sequence from amino acids 134-171 linked to BSA. More specifically, the immunogen had the sequence of (SEQ ID NO: 578):

MGYIPLVGAPLGGAARALAHGVRVLEDGVNYATGNLPG

In addition, the binding of the monoclonal antibodies to three specific N-terminally biotinylated epitope regions also was characterized and is further discussed in the Examples. Specifically, the three overlapping epitopes were derived from the above region and had the sequences of (SEQ ID NOS: 573-575, respectively, in order of appearance):

HCVc 134-154      MGYIPLVGAPLGGAARALAHG

HCVc 141-161      GAPLGGAARALAHGVRVLEDG

HCVc 151-171      LAHGVRVLEDGVNYATGNLPG

The immunogen was conjugated to BSA to produce the antibodies. In other embodiments, the immunogen was conjugated to TT and fibrils. The TT sequence is often used to provide a more robust immune response in mice. The sequence of the TT conjugate was:

Ac-Met-Gly-Tyr-Ile-Pro-Leu-Val-Gly-Ala-Pro-Leu-

Gly-Gly-Ala-Ala-Arg-Ala-Leu-Ala-His-Gly-Val-Arg-

Val-Leu-Glu-Asp-Gly-Val-Asn-Tyr-Ala-Thr-Gly-Asn-

Leu-Pro-Gly-Gln-Tyr-Ile-Lys-Ala-Asn-Ser-Lys-Phe-

Ile-Gly-Ile-Thr-Glu-Leu-NH2

The sequence of the fibrils conjugate was:

Ac-Met-Gly-Tyr-Ile-Pro-Leu-Val-Gly-Ala-Pro-Leu-

Gly-Gly-Ala-Ala-Arg-Ala-Leu-Ala-His-Gly-Val-Arg-

Val-Leu-Glu-Asp-Gly-Val-Asn-Tyr-Ala-Thr-Gly-Asn-

Leu-Pro-Gly-Gln-Gln-Lys-Phe-Gln-Phe-Gln-Phe-Glu-

Gln-Gln-NH2

B-lymphocytes were fused with a myeloma fusion partner to create hybridomas that were then screened for reactivity against the immunogen peptide, three overlapping peptides within the immunogen peptide sequence, and a recombinant HCV core antigen. Kinetic profiling using a Biacore 4000 allowed for identification of clusters of antibodies wherein the clusters are defined by their ability to bind to the immunogen peptide, or shorter peptides overlapping the 134-171 region. Combining these results with immunoreactivity, or lack thereof, for the recombinant antigen as determined by ELISA, allowed further delineation of the antibodies into groups with similar characteristics (specificities).

To briefly summarize the screening results discussed in further detail in the Examples, the greatest immune response was seen in mice immunized with the peptide linked to BSA. Additionally, the response from these mice was predominantly focused on the amino acid 141-161 region, although there was also some response to the amino acid 134-154 and 151-171 regions as well. With the HCV peptide linked to TT, an immune response was seen, however, this response was not as strong as with BSA. The response was spread over all 3 epitope regions. On the other hand, mice immunized using the amino acid 134-171 peptide linked to a peptide that would form fibril networks failed to show a significant immune response. The antibodies of the present invention are described in further detail in FIGS. 1A and 1B, and in the Examples.

The HCV core antigen used for these studies was expressed in *E. coli* and purified in a two-step process using IMAC followed by reverse-phase HPLC based on previously published methods (Boulant et al., J. Virol. (2005), 79(17):11353-11365).

In this manner a significant array of monoclonal antibodies that are specific for the lipid binding domain of HCV core have been produced. These monoclonal antibodies have utility in development of diagnostic assays for the detection of HCV core antigen in the serum and plasma of infected individuals. Prior to the present invention, there has been no reported generation of monoclonal antibodies to the multiple epitopes within the core amino acid 134-171 region that have shown binding activity to the HCV full length core peptide. The availability of the monoclonal antibodies of the present invention allows for the development of immunoassays for core antigen detection wherein two major domains of HCV core antigen are targeted. Previous core antigen assays described the use of monoclonals directed to epitopes within amino acid 1-125 (nucleic acid binding domain). Because the previously described monoclonal antibodies were only able to target the nucleic acid binding domain of HCV core, they were at best inefficient and often ineffective at detection of core protein fragments, break-down products, or smaller core proteins derived by internal translation initiation. The present invention for the first time overcomes these inadequacies in the previous assays by providing specific monoclonal antibodies that can be used as reagents to more efficiently and rapidly detect HCV core present in a test sample.

More particularly, the antibodies described herein are reagents useful for detection of HCV core antigen and are useful reagents to facilitate investigation of the life cycle of HCV. As noted above, HCV encoded proteins are expressed in a concerted process in which ribosomes bind to the internal ribosome entry site (IRES) and initiate translation, leading to synthesis of the viral polyprotein, which is cleaved to produce the classical HCV proteins, p21 core, E1, E2, p7, and the nonstructural proteins. None of the viral enzymes, including the viral polymerase, can be made without the initiation of translation in the core gene region. Because of this temporal relationship, it is believed that translation events in this region control the expression all HCV proteins. Hence, a complete understanding of the core gene and its gene products is essential to understanding the life cycle of the virus and may shed light on our understanding of mechanisms of virus pathogenicity. Recently, a new family of conserved viral proteins, referred to as minicores have been described (Eng et al., J Virol. 2009 April; 83(7):3104-3114). These proteins are encoded in the same reading frame as the core gene but, are believed to be derived from internal translation initiation events rather than post-translational processing of the full-length core protein. One of the minicore proteins described is termed "91 minicore" named for the presumed initiator codon within core. It is hypothesized that "134 minicore" also exists, being derived from translation initiation at codon 134 which encodes a methionine in many HCV isolates. However, reagents are not available that allow detection of minicores that are, essentially, derived from the lipid binding domain. Such proteins may play an important role in HCV persistence.

Since the monoclonal antibodies were raised against a linear, synthetic peptide derived from HCV core 134-171, it is unknown whether they will bind to the native, complete core antigen or processed forms of HCV core that exist in infected individuals. However, provided that the monoclonal antibodies of the present invention are able at least to bind one or more epitopes presented by the linear HCV core region from amino acids 134-171, it is contemplated that such binding will be sufficient to render these monoclonal antibodies significantly useful in HCV detection assays. Some of the monoclonal antibodies of the present invention react with recombinant core antigen while others do not, suggesting that within the core amino acid 134-171 region, there are both linear and conformational epitopes. Antibodies recognizing either linear or conformational epitopes are very useful tools for the study of virus assembly within infected cells and the virus life cycle generally.

Finally, these reagents can also be used in immunoassays where it is desirable to determine the presence of only the lipid binding domain. Since little is known about circulating levels of minicores in infected individuals it is possible that they are present at much higher levels than core proteins containing the region of amino acids 1-125. In providing antibodies that detect HCV core peptides outside of the region of amino acids 1-125, the present invention provides HCV core antigen detection assays with much greater sensitivity than those currently available.

DEFINITIONS

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CHL CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (Winter, et al. U.S. Pat. Nos. 5,648,260 and 5,624,821). The Fc portion of an antibody mediates several important effector functions e.g., cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.R5 and complement Clq, respectively. Neonatal Fc receptors (FcRn) are the critical components determining the circulating half-life of antibodies. At least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al. Nature; 264: 415-20; Thies et al 1999 J Mol Biol; 293: 67-79). Mutation of cysteine residues within the hinge regions to prevent heavy chain-heavy chain disulfide bonds will destabilize dimerization of CH3 domains. Residues responsible for CH3 dimerization have been identified (Dall'Acqua 1998 Biochemistry 37: 9266-73). Therefore, it is possible to generate a monovalent half-Ig. Interestingly, these monovalent half Ig molecules have been found in nature for both IgG and IgA subclasses (Seligman 1978 Ann Immunol 129: 855-70; Biewenga et al 1983 Clin Exp Immunol 51: 395-400). The stoichiometry of FcRn:Ig Fc region has been determined to be 2:1 (West et al. 2000 Biochemistry 39: 9698-708), and half Fc is sufficient for mediating FcRn binding (Kim et al 1994 Eur J Immunol; 24: 542-548). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2-CH3 domains. However the half Ig molecule may have certain advantage in tissue penetration due to its smaller size than that of a regular antibody. At least one amino acid residue may be replaced in the constant region of the binding protein of the present disclosure, for example the Fc region, such that the dimerization of the heavy chains is disrupted, resulting in half DVD Ig molecules. The anti-inflammatory activity of IgG is completely dependent on sialylation of the N-linked glycan of the IgG Fc fragment. The precise glycan requirements for anti-inflammatory activity has been determined, such that an appropriate IgG1 Fc fragment can be created, thereby generating a fully recombinant, sialylated IgG1 Fc with greatly enhanced potency (Anthony, R. M., et al. (2008) Science 320:373-376).

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab').sub.2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. (See, e.g., Holliger, P., et al. (1993) Proc. Natl. Acad. Sci. USA 90:6444-6448; Poljak, R. J., et al. (1994) Structure 2:1121-1123). Such antibody binding portions are known in the art. (See, e.g., Kontermann and Dubel eds., Antibody Engineering (2001) Springer-Verlag. New York. 790 pp. (ISBN 3-540-41354-5)). In addition, single chain antibodies also include "linear antibodies" comprising a pair of tandem Fv segments (VH—CH1-VH—CH1) which, together with complementary light chain polypeptides, form a pair of antigen binding regions (Zapata et al., Protein Eng. 8(10):1057-1062 (1995); and U.S. Pat. No. 5,641,870).

The term "multivalent binding protein" is used throughout this specification to denote a binding protein comprising two or more antigen binding sites. In one aspect, the multivalent binding protein is engineered to have three or more antigen binding sites, and is generally not a naturally occurring antibody. Dual variable domain (DVD) binding proteins comprise two or more antigen binding sites and are tetravalent or multivalent binding proteins. DVDs as described herein can be monospecific, i.e., capable of one antigen such as HCV core protein, or multispecific, i.e. capable of binding two or more antigens. DVD binding proteins comprising two heavy chain DVD polypeptides and two light chain DVD polypeptides are referred to as DVD-Ig, and are described for example in U.S. Pat. No. 7,612,181, the disclosure of which is herein incorporated by reference in its entirety. Each half of a DVD-Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

An "immunoglobulin constant domain" refers to a heavy or light chain constant domain. Human IgG heavy chain and light chain constant domain amino acid sequences are known in the art.

The term "monoclonal antibody" or "mAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody", as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R. (1997) TIB Tech. 15:62-70; Azzazy H., and Highsmith W. E. (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see, Taylor, L. D., et al. (1992) Nucl. Acids Res. 20:6287-6295; Kellermann S-A. and Green L. L. (2002) Current Opinion in Biotechnology 13:593-597; Little M. et al. (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. Such recombinant human antibodies can be subjected to in vitro mutagenesis (or, when an animal transgenic for human Ig sequences is used, in vivo somatic mutagenesis) such that the amino acid sequences of the VH and VL regions of the recombinant antibodies are sequences that, while derived from and related to human germline VH and VL sequences, may not naturally exist within the human antibody germline repertoire in vivo.

An "affinity matured" antibody is an antibody with one or more alterations in one or more CDRs thereof which result an improvement in the affinity of the antibody for antigen, compared to a parent antibody which does not possess those alteration(s). Exemplary affinity matured antibodies will have nanomolar or even picomolar affinities for the target antigen. Affinity matured antibodies are produced by procedures known in the art. Marks et al. BidlTechnology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); Hawkins et al, J. Mol. Biol. 226:889-896 (1992) and selective mutation at selective mutagenesis positions, contact or hypermutation positions with an activity enhancing amino acid residue as described in U.S. Pat. No. 6,914,128 B1.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E.A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region. As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

As used herein, the term "neutralizing" refers to counteracting the biological activity of an antigen when a binding protein specifically binds the antigen. In one aspect, the neutralizing binding protein binds the cytokine and reduces its biologically activity by at least about 20%, 40%, 60%, 80%, 85% or more.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it recognizes its target antigen in a complex mixture of proteins and/or macromolecules. Antibodies are said to "bind to the same epitope" if the antibodies cross-compete (one prevents the binding or modulating effect of the other). In addition structural definitions of epitopes (overlapping, similar, identical) are informative, but functional definitions are often more relevant as they encompass structural (binding) and functional (modulation, competition) parameters.

The term "surface plasmon resonance", as used herein, refers to an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "Kon", as used herein, is intended to refer to the on rate constant for association of a binding protein (e.g., an antibody) to the antigen to form the, e.g., antibody/antigen complex as is known in the art. The "Kon" also is known by the terms "association rate constant", or "ka", as used interchangeably herein. This value indicating the binding rate of an antibody to its target antigen or the rate of complex formation between an antibody and antigen.

The term "Koff", as used herein, is intended to refer to the off rate constant for dissociation, or "dissociation rate constant", of a binding protein (e.g., an antibody) from the, e.g., antibody/antigen complex as is known in the art. This value indicates the dissociation rate of an antibody from its target antigen or separation of Ab-Ag complex over time into free antibody and antigen.

The term "KD" as used herein, is intended to refer to the "equilibrium dissociation constant", and refers to the value obtained in a titration measurement at equilibrium, or by dividing the dissociation rate constant (koff) by the association rate constant (kon). The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

"Label" and "detectable label" mean a moiety attached to a specific binding partner, such as an antibody or an analyte, e.g., to render the reaction between members of a specific binding pair, such as an antibody and an analyte, detectable, and the specific binding partner, e.g., antibody or analyte, so labeled is referred to as "detectably labeled." Thus, the term "labeled binding protein" as used herein, refers to a protein with a label incorporated that provides for the identification of the binding protein. In one aspect, the label is a detectable marker that can produce a signal that is detectable by visual or instrumental means, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., 3H, 14C, 35S, 90Y, 99Tc, 111In, 125I, 131I, 177Lu, 166Ho, or 153Sm); chromogens, fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

The term "conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. In one aspect, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The terms "isolated polynucleotide" and "isolated nucleotide molecule" as used interchangeably herein mean a polynucleotide (e.g., of genomic, cDNA, or synthetic origin, or some combination thereof) that, is not associated with all or a portion of a polynucleotide with which the "isolated polynucleotide" or "isolated nucleotide molecule" is found in nature, or does not occur in nature as part of a larger sequence. An "isolated polynucleotide" or "isolated nucleotide molecule" may be operably linked to a polynucleotide that it is not linked to in nature.

The terms "regulate" and "modulate" as used interchangeably herein refer to a change or an alteration in the activity of a molecule of interest (e.g., the biological activity of a cytokine). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction. Correspondingly, the term "modulator," as used herein, is a compound capable of changing or altering an activity or function of a molecule of interest (e.g., the biological activity of a cytokine). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

"Patient" and "subject" may be used interchangeably herein to refer to an animal, such as a mammal, including a primate (for example, a human, a monkey, and a chimpanzee), a non-primate (for example, a cow, a pig, a camel, a llama, a horse, a goat, a rabbit, a sheep, a hamster, a guinea pig, a cat, a dog, a rat, a mouse, a whale), a bird (e.g., a duck or a goose), and a shark. Preferably, the patient or subject is a human, such as a human being treated or assessed for a disease, disorder or condition, a human at risk for a disease, disorder or condition, a human having a disease, disorder or condition, and/or human being treated for a disease, disorder or condition.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

"Component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide or other analyte as above, such as a composition comprising an analyte such as polypeptide, which is optionally immobilized on a solid support, such as by binding to an anti-analyte (e.g., anti-polypeptide) antibody. Some components can be in solution or lyophilized for reconstitution for use in an assay.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (e.g., polypeptide of interest) may entail release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

"Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

"Specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to analyte (or a fragment thereof) and not bind specifically to other entities.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

Monoclonal Antibodies

FIGS. 1A and 1B show the sequences of various antibodies that have been determined to be specific for HCV core antigen and more particularly, have been determined to be specific for the lipid binding domain of HCV core antigen. It has been found that these monoclonal antibodies are specifically immunoreactive with the lipid binding domain of HCV core antigen. More specifically, it is found that the antibodies of the present invention specifically bind at least one epitope formed by amino acid sequence MGYIPLVGAPLG-GAARALAHGVRVLEDGVNYATGNLPG (SEQ ID NO: 578). More particularly, the monoclonal antibodies at least are immunoreactive with an epitope formed by amino acids 141-161, 134-154 and 151-171 of HCV core antigen. Given the disclosure of these monoclonal antibodies, the present invention contemplates the uses thereof in specific immunoassays to facilitate a rapid and efficient detection of the presence of HCV in a test sample by determining the presence of HCV core antigen in such a test sample.

The anti-HCV core binding proteins, including monoclonal antibodies and any derivative (e.g., a fragment or variant) thereof that comprises the CDRs of the heavy and light chains of the monoclonal antibodies described herein (see FIGS. 1A and 1B) provided that such a derivative retains the property of binding specifically to HCV core protein lipid binding domain, can be used in immunoassays for diagnosing or prognosing hepatitis C virus infection in a mammal. As used throughout the present disclosure, "mammal" includes humans and non-human primates, as well as other animals. It will be understood that a target analyte in the immunoassays and related methods is the lipid domain of HCV core protein, and hence the target analyte is HCV core protein which would be present in the sample, such as for example, after HCV infection. Additionally, it should be understood that the immunoassay may detect two or more target analytes provided that at least one of the analytes is HCV core protein, the second or additional target analyte may be another core protein analyte (e.g., an the DNA binding domain of HCV core protein) or may be an analyte that is not HCV core protein.

The nucleotide (DNA) sequences and deduced protein sequences encoding the heavy and light chain variable domains of anti-HCV core monoclonal antibodies were obtained by immunizing mice with a synthetic peptide comprised of HCV core genotype 1 consensus sequence from amino acids 134-171 and a tetanus toxoid (TT) peptide sequence. In some embodiments, the amino acid 134-171 sequence was conjugated to BSA. However, in other embodiments, the synthetic peptide also was conjugated to the TT sequence as this is often used to provide a more robust immune response in mice, by methods known to those skilled in the art such as those described in detail herein below and in, for example, Goding, J. W. 1983. Monoclonal Antibodies: Principles and Practice, Pladermic Press, Inc., NY, N.Y., pp. 56 97. Briefly, to produce a human-human hybridoma, a human lymphocyte donor is selected. A donor who is known as infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies. Antibodies secreted by the immortalized cells are screened to determine the clones that secrete antibodies of the desired specificity. For monoclonal anti-HCV core antibodies, the antibodies must bind to HCV core protein and more specifically, the lipid binding domain of HCV core protein respectively. Cells producing antibodies of the desired specificity are selected. Other methods for obtaining monoclonal antibodies can be used, as known in the art. The Examples below describes how the anti-HCV core monoclonal antibodies were obtained and characterized following isolation of mRNA from hybridoma cells grown in cell culture. Deduced amino acid sequences of the heavy and light chain variable regions for the anti-HCV core monoclonal antibodies of the present invention are listed in FIG. 1A and FIG. 1B, respectively.

The deduced amino acid sequences of the heavy and the light chain domains were assigned SEQ ID NOs and the corresponding cDNAs sequences encoding the same are shown in the Sequence Table in Appendix A.

The cDNA sequences set forth in the Sequence Table represent exemplary embodiments of the disclosed cDNAs. Variations are contemplated in the cDNA sequences shown therein. Such variations include those that will result in a nucleic acid sequence that is capable of directing production of analogs of the corresponding protein shown in the Sequence Table. It will be understood that due to the degeneracy of the genetic code, many substitutions of nucleotides may be made that will lead to a DNA sequence that remains capable of directing production of the corresponding protein or its analogs. All such variant DNA sequences that are functionally equivalent to any of the sequences described herein, are encompassed by the present disclosure.

A variant of any of the binding proteins (as exemplified by monoclonal antibodies of the invention shown in FIGS. 1A and 1B) described herein means a protein (or polypeptide) that differs from a given protein (e.g., an anti-HCV core monoclonal antibody) in amino acid sequence by the addition (e.g., insertion), deletion, or conservative substitution of amino acids, but that retains the biological activity of the given protein. A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101, which is incorporated herein by reference). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity, e.g., the ability to bind to IL-18. Use of "variant" herein is intended to encompass fragments of a variant unless otherwise contradicted by context.

The antibodies of the present invention or antigen binding fragments of those antibodies (e.g., fragments that comprise the heavy and light chain CDRs of the antibodies of the present invention) may also be produced by genetic engineering. For example, the technology for expression of both heavy and light chain genes in E. coli is the subject of the PCT patent applications; publication number WO 901443, WO901443, and WO 9014424 and in Huse et al., 1989 Science 246:1275 1281. The present disclosure also encompasses an isolated recombinant vector comprising a nucleic acid molecule as described herein, as well as a host cell comprising such a recombinant vector. A vector is a nucleic acid molecule, which may be a construct, capable of transporting another nucleic acid to which it has been linked. A vector may include any preferred or required operational elements. Preferred vectors are those for which the restriction sites have been described and which contain the operational elements needed for transcription of the nucleic acid sequence. Such operational elements include for example at least one suitable promoter, at least one operator, at least one leader sequence, at least one terminator codon, and any other DNA sequences necessary or preferred for appropriate transcription and subsequent translation of the nucleic acid sequence. Such vectors contain at least one origin of replication recognized by the host organism along with at least one selectable marker and at least one promoter sequence capable of initiating transcription of the nucleic acid sequence. A vector may be a plasmid into which additional DNA segments may be ligated. A vector may be a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as a plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

Sequences that are operably linked are in a relationship permitting them to function in their intended manner. A control sequence operably linked to a coding sequence is ligated in such a way that expression of the coding sequence is achieved under conditions compatible with the control sequences. Operably linked sequences include both expression control sequences that are contiguous with the gene of interest and expression control sequences that act in trans or at a distance to control the gene of interest. Expression control sequences are polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. Control sequences include components whose presence is essential for expression and processing, and can also include additional components whose presence is advantageous, for example, leader sequences and fusion partner sequences.

A host cell may be transformed with a vector that introduces exogenous DNA into a host cell in order to render that cell one that recombinantly produces the antibodies of the present invention. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Transformed cells include stably transformed cells in which the inserted DNA is capable of replication either as an autonomously replicating plasmid or as part of the host chromosome, and cells which transiently express the inserted DNA or RNA for limited periods of time.

Suitable host organisms include for example a eukaryotic cell system such as but not limited to cell lines such as HeLa, MRC-5 or CV-1. Host organisms such as host cells are cultured under conditions appropriate for amplification of the vector and expression of the protein, as well known in the art. Expressed recombinant proteins may be detected by any of a number of methods also well known in the art.

Although the HCV detection aspects of the present invention merely need the antibodies to be monoclonal antibodies such that they specifically recognize HCV core antigen, it may in some embodiments be desirable to produce humanized versions of the antibodies of the present invention. Humanized" antibodies and production thereof is well known to those of skill in the art. General reviews of "humanized" antibodies are provided by Morrison S., 1985 Science 229: 1202 and by Oi et al., 1986 BioTechniques 4:214. Suitable "humanized" antibodies can be alternatively produced by CDR or CEA substitution (Jones et al., 1986 Nature 321:552; Verhoeyan et al., 1988 Science 239:1534; Biedler et al. 1988 J. Immunol. 141:4053, the entire disclosures of which are incorporated herein by reference).

In other embodiments, the monoclonal antibodies of the present invention may serve as useful starting materials for the production of engineered and derivatized binding proteins including dual variable domain immunoglobulin (DVD-Ig) binding proteins comprising one or more anti-HCV monoclonal antibodies as described herein. For example, DVD-Ig's with unique binding affinities for HCV core protein may be produced, as described for example in U.S. Pat. No. 7,612,181, the entire disclosure of which is hereby incorporated by reference. DVD-Ig binding proteins are capable of binding one or more targets. Preferably the binding protein comprises a polypeptide chain comprising VD1-(X1)n-VD2-C—(X2)n, wherein VD1 is a first variable domain, VD2 is a second variable domain, C is a constant domain, X1 represents an amino acid or polypeptide, X2 represents an Fc region and n is 0 or 1. The binding protein can be generated using various techniques.

In exemplary techniques, the DVD-Ig can be formed with four polypeptide chains which form four functional antigen binding sites. Thus, for example, the DVD-Ig is capable of binding HCV core protein. The binding protein can be capable of modulating a biological function of HCV core protein, or of neutralizing HCV core protein. Exemplary such binding proteins have at least one heavy chain variable domain comprising an amino acid sequence of at least 90% identity with one of the antibodies of the present invention and at least the corresponding light chain variable domain comprising an amino acid sequence having at least 90% identity with a sequence of that light chain variable domain.

The variable domains of a DVD binding protein can be obtained from parent antibodies, including polyclonal and monoclonal antibodies capable of binding antigens of interest. The monoclonal antibodies that specifically bind to HCV core protein described herein are suitable parent antibodies. Generally, antibodies used for the DVD binding protein may be naturally occurring or may be generated by recombinant technology.

Monoclonal antibodies can be prepared using a wide variety of techniques known in the art including the use of hybridoma, recombinant, and phage display technologies, or a combination thereof. For example, monoclonal antibodies can be produced using hybridoma techniques including those as described herein for preparing the anti-HCV core protein monoclonal antibodies, and those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Hybridomas are selected, cloned and further screened for desirable characteristics, including robust hybridoma growth, high antibody production and desirable antibody characteristics, as discussed in Example 1 below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art. In a preferred embodiment, the hybridomas are mouse hybridomas. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an antibody capable of binding a specific antigen.

Recombinant monoclonal antibodies are also generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) Proc. Natl. Acad. Sci. USA 93:7843-7848. In this method, single cells secreting antibodies of interest, e.g., lymphocytes derived from an immunized animal, are identified, and, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to the antigen of interest. The amplified immunoglobulin sequences further can be manipulated in vitro, such as by in vitro affinity maturation methods such as those described in PCT Publication WO 97/29131 and PCT Publication WO 00/56772.

Monoclonal antibodies are also produced by immunizing a non-human animal comprising some, or all, of the human immunoglobulin locus with an antigen of interest. In a preferred embodiment, the non-human animal is a XENOMOUSE® transgenic mouse, an engineered mouse strain that comprises large fragments of the human immunoglobulin loci and is deficient in mouse antibody production. See, e.g., Green et al. Nature Genetics 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE® transgenic mouse produces an adult-like human repertoire of fully human antibodies, and generates antigen-specific human Mabs. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics 15:146-156 (1997), Green and Jakobovits J. Exp. Med. 188:483-495 (1998), the disclosures of which are hereby incorporated by reference.

In vitro methods also can be used to make the parent antibodies, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, US patent application publication 20030186374, and PCT Publication No. WO 97/29131, the contents of each of which are incorporated herein by reference.

Parent antibodies can also be generated using various phage display methods known in the art. In phage display methods, functional antibody domains are displayed on the surface of phage particles that carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies as described herein include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

Alternative to screening of recombinant antibody libraries by phage display, other methodologies known in the art for screening large combinatorial libraries can be applied to the identification of parent antibodies. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) Proc. Natl. Acad. Sci. USA 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the parent antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the parent antibodies include those disclosed in Wittrup, et al. U.S. Pat. No. 6,699,658 incorporated herein by reference.

The monoclonal antibodies described herein can be further modified to generate CDR grafted and Humanized parent antibodies. CDR-grafted parent antibodies comprise heavy and light chain variable region sequences from a human antibody wherein one or more of the CDR regions of VH and/or VL are replaced with CDR sequences of murine antibodies capable of binding antigen of interest. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs has at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing such antibodies are known in the art (see EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352).

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.html; www.library.thinkquest.org/12429/Immune/Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/Immunology.html.www.immunologylink.com/; pathbox.wustl.edu/.about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Elisa.html; www.biodesign.com/table.asp; www.icnet.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.aboutjraats/linksl.html; www.recab.uni-hd.de/immuno.bme.nwu.edu/; www.mrc-cpe.cam.ac.uk/imt-doc/pu-blic/INTRO.html; www.ib-t.unam.mx/virV_-mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stataim.html; www.biosci.missouri.edu/smithgp/index.html; www.cryst.bioc.cam.ac.uk/.abo-ut.fmolina/Webpages/Pept/spottech.html; wwwjerini.de/fr roducts.htm; www.patents.ibm.con/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

Parent monoclonal antibodies may be selected from various monoclonal antibodies capable of binding specific targets including, or in addition to, HCV proteins, as well known in the art.

Parent monoclonal antibodies may also be selected from various therapeutic antibodies approved for use, in clinical trials, or in development for clinical use, particularly those that may be applicable in treating symptoms of HCV infection, or in treating conditions or diseases that co-exist with HCV infection, such as cancer, including particularly hepatocellular carcinoma.

As noted throughout the present invention, it may be desirable to label the antibodies of the present invention. A labeled antibody (or a binding protein derived from one of the antibodies of the present invention) comprises the antibody, which is derivatized or linked to another functional molecule (e.g., another peptide or protein). For example, the monoclonal antibody can be derivatized by functionally linking it (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the binding protein with another molecule (such as a streptavidin core region or a polyhistidine tag).

Useful detectable agents with which monoclonal antibody may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. The antibody may also be derivatized with detectable enzymes, such as alkaline phosphatase, horseradish peroxidase, glucose oxidase and the like. When derivatized with a detectable enzyme, the detection is achieved by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A monoclonal antibody of the invention may also be derivatized with biotin, and detected through indirect measurement of avidin or streptavidin binding, or vice versa.

While the compositions of the present invention have demonstrated use in diagnostic applications for determining the presence of HCV core antigen in a test sample, it is contemplated that the compositions of the present invention also may serve a diagnostic or therapeutic purpose for in vivo administration to a mammal. Thus, in some embodiments, the present invention provides pharmaceutical and diagnostic compositions comprising one or more anti-HCV core binding proteins disclosed herein as an active ingredient. Pharmaceutical or diagnostic compositions may comprise any monoclonal antibody described herein, or any combination thereof, and a pharmaceutically acceptable carrier, diluent and/or excipient. Generally, the pharmaceutical and diagnostic compositions are prepared by combining the active ingredient with the carrier, diluent and/or excipient.

The compositions comprising binding proteins as described herein are for use in, but not limited to, diagnosing, detecting, or monitoring a disorder, but may also find use in preventing, treating, managing, or ameliorating of a disorder or one or more symptoms thereof, and/or in research. In a specific embodiment, a composition comprises one or more monoclonal antibodies of the present invention or a binding protein derived from one or more of the monoclonal antibodies of the present invention. In another embodiment, the composition comprises one or more monoclonal antibodies or binding proteins derived therefrom as described herein and one or more diagnostic, prophylactic or therapeutic agents other than monoclonal antibodies or binding proteins derived therefrom as described herein.

Immunoassays

Immunoassays according to the present disclosure include such techniques commonly recognized in the art, including for example radioimmunoassay, Western blot assay, immunofluorescent assay, enzyme immunoassay, chemiluminescent assay, immunohistochemical assay, immunoprecipitation and the like. Standard techniques known in the art for ELISA are well-known and described for example in Methods in Immunodiagnosis, 2nd Edition, Rose and Bigazzi, eds., John Wiley and Sons, 1980 and Campbell et al., Methods of Immunology, W. A. Benjamin, Inc., 1964, both of which are incorporated herein by reference Immunoassays may be a direct, indirect, competitive, or noncompetitive immunoassay as described in the art (Oellerich, M. 1984. J. Clin. Chem. Clin. BioChem 22:895 904). Biological samples appropriate for such detection assays include, but are not limited to blood, plasma, serum, liver, saliva, lymphocytes or other mononuclear cells.

In preferred embodiments, the antibodies described herein are used in immunoassays specific for the detection of HCV. Examples include, but are not limited to, sandwich immunoassay, radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds an analyte of interest such as HCV core (or a fragment thereof) is attached to the surface of a mass spectrometry probe, such as a pre-activated protein chip array. The analyte (or a fragment thereof) is then specifically captured on the biochip, and the captured analyte (or a fragment thereof) is detected by mass spectrometry. Alternatively, the analyte (or a fragment thereof) can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay.

An immunoassay for determining the presence or amount of human hepatitis C virus in a sample may comprise, for example, combining an HCV core protein binding protein with the sample for a time sufficient for the binding protein to bind to any human hepatitis C virus that may be present in the sample, and determining the presence or amount of human hepatitis C virus present in the sample based on specific binding of the binding protein to the human hepatitis C virus core protein. The disclosure also encompasses an immunoassay device for detecting the presence or absence of human HCV in a sample, wherein the device comprises any of the antibodies described herein immobilized on a solid support. The anti-HCV core antibodies and any analogs thereof may be prepared in the form of a kit, alone, or in combinations with other reagents such as secondary antibodies, for use in immunoassays.

Methods well-known in the art for collecting, handling and processing urine, blood, serum and plasma, and other body fluids, are used in the practice of the present disclosure, for instance, when an anti-HCV core antibody of the present invention is employed as an immunodiagnostic reagent and/ or in an analyte immunoassay kit. The test sample can comprise further moieties in addition to the HCV core antigen, including for example, antibodies, antigens, haptens, hormones, drugs, enzymes, receptors, proteins, peptides, polypeptides, oligonucleotides and/or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally may be performed (e.g., as part of a regimen on a commercial platform).

The pretreatment reagent can be any reagent appropriate for use with the immunoassay and kits of the present disclosure. The pretreatment optionally comprises: (a) one or more solvents (e.g., methanol and ethylene glycol) and optionally, salt, (b) one or more solvents and salt, and optionally, detergent, (c) detergent, or (d) detergent and salt. Pretreatment reagents are known in the art, and such pretreatment can be employed as has been previously described, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay Comparison with TDx Monoclonal Whole Blood and EMIT Cyclosporine Assays, Clin. Chem. 45: 432-435 (1999)), and/or as commercially available. Additionally, pretreatment can be performed as described in U.S. Pat. No. 5,135,875, European Patent Pub. No. 0 471 293, U.S. Provisional Patent App. 60/878,017, filed Dec. 29, 2006, and U.S. Patent App. Pub. No. 2008/0020401 (incorporated by reference in its entirety for its teachings regarding pretreatment).

With use of a pretreatment reagent the assay is rendered more sensitive by disruption of preformed/preexisting immune complexes or viral particles in the test sample. In such a pretreated test sample, the anti-HCV core antibody in the sample is separated from the antigen and the remaining antigen in the sample is then tested for the presence of HCV core antigen using the monoclonal antibodies of the present invention. The HCV core antigen in the test sample is thus subjected to an antibody capture step to capture any HCV antigen present in the test sample.

In some other embodiments, use of the pretreatment does not require such a separation step. The entire mixture of test sample and pretreatment reagent are contacted with an antibody specific for the targeted antigen (in this case HCV core antigen, or more particularly, HCV core antigen lipid binding domain). The pretreatment reagent employed for such an assay typically is diluted in the pretreated test sample mixture, either before or during capture by the first antibody that is used to capture the HCV antigen. Despite such dilution, a certain amount of the pretreatment reagent may still be present in the test sample mixture during capture. The capture reagents may be an antibody of the present invention, alternatively, it may be another anti-HCV core antigen antibody or indeed it may be an antibody directed against a non-core protein antigen of HCV (e.g., an antibody against an envelope protein, E1, or E2 or other portion of HCV).

In one assay format, after the test sample is obtained from a subject, a first mixture is prepared. The mixture contains the test sample being assessed for the presence of a given antigen (e.g., in the present case, for the presence of HCV core antigen) and a first specific binding partner (typically an antibody that recognizes an HCV epitope), wherein the first specific binding partner and any HCV antigen contained in the test sample form a first antibody-antigen complex. The order in which the test sample and the first specific binding partner are added to form the mixture is not critical. The first specific binding partner may be immobilized on a solid phase, but in alternative embodiments, the first specific binding partner may be in a solution phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

The methods described are amenable for adaption to systems that utilize microparticle technology including in automated and semi-automated systems wherein the solid phase comprises a microparticle. Such systems include those described in pending U.S. patent application Ser. Nos. 425,651 and 425,643, which correspond to published EPO applications Nos. EP 0 425 633 and EP 0 424 634, respectively, which are incorporated herein by reference.

After the mixture containing the first specific binding partner-analyte complex is formed, any unbound analyte is removed from the complex using any technique known in the art. For example, the unbound analyte can be removed by washing. Desirably, however, the first specific binding partner is present in excess of any analyte present in the test sample in order to optimize maximal binding of the analyte present in the test sample by the first specific binding partner.

After removal of unbound analyte, a second specific binding partner is added to the mixture to form a first specific binding partner-analyte-second specific binding partner complex. The second specific binding partner is preferably an anti-analyte antibody that binds to an epitope on the analyte that differs from the epitope on analyte bound by the first specific binding partner. Simply by way of example, assuming that the assay is for detection of HCV core antigen, a first "capture" antibody is used that is specific for the DNA binding domain of HCV core antigen (alternatively, the first antibody is an anti HCV core antibody that is specific for the HCV core antigen lipid binding domain, such as the antibodies described herein), once this first capture antibody captures HCV core protein from the sample, a second anti-core antigen antibody that binds the lipid binding domain of HCV core antigen (where the first antibody bound the DNA binding domain, or alternatively, where the first antibody is first antibody is specific for the HCV core antigen lipid binding domain, the second antibody could be specific for the DNA binding domain of HCV core antigen). Preferably, in such embodiments, the second specific binding partner is labeled with or contains a detectable label as described above in order to facilitate detection of the [capture antibody-antigen-second antibody] complex.

Any suitable detectable label as is known in the art can be used. For example, the detectable label can be a radioactive label (such as $^3$H, $^{125}$I, $^{35}$S, $^{14}$C, $^{32}$P, and $^{33}$P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2.sup.nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with a chemiluminescent agent such as an acridinium compound, detectably labeled first specific binding partner-analyte complexes form. Alternatively, if a second specific binding partner is used and the second specific binding partner is detectably labeled with a chemiluminescent agent such as an acridinium compound, detectably labeled first specific binding partner-analyte-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture (e.g., the source of the hydrogen peroxide being one or more buffers or other solutions that are known to contain hydrogen peroxide) before, simultaneously with, or after the addition of an above-described acridinium compound. Hydrogen peroxide can be generated in situ in a number of ways such as would be apparent to one skilled in the art.

Upon the simultaneous or subsequent addition of at least one basic solution to the sample, a detectable signal, namely, a chemiluminescent signal, indicative of the presence of analyte is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of analyte in the sample can be quantified. Specifically, the amount of analyte in the sample is proportional to the intensity of the signal generated. The amount of analyte present can be quantified by comparing the amount of light generated to a standard curve for analyte or by comparison to a reference standard. The standard curve can be generated using serial dilutions or solutions of known concentrations of analyte by mass spectroscopy, gravimetric methods, and other techniques known in the art. While the above is described with emphasis on use of an acridinium compound as the chemiluminescent agent, one of ordinary skill in the art can readily adapt this description for use of other chemiluminescent agents.

Analyte immunoassays generally can be conducted using any format known in the art, such as, but not limited to, a sandwich format. Specifically, in one immunoassay format, at least two antibodies are employed to capture and quantify analyte, such as human analyte, or a fragment thereof in a sample. More specifically, preferably, the at least two antibodies bind to different epitopes on an analyte (or a fragment thereof) forming an immune complex, which is referred to as a "sandwich." Generally, in the immunoassays one or more antibodies can be used to capture the analyte (or a fragment thereof) in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody," the "detection antibodies," the "conjugate," or the "conjugates"). Thus, in the context of a sandwich immunoassay format, an anti-HCV core antibody of the present invention can be used as a capture antibody, a detection antibody, or both. For example, one anti-HCV core antibody having a domain that can bind a first epitope (e.g., the lipid binding domain of HCV core antigen) on an analyte can be used as a capture antibody and/or another anti-HCV core antibody having a domain that can bind a second epitope (e.g., the DNA binding domain of HCV core antigen) can be used as a detection antibody, or vice versa. Alternatively, one antibody having a first domain that can bind an epitope on a HCV core antigen and a second antibody that binds an epitope on a different HCV antigen can be used as a capture antibody and/or a detection antibody to detect, and optionally quantify, two or more analytes.

Generally speaking, a sample being tested for (for example, suspected of containing) analyte can be contacted with at least one capture antibody (or antibodies) and at least one detection antibody (which can be a second detection antibody or a third detection antibody or even a successively numbered antibody, e.g., as where the capture and/or detection antibody comprise multiple antibodies) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a sample suspected of containing analyte (or a fragment thereof) is first brought into contact with at least one first capture antibody under conditions that allow the formation of a first antibody/analyte complex. If more than one capture antibody is used, a first capture antibody/analyte complex comprising two or more capture antibodies is formed. In a sandwich assay, the antibodies, i.e., preferably, the at least one capture antibody, are used in molar excess amounts of the maximum amount of analyte (or a fragment thereof) expected in the test sample. For example, from about 5 µg to about 1 mg of antibody per mL of buffer (e.g., microparticle coating buffer) can be used.

Competitive inhibition immunoassays, which are often used to measure small analytes because binding by only one antibody is required, comprise sequential and classic formats. In a sequential competitive inhibition immunoassay a capture antibody to an analyte of interest is coated onto a well of a microtiter plate or other solid support. When the sample containing the analyte of interest is added to the well, the analyte of interest binds to the capture antibody. After washing, a known amount of labeled (e.g., biotin or horseradish peroxidase (HRP)) analyte is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay an antibody to an analyte of interest is coated onto a solid support (e.g., a well of a microtiter plate). However, unlike the sequential competitive inhibition immunoassay, the sample and the labeled analyte are added to the well at the same time. Any analyte in the sample competes with labeled analyte for binding to the capture antibody. After washing, the signal generated by the labeled analyte is measured and is inversely proportional to the amount of analyte in the sample.

Optionally, prior to contacting the test sample with the at least one capture antibody (for example, the first capture antibody), the at least one capture antibody can be bound to a solid support, which facilitates the separation of the first antibody/analyte (or a fragment thereof) complex from the test sample. The substrate to which the capture antibody is bound can be any suitable solid support or solid phase that facilitates separation of the capture antibody-analyte complex from the sample.

Examples of solid phases or supports are well known to those of skill in the art and include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen or the antibody to the substrate results; alternatively, a chemical coupling agent or other means can be used to bind covalently the antibody to the substrate, provided that such binding does not interfere with the ability of the antibody to bind to analyte. Alternatively, the antibody can be bound with microparticles, which have been previously coated with streptavidin (e.g., DYNAL® Magnetic Beads, Invitrogen, Carlsbad, Calif.) or biotin (e.g., using Power-Bind™-SA-MP streptavidin-coated microparticles (Seradyn, Indianapolis, Ind.)) or anti-species-specific monoclonal antibodies. If necessary, the substrate can be derivatized to allow reactivity with various functional groups on the antibody. Such derivatization requires the use of certain coupling agents, examples of which include, but are not limited to, maleic anhydride, N-hydroxysuccinimide, and 1-ethyl-3-(3-dimethylaminopropyl) carbodiimide. If desired, one or more capture reagents, such as antibodies (or fragments thereof), each of which is specific for analyte(s) can be attached to solid phases in different physical or addressable locations (e.g., such as in a biochip configuration (see, e.g., U.S. Pat. No. 6,225,047; Intl Patent App. Pub. No. WO 99/51773; U.S. Pat. No. 6,329,209; International Patent App. Pub. No. WO 00/56934, and U.S. Pat. No. 5,242,828). If the capture reagent is attached to a mass spectrometry probe as the solid support, the amount of analyte bound to the probe can be detected by laser desorption ionization mass spectrometry. Alternatively, a single column can be packed with different beads, which are derivatized with the one or more capture reagents, thereby capturing the analyte in a single place (see, antibody-derivatized, bead-based technologies, e.g., the xMAP technology of Luminex (Austin, Tex.)).

After the test sample being assayed for analyte (or a fragment thereof) is brought into contact with the at least one capture antibody (for example, the first capture antibody), the mixture is incubated in order to allow for the formation of a first antibody (or multiple antibody)-analyte (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/analyte complex, the complex is then contacted with at least one detection antibody under conditions which allow for the formation of a (first or multiple) capture antibody/analyte/second detection antibody complex). While captioned for clarity as the "second" antibody (e.g., second detection antibody), in fact, where multiple antibodies are used for capture and/or detection, the at least one detection antibody can be the second, third, fourth, etc. antibodies used in the immunoassay. If the capture antibody/analyte complex is contacted with more than one detection antibody, then a (first or multiple) capture antibody/analyte (or a fragment thereof)/(multiple) detection antibody complex is formed. As with the capture antibody (e.g., the first capture antibody), when the at least one (e.g., second and any subsequent) detection antibody is brought into contact with the capture antibody/analyte (or a fragment thereof) complex, a period of incubation under conditions similar to those described above is required for the formation of the (first or multiple) capture antibody/analyte/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antibody/analyte/(second or multiple) detection antibody complex. Any detectable label known in the art can be used (see discussion above).

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SP SP-Acridinium Ester (i.e., N10-(3-sulfopropyl)-N-(3-sulfopropyl)-acridinium-9-carboxamide).

The (first or multiple) capture antibody/analyte/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support, it can be simultaneously contacted with the analyte-containing sample and the at least one second detection antibody to form a first (multiple) antibody/analyte/second (multiple) antibody complex, followed by removal of the fluid (test sample) from contact with the solid support. If the at least one first capture antibody is not bound to a solid support, then the (first or multiple) capture antibody/analyte/(second or multiple) detection antibody complex does not have to be removed from the test sample for quantification of the amount of the label.

After formation of the labeled capture antibody/analyte/detection antibody complex (e.g., the first capture antibody/analyte/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using appropriate means, such as a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of analyte or a fragment thereof in the test sample is determined by appropriate means, such as by use of a standard curve that has been generated using serial dilutions of analyte or a fragment thereof of known concentration. Other than using serial dilutions of analyte or a fragment thereof, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at about room temperature (i.e., at from about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

In view of the above, a method of determining the presence, amount, or concentration of HCV core (or a fragment thereof) in a test sample is provided. The method comprises assaying the test sample for an HCV core antigen (or a fragment thereof) by an assay (i) employing (i') at least one of an antibody, a fragment of an antibody that can bind to an analyte, a variant of an antibody that can bind to an analyte, a fragment of a variant of an antibody that can bind to an analyte, or a DVD-Ig (or a fragment, a variant, or a fragment of a variant thereof) that can bind to an HCV core antigen, and (ii') at least one detectable label and (ii) comprising comparing a signal generated by the detectable label as a direct or indirect indication of the presence, amount or concentration of the HCV core antigen (or a fragment thereof) in the test sample to a signal generated as a direct or indirect indication of the presence, amount or concentration of HCV core antigen (or a fragment thereof) in a control or calibrator. The calibrator is optionally part of a series of calibrators, in which each of the calibrators differs from the other calibrators by the concentration of analyte.

The method can comprise (i) contacting the test sample with at least one first specific binding partner for HCV core (or a fragment thereof) selected from the group consisting of an antibody of the present invention, a fragment of such an antibody that can bind to an HCV core antigen, a variant of an antibody that can bind to an HCV core antigen, a fragment of a variant of an antibody that can bind to an HCV core antigen, or a DVD-Ig (or a fragment, a variant, or a fragment of a variant thereof) that can bind to an HCV core antigen so as to form a first specific binding partner/HCV core antigen (or fragment thereof) complex, (ii) contacting the first specific binding partner/HCV core antigen (or fragment thereof) complex with at least one second specific binding partner for the HCV core antigen (or fragment thereof) selected from the group consisting of a detectably labeled anti-HCV core antibody, a detectably labeled fragment of an anti-HCV core antibody that can bind to HCV core antigen, a detectably labeled variant of an anti-HCV core antibody that can bind to HCV core antigen, a detectably labeled fragment of a variant of an anti-HCV core antibody that can bind to HCV core antigen, and a detectably labeled DVD-Ig (or a fragment, a variant, or a fragment of a variant thereof) so as to form a first specific binding partner/HCV core antigen (or fragment thereof)/second specific binding partner complex, and (iii) determining the presence, amount or concentration of HCV core antigen in the test sample by detecting or measuring the signal generated by the detectable label in the first specific binding partner/HCV core antigen (or fragment thereof)/second specific binding partner complex formed in (ii).

Alternatively, the method can comprise contacting the test sample with at least one first specific binding partner for HCV core (or a fragment thereof) selected from the group consisting of an antibody, a fragment of an antibody that can bind to an HCV core, a variant of an antibody that can bind to an HCV core, a fragment of a variant of an antibody that can bind to an HCV core, and a DVD-Ig (or a fragment, a variant, or a fragment of a variant thereof) and simultaneously or sequentially, in either order, contacting the test sample with at least one second specific binding partner, which can compete with HCV core (or a fragment thereof) for binding to the at least one first specific binding partner and which is selected from the group consisting of a detectably labeled HCV core, a detectably labeled fragment of HCV core that can bind to the first specific binding partner, a detectably labeled variant of HCV core that can bind to the first specific binding partner, and a detectably labeled fragment of a variant of HCV core that can bind to the first specific binding partner. Any HCV core (or a fragment thereof) present in the test sample and the at least one second specific binding partner compete with each other to form a first specific binding partner/HCV core (or fragment thereof) complex and a first specific binding partner/second specific binding partner complex, respectively. The method further comprises determining the presence, amount or concentration of HCV core in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of HCV core in the test sample.

The above methods can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

With regard to the methods of assay (and kit therefor), it may be possible to employ commercially available anti-HCV core antibodies or methods for production of anti-HCV core as described in the literature. Commercial supplies of various antibodies include, but are not limited to, Santa Cruz Biotechnology Inc. (Santa Cruz, Calif.), GenWay Biotech, Inc. (San Diego, Calif.), and R&D Systems (RDS; Minneapolis, Minn.).

Generally, a predetermined level can be employed as a benchmark against which to assess results obtained upon assaying a test sample for HCV core or a fragment thereof, e.g., for detecting disease or risk of disease. Generally, in making such a comparison, the predetermined level is obtained by running a particular assay a sufficient number of times and under appropriate conditions such that a linkage or association of HCV core presence, amount or concentration with a particular stage or endpoint of a disease, disorder or condition or with particular clinical indicia can be made. Typically, the predetermined level is obtained with assays of reference subjects (or populations of subjects). The HCV core measured can include fragments thereof, degradation products thereof, and/or enzymatic cleavage products thereof.

In particular, with respect to a predetermined level as employed for monitoring HCV disease progression and/or treatment, the amount or concentration of analyte or a fragment thereof may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for HCV core antigen is defined in accordance with standard practice. Because the levels of HCV core in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable disease, for example, and a "normal" (sometimes termed "control") patient or population is/are one(s) that exhibit(s) no detectable disease, respectively, for example. Furthermore, given that HCV core is not routinely found at a high level in the majority of the human population, a "normal subject" can be considered an individual with no substantial detectable increased or elevated amount or concentration of HCV core, and a "normal" (sometimes termed "control") patient or population is/are one(s) that exhibit(s) no substantial detectable increased or elevated amount or concentration of HCV core. An "apparently normal subject" is one in which HCV core has not yet been or currently is being assessed. The level of an HCV core is said to be "elevated" when the HCV core is normally undetectable (e.g., the normal level is zero, or within a range of from about 25 to about 75 percentiles of normal populations), but is detected in a test sample, as well as when the HCV core is present in the test sample at a higher than normal level. Thus, inter alia, the disclosure provides a method of screening for a subject having, or at risk of having, a particular disease, disorder, or condition. The method of assay can also involve the assay of other markers and the like.

Accordingly, the methods described herein also can be used to determine whether or not a subject has or is at risk of developing a HCV disease, disorder or condition. Specifically, such a method can comprise the steps of:

(a) determining the concentration or amount in a test sample from a subject of HCV core (or a fragment thereof) (e.g., using the methods described herein, or methods known in the art); and (b) comparing the concentration or amount of HCV core (or a fragment thereof) determined in step (a) with a predetermined level, wherein, if the concentration or amount of HCV core determined in step (a) is favorable with respect to a predetermined level, then the subject is determined not to have or be at risk for a given disease, disorder or condition. However, if the concentration or amount of HCV core determined in step (a) is unfavorable with respect to the predetermined level, then the subject is determined to have or be at risk for a given disease, disorder or condition.

Additionally, provided herein is method of monitoring the progression of disease in a subject. Optimally the method comprising the steps of:

(a) determining the concentration or amount in a test sample from a subject of HCV core;

(b) determining the concentration or amount in a later test sample from the subject of HCV core; and (c) comparing the concentration or amount of HCV core as determined in step (b) with the concentration or amount of HCV core determined in step (a), wherein if the concentration or amount determined in step (b) is unchanged or is unfavorable when compared to the concentration or amount of HCV core determined in step (a), then the disease in the subject is determined to have continued, progressed or worsened. By comparison, if the concentration or amount of HCV core as determined in step (b) is favorable when compared to the concentration or amount of HCV core as determined in step (a), then the disease in the subject is determined to have discontinued, regressed or improved.

Optionally, the method further comprises comparing the concentration or amount of HCV core as determined in step (b), for example, with a predetermined level. Further, optionally the method comprises treating the subject with one or more pharmaceutical compositions for a period of time if the comparison shows that the concentration or amount of HCV core as determined in step (b), for example, is unfavorably altered with respect to the predetermined level.

In still other embodiments, any of the assays described herein for monitoring presence or levels of HCV core antigen can advantageously be combined with other assays that also determine HCV infection. For example, any of the HCV core determining methods of the invention may further comprise determining the level of another HCV antigen or HCV antibody directed to an antigen other than core protein, including but not limited to determining the presence of HCV Core, E1, E2, NS2, NS3, NS4a, NS4b and NS5.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of HCV core is determined (e.g., using the methods described herein or as known in the art). After the concentration or amount of HCV core is determined, optionally the concentration or amount of HCV core is then compared with a predetermined level. If the concentration or amount of HCV core as determined in the first test sample is lower than the predetermined level, then the subject is not treated with one or more pharmaceutical compositions. However, if the concentration or amount of HCV core as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of HCV core is determined in the second or subsequent test sample is determined (e.g., using the methods described herein or as known in the art). The concentration or amount of HCV core as determined in each of the second and subsequent test samples is then compared with the concentration or amount of HCV core as determined in the first test sample (e.g., the test sample that was originally optionally compared to the predetermined level). If the concentration or amount of HCV core as determined in step (c) is favorable when compared to the concentration or amount of HCV core as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of HCV core as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's HCV core level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained.

When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally, the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from a given disease, disorder or condition will benefit from treatment. In particular, the disclosure relates to HCV core companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, a given disease, disorder or condition is a candidate for therapy. Generally, the subject is one who has experienced some symptom of a given disease, disorder or condition or who has actually been diagnosed as having, or being at risk for, a given disease, disorder or condition, and/or who demonstrates an unfavorable concentration or amount of HCV core or a fragment thereof, as described herein.

The method optionally comprises an assay as described herein, where HCV core is assessed before and following treatment of a subject with one or more pharmaceutical compositions (e.g., particularly with a pharmaceutical related to a mechanism of action involving HCV core), with immunosuppressive therapy, or by immunoabsorption therapy, or where HCV core is assessed following such treatment and the concentration or the amount of HCV core is compared against a predetermined level. An unfavorable concentration of amount of HCV core observed following treatment confirms that the subject will not benefit from receiving further or continued treatment, whereas a favorable concentration or amount of HCV core observed following treatment confirms that the subject will benefit from receiving further or continued treatment. This confirmation assists with management of clinical studies, and provision of improved patient care.

The method of assay also can be used to identify a compound that ameliorates a given disease, disorder or condition. For example, a cell that expresses HCV core can be contacted with a candidate compound. The level of expression of HCV core in the cell contacted with the compound can be compared to that in a control cell using the method of assay described herein.

In yet another detection method, each of the binding proteins as described herein can be employed in the detection of HCV antigens in fixed tissue sections, as well as fixed cells by immunohistochemical analysis.

In addition, these binding proteins can be bound to matrices similar to CNBr-activated Sepharose and used for the affinity purification of specific HCV proteins from cell cultures, or biological tissues such as blood and liver.

The monoclonal antibodies as described herein can also be used for the generation of chimeric antibodies for therapeutic use, or other similar applications. In addition, as discussed herein throughout the antibodies also could be used in the production of DVD-Ig molecules.

The monoclonal antibodies or fragments thereof can be provided individually to detect HCV core antigens. It is contemplated that combinations of the monoclonal antibodies (and fragments thereof) provided herein also may be used together as components in a mixture or "cocktail" of at least one anti-HCV core antibody as described herein with antibodies to other HCV regions, each having different binding specificities. Thus, this cocktail can include the monoclonal antibodies as described herein, which are directed to HCV core protein, and other monoclonal antibodies to other antigenic determinants of the HCV genome. Examples of other monoclonal antibodies useful for these contemplated cocktails include those to HCV C-100, HCV 33C, HCV CORE, HCV NS5 and/or HCV putative ENV, which are disclosed in, for example, U.S. Ser. No. 07/610,175 entitled MONOCLONAL ANTIBODIES TO HEPATITIS C VIRUS AND METHOD FOR USING SAME, U.S. Ser. No. 07/610,175 entitled MONOCLONAL ANTIBODIES TO HCV 33C PROTEINS AND METHODS FOR USING SAME, U.S. Ser. No. 07/648,475 entitled MONOCLONAL ANTIBODIES TO PUTATIVE HCV ENVELOPE REGION AND METHODS FOR USING SAME, U.S. Ser. No. 07/648,473 entitled MONOCLONAL ANTIBODIES TO HCV CORE PROTEINS AND METHODS FOR USING SAME and in co-filed patent application entitled MONOCLONAL ANTIBODIES TO HCV NS5 PROTEIN AND METHODS FOR USING SAME, U.S. Ser. No. 07/748,563, all of which enjoy common ownership and are incorporated herein by reference. This cocktail of monoclonal antibodies as described herein would be used in the assay formats detailed herein in place of the monoclonal antibody to HCV core, and thus would be able to detect the HCV core and other HCV antigens.

The polyclonal antibody or fragment thereof which can be used in the assay formats should specifically bind to HCV core or other HCV proteins used in the assay, such as HCV C-100 protein, HCV 33C protein, HCV ENV, HCV E2/NS1 or HCV NS5 protein. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having different HCV specificity, they would be useful for diagnosis, evaluation and prognosis of HCV infection, as well as for studying HCV protein differentiation and specificity.

As noted elsewhere herein throughout, the test samples which can be tested by the methods as described herein described herein include human and animal body fluids such as whole blood, serum, plasma, cerebrospinal fluid, urine, biological fluids such as cell culture supernatants, fixed tissue specimens and fixed ceil specimens.

The indicator reagent comprises a signal-generating compound (label) that is capable of generating a measurable signal detectable by external means conjugated (attached) to a specific binding member for HCV core. "Specific binding member" as used herein means a member of a specific binding pair. That is, two different molecules where one of the molecules through chemical or physical means specifically binds to the second molecule. In addition to being an antibody member of a specific binding pair for HCV core, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HCV core as in a sandwich assay, to the capture reagent as in a competitive assay, or to the ancillary specific binding member as in an indirect assay.

The various signal generating compounds (labels) contemplated include chromogens, catalysts such as enzymes, luminescent compounds such as fluorescein and rhodamine, chemiluminescent compounds such as acridinium, phenanthridinium and dioxetane compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The use of scanning probe microscopy (SPM) for immunoassays also is a technology to which the monoclonal antibodies as described herein are easily adaptable. In scanning probe microscopy, in particular in atomic force microscopy, the capture phase, for example, at least one of the monoclonal antibodies as described herein, is adhered to a solid phase and a scanning probe microscope is utilized to detect antigen/antibody complexes which may be present on the surface of the solid phase. The use of scanning tunnelling microscopy eliminates the need for labels that normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (the HCV core specific substance, which is the monoclonal antibody as described herein) is attached to a surface suitable for scanning. The attachment of the HCV core specific substance may be by adsorption to a test piece, which comprises a solid phase of a plastic or metal surface, following methods known to those of ordinary skill in the art. Or, covalent attachment of a specific binding partner (HCV core specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis(succinimidyl) suberate, SPPD 9 succinimidyl 3-[2-pyridyldithio]propionate), SMCC (succinimidyl-4-[N-maleimidomethyl]cyclohexane-1-carboxylate), STAB (succinimidyl [4-iodoacetyl]aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent application Ser. Nos. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present disclosure expresses a preference for the use of solid phases, it is contemplated that the monoclonal antibodies as described herein can be utilized in non-solid phase assay systems. These assay systems are known to those skilled in the art, and are considered to be within the scope of the disclosure.

It is contemplated that the reagent employed for the assay can be provided in the form of a kit with one or more containers such as vials or bottles, with each container containing a separate reagent such as a monoclonal antibody, or a cocktail of monoclonal antibodies, detection reagents and washing reagents employed in the assay.

The antibodies can also be used as a means of enhancing the immune response. The antibodies can be administered in amount similar to those used for other therapeutic administrations of antibody. For example, normal immune globulin is administered at 0.02 0.1 ml/lb body weight during the early incubation period of other viral diseases such as rabies, measles, and hepatitis B to interfere with viral entry into cells. Thus, antibodies reactive with the HCV core proteins can be passively administered alone or in conjunction with another anti-viral agent to a host infected with an HCV to enhance the immune response and/or the effectiveness of an antiviral drug.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

Kits

Also contemplated herein are kits for assaying a test sample for the presence, amount or concentration of HCV core protein (or a fragment thereof) in a test sample. Such a kit comprises at least one component for assaying the test sample for HCV core protein (or a fragment thereof) and instructions for assaying the test sample for the HCV core (or a fragment thereof). The at least one component for assaying the test sample for the HCV core (or a fragment thereof) can include a composition comprising an anti-HCV core protein monoclonal antibody or an anti-HCV core protein DVD-Ig (or a fragment, a variant, or a fragment of a variant thereof), which is optionally immobilized or capable of being immobilized on a solid phase.

The kit can comprise at least one component for assaying the test sample for HCV core protein by immunoassay, e.g., chemiluminescent microparticle immunoassay, and instructions for assaying the test sample for an HCV core by immunoassay, e.g., chemiluminescent microparticle immunoassay. For example, the kit can comprise at least one specific binding partner for an HCV core, such as an anti-HCV core, monoclonal/polyclonal antibody (or a fragment thereof that can bind to the HCV core, a variant thereof that can bind to the HCV core, or a fragment of a variant that can bind to the HCV core) or an anti-HCV core DVD-Ig (or a fragment, a variant, or a fragment of a variant thereof), either of which can be detectably labeled. Alternatively or additionally, the kit can comprise detectably labeled HCV core (or a fragment thereof that can bind to an anti-HCV core, monoclonal/polyclonal antibody or an anti-HCV core DVD-Ig (or a fragment, a variant, or a fragment of a variant thereof)), which can compete with any HCV core in a test sample for binding to an anti-HCV core, monoclonal/polyclonal antibody (or a fragment thereof that can bind to the HCV core, a variant thereof that can bind to the HCV core, or a fragment of a variant that can bind to the HCV core) or an anti-HCV core DVD-Ig (or a fragment, a variant, or a fragment of a variant thereof), either of which can be immobilized on a solid support. The kit can comprise a calibrator or control, e.g., isolated or purified HCV core. The kit can comprise at least one container (e.g., tube, microtiter plates or strips, which can be already coated with a first specific binding partner, for example) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions can be in paper form or computer-readable form, such as a disk, CD, DVD, or the like.

Any antibodies, such as an anti-HCV core antibody or an anti-HCV core DVD-Ig, or tracer can incorporate a detectable label as described herein, such as a fluorophore, a radioactive moiety, an enzyme, a biotin/avidin label, a chromophore, a chemiluminescent label, or the like, or the kit can include reagents for carrying out detectable labeling. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, a solution, and/or at least one basic solution. If desired, the kit can contain a solid phase, such as a magnetic particle, bead, test tube, microtiter plate, cuvette, membrane, scaffolding molecule, film, filter paper, disc or chip.

The kit (or components thereof), as well as the method of determining the presence, amount or concentration of an HCV core in a test sample by an assay, such as an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., an anti-HCV core, monoclonal/polyclonal antibody (or a fragment thereof, a variant thereof, or a fragment of a variant thereof) or an anti-HCV core DVD-Ig (or a fragment thereof, a variant thereof, or a fragment of a variant thereof) is attached; either way, sandwich formation and HCV core reactivity can be impacted), and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format, such as an ELISA, may incubate a detection antibody, such as the conjugate reagent, for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Patent App. Pub. No. 2003/0170881, U.S. Patent App. Pub. No. 2004/0018577, U.S. Patent App. Pub. No. 2005/0054078, and U.S. Patent App. Pub. No. 2006/0160164, which are incorporated in their entireties by reference for their teachings regarding same.

In particular, with regard to the adaptation of an HCV core assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized anti-HCV core, monoclonal/polyclonal antibody (or a fragment thereof, a variant thereof, or a fragment of a variant thereof) or anti-HCV core DVD-Ig (or a fragment thereof, a variant thereof, or a fragment of a variant thereof), are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising a specific binding partner for an HCV core, such as an anti-HCV core, monoclonal/polyclonal antibody (or a fragment thereof, a variant thereof, or a fragment of a variant thereof that can bind the HCV core) or an anti-HCV core DVD-Ig (or a fragment thereof, a variant thereof, or a fragment of a variant thereof that can bind the HCV core), either of which can be detectably labeled. Within the fluid pouch of the cartridge is an aqueous reagent that includes p-aminophenol phosphate.

In operation, a sample suspected of containing an HCV core is added to the holding chamber of the test cartridge, and the cartridge is inserted into the I-STAT® reader. After the specific binding partner for an HCV core has dissolved into the sample, a pump element within the cartridge forces the sample into a conduit containing the chip. Here it is oscillated to promote formation of the sandwich. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of HCV core in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, microparticle diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-Stat cartridge format, using a nucleic acid sequence linked to the signal antibody as a signal amplifier.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Animal Immunizations

Female CAF1/J and RBF/DnJ mice (both from The Jackson Laboratory, Bar Harbor, Me.) were immunized on weeks 0, 4 and 10 with 50 µg of an HCV core peptide corresponding to amino acids (all numbering per HCV-1) 134-171 covalently linked to BSA (ALRZ-8 immunogen).

HCV core peptide-BSA was prepared by AnaSpec, Inc. (Fremont, Calif.). The immunogen peptide was emulsified in Complete or Incomplete Adjulite Freund's Adjuvant (Pacific Immunology, Ramona, Calif.). Complete Freund's adjuvant was used for the primary immunization and Incomplete Freund's adjuvant for the second and third immunizations. Each inoculum was prepared by first diluting the HCV peptide-BSA to the appropriate concentration in sterile saline (0.9% sodium chloride), adding an equal volume of adjuvant and then mixing by passing back and forth between two syringes via a 3-way stopcock until a thick, stable emulsion was formed. Sera samples were taken 10-14 days following the 3rd immunization. On the $4^{th}$ and $3^{rd}$ days prior to B cell harvest, RBF/DnJ mice #306 and 315 were administered 50 µg peptide-BSA diluted in sterile saline. This inoculum was delivered into the body cavity near the spleen.

```
ALRZ-8 immunogen
Ac-MGYIPLVGAPLGGAARALAHGVRVLEDGVNYATGNLPGC-BSA
```

Example 2

Screening of Mouse Sera for Antigen Immunoreactivity

Mouse sera samples collected 7-10 days after their final immunization were first tested in a 96-well micro titer enzyme immunoassay (EIA) for reactivity to each of three synthetic (Anaspec, Inc.) carboxy-terminal biotinylated HCV core peptides. The peptides used for screening were derived from the immunogen sequence described in Example 1 and had the following designations and sequences: Peptide 1 (all numbering per HCV-1), amino acids 134-151: MGYIPLVGAPLGGAARALAHG (SEQ ID NO: 573); Peptide 2, amino acids 141-161: GAPLGGAARALAHGVRVLEDG (SEQ ID NO: 574), Peptide 3, amino acids 151-171, LAHGVRVLEDGVNYATGNLPG (SEQ ID NO: 575). Assay plates (NUNC Corporation, Naperville, Ill.) were coated with 100 µL/well of sheep anti-mouse IgG Fc specific antibody (Jackson ImmunoResearch, West Grove, Pa.) diluted to 2 µg/mL in phosphate-buffered saline (PBS). Plates were incubated at 37 deg C for about 2 hours and then at about 21 deg C for about 2 hours. The capture antibody was then removed and 200 µL/well of blocking solution (3% w/v [weight/volume] bovine serum albumin (BSA) and 0.5% v/v [volume/volume] polysorbate-20 diluted in PBS added. The plates were incubated for about 30 minutes and then washed with distilled water. Next, serial dilutions (in block solution) of the mouse sera or a positive control were added to the assay plates (100 µL/well), incubated for between 2 and 20 hours and then washed with dH₂O. Next, 100 µL/well of normal serum solution (NSS; block solution containing 2% v/v normal mouse serum) was added for additional blocking. This solution helps to prevent non-specific binding in the assay well. The plates were incubated for about 30 minutes and then washed with dH₂O. Subsequently, 100 µL/well of a 224 nM solution of each peptide was added to the assay wells for a brief incubation, after which the plates were washed with dH₂O (sera samples were tested for reactivity to individual peptides, rather than a mixture of all three). Next, 100 µL/well horse radish peroxidase labeled streptavidin (Jackson ImmunoResearch) diluted to 200 ng/mL in blocking solution was added, allowed to incubate for about 30 minutes and then the plates washed; o-phenylenediamine substrate (OPD) was used as the chromagen to generate signal, and the reaction was quenched using 1 N sulfuric acid. Signal was read at a wavelength of 492 nm.

Example 3

Screening of Mouse Sera for Relative Affinity

Relative affinity testing was completed for each sera sample—peptide combination for which a strong signal was seen in the previous assay. To determine the relative affinity of each serum sample for the individual core peptides, samples were tested for reactivity to limiting concentrations of each biotin labeled peptide. The assay format was identical to that described above, except that instead of preparing serial dilutions of mouse sera test samples, each sample was prepared at a single dilution, in blocking solution. Additionally, the individual peptides were tested at varying concentrations, beginning with a 500 nM solution in blocking solution followed by ten log 2 dilutions, also in blocking solution. Binding curves were generate and used to determine relative affinity for each sera sample. Based on these results, RBF/DnJ mice #306 and 315 were chosen for B cell fusion.

Example 4

Mouse Splenocyte Fusion

On the day of fusion, the mice were euthanized and their splenocytes were harvested and placed into Iscoves Modified Dulbeccos Medium (IMDM) supplemented with Pen Strep (Invitrogen Corporation). A cell fusion was performed as described by Kohler and Milstein (Nature 1975; 256:495-7). Each mouse spleen was placed into a petri dish containing IMDM. The splenocytes were perfused out of each spleen using a syringe containing IMDM and a cell scraper. All splenocytes from mouse #306 and 315 were isolated and pooled in a 50 ml centrifuge tube, then counted using a hemocytometer with trypan blue dye exclusion to determine viability. Approximately $8.0 \times 10^8$ total cells at 89% viability were recovered from these spleens. Approximately $7.6 \times 10^6$ cells/ml were estimated to be B-cells based on their physical appearance under the microscope. Approximately 5 mL of this cell suspension was used for a first fusion experiment (fusion 208A), and the remaining cells were processed using magnetic activated cell sorting (MACS) and a Pan B-cell isolation kit (Miltenyi Biotech) to enrich the cell population for B-cells and deplete other cell types. Approximately $6.7 \times 10^8$ total cells were incubated with the Pan B-cell biotin labeled antibody cocktail followed by the anti-biotin microbeads per manufacturer's instructions. The cell suspension/microbead mixture was washed by centrifugation and passed over a Miltenyi Biotech LS column contained within a magnetic field. B-cells flow freely through the column and other cell types are retained in the column. The columns were washed 3 times with PBS containing 2% FBS to wash out all B-cells. The B-cell suspension was centrifuged and the pellet was resuspended in IMDM, and then counted using a hemocytometer. Approximately $1.4 \times 10^8$ B-cells were recovered from the enrichment procedure. Approximately $7.0 \times 10^7$ B-cells from that suspension were used for a second fusion experiment (fusion 208B) and the remaining B-cells were cryopreserved for later usage.

The unenriched splenocytes from the spleens (~$3.8 \times 10^7$ B-cells for fusion 208A) and the enriched B-cell pool (~$7.0 \times 10^7$ B-cells for fusion 208B) were washed by centrifugation in separate tubes and the cell pellets were re-suspended in IMDM. These splenocytes were mixed with an equal number of NS/0 myeloma cells and centrifuged into a pellet. The fusion was accomplished by exposing the splenocytes and NS/0 cells to 50% Polyethylene glycol (PEG) (American Type Culture Collection—Molecular Weight 1300-1600) in HSFM. One mL of the PEG solution was added to each cell pellet over 30 seconds, followed by one additional minute of incubation. The PEG and cell pellet was diluted by slowly adding 30 mL of IMDM over 30 seconds. The fused cells were then removed from suspension by centrifugation and decanting the supernatant. The cell pellet from each fusion (208A and 208B) was re-suspended into ~250 mL of IMDM supplemented with ~10% FBS (Hyclone Laboratories), HAT (Hypoxanthine, Aminopterin, Thymidine) (Sigma Laboratories), HT Supplement (Invitrogen Corporation), BM Condimed H1 (Roche Applied Science), Cholesterol and L-Glutamine (Invitrogen Corporation) in order to select for hybridomas. The fused cells were seeded into T162 culture flasks containing the HAT medium and cultured in bulk for approximately 48 hours at 37° C. with 5% $CO_2$. Following 48 hours of HAT selection, the bulk culture was centrifuged and the pellet was re-suspended into semi-solid tissue culture medium. The semi-solid tissue culture medium consisted of a 50% mixture of 2×IMDM (Invitrogen) with Clone Matrix (Molecular Devices) supplemented with 10% FBS, HT Supplement, Penn/Strep, L-Glutamine, and anti-mouse IgG-FITC Clone Detect (Molecular Devices). The semi-solid culture plates were allowed to incubate for 7-10 days before colony selection on the ClonepixFL (Molecular Devices). A colony grown in the semi-solid medium was considered a clone because the single cell initiating it had not been allowed to move and mix with other cells during growth, but all cell lines of interest will be subcloned at a later date to ensure clonality. An immunoprecipitation reaction occurs between the antibody being produced by the colony and the goat anti-mouse IgG Fc-FITC that fluoresces. The brighter the fluorescence signal observed, the more antibody being produced. Colonies were analyzed for fluorescence on the ClonepixFL and the ones with the brightest fluorescent signal were selected for automated transfer to 96 well tissue culture plates containing IMDM supplemented with 10% FBS, HT supplement, cholesterol, L-Glutamine, and Pen Strep. The 96 well tissue culture plates were allowed to grow for 3 to 7 days at 37° C. prior to supernatant screening for antibody production.

Example 5

Hybridoma Screening and Selection Using Peptides

Cell supernatant samples were analyzed for anti-HCV antibodies by EIA. Sheep anti-mouse IgG Fc (Jackson Immunoresearch) was coated on 96 well micro-titer EIA plates at 1 μg/mL. After the capture reagent had been coated on the solid phase, remaining solution was removed and the plates were blocked using 3% BSA in PBS. The wells were washed with distilled water and cell supernatants were added to the blocked plates and allowed to incubate at room temperature for at least one hour. The anti-mouse IgG Fc captures the anti-HCV mouse antibody from the supernatant. Following the incubation, the plates were washed using distilled water. A 3% normal mouse serum in BSA block solution was added to all wells and incubated at room temperature for 30 minutes to block any unbound sheep anti-mouse IgG Fc capture sites coated on the plate. The wells were washed with distilled water and a mixture of the biotinylated HCV peptides described in Example 2 (i.e. corresponding to amino acids 134-154, 141-161, and 151-171 of HCV-1), each at 100 ng/mL, was added and incubated for 30 minutes at room temperature. Following this incubation, the biotinylated antigens were washed from the plates using distilled water and streptavidin-HRPO (Jackson Immunoresearch) diluted to approximately 200 ng/mL was added to the plates and allowed to incubate for 30 minutes. The plates were washed with distilled water and o-phenylenediamine substrate was used as the chromogen to generate signal. Plates were read at 492 nm and the results were analyzed. Wells were considered positive if they had an EIA signal at least 3 times greater than background. Positive wells were expanded to 24 well plates in IMDM supplemented with 10% FBS, HT supplement, cholesterol, and L-Glutamine.

Following 5-14 days of growth, the 24 well cultures were evaluated by EIA in the same manner as previously described, except the supernatant samples were titrated against each of the biotinylated HCV core peptides individually and BSA to identify clones that might bind nonspecifically to the peptides or the blocking protein. The 24 well cultures generating signal at least 5 times greater than the average BSA background value of 0.08 OD units with at least one of the screening peptides were considered positive and selected for further evaluation. Values are listed in Table 1.

TABLE 1

| Clone # | Reactivity to HCV bt-134-154 | Reactivity to HCV bt-141-161 | Reactivity to HCV bt-151-171 | BSA (Pep) |
|---|---|---|---|---|
| HCV 208A-1006 | 0.15 | 3.56 | 0.07 | 0.08 |
| HCV 208A-1007 | 0.07 | 3.53 | 0.08 | 0.07 |
| HCV 208A-1015 | 0.07 | 0.42 | 0.11 | 0.08 |
| HCV 208A-1022 | 0.08 | 1.63 | 0.08 | 0.09 |
| HCV 208A-1032 | 0.12 | 3.73 | 0.09 | 0.08 |
| HCV 208A-1064 | 0.10 | 3.50 | 0.12 | 0.07 |
| HCV 208A-1081 | 0.06 | 3.52 | 0.06 | 0.05 |
| HCV 208A-110 | 0.07 | 2.88 | 0.11 | 0.06 |
| HCV 208A-122 | 0.06 | 2.65 | 0.09 | 0.06 |
| HCV 208A-126 | 0.20 | 2.08 | 0.10 | 0.10 |
| HCV 208A-133 | 0.10 | 3.68 | 0.13 | 0.06 |
| HCV 208A-134 | 2.06 | 0.08 | 0.06 | 0.07 |
| HCV 208A-147 | 0.67 | 0.07 | 0.06 | 0.20 |
| HCV 208A-152 | 0.08 | 3.55 | 0.09 | 0.07 |
| HCV 208A-158 | 0.10 | 2.70 | 0.09 | 0.07 |
| HCV 208A-159 | 0.15 | 3.77 | 0.19 | 0.08 |
| HCV 208A-160 | 0.11 | 3.28 | 0.09 | 0.09 |
| HCV 208A-194 | 0.07 | 0.20 | 0.06 | 0.07 |
| HCV 208A-207 | 1.24 | 0.17 | 0.08 | 0.07 |
| HCV 208A-208 | 0.09 | 3.22 | 0.29 | 0.10 |
| HCV 208A-210 | 0.06 | 1.15 | 0.05 | 0.06 |
| HCV 208A-222 | 0.06 | 2.70 | 0.08 | 0.07 |
| HCV 208A-227 | 0.08 | 0.24 | 0.43 | 0.07 |
| HCV 208A-230 | 0.08 | 0.42 | 0.07 | 0.07 |
| HCV 208A-264 | 0.05 | 0.07 | 0.37 | 0.09 |
| HCV 208A-286 | 0.11 | 2.62 | 0.11 | 0.06 |
| HCV 208A-293 | 0.08 | 2.42 | 0.11 | 0.07 |
| HCV 208A-312 | 0.22 | 3.70 | 0.06 | 0.06 |
| HCV 208A-334 | 0.05 | 3.07 | 0.05 | 0.05 |
| HCV 208A-352 | 1.08 | 0.07 | 0.06 | 0.07 |
| HCV 208A-367 | 0.08 | 1.79 | 0.10 | 0.08 |
| HCV 208A-381 | 0.07 | 3.69 | 0.12 | 0.08 |
| HCV 208A-382 | 0.10 | 0.07 | 0.43 | 0.08 |
| HCV 208A-393 | 0.06 | 1.04 | 0.06 | 0.05 |
| HCV 208A-422 | 0.05 | 0.84 | 0.10 | 0.07 |
| HCV 208A-427 | 0.20 | 3.82 | 0.11 | 0.11 |
| HCV 208A-442 | 0.08 | 3.04 | 0.06 | 0.06 |
| HCV 208A-460 | 0.09 | 2.69 | 0.10 | 0.07 |
| HCV 208A-470 | 0.08 | 0.10 | 0.08 | 0.08 |
| HCV 208A-489 | 0.06 | 3.11 | 0.07 | 0.06 |
| HCV 208A-493 | 0.09 | 3.60 | 0.07 | 0.07 |
| HCV 208A-557 | 0.05 | 2.41 | 0.06 | 0.05 |
| HCV 208A-558 | 0.12 | 0.95 | 0.14 | 0.10 |
| HCV 208A-562 | 0.21 | 3.71 | 0.12 | 0.09 |
| HCV 208A-575 | 0.07 | 1.55 | 0.13 | 0.12 |
| HCV 208A-576 | 0.08 | 3.05 | 0.09 | 0.06 |
| HCV 208A-584 | 0.89 | 0.10 | 0.06 | 0.08 |
| HCV 208A-603 | 0.07 | 1.35 | 0.09 | 0.07 |
| HCV 208A-604 | 0.05 | 2.27 | 0.06 | 0.05 |
| HCV 208A-605 | 0.22 | 3.71 | 0.16 | 0.11 |
| HCV 208A-638 | 0.07 | 2.96 | 0.09 | 0.06 |
| HCV 208A-641 | 0.10 | 0.93 | 0.11 | 0.09 |
| HCV 208A-658 | 0.06 | 1.10 | 0.08 | 0.20 |
| HCV 208A-692 | 3.67 | 0.38 | 0.07 | 0.06 |
| HCV 208A-695 | 0.08 | 3.82 | 0.11 | 0.07 |
| HCV 208A-719 | 0.07 | 3.60 | 0.09 | 0.06 |
| HCV 208A-736 | 3.24 | 0.12 | 0.06 | 0.07 |
| HCV 208A-741 | 1.20 | 3.37 | 0.06 | 0.07 |
| HCV 208A-744 | 0.12 | 3.88 | 0.10 | 0.08 |
| HCV 208A-759 | 0.16 | 3.95 | 0.14 | 0.08 |
| HCV 208A-768 | 0.11 | 3.28 | 0.09 | 0.09 |
| HCV 208A-774 | 0.14 | 3.53 | 0.12 | 0.07 |
| HCV 208A-793 | 0.07 | 2.96 | 0.10 | 0.07 |
| HCV 208A-807 | 0.79 | 0.07 | 0.06 | 0.06 |
| HCV 208A-826 | 3.28 | 0.11 | 0.11 | 0.10 |
| HCV 208A-828 | 0.07 | 3.35 | 0.10 | 0.07 |
| HCV 208A-830 | 0.07 | 2.88 | 0.08 | 0.06 |
| HCV 208A-850 | 0.07 | 3.49 | 0.10 | 0.06 |
| HCV 208A-863 | 0.07 | 4.00 | 0.08 | 0.06 |
| HCV 208A-874 | 0.05 | 0.73 | 0.06 | 0.05 |
| HCV 208A-877 | 0.06 | 1.21 | 0.05 | 0.06 |
| HCV 208A-879 | 0.09 | 0.17 | 0.79 | 0.19 |
| HCV 208A-920 | 0.17 | 4.00 | 0.08 | 0.08 |
| HCV 208A-926 | 0.06 | 3.32 | 0.07 | 0.09 |
| HCV 208A-938 | 0.09 | 3.49 | 0.09 | 0.10 |
| HCV 208A-939 | 3.33 | 0.17 | 0.05 | 0.05 |
| HCV 208A-967 | 0.52 | 0.73 | 0.18 | 0.07 |
| HCV 208A-982 | 0.08 | 3.40 | 0.06 | 0.07 |
| HCV 208A-983 | 3.03 | 0.40 | 0.05 | 0.05 |
| HCV 208B-1024 | 0.08 | 0.75 | 0.15 | 0.10 |
| HCV 208B-1029 | 0.07 | 0.51 | 0.10 | 0.06 |
| HCV 208B-1043 | 0.16 | 0.12 | 3.88 | 0.07 |
| HCV 208B-1070 | 0.07 | 3.50 | 0.05 | 0.05 |
| HCV 208B-1072 | 0.09 | 2.28 | 0.09 | 0.12 |
| HCV 208B-109 | 0.08 | 3.46 | 0.11 | 0.07 |
| HCV 208B-1094 | 0.12 | 3.28 | 0.13 | 0.10 |
| HCV 208B-1096 | 0.34 | 0.13 | 3.56 | 0.08 |
| HCV 208B-131 | 0.13 | 0.18 | 3.89 | 0.10 |
| HCV 208B-141 | 1.66 | 0.09 | 0.06 | 0.06 |
| HCV 208B-174 | 0.08 | 1.26 | 0.07 | 0.08 |
| HCV 208B-178 | 0.10 | 0.07 | 1.69 | 0.07 |
| HCV 208B-181 | 0.12 | 2.44 | 0.07 | 0.06 |
| HCV 208B-183 | 0.31 | 0.14 | 0.09 | 0.11 |
| HCV 208B-189 | 0.55 | 0.15 | 3.95 | 0.09 |
| HCV 208B-207 | 0.19 | 0.09 | 0.50 | 0.07 |
| HCV 208B-214 | 0.16 | 0.07 | 0.60 | 0.06 |
| HCV 208B-230 | 0.41 | 0.12 | 0.08 | 0.08 |
| HCV 208B-251 | 0.11 | 2.35 | 0.41 | 0.10 |
| HCV 208B-281 | 1.48 | 0.16 | 0.12 | 0.07 |
| HCV 208B-309 | 0.11 | 2.34 | 0.09 | 0.09 |
| HCV 208B-319 | 0.17 | 3.43 | 0.13 | 0.13 |
| HCV 208B-327 | 0.07 | 0.05 | 0.49 | 0.05 |
| HCV 208B-348 | 0.07 | 0.20 | 0.07 | 0.07 |
| HCV 208B-353 | 0.07 | 2.47 | 0.07 | 0.07 |
| HCV 208B-395 | 0.54 | 0.13 | 3.69 | 0.11 |
| HCV 208B-408 | 0.81 | 0.20 | 0.16 | 0.06 |
| HCV 208B-409 | 0.09 | 3.21 | 0.14 | 0.07 |
| HCV 208B-446 | 0.06 | 2.50 | 0.08 | 0.06 |
| HCV 208B-457 | 0.75 | 0.66 | 0.24 | 0.17 |
| HCV 208B-471 | 1.62 | 0.11 | 0.08 | 0.10 |
| HCV 208B-488 | 0.08 | 0.07 | 0.30 | 0.08 |
| HCV 208B-515 | 0.51 | 0.13 | 0.06 | 0.06 |
| HCV 208B-517 | 0.10 | 0.41 | 0.70 | 0.11 |
| HCV 208B-547 | 0.12 | 0.08 | 2.90 | 0.08 |
| HCV 208B-556 | 0.13 | 3.07 | 0.18 | 0.08 |
| HCV 208B-560 | 0.11 | 3.90 | 0.14 | 0.07 |
| HCV 208B-589 | 0.27 | 0.10 | 2.85 | 0.12 |
| HCV 208B-591 | 0.08 | 3.10 | 0.07 | 0.07 |
| HCV 208B-602 | 0.20 | 1.87 | 0.20 | 0.07 |

TABLE 1-continued

| Clone # | Reactivity to HCV bt-134-154 | Reactivity to HCV bt-141-161 | Reactivity to HCV bt-151-171 | BSA (Pep) |
|---|---|---|---|---|
| HCV 208B-608 | 0.19 | 0.37 | 0.13 | 0.07 |
| HCV 208B-612 | 3.05 | 3.04 | 0.15 | 0.08 |
| HCV 208B-616 | 0.10 | 0.71 | 0.11 | 0.09 |
| HCV 208B-617 | 0.45 | 0.51 | 0.13 | 0.10 |
| HCV 208B-646 | 0.15 | 3.94 | 0.18 | 0.10 |
| HCV 208B-652 | 0.21 | 0.55 | 0.10 | 0.09 |
| HCV 208B-672 | 0.08 | 2.79 | 0.10 | 0.08 |
| HCV 208B-739 | 1.13 | 0.11 | 0.07 | 0.08 |
| HCV 208B-742 | 0.08 | 0.44 | 0.07 | 0.09 |
| HCV 208B-750 | 0.10 | 3.41 | 0.12 | 0.09 |
| HCV 208B-762 | 0.07 | 0.65 | 0.05 | 0.05 |
| HCV 208B-765 | 0.10 | 0.64 | 0.16 | 0.08 |
| HCV 208B-778 | 0.11 | 0.06 | 0.23 | 0.06 |
| HCV 208B-780 | 0.07 | 1.02 | 0.17 | 0.10 |
| HCV 208B-788 | 0.09 | 0.49 | 0.10 | 0.16 |
| HCV 208B-793 | 0.09 | 0.72 | 0.09 | 0.13 |
| HCV 208B-796 | 0.07 | 3.03 | 0.07 | 0.09 |
| HCV 208B-822 | 0.08 | 1.35 | 0.07 | 0.05 |
| HCV 208B-826 | 0.53 | 1.35 | 0.08 | 0.07 |
| HCV 208B-853 | 0.09 | 0.74 | 0.12 | 0.13 |
| HCV 208B-860 | 0.12 | 0.73 | 0.12 | 0.07 |
| HCV 208B-862 | 0.21 | 3.28 | 0.10 | 0.09 |
| HCV 208B-894 | 0.07 | 0.09 | 0.48 | 0.07 |
| HCV 208B-909 | 0.09 | 3.11 | 0.11 | 0.07 |
| HCV 208B-911 | 0.09 | 0.09 | 0.71 | 0.10 |
| HCV 208B-922 | 0.93 | 0.11 | 0.11 | 0.09 |
| HCV 208B-952 | 0.07 | 0.64 | 0.07 | 0.09 |
| HCV 208B-954 | 0.06 | 3.43 | 0.06 | 0.06 |
| HCV 208B-956 | 0.10 | 0.85 | 0.05 | 0.05 |
| HCV 208B-960 | 0.09 | 3.38 | 0.11 | 0.08 |
| HCV 208B-982 | 0.20 | 1.10 | 0.13 | 0.09 |

Example 6

Cloning and Expression of Recombinant HCV Core1-169

The nucleotide sequence encoding amino acids 1-169 of HCV-1 was codon optimized for *E. coli* expression and cloned into a modified pET32a vector wherein the sequence encoding a thioredoxin fusion protein was eliminated and replaced with Methionine (M). In addition, a carboxy-terminal hexahistidine tag (SEQ ID NO: 580) was included immediately after codon 169 of HCV core to facilitate purification via immobilized metal affinity chromatography (IMAC). *E. coli* BL21(DE3) cells were transformed with purified plasmid DNA and a clone harboring the plasmid pET-HCVCore1-169 identified. The protein expressed therefrom was designated as HCV Core1-169.

Protein expression was achieved by culturing the pET-HCVCore1-169-transformed *E. coli* BL21(DE3) cells in terrific broth (TB) medium. Cells were grown in a fermentor to an OD600 nm of 10 and then induced with 1 mM IPTG and grown at 37° C. for approximately three hours until an OD600 nm of approximately 20 was obtained. Cells were harvested by centrifugation and lysed by sonication in 25 mM Tris-HCl buffer (pH 7.4) containing 150 mM NaCl, 1 mM DTT, 5 mM MgCl$_2$, lysozyme and benzonase. The lysate was clarified by centrifugation and the insoluble fraction was dissolved in 25 mM Tris-HCl buffer (pH 7.4) containing 150 mM NaCl, 6 M urea, 1.0% n-dodecyl-β-D-maltoside, 1 mM DTT, and 5 mM MgCl$_2$. The dissolved lysate was again clarified by centrifugation and the soluble fraction was loaded onto a HisTrap Fast Flow column (GE Healthcare). The column was then washed with 25 column volumes of 25 mM Tris-HCl buffer (pH 7.4) containing 150 mM NaCl, 1 mM DTT, 5 mM MgCl$_2$, 6 M urea, 0.1% n-dodecyl-β-D-maltoside, and 10 mM imidazole. Elution was done using the same buffer and a linear gradient of imidazole (0-500 mM). Eluted fractions containing the desired protein of interest (determined by SDS-PAGE) were pooled and dialyzed against 25 mM Tris-HCl buffer (pH 7.4) containing 150 mM NaCl, 1 mM DTT, 5 mM MgCl$_2$, with and without 6 M urea and 0.1% n-dodecyl-β-D-maltoside.

```
HCV Core1-169 Nucleotide Sequence
atgtctaccaacccgaaaccgcagaaaaaaaacaaacgtaacaccaaccg
tcgtccgcaggacgttaaatttcccgggtggtggtcagatcgttggtggtg
tttacctgctgccgcgtcgtggtccgcgtctgggtgttcgtgctacgcgt
aaaacctctgaacgttctcagccgcgtgggcgtcgtcagccgatcccgaa
agctcgtcgtccggaaggtcgtacctgggctcagccgggttacccgtggc
cgctgtacggtaacgaaggttgcggttgggctggttggctgctgtctccg
cgtggatctcgtccgtcttggggtccgaccgaccgcgtcgtcgttctcg
taaccttggtaaagttatcgataccctgacctgcggtttcgctgacctga
tggttacataccgctggttggagctccgctgggtggtgctgctcgtgct
ctggcgcatggcgtgcgtgttctggaagatggcgtcaactatgccaccgg
taatctg HCV Core1-169 Amino Acid Sequence
mstnpkpqkknkrntnrrpqdvkfpgggqivggvyllprrgprlgvratr
ktsersqprgrrqpipkarrpegrtwaqpgypwplygnegcgwagwllsp
rgsrpswgptdprrrsrnlgkvidtltcgfadlmgyiplvgaplggaara
lahgvrvledgvnyatgnl
```

Example 7

Hybridoma Screening Using Core Antigen

The 24 well cultures were then evaluated by EIA for their ability bind HCV core1-169 (as described in Example 6) coated directly onto microtiter plates (solid phase assay). HCV core1-169 was coated onto 96 well micro-titer EIA plates at 1 μg/mL. After the capture reagent had been coated on the solid phase, the solution was removed and the plates were blocked using 3% BSA in PBS. The wells were washed with distilled water and 5 fold serial dilutions of the cell culture supernatants were added and allowed to incubate at room temperature for at least one hour. The plates were washed with distilled water and a HRP labeled goat anti-mouse IgG FC antibody diluted at approximately 200 ng/ml in BSA block solution was added to the plates and allowed to incubate for 30 minutes at room temperature. The plates were washed with distilled water and o-phenylenediamine substrate was used as the chromogen to generate signal. Plates were read at 492 nm and the results were analyzed.

Antibodies with BSA background reactivity greater than or equal to the core 1-169 reactivity value were considered negative and not used in calculating the average BSA background value. For the remainder of antibodies to be considered positive for core 1-169, they had to have an EIA signal of, at least, 0.50 OD units, or at least 5 times greater than the average BSA background signal of 0.10 OD units. Values are listed in Table 2.

TABLE 2

| Clone # | Solid Phase HCV Core OD (A492) | BSA OD (A492) |
|---|---|---|
| HCV 208A-1006 | 0.75 | 0.09 |
| HCV 208A-1007 | 0.39 | 0.06 |
| HCV 208A-1015 | 0.16 | 0.08 |
| HCV 208A-1022 | 0.09 | 0.07 |
| HCV 208A-1032 | 1.27 | 0.08 |
| HCV 208A-1064 | 0.94 | 0.08 |
| HCV 208A-1081 | 1.25 | 0.06 |
| HCV 208A-110 | 1.60 | 0.08 |

TABLE 2-continued

| Clone # | Solid Phase HCV Core OD (A492) | BSA OD (A492) |
|---|---|---|
| HCV 208A-122 | 1.36 | 0.06 |
| HCV 208A-126 | 0.69 | 0.24 |
| HCV 208A-133 | 1.73 | 0.07 |
| HCV 208A-134 | 0.10 | 0.07 |
| HCV 208A-147 | 0.08 | 0.10 |
| HCV 208A-152 | 1.31 | 0.07 |
| HCV 208A-158 | 1.16 | 0.06 |
| HCV 208A-159 | 0.57 | 0.35 |
| HCV 208A-160 | 1.65 | 0.08 |
| HCV 208A-194 | 0.08 | 0.07 |
| HCV 208A-207 | 0.11 | 0.06 |
| HCV 208A-208 | 0.77 | 0.28 |
| HCV 208A-210 | 0.87 | 0.06 |
| HCV 208A-222 | 1.06 | 0.07 |
| HCV 208A-227 | 0.06 | 0.08 |
| HCV 208A-230 | 0.08 | 0.06 |
| HCV 208A-264 | 0.09 | 0.07 |
| HCV 208A-286 | 1.20 | 0.08 |
| HCV 208A-293 | 1.41 | 0.07 |
| HCV 208A-312 | 1.39 | 0.07 |
| HCV 208A-334 | 1.28 | 0.09 |
| HCV 208A-352 | 0.10 | 0.08 |
| HCV 208A-367 | 0.88 | 0.07 |
| HCV 208A-381 | 1.43 | 0.13 |
| HCV 208A-382 | 0.08 | 0.07 |
| HCV 208A-393 | 0.24 | 0.07 |
| HCV 208A-422 | 1.68 | 1.10 |
| HCV 208A-427 | 0.62 | 0.11 |
| HCV 208A-442 | 1.61 | 0.06 |
| HCV 208A-460 | 1.68 | 0.07 |
| HCV 208A-470 | 0.08 | 0.07 |
| HCV 208A-489 | 1.37 | 0.07 |
| HCV 208A-493 | 1.58 | 0.06 |
| HCV 208A-557 | 1.40 | 0.07 |
| HCV 208A-558 | 0.40 | 0.25 |
| HCV 208A-562 | 1.29 | 0.07 |
| HCV 208A-575 | 0.12 | 0.06 |
| HCV 208A-576 | 1.13 | 0.06 |
| HCV 208A-584 | 0.07 | 0.06 |
| HCV 208A-603 | 0.25 | 0.07 |
| HCV 208A-604 | 1.27 | 0.06 |
| HCV 208A-605 | 0.55 | 0.06 |
| HCV 208A-638 | 1.07 | 0.06 |
| HCV 208A-641 | 0.20 | 0.07 |
| HCV 208A-658 | 0.83 | 0.07 |
| HCV 208A-692 | 0.07 | 0.06 |
| HCV 208A-695 | 0.61 | 0.17 |
| HCV 208A-719 | 1.12 | 0.06 |
| HCV 208A-736 | 0.07 | 0.07 |
| HCV 208A-741 | 1.20 | 0.06 |
| HCV 208A-744 | 1.57 | 0.07 |
| HCV 208A-759 | 0.36 | 0.22 |
| HCV 208A-768 | 1.12 | 0.07 |
| HCV 208A-774 | 1.41 | 0.06 |
| HCV 208A-793 | 1.24 | 0.06 |
| HCV 208A-807 | 0.14 | 0.10 |
| HCV 208A-826 | 0.09 | 0.06 |
| HCV 208A-828 | 1.49 | 0.07 |
| HCV 208A-830 | 1.16 | 0.06 |
| HCV 208A-850 | 1.18 | 0.06 |
| HCV 208A-863 | 1.55 | 0.07 |
| HCV 208A-874 | 0.45 | 0.06 |
| HCV 208A-877 | 0.90 | 0.07 |
| HCV 208A-879 | 0.32 | 0.30 |
| HCV 208A-920 | 1.14 | 0.07 |
| HCV 208A-926 | 1.14 | 0.09 |
| HCV 208A-938 | 0.83 | 0.13 |
| HCV 208A-939 | 0.07 | 0.06 |
| HCV 208A-967 | 1.08 | 1.30 |
| HCV 208A-982 | 1.25 | 0.07 |
| HCV 208A-983 | 0.12 | 0.06 |
| HCV 208B-1024 | 0.60 | 0.40 |
| HCV 208B-1029 | 0.07 | 0.07 |
| HCV 208B-1043 | 0.86 | 0.15 |
| HCV 208B-1070 | 1.24 | 0.08 |
| HCV 208B-1072 | 0.89 | 0.07 |
| HCV 208B-109 | 0.62 | 0.15 |
| HCV 208B-1094 | 0.90 | 0.17 |
| HCV 208B-1096 | 0.49 | 0.15 |
| HCV 208B-131 | 0.74 | 0.06 |
| HCV 208B-141 | 0.07 | 0.08 |
| HCV 208B-174 | 0.15 | 0.06 |
| HCV 208B-178 | 0.89 | 0.07 |
| HCV 208B-181 | 0.47 | 0.07 |
| HCV 208B-183 | 0.84 | 0.85 |
| HCV 208B-189 | 0.49 | 0.11 |
| HCV 208B-207 | 0.06 | 0.08 |
| HCV 208B-214 | 0.09 | 0.06 |
| HCV 208B-230 | 0.08 | 0.09 |
| HCV 208B-251 | 0.79 | 0.08 |
| HCV 208B-281 | 0.09 | 0.07 |
| HCV 208B-309 | 0.77 | 0.07 |
| HCV 208B-319 | 0.50 | 0.11 |
| HCV 208B-327 | 0.14 | 0.08 |
| HCV 208B-348 | 0.90 | 0.67 |
| HCV 208B-353 | 0.30 | 0.06 |
| HCV 208B-395 | 0.50 | 0.12 |
| HCV 208B-408 | 0.09 | 0.08 |
| HCV 208B-409 | 0.52 | 0.13 |
| HCV 208B-446 | 0.78 | 0.24 |
| HCV 208B-457 | 0.13 | 0.11 |
| HCV 208B-471 | 0.24 | 0.12 |
| HCV 208B-488 | 0.34 | 0.07 |
| HCV 208B-515 | 0.06 | 0.07 |
| HCV 208B-517 | 0.79 | 0.07 |
| HCV 208B-547 | 0.46 | 0.13 |
| HCV 208B-556 | 0.74 | 0.36 |
| HCV 208B-560 | 1.07 | 0.07 |
| HCV 208B-589 | 0.68 | 0.17 |
| HCV 208B-591 | 0.72 | 0.08 |
| HCV 208B-602 | 0.14 | 0.06 |
| HCV 208B-608 | 0.07 | 0.06 |
| HCV 208B-612 | 0.18 | 0.06 |
| HCV 208B-616 | 0.19 | 0.15 |
| HCV 208B-617 | 0.93 | 1.21 |
| HCV 208B-646 | 1.24 | 0.07 |
| HCV 208B-652 | 0.10 | 0.07 |
| HCV 208B-672 | 1.77 | 0.79 |
| HCV 208B-739 | 0.19 | 0.17 |
| HCV 208B-742 | 0.29 | 0.08 |
| HCV 208B-750 | 0.98 | 0.07 |
| HCV 208B-762 | 1.62 | 1.49 |
| HCV 208B-765 | 0.15 | 0.12 |
| HCV 208B-778 | 0.10 | 0.08 |
| HCV 208B-780 | 1.05 | 0.97 |
| HCV 208B-788 | 0.21 | 0.21 |
| HCV 208B-793 | 0.85 | 0.42 |
| HCV 208B-796 | 0.49 | 0.14 |
| HCV 208B-822 | 0.22 | 0.06 |
| HCV 208B-826 | 0.65 | 0.08 |
| HCV 208B-853 | 0.10 | 0.06 |
| HCV 208B-860 | 0.12 | 0.08 |
| HCV 208B-862 | 0.49 | 0.12 |
| HCV 208B-894 | 0.07 | 0.07 |
| HCV 208B-909 | 0.66 | 0.23 |
| HCV 208B-911 | 1.18 | 1.17 |
| HCV 208B-922 | 0.07 | 0.08 |
| HCV 208B-952 | 0.16 | 0.07 |
| HCV 208B-954 | 1.10 | 0.07 |
| HCV 208B-956 | 0.12 | 0.07 |
| HCV 208B-960 | 1.16 | 0.09 |
| HCV 208B-982 | 0.46 | 0.08 |

Example 8

Hybridoma Screening Via Core Antigen Capture Assay

The cell lines that were identified as positive at the 24 well stage by peptide-based EIA (Example 5) or HCV Core1-169 solid phase immunoassay (Example 7) were expanded for cryopreservation, followed by generation of high-density spent-cell supernatant. The high density exhausted supernatant from fusion 208A and 208B cell lines were tested for their ability to detect HCV Core1-169 captured from solution by a monoclonal antibody (14-153-229, U.S. Pat. No. 7,858,752) directed against an epitope within the nucleic acid binding domain of HCV Core (e.g. amino acids 1-125), also known as Domain 1. An anti-domain 1 monoclonal antibody was coated on the solid phase of 96 well micro-titer EIA plates at 1 µg/mL. After the capture reagent had been coated on the solid phase, it was removed and the plates were blocked for 30 minutes at room temperature using a 5×PBS buffer containing 2% fish gelatin, 0.5% Tween20, and 0.1% n-Dodecyl-N,N-Dimethylamine-N-Oxide (Affymetrix). The plates were washed with distilled water and a 50 ng/ml solution of Core1-169 antigen diluted in the fish gelatin/detergent solution was added to all wells and allowed to incubate for at least 30 minutes at room temperature. The wells were washed with distilled water and cell supernatants were titrated down the blocked plates and allowed to incubate at room temperature for at least 30 minutes at room temperature. The plates were washed with distilled water and a HRP labeled goat anti-mouse IgG FC antibody diluted to approximately 200 ng/ml in BSA block solution was added to the plates and allowed to incubate for 30 minutes at room temperature. The plates were washed with distilled water and o-phenylenediamine substrate was used as the chromogen to generate signal. Plates were read at 492 nm and the results were analyzed. Antibodies were considered positive for Core1-169 if they had EIA signal of, at least, 0.50 OD units, or at least 5 times greater than the average BSA background signal of 0.10 OD units. Values are listed in Table 3.

TABLE 3

| Clone # | Captured HCV Core OD (A492) | BSA OD (A492) |
|---|---|---|
| HCV 208A-1006 | 0.97 | 0.10 |
| HCV 208A-1007 | 1.25 | 0.13 |
| HCV 208A-1015 | 0.15 | 0.14 |
| HCV 208A-1022 | 0.33 | 0.22 |
| HCV 208A-1032 | 1.53 | 0.08 |
| HCV 208A-1064 | 1.57 | 0.09 |
| HCV 208A-1081 | 1.95 | 0.09 |
| HCV 208A-110 | 1.87 | 0.07 |
| HCV 208A-122 | 2.10 | 0.07 |
| HCV 208A-126 | 1.20 | 0.07 |
| HCV 208A-133 | 1.46 | 0.08 |
| HCV 208A-134 | 0.13 | 0.09 |
| HCV 208A-147 | 0.14 | 0.08 |
| HCV 208A-152 | 1.60 | 0.06 |
| HCV 208A-158 | 1.84 | 0.08 |
| HCV 208A-159 | 1.29 | 0.08 |
| HCV 208A-160 | 1.54 | 0.08 |
| HCV 208A-194 | 0.14 | 0.14 |
| HCV 208A-207 | 0.41 | 0.09 |
| HCV 208A-208 | 1.77 | 0.07 |
| HCV 208A-210 | 0.87 | 0.08 |
| HCV 208A-222 | 2.07 | 0.08 |
| HCV 208A-227 | 0.09 | 0.08 |
| HCV 208A-230 | 0.07 | 0.08 |
| HCV 208A-264 | 0.09 | 0.08 |
| HCV 208A-286 | 2.06 | 0.14 |
| HCV 208A-293 | 2.31 | 0.07 |
| HCV 208A-312 | 2.07 | 0.08 |
| HCV 208A-334 | 1.90 | 0.10 |
| HCV 208A-352 | 0.53 | 0.08 |
| HCV 208A-367 | 1.41 | 0.08 |
| HCV 208A-381 | 2.18 | 0.07 |
| HCV 208A-382 | 0.11 | 0.08 |
| HCV 208A-393 | 0.07 | 0.09 |
| HCV 208A-422 | 0.18 | 0.11 |
| HCV 208A-427 | 1.84 | 0.08 |

TABLE 3-continued

| Clone # | Captured HCV Core OD (A492) | BSA OD (A492) |
|---|---|---|
| HCV 208A-442 | 0.36 | 0.14 |
| HCV 208A-460 | 1.50 | 0.08 |
| HCV 208A-470 | 0.09 | 0.09 |
| HCV 208A-489 | 1.46 | 0.07 |
| HCV 208A-493 | 1.44 | 0.08 |
| HCV 208A-557 | 2.39 | 0.08 |
| HCV 208A-558 | 0.23 | 0.18 |
| HCV 208A-562 | 2.15 | 0.07 |
| HCV 208A-575 | 0.30 | 0.10 |
| HCV 208A-576 | 1.44 | 0.07 |
| HCV 208A-584 | 1.10 | 1.20 |
| HCV 208A-603 | 1.55 | 0.09 |
| HCV 208A-604 | 1.75 | 0.07 |
| HCV 208A-605 | 2.21 | 0.08 |
| HCV 208A-638 | 2.24 | 0.08 |
| HCV 208A-641 | 0.11 | 0.10 |
| HCV 208A-658 | 0.91 | 0.08 |
| HCV 208A-692 | 0.57 | 0.09 |
| HCV 208A-695 | 1.77 | 0.09 |
| HCV 208A-719 | 1.68 | 0.08 |
| HCV 208A-736 | 0.32 | 0.10 |
| HCV 208A-741 | 1.90 | 0.08 |
| HCV 208A-744 | 1.62 | 0.10 |
| HCV 208A-759 | 0.63 | 0.08 |
| HCV 208A-768 | 2.29 | 0.08 |
| HCV 208A-774 | 1.91 | 0.09 |
| HCV 208A-793 | 1.19 | 0.08 |
| HCV 208A-807 | 0.09 | 0.08 |
| HCV 208A-826 | 0.17 | 0.08 |
| HCV 208A-828 | 1.55 | 0.08 |
| HCV 208A-830 | 2.09 | 0.08 |
| HCV 208A-850 | 1.50 | 0.09 |
| HCV 208A-863 | 1.88 | 0.08 |
| HCV 208A-874 | 0.18 | 0.10 |
| HCV 208A-877 | 1.25 | 0.08 |
| HCV 208B-672 | 0.99 | 0.08 |
| HCV 208B-739 | 0.88 | 0.09 |
| HCV 208B-742 | 0.12 | 0.08 |
| HCV 208B-750 | 1.53 | 0.08 |
| HCV 208B-762 | 0.28 | 0.21 |
| HCV 208B-765 | 0.36 | 0.44 |
| HCV 208B-778 | 0.08 | 0.07 |
| HCV 208B-780 | 0.10 | 0.08 |
| HCV 208B-788 | 0.09 | 0.07 |
| HCV 208B-793 | 0.17 | 0.20 |
| HCV 208B-796 | 1.19 | 0.09 |
| HCV 208B-822 | 0.12 | 0.11 |
| HCV 208B-826 | 0.72 | 0.41 |
| HCV 208B-853 | 0.08 | 0.09 |
| HCV 208B-860 | 0.09 | 0.09 |
| HCV 208B-862 | 1.07 | 0.07 |
| HCV 208B-894 | 0.09 | 0.09 |
| HCV 208B-909 | 0.39 | 0.10 |
| HCV 208B-911 | 0.14 | 0.17 |
| HCV 208B-922 | 0.08 | 0.08 |
| HCV 208B-952 | 0.09 | 0.08 |
| HCV 208B-954 | 1.53 | 0.07 |
| HCV 208B-956 | 0.14 | 0.12 |
| HCV 208B-960 | 1.19 | 0.08 |
| HCV 208B-982 | 0.99 | 0.08 |

Example 9

Determination of Anti-HCV Core Antibody Binding Kinetics

The affinities/kinetics of the anti-HCV core peptide 134-171 monoclonal antibodies were determined using a Biacore 4000 instrument (GE Healthcare Bio-Sciences AB, Uppsala, Sweden). First, after pre-treating a CM5 Series S biosensor chip (GE Healthcare) with duplicate injections of 100 mM HCl, 50 mM NaOH, and 0.1% SDS, a rabbit anti-mouse IgG Capture Biosensor was created by amine-coupling rabbit anti-mouse IgG antibody (GE Healthcare, Piscataway, N.J.) on Spots 1, 2, 4, and 5 in all four flow cells of the biosensor chip via EDC/NHS/ethanolamine chemistry provided in an Amine Coupling Kit (GE Healthcare). Clarified anti-HCV Core antibody exhausted hybridoma supernatants and HCV Core peptide were diluted into a filtered buffer composed of 10×HBS-EP+ buffer (GE Healthcare; hereinafter "running buffer") diluted 10-fold into distilled $H_2O$, supplemented with 0.1% BSA and 0.1% CM-Dextran, and 0.2 μm filtered. Each HCV Core antibody supernatant was diluted 1:1 with running buffer and 0.2 μm filtered again. A 53 amino acid custom peptide (ALRZ-9 peptide, Anaspec, Fremont, Calif.) was chemically synthesized to contain HCV Core residues 134-171 and a carboxy-terminal tetanus toxoid (TT) immunogenic T-cell epitope peptide (Eur. J. Immunol. (1989), 19:2237-2242) with the terminal amino and carboxy groups acetylated and amidated, respectively. The lyophilized HCV core 134-171-tetanus toxoid synthetic peptide immunogen was diluted in distilled water to a stock concentration of 0.7 or 1 mg/mL and further diluted into running buffer to concentrations of either 0.457 to 3,000 nM or 0.412 to 2,700 nM, both using a 3-fold dilution series. All antigen solutions were 0.2 μm filtered prior to use.

The HCV Core 134-171-TT peptide procedure was as follows: 10 μL of HCV Core antibody was separately injected over Spots 1 and 5 in all four flow cells at 10 μL/minute. After all the spots contained captured antibody, the flow rate was increased to 30 μL/minute and the biosensor was equilibrated at this new flow rate for 2 minutes; then, a 3 minute injection (90 μL) of HCV Core peptide followed by 4 minutes of running buffer. All biosensor surfaces were regenerated with one 30 μL injection of 10 mM glycine, pH 1.7 (GE Healthcare), at a flow rate of 10 μL/minute. All concentrations were tested in duplicate. The binding kinetics (association and dissociation) were monitored via sensorgrams during antigen injection followed by running buffer. The sensorgrams were double-referenced and fit to a 1:1 binding model using Biacore 4000 Evaluation software (GE Healthcare Bio-Sciences AB) to determine association and dissociation rates, as well as overall $K_D$. Kinetic and affinity values are listed in Table 4. If values are not present, then either binding kinetics could not be determined or the antibody did not interact with the HCV Core 134-171-TT peptide in this assay.

ALRZ-9 peptide
Ac-MGYIPLVGAPLGGAARALAHGVRVLEDGVNYATGNLPGQYIKANSKFIGITEL-NH2

TABLE 4

| | Binding Interactions with HCV Core 134-171-TT Peptide | | |
|---|---|---|---|
| Clone # | ka (1/Ms) | kd (1/s) | KD (M) |
| HCV 208A-1006 | 1.8E+06 | 6.2E-04 | 3.5E-10 |
| HCV 208A-1007 | 1.8E+06 | 7.4E-04 | 4.1E-10 |
| HCV 208A-1022 | 1.6E+05 | 2.5E-03 | 1.6E-08 |
| HCV 208A-1032 | 1.2E+06 | 5.5E-04 | 4.5E-10 |
| HCV 208A-1064 | 1.6E+06 | 3.4E-04 | 2.1E-10 |
| HCV 208A-1081 | 1.3E+06 | 5.7E-04 | 4.5E-10 |
| HCV 208A-110 | 1.7E+06 | 5.5E-04 | 3.3E-10 |
| HCV 208A-122 | 1.8E+06 | 2.1E-04 | 1.2E-10 |
| HCV 208A-133 | 1.2E+06 | 5.0E-04 | 4.1E-10 |
| HCV 208A-134 | 1.8E+04 | 3.8E-05 | 2.1E-09 |
| HCV 208A-152 | 7.7E+05 | 4.0E-04 | 5.2E-10 |
| HCV 208A-158 | 1.3E+06 | 4.4E-04 | 3.3E-10 |
| HCV 208A-159 | 1.4E+06 | 6.5E-04 | 4.5E-10 |
| HCV 208A-160 | 1.6E+06 | 6.1E-04 | 3.8E-10 |

TABLE 4-continued

| | Binding Interactions with HCV Core 134-171-TT Peptide | | |
|---|---|---|---|
| Clone # | ka (1/Ms) | kd (1/s) | KD (M) |
| HCV 208A-207 | 3.1E+05 | <1E-05 | <3.2E-11 |
| HCV 208A-208 | 1.6E+06 | 5.4E-04 | 3.4E-10 |
| HCV 208A-222 | 1.1E+06 | 3.5E-04 | 3.1E-10 |
| HCV 208A-286 | 2.0E+06 | 2.5E-04 | 1.2E-10 |
| HCV 208A-293 | 2.1E+06 | 2.3E-04 | 1.1E-10 |
| HCV 208A-312 | 2.1E+06 | 2.6E-04 | 1.3E-10 |
| HCV 208A-334 | 1.7E+06 | 5.7E-04 | 3.4E-10 |
| HCV 208A-352 | 1.0E+05 | 5.4E-05 | 5.2E-10 |
| HCV 208A-367 | 1.5E+06 | 5.9E-04 | 3.9E-10 |
| HCV 208A-381 | 2.0E+06 | 2.7E-04 | 1.3E-10 |
| HCV 208A-427 | 1.2E+06 | 5.6E-04 | 4.5E-10 |
| HCV 208A-460 | 1.3E+06 | 5.6E-04 | 4.4E-10 |
| HCV 208A-489 | 1.3E+06 | 6.6E-04 | 4.9E-10 |
| HCV 208A-493 | 1.4E+06 | 5.7E-04 | 4.1E-10 |
| HCV 208A-557 | 2.4E+06 | 2.1E-04 | 9.1E-11 |
| HCV 208A-562 | 1.7E+06 | 6.6E-04 | 4.0E-10 |
| HCV 208A-576 | 1.2E+06 | 5.8E-04 | 4.9E-10 |
| HCV 208A-603 | 1.5E+06 | 5.6E-04 | 3.9E-10 |
| HCV 208A-604 | 1.3E+06 | 5.8E-04 | 4.5E-10 |
| HCV 208A-605 | 8.7E+05 | 3.7E-04 | 4.3E-10 |
| HCV 208A-638 | 2.7E+06 | 5.3E-04 | 2.0E-10 |
| HCV 208A-695 | 2.0E+06 | 7.1E-04 | 3.5E-10 |
| HCV 208A-719 | 1.9E+06 | 5.7E-04 | 3.0E-10 |
| HCV 208A-736 | 2.2E+04 | 1.7E-05 | 7.6E-10 |
| HCV 208A-741 | 1.7E+06 | 6.9E-04 | 4.1E-10 |
| HCV 208A-744 | 1.3E+06 | 6.0E-04 | 4.5E-10 |
| HCV 208A-768 | 1.1E+06 | 3.6E-04 | 3.3E-10 |
| HCV 208A-774 | 1.3E+06 | 5.9E-04 | 4.5E-10 |
| HCV 208A-793 | 1.8E+06 | 6.6E-04 | 3.7E-10 |
| HCV 208A-826 | 1.8E+04 | 7.4E-05 | 4.2E-09 |
| HCV 208A-828 | 1.4E+06 | 5.7E-04 | 4.2E-10 |
| HCV 208A-830 | 3.4E+06 | 5.4E-04 | 1.6E-10 |
| HCV 208A-850 | 1.6E+06 | 6.0E-04 | 3.9E-10 |
| HCV 208A-863 | 1.3E+06 | 6.1E-04 | 4.6E-10 |
| HCV 208A-877 | 1.1E+06 | 2.4E-03 | 2.2E-09 |
| HCV 208A-920 | 1.5E+06 | 5.6E-04 | 3.9E-10 |
| HCV 208A-926 | 1.7E+06 | 5.6E-04 | 3.3E-10 |
| HCV 208A-938 | 1.6E+06 | 5.2E-04 | 3.2E-10 |
| HCV 208A-939 | 2.5E+04 | 2.2E-04 | 9.0E-09 |
| HCV 208A-982 | 1.3E+06 | 6.2E-04 | 4.9E-10 |
| HCV 208A-983 | 9.7E+04 | 4.6E-05 | 4.6E-10 |
| HCV 208B-1024 | 1.0E+06 | 1.4E-02 | 1.5E-08 |
| HCV 208B-1043 | 1.1E+06 | 6.0E-04 | 5.4E-10 |
| HCV 208B-1070 | 1.6E+06 | 5.2E-04 | 3.2E-10 |
| HCV 208B-1072 | 1.3E+06 | 5.5E-04 | 4.2E-10 |
| HCV 208B-109 | 1.4E+06 | 5.1E-04 | 3.7E-10 |
| HCV 208B-1094 | 1.5E+06 | 2.5E-04 | 1.6E-10 |
| HCV 208B-1096 | 1.3E+06 | 6.0E-04 | 4.6E-10 |
| HCV 208B-131 | 1.3E+06 | 1.7E-03 | 1.3E-09 |
| HCV 208B-141 | 3.1E+04 | 1.6E-04 | 5.3E-09 |
| HCV 208B-174 | 7.6E+05 | 1.8E-04 | 2.5E-10 |
| HCV 208B-181 | 2.0E+06 | 3.6E-04 | 1.8E-10 |
| HCV 208B-189 | 8.8E+05 | 1.5E-04 | 1.7E-10 |
| HCV 208B-251 | 1.1E+06 | 6.5E-04 | 5.8E-10 |
| HCV 208B-281 | 2.2E+03 | 2.5E-04 | 9.6E-08 |
| HCV 208B-309 | 1.2E+06 | 6.8E-04 | 5.7E-10 |
| HCV 208B-319 | 2.2E+06 | 2.8E-04 | 1.3E-10 |
| HCV 208B-395 | 1.3E+06 | 4.7E-04 | 3.6E-10 |
| HCV 208B-409 | 1.9E+06 | 2.8E-04 | 1.5E-10 |
| HCV 208B-446 | 2.1E+06 | 2.8E-04 | 1.4E-10 |
| HCV 208B-471 | 2.2E+05 | 5.5E-05 | 2.5E-10 |
| HCV 208B-547 | 1.6E+06 | 4.9E-03 | 3.2E-09 |
| HCV 208B-556 | 1.5E+06 | 6.0E-04 | 4.0E-10 |
| HCV 208B-560 | 1.1E+06 | 2.6E-04 | 2.3E-10 |
| HCV 208B-589 | 9.6E+05 | 6.1E-04 | 6.3E-10 |
| HCV 208B-591 | 2.2E+06 | 2.0E-04 | 9.3E-11 |
| HCV 208B-612 | 1.8E+05 | 6.5E-05 | 3.5E-10 |
| HCV 208B-646 | 1.8E+06 | 6.0E-04 | 3.4E-10 |
| HCV 208B-672 | 2.2E+06 | 3.4E-04 | 1.6E-10 |
| HCV 208B-739 | 2.8E+05 | 5.5E-05 | 2.0E-10 |
| HCV 208B-750 | 2.0E+06 | 2.6E-04 | 1.3E-10 |
| HCV 208B-796 | 1.5E+06 | 6.8E-04 | 4.6E-10 |
| HCV 208B-862 | 1.4E+06 | 1.0E-04 | 7.0E-11 |
| HCV 208B-954 | 1.6E+06 | 5.5E-04 | 3.4E-10 |

TABLE 4-continued

| | Binding Interactions with HCV Core 134-171-TT Peptide | | |
|---|---|---|---|
| Clone # | ka (1/Ms) | kd (1/s) | KD (M) |
| HCV 208B-960 | 1.6E+06 | 5.6E−04 | 3.5E−10 |
| HCV 208B-982 | 2.2E+06 | 8.0E−04 | 3.5E−10 |

Example 10

BIACore Antibody Binding Pair Analysis with Nucleic Acid Binding Domain mAbs

The ability of the anti-HCV core peptide 134-171 monoclonal antibodies to form antibody binding pairs with anti-HCV Core C11-3, C11-7, C11-9, and C11-14 (U.S. Pat. No. 6,727,092; Morota, et al, J. Virol. Meth., 2009, 157:8-14) antibodies and recombinant HCV Core1-169 antigen was determined using a Biacore 4000 instrument (GE Healthcare Bio-Sciences AB). First, after pre-treating a CM5 Series S biosensor chip (GE Healthcare) with duplicate injections of 100 mM HCl, 50 mM NaOH, and 0.1% SDS, a rabbit anti-mouse IgG Capture Biosensor was created by amine-coupling rabbit anti-mouse IgG antibody (GE Healthcare, Piscataway, N.J.) on Spots 1, 2, 4, and 5 in all four flow cells of the biosensor chip via EDC/NHS/ethanolamine chemistry provided in an Amine Coupling Kit (GE Healthcare).

Clarified anti-HCV Core (peptide aa 134-171) antibody exhausted hybridoma supernatants, recombinant HCV Core1-169 antigen, 3 different purified mouse monoclonal IgG representing isotypes IgG1, IgG2a, and IgG2b non-reactive to HCV Core used as blocking reagents, and anti-HCV Core C11-3, C11-7, C11-9, and C11-14 mAbs were diluted into a filtered running buffer (hereinafter "running buffer") composed of 10×PBS buffer (GE Healthcare) diluted 5-fold into distilled $H_2O$, supplemented with 3 mM EDTA, 0.1% BSA, 0.1% CM-Dextran, 0.1% n-Dodecyl-N,N-Dimethylamine-N-Oxide, an extra 500 mM NaCl, and 0.2 μm filtered. Each HCV Core antibody supernatant was diluted 1:1, the recombinant HCV Core1-169 antigen was diluted to 500 nM per the calculated dimer molecular weight (39,453 Da), the anti-HCV Core C11-3, C11-7, C11-9, and C11-14 purified monoclonal antibodies were individually diluted to 20 μg/mL, and the 3 mouse IgG blocking reagents were all diluted as a pool with each isotype having a concentration of at least 100 μg/mL in running buffer. All dilutions were 0.2 μm filtered prior to use.

The HCV Core antibody-antigen-antibody sandwich procedure was as follows. 20 μL of the HCV Core C11 antibodies were injected over Spots 1 and 5 in all four flow cells at 10 μL/minute: C11-3 in flow cell 1, C11-7 in flow cell 2, C11-9 in flow cell 3, and c11-14 in flow cell 4. The flow rate was increased to 30 μL/minute and the remaining available anti-mouse IgG binding sites on the biosensor were blocked with the mouse IgG1, IgG2a, and IgG2b isotype pool by injecting 60 μL over Spots 1 and 2 and then 60 μL over Spots 4 and 5 in all flow cells. 60 μL of HCV Core1-169 antigen was injected over Spot 1 and then another 60 μL over Spot 5 in all flow cells. 60 μL of one HCV Core antibody diluted supernatant was inject over Spots 1 and 2 over all flow cells and another diluted supernatant over Spots 4 and 5 in all flow cells. The flow rate was decreased 10 μL/minute and all biosensor surfaces were regenerated with one 30 μL injection of 10 mM glycine, pH 1.7 (GE Healthcare).

Using the Biacore 4000 Evaluation Epitope Mapping software module (GE Healthcare Bio-Sciences AB), the binding response for each C11 antibody, antigen, and HCV Core antibody supernatant was determined after each injection and used to calculate an expected response reference value using the dimeric antigen and antibody (150,000 Da) molecular weights. An expected percent binding value was determined using individual samples versus the reference value. Any expected percent binding values that were greater than 5.0 were considered positive for the ability to form an antibody sandwich with the recombinant HCV Core1-169 antigen. Expected percent values are listed in Table 5.

TABLE 5

| Secondary Conjugate Antibody Anti-HCV Core 134-171 antibodies | Primary Capture Antibody Anti-HCV Core antibody | | | |
|---|---|---|---|---|
| | C11-3 | C11-7 | C11-9 | C11-14 |
| HCV 208A-1006 | 2.4 | 3.1 | ≤1.0 | 2.5 |
| HCV 208A-1007 | 4.4 | 6.1 | 2.7 | 4.2 |
| HCV 208A-1015 | ≤1.0 | ≤1.0 | ≤1.0 | ≤1.0 |
| HCV 208A-1022 | ≤1.0 | 1.3 | ≤1.0 | ≤1.0 |
| HCV 208A-1032 | 19.5 | 26.7 | 15.7 | 21.8 |
| HCV 208A-1064 | 16.3 | 19.6 | 10.5 | 16.3 |
| HCV 208A-1081 | 19.0 | 25.9 | 14.9 | 20.8 |
| HCV 208A-110 | 15.7 | 21.1 | 9.4 | 14.8 |
| HCV 208A-122 | 17.3 | 19.7 | 9.6 | 14.8 |
| HCV 208A-126 | 1.2 | 2.0 | ≤1.0 | 1.3 |
| HCV 208A-133 | 9.8 | 13.9 | 5.8 | 9.3 |
| HCV 208A-134 | ≤1.0 | ≤1.0 | ≤1.0 | ≤1.0 |
| HCV 208A-147 | ≤1.0 | ≤1.0 | ≤1.0 | ≤1.0 |
| HCV 208A-152 | 10.0 | 12.5 | 6.9 | 9.8 |
| HCV 208A-158 | 14.0 | 16.5 | 7.8 | 12.4 |
| HCV 208A-159 | 4.6 | 7.0 | 3.3 | 5.5 |
| HCV 208A-160 | 15.5 | 20.9 | 8.7 | 13.8 |
| HCV 208A-194 | ≤1.0 | ≤1.0 | ≤1.0 | ≤1.0 |
| HCV 208A-207 | ≤1.0 | ≤1.0 | ≤1.0 | ≤1.0 |
| HCV 208A-208 | 2.6 | 3.2 | ≤1.0 | 2.5 |
| HCV 208A-210 | 1.2 | 1.6 | ≤1.0 | ≤1.0 |
| HCV 208A-222 | 15.6 | 18.8 | 10.7 | 15.0 |
| HCV 208A-227 | ≤1.0 | 1.1 | ≤1.0 | ≤1.0 |
| HCV 208A-230 | ≤1.0 | ≤1.0 | ≤1.0 | ≤1.0 |
| HCV 208A-264 | ≤1.0 | 1.1 | ≤1.0 | ≤1.0 |
| HCV 208A-286 | 18.9 | 22.1 | 13.0 | 18.5 |
| HCV 208A-293 | 17.9 | 20.9 | 11.0 | 16.4 |
| HCV 208A-312 | 16.3 | 19.7 | 11.8 | 16.4 |
| HCV 208A-334 | 17.2 | 20.6 | 10.3 | 15.9 |
| HCV 208A-352 | ≤1.0 | ≤1.0 | ≤1.0 | ≤1.0 |
| HCV 208A-367 | 9.7 | 14.5 | 6.1 | 9.3 |
| HCV 208A-381 | 17.2 | 20.3 | 12.3 | 17.4 |
| HCV 208A-382 | ≤1.0 | 1.5 | ≤1.0 | ≤1.0 |
| HCV 208A-393 | ≤1.0 | ≤1.0 | ≤1.0 | ≤1.0 |
| HCV 208A-422 | ≤1.0 | ≤1.0 | ≤1.0 | ≤1.0 |
| HCV 208A-427 | 15.5 | 22.1 | 11.7 | 16.5 |
| HCV 208A-442 | ≤1.0 | 1.6 | ≤1.0 | ≤1.0 |
| HCV 208A-460 | 17.5 | 24.3 | 12.9 | 18.3 |
| HCV 208A-470 | ≤1.0 | ≤1.0 | ≤1.0 | ≤1.0 |
| HCV 208A-489 | 15.9 | 21.9 | 11.5 | 16.6 |
| HCV 208A-493 | 12.6 | 17.7 | 7.8 | 12.2 |
| HCV 208A-557 | 17.7 | 21.4 | 13.3 | 17.6 |
| HCV 208A-558 | ≤1.0 | 1.1 | ≤1.0 | ≤1.0 |
| HCV 208A-562 | 13.8 | 17.1 | 9.5 | 14.8 |
| HCV 208A-575 | ≤1.0 | ≤1.0 | ≤1.0 | ≤1.0 |
| HCV 208A-576 | 12.6 | 16.9 | 9.1 | 13.3 |
| HCV 208A-584 | ≤1.0 | 1.6 | ≤1.0 | ≤1.0 |
| HCV 208A-603 | 6.7 | 9.1 | 4.0 | 6.8 |
| HCV 208A-604 | 15.4 | 20.8 | 9.8 | 14.8 |
| HCV 208A-605 | 15.9 | 19.3 | 11.9 | 15.8 |
| HCV 208A-638 | 14.1 | 16.9 | 9.2 | 13.3 |
| HCV 208A-641 | ≤1.0 | ≤1.0 | ≤1.0 | ≤1.0 |
| HCV 208A-658 | 1.8 | 2.5 | ≤1.0 | ≤1.0 |
| HCV 208A-692 | ≤1.0 | ≤1.0 | ≤1.0 | ≤1.0 |
| HCV 208A-695 | 14.2 | 20.4 | 9.5 | 15.0 |
| HCV 208A-719 | 7.5 | 10.0 | 4.9 | 8.0 |
| HCV 208A-736 | ≤1.0 | ≤1.0 | ≤1.0 | ≤1.0 |
| HCV 208A-741 | 19.4 | 22.7 | 14.2 | 21.2 |

TABLE 5-continued

| Secondary Conjugate Antibody Anti-HCV Core 134-171 antibodies | Primary Capture Antibody Anti-HCV Core antibody | | | |
|---|---|---|---|---|
| | C11-3 | C11-7 | C11-9 | C11-14 |
| HCV 208A-744 | 16.7 | 22.5 | 10.5 | 16.1 |
| HCV 208A-759 | ≤1.0 | ≤1.0 | ≤1.0 | ≤1.0 |
| HCV 208A-768 | 12.7 | 17.1 | 8.8 | 12.6 |
| HCV 208A-774 | 18.5 | 24.5 | 13.4 | 19.3 |
| HCV 208A-793 | 3.8 | 6.2 | 2.5 | 3.9 |
| HCV 208A-807 | ≤1.0 | ≤1.0 | ≤1.0 | ≤1.0 |
| HCV 208A-826 | ≤1.0 | 1.3 | ≤1.0 | ≤1.0 |
| HCV 208A-828 | 14.8 | 20.7 | 10.9 | 16.5 |
| HCV 208A-830 | 11.9 | 14.7 | 7.9 | 11.7 |
| HCV 208A-850 | 7.3 | 9.7 | 4.4 | 7.5 |
| HCV 208A-863 | 18.0 | 24.9 | 12.1 | 18.0 |
| HCV 208A-874 | ≤1.0 | ≤1.0 | ≤1.0 | ≤1.0 |
| HCV 208A-877 | 9.4 | 12.1 | 5.9 | 10.7 |
| HCV 208A-879 | ≤1.0 | ≤1.0 | ≤1.0 | ≤1.0 |
| HCV 208A-920 | 19.3 | 22.9 | 13.2 | 19.1 |
| HCV 208A-926 | 19.3 | 26.3 | 14.7 | 21.1 |
| HCV 208A-938 | 14.1 | 21.0 | 10.4 | 15.5 |
| HCV 208A-939 | ≤1.0 | ≤1.0 | ≤1.0 | ≤1.0 |
| HCV 208A-967 | ≤1.0 | ≤1.0 | ≤1.0 | ≤1.0 |
| HCV 208A-982 | 19.2 | 26.3 | 15.0 | 20.6 |
| HCV 208A-983 | ≤1.0 | ≤1.0 | ≤1.0 | ≤1.0 |
| HCV 208B-1024 | 10.9 | 14.3 | 7.1 | 12.2 |
| HCV 208B-1029 | ≤1.0 | ≤1.0 | ≤1.0 | ≤1.0 |
| HCV 208B-1043 | 17.4 | 20.7 | 12.0 | 17.9 |
| HCV 208B-1070 | 22.0 | 28.6 | 17.7 | 25.3 |
| HCV 208B-1072 | 25.0 | 30.2 | 19.3 | 27.4 |
| HCV 208B-109 | 12.5 | 16.0 | 8.6 | 13.3 |
| HCV 208B-1094 | 24.4 | 28.4 | 19.8 | 27.8 |
| HCV 208B-1096 | 15.1 | 16.9 | 11.4 | 16.3 |
| HCV 208B-131 | 11.4 | 12.4 | 6.8 | 11.6 |
| HCV 208B-141 | ≤1.0 | ≤1.0 | ≤1.0 | ≤1.0 |
| HCV 208B-174 | 1.6 | 1.5 | ≤1.0 | 1.6 |
| HCV 208B-178 | ≤1.0 | 1.7 | ≤1.0 | ≤1.0 |
| HCV 208B-181 | 7.4 | 10.0 | 5.4 | 8.1 |
| HCV 208B-183 | ≤1.0 | ≤1.0 | ≤1.0 | ≤1.0 |
| HCV 208B-189 | 2.3 | 2.9 | ≤1.0 | 2.7 |
| HCV 208B-207 | ≤1.0 | ≤1.0 | ≤1.0 | ≤1.0 |
| HCV 208B-214 | ≤1.0 | ≤1.0 | ≤1.0 | ≤1.0 |
| HCV 208B-230 | ≤1.0 | ≤1.0 | ≤1.0 | ≤1.0 |
| HCV 208B-251 | 16.6 | 20.1 | 12.3 | 18.2 |
| HCV 208B-281 | ≤1.0 | ≤1.0 | ≤1.0 | ≤1.0 |
| HCV 208B-309 | 13.6 | 17.5 | 10.2 | 15.5 |
| HCV 208B-319 | 6.0 | 8.5 | 4.2 | 6.3 |
| HCV 208B-327 | ≤1.0 | ≤1.0 | ≤1.0 | ≤1.0 |
| HCV 208B-348 | ≤1.0 | 1.5 | ≤1.0 | ≤1.0 |
| HCV 208B-353 | 1.9 | 2.6 | ≤1.0 | 2.4 |
| HCV 208B-395 | 7.6 | 9.4 | 5.2 | 7.8 |
| HCV 208B-408 | ≤1.0 | ≤1.0 | ≤1.0 | ≤1.0 |
| HCV 208B-409 | 1.8 | 2.7 | ≤1.0 | 2.0 |
| HCV 208B-446 | 10.0 | 12.2 | 7.8 | 10.3 |
| HCV 208B-457 | ≤1.0 | ≤1.0 | ≤1.0 | ≤1.0 |
| HCV 208B-471 | ≤1.0 | ≤1.0 | ≤1.0 | ≤1.0 |
| HCV 208B-488 | ≤1.0 | ≤1.0 | ≤1.0 | ≤1.0 |
| HCV 208B-515 | ≤1.0 | ≤1.0 | ≤1.0 | ≤1.0 |
| HCV 208B-517 | ≤1.0 | ≤1.0 | ≤1.0 | ≤1.0 |
| HCV 208B-547 | 7.2 | 8.3 | 4.9 | 8.2 |
| HCV 208B-556 | 11.5 | 15.3 | 8.3 | 12.7 |
| HCV 208B-560 | 10.6 | 15.5 | 8.3 | 12.0 |
| HCV 208B-589 | 9.4 | 11.7 | 6.7 | 9.9 |
| HCV 208B-591 | 19.1 | 23.0 | 15.1 | 21.7 |
| HCV 208B-602 | 1.3 | 1.8 | ≤1.0 | ≤1.0 |
| HCV 208B-608 | ≤1.0 | ≤1.0 | ≤1.0 | ≤1.0 |
| HCV 208B-612 | 3.8 | 4.4 | ≤1.0 | 3.1 |
| HCV 208B-616 | ≤1.0 | ≤1.0 | ≤1.0 | ≤1.0 |
| HCV 208B-617 | ≤1.0 | ≤1.0 | ≤1.0 | ≤1.0 |
| HCV 208B-646 | 22.0 | 30.2 | 17.8 | 25.6 |
| HCV 208B-652 | ≤1.0 | 1.3 | ≤1.0 | ≤1.0 |
| HCV 208B-672 | 2.6 | 2.8 | ≤1.0 | 2.7 |
| HCV 208B-739 | ≤1.0 | ≤1.0 | ≤1.0 | ≤1.0 |
| HCV 208B-742 | ≤1.0 | ≤1.0 | ≤1.0 | ≤1.0 |
| HCV 208B-750 | 22.8 | 27.3 | 17.2 | 24.1 |
| HCV 208B-762 | ≤1.0 | ≤1.0 | ≤1.0 | ≤1.0 |
| HCV 208B-765 | ≤1.0 | ≤1.0 | ≤1.0 | ≤1.0 |
| HCV 208B-778 | ≤1.0 | ≤1.0 | ≤1.0 | ≤1.0 |
| HCV 208B-780 | ≤1.0 | ≤1.0 | ≤1.0 | ≤1.0 |
| HCV 208B-788 | ≤1.0 | ≤1.0 | ≤1.0 | ≤1.0 |
| HCV 208B-793 | ≤1.0 | ≤1.0 | ≤1.0 | ≤1.0 |
| HCV 208B-796 | 20.2 | 27.7 | 17.3 | 25.2 |
| HCV 208B-822 | ≤1.0 | ≤1.0 | ≤1.0 | ≤1.0 |
| HCV 208B-826 | ≤1.0 | ≤1.0 | ≤1.0 | ≤1.0 |
| HCV 208B-853 | ≤1.0 | ≤1.0 | ≤1.0 | ≤1.0 |
| HCV 208B-860 | ≤1.0 | ≤1.0 | ≤1.0 | ≤1.0 |
| HCV 208B-862 | 11.2 | 15.2 | 8.9 | 12.6 |
| HCV 208B-894 | ≤1.0 | ≤1.0 | ≤1.0 | ≤1.0 |
| HCV 208B-909 | 1.6 | 2.5 | ≤1.0 | ≤1.0 |
| HCV 208B-911 | ≤1.0 | ≤1.0 | ≤1.0 | ≤1.0 |
| HCV 208B-922 | ≤1.0 | ≤1.0 | ≤1.0 | ≤1.0 |
| HCV 208B-952 | ≤1.0 | ≤1.0 | ≤1.0 | ≤1.0 |
| HCV 208B-954 | 23.9 | 32.7 | 18.4 | 26.0 |
| HCV 208B-956 | ≤1.0 | ≤1.0 | ≤1.0 | ≤1.0 |
| HCV 208B-960 | 21.0 | 28.1 | 15.8 | 22.9 |
| HCV 208B-982 | 4.5 | 5.4 | ≤1.0 | 4.9 |

Example 11

Immunoglobulin Purification and Labeling

Anti-HCV core hybridomas were expanded in Hybridoma Serum Free Medium (Invitrogen Corporation) supplemented with L-glutamine and 10% Ultra Low IgG FBS (Invitrogen Corporation) and seeded into roller bottles at approximately $0.5 \times 10E^5$ cells/mL. The cultures were incubated at 37° C. while rotating at approximately 1 revolution per minute for 10-14 days, or until a terminal end culture was obtained. The terminal roller bottle supernatant was harvested and clarified with a 0.45 micron filter. The clarified supernatant was diluted with an equal volume of 1.5 M glycine, 3M NaCl buffer, pH 8.9, then loaded onto a pre-equilibrated 5 ml Protein A column using the AKTA automated purification system (Amersham/Pharmacia/GE). The column was then washed with approximately 5 column volumes of binding buffer and when a stable baseline is achieved, the mAb was eluted with 0.1 M sodium citrate buffer, pH 2.8. The IgG was then transferred to a desalting column and exchanges into PBS, pH 7.2-7.4, and then further dialyzed in PBS pH 7.2-7.4, using 10,000 molecular weight cut-off dialysis membrane (Pierce Chemical). Selected antibodies were biotinylated by using Sulfo-NHS-LC-Biotin (Pierce) at a 20-fold molar excess and incubated for 30 minutes at room temperature. Unbound biotin was removed through dialysis in PBS pH 7.2-7.4. All biotinylated monoclonals were tested by EIA to confirm successful labeling.

Example 12

HCV Core Antigen Capture Assays

Purified anti-HCV core134-171 monoclonal antibodies were evaluated for their ability to form binding pairs with themselves and two other domain 1 monoclonal antibodies using HCV core1-169 recombinant antigen in an EIA format. Anti-HCV Domain 1 monoclonal antibodies, C11-7 and C11-9, and anti-HCV core134-171 monoclonals were coated onto microtiter plates at approximately 1000 ng/ml and allowed to incubate overnight at 2-8 degrees C. After the capture reagent had been coated on the solid phase, the plates were blocked using a 5×PBS buffer containing 2% fish gelatin, 0.5% Tween 20, and 0.1% n-dodecyl-N,N-dimethylamine-N-oxide. The wells were washed with distilled water and purified core 1-169 antigen was added to the blocked plates in serial dilutions from 50 to 0.78 ng/ml diluted in fish gelatin block, and then allowed to incubate at room temperature for approximately 30 minutes. The wells were washed with distilled water and biotin labeled anti-HCV core monoclonals were added to the plates at concentrations ranging from 100 to 5000 ng/ml, and then incubated for 30 minutes at room temperature. The plates were washed with distilled water and streptavidin-HRPO diluted to approximately 200 ng/mL was added to the plates and allowed to incubate for 30 minutes at room temperature. The plates were washed with distilled water and o-phenylenediamine substrate was used as the chromagen to generate signal and the optical density at 492 nm was measured.

Table 6 summarizes the assay signal (OD492 nm) for each antibody pair combination using 25 ng/ml of core1-169 antigen, which indicates whether or not each binding pair is capable of forming a sandwich. An OD492 value of at least 3× greater than the value generated by a negative control (NC) monoclonal antibody as a capture or conjugate reagent are considered positive for core antigen detection.

and oligo dT primers following standard protocols. The 5' RACE (rapid amplification of cDNA ends) protocol was used to amplify the variable heavy and light chain cDNA sequences using a dC anchor primer (5'-AAGCAGTGGTATCAACGCAGAGTACCCCCCCCCCCCCCCCC-3' (SEQ ID NO: 581)) and a generic primer specific to the constant region of the mouse heavy or light chain (Novogen). Amplicons were cloned into a commercially available vector (pCR2.1-TOPO cloning kit, Invitrogen) per the manufacturer's directions and transformed into TOP10 *E. coli*. At least eight colonies were selected for PCR amplification of cloned variable domain sequences using M13 forward and reverse primers. Amplicons were treated with ExoSap (Affymetrix) prior to sequencing using M13 forward primer and BigDye Terminator v3.1 cycle sequencing kit (Applied Biosystems, Foster City, Calif.). Sequences were obtained using ABI3130xl automated sequencer and assembled and analyzed using Vector NTI software (Invitrogen).

Deduced amino acid sequences were aligned using ClustalW (Higgins et al., Nucleic Acids Res. 22:4673-4680, 1994) as implemented in the MEGA5 software package (Tamura et al., Molecular Biology and Evolution 28: 2731-2739, 2011). MEGA5 software was used to determine groupings or clusters of related heavy chain amino acid sequences from the

TABLE 6

|  | 208A-110 (aa 141-161) | 208A-692 (aa 134-154) | 208A-293 (aa 141-161) | 208A-557 (aa 141-161) | 208A-207-271 (aa 134-154) | 208B-741 (aa 134-154 & 141-161) | 208B-1096 (aa 151-171) |
|---|---|---|---|---|---|---|---|
| 208A-110-Bt | 0.18 | 0.14 | 0.20 | 0.17 | 0.17 | 0.20 | 0.21 |
| 208A-692-Bt | 0.54 | 0.35 | 0.51 | 0.53 | 0.39 | 0.44 | 0.38 |
| 208A-293-Bt | 0.52 | 0.34 | 0.49 | 0.52 | 0.39 | 0.50 | 0.41 |
| 208A-557-Bt | 0.44 | 0.13 | 0.41 | 0.32 | 0.18 | 0.38 | 0.35 |
| 208A-207-271-Bt | 0.38 | 0.42 | 0.42 | 0.82 | 0.36 | 0.30 | 0.33 |
| 208B-741-Bt | 0.42 | 0.32 | 0.42 | 0.40 | 0.33 | 0.36 | 0.52 |
| 208B-1096-Bt | 0.19 | 0.15 | 0.24 | 0.17 | 0.18 | 0.23 | 0.26 |
| 208B-395-334-Bt | 0.21 | 0.15 | 0.26 | 0.21 | 0.20 | 0.21 | 0.23 |
| 208B-612-226-Bt | 0.26 | 0.18 | 0.28 | 0.23 | 0.24 | 0.23 | 0.70 |
| NC mAb-Bt | 0.16 | 0.15 | 0.23 | 0.18 | 0.17 | 0.18 | 0.21 |
| C11-7-Bt | 1.78 | 0.18 | 1.55 | 0.64 | 0.22 | 1.76 | 0.45 |
| C11-9-Bt | 2.59 | 0.58 | 1.84 | 1.18 | 0.44 | 2.32 | 0.82 |

|  | 208B-395-334 (aa 151-171) | 208B-612-226 (aa 134-154 & 141-161) | NC capture mAb | C11-7 (aa 115-121) | C11-9 (aa 29-37) |
|---|---|---|---|---|---|
| 208A-110-Bt | 0.22 | 0.20 | 0.15 | 0.18 | 0.13 |
| 208A-692-Bt | 0.44 | 0.37 | 0.40 | 2.92 | 2.66 |
| 208A-293-Bt | 0.44 | 0.37 | 0.37 | 2.87 | 2.60 |
| 208A-557-Bt | 0.28 | 0.25 | 0.18 | 0.22 | 0.14 |
| 208A-207-271-Bt | 0.37 | 0.33 | 0.37 | 2.47 | 2.20 |
| 208B-741-Bt | 0.34 | 0.29 | 0.29 | 2.36 | 2.13 |
| 208B-1096-Bt | 0.20 | 0.24 | 0.17 | 1.06 | 0.33 |
| 208B-395-334-Bt | 0.23 | 0.26 | 0.20 | 0.89 | 0.32 |
| 208B-612-226-Bt | 0.83 | 0.23 | 0.21 | 1.52 | 0.64 |
| NC mAb-Bt | 0.22 | 0.22 | 0.18 | 0.17 | 0.14 |
| C11-7-Bt | 0.46 | 0.53 | 0.22 | 0.23 | 1.04 |
| C11-9-Bt | 0.95 | 0.63 | 0.62 | 1.91 | 2.75 |

Example 13

Sequences of Anti-Core 134-171 Variable Domains

Figure 2:
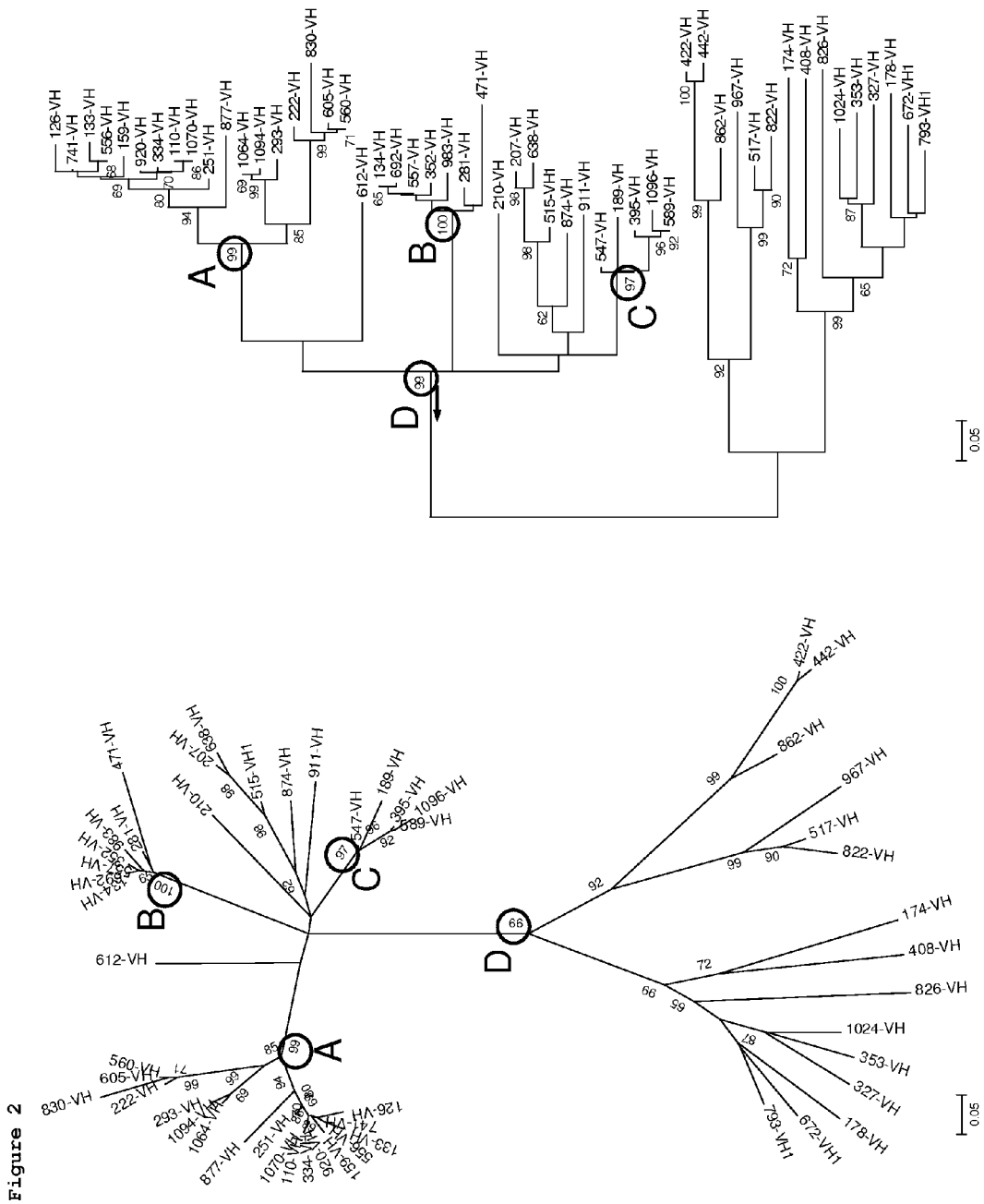

A subset of the anti-HCV core 134-171 hybridomas were selected for determination of variable heavy (VH) and variable light (VL) chain nucleotide and deduced amino acid sequences. Total RNA was extracted from the hybridoma cells using Trizol (Invitrogen) or Tri-Reagent (Sigma) according to the manufacturer's recommendations. The heavy chain and light chain cDNA was generated from the extracted total RNA using Superscript III (Life Technologies)

alignments and phylogenetic tree construction using the Neighbor Joining method with complete deletion of sequence gaps in the alignment. Tree topology, and hence clusters or groups therein, was examined for reliability by using a bootstrap test from 1000 replicates. As a general rule, if the bootstrap value for a given interior branch is 95% or higher, then the topology at that branch is considered "correct" (Nei and Kumar, Molecular Evolution and Phylogenetics, 2000; Oxford University Press, New York). Analysis of heavy chain variable domain sequences from 52 anti-HCV core 134-171 monoclonals revealed the existence of 4 main groups with bootstrap values >95%. Antibodies comprising three of these groups exhibited specificity for binding to one of each of the peptides used for screening, i.e. Group B with peptide 1 (134-154), Group A with peptide 2 (141-161), and Group C with peptide 3 (151-171). FIG. 2 provides two representations of the tree topology.

APPENDIX A

DESCRIPTION OF SEQUENCES

| mAb Clone | SEQ ID | Nucleic Acid Seq | SEQ ID | mAb Clone | Amino Acid Seq |
|---|---|---|---|---|---|
| 208A-1064H | 1 | GAGGTCCAGCTGCAACAGTCTGGACCTGAGTTGGTGAAGCCTGGGGCCTCAGTGAAGATATCTTGCAAGACTTCTGGATACACTTTCACTGAATACGCCATGCACTGGATGAAGCAGAGCCATGGAAAGAGCCTTGAGTGGATTGGAGGTATCAATCCTACTAATGGTGATACAATCTACAACCAGAAGTTCAAGGACAAGGCCAAATTGACTGTAGACAGGTCCTCCAGCACAGCCTACATGGAGCTCCGCAGCCTGACATCTGACGATTCTGCATTATTTTATTGTGCAAGACGGGAACTGGACTACTTTGCCTCCTGGGGCCAAGGCACCACTCTCACAGTCTCCTCA | 2 | 208A-1064H | EVQLQQSGPELVKPGASVKISCKTSGYTFTEYAMHWMKQSHGKSLEWIGGINPTNGDTIYNQKFKDKAKLTVDRSSSTAYMELRSLTSDDSALFYCARRELDYFASWGQGTTLTVSS |
| 208B-1094H | 3 | GAGGTCCAGCTGCAACAGTCTGGACCTGAGCTGGTGAAGCCTGGGGCCTCAGTGAAGATATCCTGCAAGACTTCTGGATACACTTTCACTGAATACGCCATGCACTGGATGAAGCAGAGCCATGGAAAGAGCCTTGAGTGGATTGGCGGTATCAATCCTACTAATGGTGATACAATCTACAACCAGAGGTTCAAGGACAAGGCCAAATTGACTGTAGACAGGTCCTCCAGCACAGCCTACATGGAGCTCCGCAGCCTGACATCTGACGATTCTGCATTATTTTATTGTGCAAGACGGGAACTGGACTACTTTGCCTCCTGGGGCCAAGGCACCACTCTCACAGTCTCCTCA | 4 | 208B-1094H | EVQLQQSGPELVKPGASVKISCKTSGYTFTEYAMHWMKQSHGKSLEWIGGINPTNGDTIYNQRFKDKAKLTVDRSSSTAYMELRSLTSDDSALFYCARRELDYFASWGQGTTLTVSS |
| 208A-293H | 5 | GAGGTCCAGCTGCAACAGTCTGGACCTGAACTGGTGAAGCCTGGGGCCTCAGTGAAGATATCCTGTAAGGCTTCGGGATTCACTTTCACTGAATACGCCATGCACTGGATGAAACAGAGCCATGGAAAGAGCCTTGAGTGGATTGGAGGTATCAATCCTACTAACGGTGATGCAATCTACAACCAGAAGTTCAAGGACAAGGCCAAGTTGACTGTAGACAGGTCCTCCAGCACAGCCTACATGGAGCTCCGCAGCCTGACATCTGACGATTCTGCATTATTTTATTGTGCAAGACGGGAACTGGACTACTTTCCCTCCTGGGGCCAAGGCACCACTCTCACAGTCTCCTCA | 6 | 208A-293H | EVQLQQSGPELVKPGASVKISCKASGFTFTEYAMHWMKQSHGKSLEWIGGINPTNGDAIYNQKFKDKAKLTVDRSSSTAYMELRSLTSDDSALFYCARRELDYFPSWGQGTTLTVSS |
| 208A-222H | 7 | GAGGTCCAGCTGCAACAGTCTGGACCTGAACTGGAAAAGCCTGGGGCTTCAGTGAGGATATCCTGCAAGACTTCTGGATACACATTCACTGAATACGCCATGCACTGG | 8 | 208A-222H | EVQLQQSGPELEKPGASVRISCKTSGYTFTEYAMHWVKQSHGKSLEWIGGINPNNGNAIYNQIFKDKATLVDRSSSTAYMGLRSLTFGDSGVYFCVRRQLDYFDYWG |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GTGAAGCAGAGCCATGGA AAGAGCCTTGAGTGGATT GGAGGTATTAATCCTAAC AATGGCAATGCTATCTAC AACCAGATATTCAAGGAC AAGGCCACACTGACTGTG GACAGGTCCTCCAGCACA GCCTACATGGGCCTCCGC AGCCTGACATTCGGGGAT TCTGGAGTCTACTTCTGT GTAAGACGACAACTGGAC TACTTTGACTATTGGGGC CAGGGCGCCTCTCTCACA GTCTCCTCA | | | QGASLTVSS |
| 208A-605H | 9 | GAGGTCCAGCTGCAACAG TCTGGACCTGAGCTGGAA AAGCCTGGGGCTTCAGTG AAGATATCCTGCAAGACT TCTGGATACACATTCACT GAATACGCCATACACTGG GTGAAGCAGAGCCATGGA ATGAGCCTTGAGTGGATT GGAGGTATTAATCCTAGC AATGGCAATGCTATCTAC AACCAAATATTCAAGGAC AAGGCCACACTGACTGTG GACAGGTCCTCCAGCACA GCCTACATGGGCCTCCGC AGCCTGACATTTGGGGAT TCTGGAGTCTACTTCTGT GTAAGACGACAACTGGAC TTCTTTGACTATTGGGGC CAGGGCGCCTCTCTCACA GTCTCCTCA | 10 | 208A-605H | EVQLQQSGPELEKPGASV KISCKTSGYTFTEYAIHW VKQSHGMSLEWIGGINPS NGNAIYNQIFKDKATLTV DRSSSTAYMGLRSLTFGD SGVYFCVRRQLDFFDYWG QGASLTVSS |
| 208B-560H | 11 | GAGGTCCAGCTGCAACAG TCTGGACCTGAGCTGGAA AAGCCTGGGGCTTCAGTG AAGATATCCTGCAAGACT TCTGGATACACATTCACT GAATACGCCATGCACTGG GTGAAGCAGAGCCATGGA ATGAGCCTTGAGTGGATT GGAGGTATTAATCCTAGC AATGGCAATGCTATCTAC AACCAGATATTCAAGGAC AAGGCCACACTGACTGTG GACAGGTCCTCCAGCACA GCCTACATGGGCCTCCGC AGCCTGACATTTGGGGAT TCTGGAGTCTACTTCTGT GTAAGACGACAACTGGAC TTCTTTGACTATTGGGGC CAGGGCGCCTCTCTCACA GTCTCCTCA | 12 | 208B-560H | EVQLQQSGPELEKPGASV KISCKTSGYTFTEYAMHW VKQSHGMSLEWIGGINPS NGNAIYNQIFKDKATLTV DRSSSTAYMGLRSLTFGD SGVYFCVRRQLDFFDYWG QGASLTVSS |
| 208A-830H | 13 | GAGGTCCGGCTGCAGCAG CCTGGACCTGAGGTGGAA AAGCCTGGGGCTTCAGTG AAGATATCCTGCAAGACT TCTGGATACACATTCACT GAATACGCCATCCACTGG GTGAAACAGAGCCATGGA GAGAGCCTTGAGTGGATT GGAGGTATTAATCCTAGC AATGGCGATCCTATCTAT AACCAGATATTCAAGGAC AAGGCCACACTGACTGTG GACAGGTCCTCCAACACA GCCTACATGGGCCTCCGC AGCCTGACAGTTGGGGAT TCTGGAGTCTACTTCTGT GTTAGACGACAACTGGAC TACTTTGACTTTTGGGGC | 14 | 208A-830H | EVRLQQPGPEVEKPGASV KISCKTSGYTFTEYAIHW VKQSHGESLEWIGGINPS NGDPIYNQIFKDKATLTV DRSSNTAYMGLRSLTVGD SGVYFCVRRQLDYFDFWG QGASLTVSS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | CAGGGCGCCTCTCTCACA GTCTCCTCA | | | |
| 208A-134H | 15 | CAGGGTCAGATGCAGCAG TCTGGAGCTGAACTGGCG AAGCCTGGGGCTTCAGTG AAGCTGTCCTGCAAGACT TCTGGCTTCACCTTCAGC AGTAGTTATATAAGTTGG TTGAAGCAAAAGCCTGGA CAGAGTCTTGAGTGGATT GCATGGATTTATGCTGGA ACTGGTAATACTAACTAT AATCAGAAGTTCACAGAC AAGGCCCAACTGACTGTA GACACATCCTCCAGTACA GCCTACATGCAACTCAGC AGCCTGACAACTGAGGAC TCTGCCATCTATTACTGT GCGATAAGTGGGACGGGA TTTACTTACTGGGGCCAA GGGACTCTGGTCACTGTC TCTGCAACA | 16 | 208A-134H | QGQMQQSGAELAKPGASV KLSCKTSGFTFSSSYISW LKQKPGQSLEWIAWIYAG TGNTNYNQKFTDKAQLTV DTSSSTAYMQLSSLTTED SAIYYCAISGTGFTYWGQ GTLVTVSA |
| 208A-692H | 17 | CAGGGTCAGATGCAGCAG TCTGGAGCTGAACTGGTG AAGCCTGGGGCTTCAGTG AAGCTGTCCTGCAAGACT TCTGGCTTCACCTTCAGC AGTAGTTATATAAGTTGG TTGAAGCAAAAGCCTGGA CAGAGTCTTGAGTGGATT GCATGGATTTATGCTGGA ACTGGTAATACTAACTAT AATCAGAAGTTCACAGAC AAGGCCCAACTGACTGTA GACACATCCTCCAGTACA GCCTACATGCAACTCAGC AGCCTGACAACTGAGGAC TCTGCCATCTATTACTGT GCGATAAGTGGGACGGGA TTTACTTACTGGGGCCAA GGGACTCTGGTCACTGTC TCTGCAACA | 18 | 208A-692H | QGQMQQSGAELAKPGASV KLSCKTSGFTFSSSYISW LKQKPGQSLEWIAWIFAG TGNTNYNQKFTDKAQLTV DTSSSTAYMQLSSLTTED SAIYYCAISGTGFTYWGQ GTLVTVSA |
| 208A-557H | 19 | CAGGGTCAGATGCAGCAG TCTGGAGCTGAGCTGGCG AAGCCTGGGGCTTCAGTG AAACTGTCCTGCAAGACT TCTGGCTTCACCTTCAGC AGTAGTTATATAAGTTGG TTGAAGCAAAAGCCTGGA CAGAGTCTTGAGTGGATT GCATGGATTTTTGCTGGA ACTGGTAATACTAATTAT AATCAGAAGTTCACAGAC AAGGCCCAACTGACTGTA GACACATCCTCCAGTACA GCCTACATGCAACTCAGC AGCCTGACAACTGAGGAC TCTGCCATCTATTACTGT GCGATAAGTGGGACGGGA TTTACTTACTGGGGCCAA GGGACTCTGGTCACTGTC TCTGCA | 20 | 208A-557H | QGQMQQSGAELVKPGASV KLSCKTSGFTFSSSYISW LKQKPGQSLEWIAWIYAG TGNTNYNQKFTDKAQLTV DTSSSTAYMQLSSLTTED SAIYYCAISGTGFTYWGQ GTLVTVSA |
| 208A-352H | 21 | CAGGGTCAGATGCAGCAG TCTGGAGCTGAGCTGGTG AAGCCTGGGGCTTCAGTG AAGCTGTCCTGCAAGACT TCTGGCTTCACCTTCAGC AGTAGTTTTATAAGTTGG TTGAAGCAAAAGCCTGGA CAGAGTCTTGAGTGGATT GCATGGATTTATGCTGGA ACTGGAAATACTAACTAT | 22 | 208A-352H | QGQMQQSGAELVKPGASV KLSCKTSGFTFSSSFISW LKQKPGQSLEWIAWIYAG TGNTNYNQKFTDKAQLTV DTSSSTAYMQFSSLTTED SAIYYCAISGTGFTYWGQ GTLVTVSA |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | AATCAGAAGTTCACAGAC AAGGCCCAACTGACTGTA GACACATCCTCCAGCACA GCCTACATGCAATTCAGC AGCCTGACGACTGAGGAC TCTGCCATCTATTACTGT GCGATAAGTGGGACGGGG TTTACTTACTGGGGCCAA GGGACTCTGGTCACTGTC TCTGCA | | | |
| 208A-983H | 23 | CAGGGTCAGATGCAGCAG TCTGGAGCTGAGCTGGTG AAGCCTGGGGCTTCAGTG AAGCTGTCCTGCAAGACT TCTGGCTTCACCTTCAGC AGTAGTTATTTTAGTTGG TTGAAGCAAAAGCCTGGA CAGAGTCTTGAGTGGATT GCATGGATTTATGCTGGA ACTGGTAATACTATCTAT AATCAGAAGTTCACAGAC AAGGCCCAACTGACTGTA GACACAGCCTCCAGCACA GCCTTCATGCAACTCAGC AGCCTGACAATTGAGGAC TCTGCCATCTACTACTGT GCGATAAGTGGGACGGGG TTTACTTACTGGGGCCAA GGGACTCTGGTCACTGTC TCTGCAACA | 24 | 208A-983H | QGQMQQSGAELVKPGASV KLSCKTSGFTFSSSYFSW LKQKPGQSLEWIAWIYAG TGNTIYNQKFTDKAQLTV DTASSTAFMQLSSLTIED SAIYYCAISGTGFTYWGQ GTLVTVSA |
| 208B-281H | 25 | CAGGGTCAGCTGCAGCAG TCTGGAGCTGAGCTGGTG AAGCCTGGGGCTTCAGTG AAGCTGTCCTGCAAGACT TCTGGCTTCACCTTCAGC AGTAGTTATATAAGTTGG TTGAAGCAAAGGCCTGGA CAGAGTCTTGAGTGGATT GCATGGATTTATGCTGGA ACTGGTGGTACTAACTAT AATCAGAAGTTCACAGAC AAGGCCCAACTGACTGTA GACACATCCTCCAGCACA GCCTACATGCAATTCAGC AGCCTGACAACTGAGGAC TCTGCCATCTATTACTGT GCGATAAGTGGGACGGGG TTTATTTACTGGGGCCAA GGGACTCTGGTCACTGTC TCTGCA | 26 | 208B-281H | QGQLQQSGAELVKPGASV KLSCKTSGFTFSSSYISW LKQRPGQSLEWIAWIYAG TGGTNYNQKFTDKAQLTV DTSSSTAYMQFSSLTTED SAIYYCAISGTGFIYWGQ GTLVTVSA |
| 208B-471H | 27 | CAGGGTCAGTTGCAGCAG TCTGGACCAGTACTGGTG AAGCCTGGGGCTTCAGAA ATACTATACTGCAAGACT TCTGGCTTCACCTTCAGC AGTACCTATATAAGTTGG TTGAAGCAAAAGCCTGGA CAGAGTCTTGAGTGGATT GCGTGGATTTATGCTGGA ACTGGTGCTACTAATTAT AATCAGAAGTTCACAGGC AAGGCCCAACTGACTGTA GACGCTTCCTCCAACACA GCCTACATGCACTTCAGC GGCCTGACACCTGAGGAC TCTGCCATCTATTACTGT GCAATTTCTGGGGCGGGG GTTTACTGGGGCCAAGGG ACTCTGGTCACTGTCTCT GCA | 28 | 208B-471H | QGQLQQSGPVLVKPGASE ILYCKTSGFTFSSTYISW LKQKPGQSLEWIAWIYAG TGATNYNQKFTDKAQLTV DASSNTAYMHFSGLTPED SAIYYCAISGAGVYWGQG TLVTVSA |
| 208A-207H | 29 | CAGGGCCAACTGCAGCAG CCTGGGGCTGAGTTTGTG | 30 | 208A-207H | QGQLQQPGAEFVKPGASL KLSCRASGYTFTSYWIHW |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | AAGCCTGGGGCTTCACTG AAGCTGTCCTGCAGGGCT TCTGGCTACACCTTCACC AGCTACTGGATACACTGG GTGAAGCAGAGGCCTGGA CAAGGCCTTGAGTGGATT GGAGAAATTGATCCTTCT GACAGTTATATTAACCAG AATCAAAAGTTCAGGGGC AAGGCCACATTGACTGTG GACAAATCCTCCAGCACA GCCTACATGGAACTCAGC GGCCTGACATCTGAAGAC TCTGCGGTCTATTACTGT GCAAGACATTACTACGGT GTTCTTGACTCCTGGGGC CAAGGTACCACTCTCACA GTCTCCTCAACA | | | VKQRPGQGLEWIGEIDPS DSYINQNQKFRGKATLTV DKSSSTAYMELSGLTSED SAVYYCARHYYGVLDSWG QGTTLTVSS |
| 208A-638H | 31 | CAGGGCCAACTGCAGCAG CCTGGGGCTGAGTTTGTG AAGCCTGGGGCTTCACTG AAGCTGTCCTGCAGGGCT TCTGGCTACACCTTCACC AGCTACTGGATTCACTGG GTGAAGCAGAGGCCTGGA CAAGGCCTTGAGTGGATC GGAGAAGTTGATCCTTCT GACAGTTATATTAACCAG AATGAAAAGTTCAGGGGC AAGGCCACATTGACTGTG GACAAATCCTCCAGCACA GCCTACATGCAGCTCGGC AGCCTGACATCTGAAGAC TCTGCGGTCTATTACTGT GCAAGACATTACTACGGT GTTCTTGACTCCTGGGGC CAAGGCACCGCTCTCACA GTCTCCTCA | 32 | 208A-638H | QGQLQQPGAEFVKPGASL KLSCRASGYTFTSYWIHW VKQRPGQGLEWIGEVDPS DSYINQNEKFRGKATLTV DKSSSTAYMQLGSLTSED SAVYYCARHYYGVLDSWG QGTALTVSS |
| 208B-515H | 33 | CAGGTCCAACTGCAGCAG CCTGGGGCTGAACTTGTG AAGCCTGGGGCTTCACTG AAGCTGTCCTGCAGGGCC TCTGGCTACACCTTCACC AGCTACTGGATTCACTGG GTGAAGCAGAGGCCTGGA CAAGGCCTTGAGTGGATC GGAGAGATTGATCCTTCT GATAGTTATACTAACTAC AATCAAAAGTTCAAGGGC AAGGCCACATTGACTGTA GACAAATCCTCCAGGGCA GCCTACATGCAGCTCAGC AGCCTGACATCTGAGGAC TCTGCGGTCTATTACTGT GCAAGACATTACTACGGT GTCTTTGACTCCTGGGGC CAAGGCACCAAACTCACA GTCTCCTCA | 34 | 208B-515H | QVQLQQPGAELVKPGASL KLSCRASGYTFTSYWIHW VKQRPGQGLEWIGEIDPS DSYTNYNQKFKGKATLTV DKSSRAAYMQLSSLTSED SAVYYCARHYYGVFDSWG QGTKLTVSS |
| 208A-874H | 35 | CAGGTCCAACTGCAGCAG CCTGGGGCTGAGCTTGTG AAGCCTGGGGCTTCAGTG AAGCTGTCCTGCAAGGCT TCTGGCTACACCCTCAGT AGCTATTGGATGCACTGG GTGAAGCAGAGGCCTGGA CAAGGCCTTGAGTGGATC GGAGAGATTCATCCTTCT GATAGTTATACTAGCTAC AATCAAAAGTTCAAGGAC AAGGCCACATTGACTGTA GACAAATCCTCCAGCACA GCCTACATGCAGCTCAGC AGCCTGACATCTGAGGAC | 36 | 208A-874H | QVQLQQPGAELVKPGASV KLSCKASGYTLSSYWMHW VKQRPGQGLEWIGEIHPS DSYTSYNQKFKDKATLTV DKSSSTAYMQLSSLTSED SAVYYCARGGYYRYDEFA YWGQGTLVTVSA |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | TCTGCAGTCTATTACTGT GCAAGGGGGGGCTACTAT AGGTACGACGAGTTTGCT TACTGGGGCCAAGGGACT CTGGTCACTGTCTCTGCA | | | |
| 208B-911H | 37 | CAGGTCCATCTGCAGCAG CCTGGGGCTGAGCTGGTG AGGCCTGGGGTTTCAGTG AAGCTGTCCTGCAAGGCT TCTGGCTACACCTTCACC ACCTACTCGATAAACTGG ATGAAGCAGAGGCCTGGA CAAGGCCTTGAGTGGATC GGAAATATTTATCCTTCT ACCAGTCATACTAACTAC AATCAAAAGTTCAGGGAC AAGGCCACAATGACTGTA GACAAATCCTCCAGCACA GCCTACATGCAGCTCAGC AGCCCGACATCTGAGGAC TCTGCGGTCTATTATTGT ACAATAAATGCCTATTCT ATGGACTACTGGGGTCAA GGAACCTCAGTCACCGTC TCCTCA | 38 | 208B-911H | QVHLQQPGAELVRPGVSV KLSCKASGYTFTTYSINW MKQRPGQGLEWIGNIYPS TSHTNYNQKFRDKATMTV DKSSSTAYMQLSSPTSED SAVYYCTINAYSMDYWGQ GTSVTVSS |
| 208B-1096H | 39 | CAGGTCCAGCTTCAGCAG TCTGGGGCTGGACTGGCA AAACCTGGGGCCTCAGTG AAGATGTCCTGCAAGGCT TCTGGCTACACCTTTACT GCCAACAAGATGCACTGG GCAAAACAGCGGCCTGGA CAGGGTCTGGAATGGATT GGATACATTGATCCTAGC TCTGGTTATACTGAATAC AATCATAAGATCCAGTAC AAGGCCACTTTGACTGCA GACACATCCTCCAGCACA GCCTACATGCAACTGAGC ACCCTAACATTTGAAGAC TCTGCAGTCTATTACTGT ACAAATTTTGCTTACTGG GGCCAAGGGACTCTGGTC ACTGTCTCAGCAACA | 40 | 208B-1096H | QVQLQQSGAGLAKPGASV KMSCKASGYTFTANKMHW AKQRPGQGLEWIGYIDPS SGYTEYNHKIQYKATLTA DTSSSTAYMQLSTLTFED SAVYYCTNFAYWGQGTLV TVSA |
| 208B-589H | 41 | CAGGTCCAGCTTCAGCAG TCTGGGGCTGGACTGGCA AAACCTGGGGCCTCAGTG AAGATGTCCTGCAAGGCT TCTGGCTACACCTTTACT GCCAACAAGATGCACTGG GCAAAACAGCGGCCTGGA CAGGGTCTGGAATGGATT GGATACATTGATCCTAGC TCTGGTTATACTGAATAC AATCATAAGATCCAGGAC AAGGCCACATTGACTGCA GACACATCCTCCAGCACA GCCTACATGCAACTGAGC AGCCTAACATTTGAAGAC TCTGCAGTCTATTACTGT ACAAATTTTGCTTACTGG GGCCAAGGGACTCTGGTC ACTGTCTCAGCA | 42 | 208B-589H | QVQLQQSGAGLAKPGASV KMSCKASGYTFTANKMHW AKQRPGQGLEWIGYIDPS SGYTEYNHKIQDKATLTA DTSSSTAYMQLSSLTFED SAVYYCTNFAYWGQGTLV TVSA |
| 208B-395H | 43 | CAGGTCCAGCTTCAGCAG TCTGGGGCTGGACTGGCA AAACCTGGGGCCTCAGTG AAGATGTCCTGCAAGGCT TCTGGCTATACCTTTACT GCCAACAAGATGCACTGG ACAAAACAGCGGCCTGGA CAGGGTCTGGAATGGATT GGATACATTGATCCTAGC | 44 | 208B-395H | QVQLQQSGAGLAKPGASV KMSCKASGYTFTANKMHW TKQRPGQGLEWIGYIDPS SGYTQYNHKIQDKATLTA DTSSSTAYMQLSSLTFED SAVYYCTNFAYWGQGTLV TVSA |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | TCTGGTTATACTCAATAC AATCATAAGATCCAGGAC AAGGCCACATTGACTGCA GACACATCCTCCAGCACA GCCTACATGCAACTGAGC AGCCTAACATTTGAAGAC TCTGCAGTCTATTACTGT ACAAATTTTGCTTACTGG GGCCAAGGGACTCTGGTC ACTGTCTCAGCA | | | |
| 208B-189H | 45 | CAGGTCCACCTTCAGCAG TCTGGGGCTGAACTGGCC AAACCTGGGGCCTCAGTG CAGATGTCCTGCAAGGCT TCTGGCTACACCTTTACT GCCAACAAGATGCACTGG GCAAGACAGCGGCCTAGA CAGGGTCTGGAATGGATT GGATACATTGATCCTGCC TCTGGCTATACTGAATAC AATCAGAAGATCAAGGAC AGGGCCACATTGACTGCA GACAAATCCTCCAGCACA GCCTACATGCAACTGAGC AGCCTGACATCTGAGGAC TCTGCAGTCTATTACTGT ACAAATTTTGCTTACTGG GGCCAAGGGACTCTGGTC ACTGTCTCTACAACA | 46 | 208B-189H | QVHLQQSGAELAKPGASV QMSCKASGYTFTANKMHW ARQRPRQGLEWIGYIDPA SGYTEYNQKIKDRATLTA DKSSSTAYMQLSSLTSED SAVYYCTNFAYWGQGTLV TVST |
| 208B-547H | 47 | CAGGTCCAGCTTCAGCAG TCTGGGGCTGAACTGGCA AAACCTGGGGCCTCAGTG AAGATGTCCTGCAAGGCT TCTGGCTACACCTTTACT AGCAACAAGATGCACTGG GCAAAACAGCGGCCTGGA CAGGGTCTGGAATGGATT GGATACATTGATCCTAGC TCTGGTTATACTGAATAC AATCAGAAGATCAAGGAC AAGGCCACATTGACTGCA GACAAATCCTCCAGCACA GCCTACATGCAACTGAGC AGCCTGACATCTGAGGAC TCTGCAGTCTATTACTGT ACAAATTTTGCTTACTGG GGCCAAGGGACTCTGGTC ACTGTCTCTGCAACA | 48 | 208B-547H | QVQLQQSGAELAKPGASV KMSCKASGYTFTSNKMHW AKQRPGQGLEWIGYIDPS SGYTEYNQKIKDKATLTA DKSSSTAYMQLSSLTSED SAVYYCTNFAYWGQGTLV TVSA |
| 208A-210H | 49 | CAGGTCCAGTTGCAGCAG TCTGGACCTGAGTTGGTG AAGCCTGGGGCTTCAATG AGGATATCCTGCAAGGCT TCTGGCTACACCTTCACA AGCTACTATGTACACTGG ATAAAGCAGAGGCCTGGA CAGGGACTTGAGTGGATT GGATGTATTTATCCTGGA GATGTTAATACTGACTAT AATGAGAAGTTCAAGGGC AAGGCCACGCTGACTGCA GACAAATCCTCCAGCACA GCCTACATGCAGGTCAGC ACCCTGACCTCTGAGGAC TCTGCGATCTATTTCTGT GTCCTTTATTACTACGGT AGTTTTGCTTACTGGGGC CAAGGGACTCTGGTCACT GTCTCTGCA | 50 | 208A-210H | QVQLQQSGPELVKPGASM RISCKASGYTFTSYYVHW IKQRPGQGLEWIGCIYPG DVNTDYNEKFKGKATLTA DKSSSTAYMQVSTLTSED SAIYFCVLYYYGSFAYWG QGTLVTVSA |
| 208A-422H | 51 | GATGTACAGCTTCAGGAG TCAGGACCTGGCCTCGTG AATCCTTCTCAGTCTCTG TCTCTCACCTGCTCTGTC | 52 | 208A-422H | DVQLQESGPGLVNPSQSL SLTCSVTGYSITSGYYWI WIQQSPGNKLEWMGYIKY DGGNNYSPSLKNRISIAR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | ACTGGCTACTCCATCACC AGTGGTTATTACTGGATC TGGATCCAGCAGTCTCCA GGAAACAAACTGGAATGG ATGGGCTACATAAAGTAC GACGGTGGCAATAACTAC AGCCCATCTCTCAAAAAT CGAATCTCCATCGCTCGT GACACATCTAAGAACCAG TGTTTCCTGAAGTTGAAT TCTGTGACTATTGAGGAC ACAGCTACATATTACTGT ACAAGAGGGTCGGACTCC TTTGACTACTGGGGCCAA GGCACCACTCTCACAGTC TCCTCA | | | DTSKNQCFLKLNSVTIED TATYYCTRGSDSFDYWGQ GTTLTVSS |
| 208A-442H | 53 | GATGTACAGCTTCAGGAG TCAGGACCTGGCCTCGTG AATCCTTCTCAGTCTCTG TCTCTCACCTGCTCTGTC ACTGGCTACTCCATCACC AGTGGTTATTACTGGATC TGGATCCGGCAGTTTCCA GGAAACAAACTGGAATGG ATGGGCTACATAAAGTAC GACGGTGGCAATAACTAC AGCCCATCTCTCAAAAAT CGAATCTCCATCGCTCGT GACACATCTAAGAACCAG TTTTTCCTGAAGTTGAAT TCTGTGACTATTGAGGAC ACAGCTACATATTACTGT ACAAGAGGGTCGGACTCC TTTGACTACTGGGGCCAA GGCACCACTCTCACAGTC TCCTCA | 54 | 208A-442H | DVQLQESGPGLVNPSQSL SLTCSVTGYSITSGYYWI WIRQFPGNKLEWMGYIKY DGGNNYSPSLKNRISIAR DTSKNFFLKLNSVTIED TATYYCTRGSDSFDYWGQ GTTLTVSS |
| 208B-862H | 55 | GATGTGCAGCTTCAGGAG TCGGGACCTGGCCTGGTG AAACCTTCTCAGTCTCTG TCCCTCACCTGCACTGTC ACTGGCTACTCAATCACC AGTGATTATGCCTGGAAC TGGATCCGGCAGTTTCCT GGAAACAAACTGGAGTGG ATGGGCTACATAAGCTAC AGTGGTACCACTGTCTAC AGCCCATCTCTCAAAAGT CGAATCTCCATCACTCGG GACACATCCAAAAACCAG TTCTTCCTGCAATTGAAT TCTGTGACTATTGAGGAC TCAGCCACGTATTATTGT GGGGGTAATTACTGGGGC CAAGGGACTCTGGTCACT GTCTCTGCA | 56 | 208B-862H | DVQLQESGPGLVKPSQSL SLTCTVTGYSITSDYAWN WIRQFPGNKLEWMGYISY SGTTVYSPSLKSRISITR DTSKNFFLQLNSVTIED SATYYCGGNYWGQGTLVT VSA |
| 208A-967H | 57 | CAGGTGCAGCTGGAGGAG TCAGGACCTGGCCTGGTG GCGCCCTCACAGAGCCTG TCCATCACTTGCACTGTC TCTGGATTTTCATTAACC AGCTATGTGTACACTGG GTTCGCCAGCCTCCAGGA AAGGGTCTGGAGTGGCTG GGAGTAATATGGGCTGTT GGAAGTATAAATTATAAT TCGGCTCTCATGTCCAGA CTGAGCATCAGCAAAGAC AACTCCAAGAGCCAAGTT TTCTTAAAAATGAACAGT CTACGAACTGATGACACA GCCATGTACTACTGTGCC AGAGATCGGACTACGGCT ACCCCCTTCTTTGACTAC | 58 | 208A-967H | QVQLEESGPGLVAPSQSL SITCTVSGFSLTSYGVHW VRQPPGKGLEWLGVIWAV GSINYNSALMSRLSISKD NSKSQVFLKMNSLRTDDT AMYYCARDRTTATPFFDY WGQGTTLTVSS |

| mAb Clone | SEQ ID | Nucleic Acid Seq | SEQ ID | mAb Clone | Amino Acid Seq |
|---|---|---|---|---|---|
| | | TGGGGCCAAGGCACCACT CTCACAGTCTCCTCATCC AAAACA | | | |
| 208B-517H | 59 | CAGGTGCAGCTGAAGCAG TCAGGACCTGGCCTAGTG CAGCCCTCACAGAGCCTG TCCATCACCTGCACAGTC TCTGGTTTCTCATTAATT ACCCATGGTGTACACTGG GTTCGCCAGTCTCCAGGA AAGGGTCTGGAGTGGCTG GGAGTGATATGGAGTGGT GGAAGCACAGACTATAAT GCAGCTTTCATATCCAGA CTGAGCATCAGCAAGGAC ACCTCCAAGAGCCAAGTT TTCCTTAAAATGAGCAGT CTGCAAGCTGATGACACA GCCATATACTACTGTGCC AGAAATGGGGGGCTACG GCCTTTGACTACTGGGGC CAAGGCACCACTCTCACA GTCTCCTCA | 60 | 208B-517H | QVQLKQSGPGLVQPSQSL SITCTVSGFSLITHGVHW VRQSPGKGLEWLGVIWSG GSTDYNAAFISRLSISKD TSKSQVFLKMSSLQADDT AIYYCARNGGATAFDYWG QGTTLTVSS |
| 208B-822H | 61 | CAGGTACAGCTGAAGCAG TCAGGACCTGGCCTAGTG CAGCCCTCACAGAGCCTG TCCATCACCTGCACAGTC TCTGGTTTCTCATTAATT ACCTATGGTGTACACTGG GTTCGCCAGTCTCCAGGA AAGGGTCTGGAGTGGCTG GGAGTGATATGGGGTGGT GGAAGCACAGGCTATAAT GCAGCTTTCGTATCCAGA CTGAACATCACCAAGGAC AACTCCAAGAGCCAAGTT TTCTTTAAAATGAACAGT CTGCAACCTGATGACACA GCCATATACTACTGTGCC AGAAATGGAGGGGCTACG GTCTTTGACTACTGGGGC CAAGGCACCACTCTCACA GTCTCCTCA | 62 | 208B-822H | QVQLKQSGPGLVQPSQSL SITCTVSGFSLITYGVHW VRQSPGKGLEWLGVIWGG GSTGYNAAFVSRLNITKD NSKSQVFFKMNSLQPDDT AIYYCARNGGATVFDYWG QGTTLTVSS |
| 208B-1024H | 63 | GAGGTGCAGCTGGTGGAG TCTGGGGGAGACTTAGTG AAGCCTGGAGGGTCCCTG AAACTCTCCTGTGCAGCC TCTGGATTCACTTTCAGT AACTATGGCATGTCTTGG GTTCGCCAGACTCCAGAC AAGAGGCTGGAGTGGGTC GCAACCATTAGTAGTGGT GGTAGTTATAGCTACTAT CCAGACAGTGTAAAGGGG CGGTTCACCATCTCCAGA GACAATGCCAAGAACATC CTGTACCTGCAAATGAGC AGTCTGAAGTCTGAGGAC ACAGCCATGTATTACTGT GCAAGTCTCTACTACGGC TACGGGGACTACTGGGGC CAAGGCACCGCTTTCACA GTCTCCTCA | 64 | 208B-1024H | EVQLVESGGDLVKPGGSL KLSCAASGFTFSNYGMSW VRQTPDKRLEWVATISSG GSYSYYPDSVKGRFTISR DNAKNILYLQMSSLKSED TAMYYCASLYYGYGDYWG QGTAFTVSS |
| 208B-327H | 65 | GAAGTGCAGCTGGTGGAG TCTGGGGGAGGCTTGGTG AAGCCTGGAGGGTCCCTG AAACTCTCCTGTGCAGCC TCTGGATTCACTTTCAGT GACTCTTATATGTATTGG GTTCGCCAGACTCCGGAC CAGAGGCTGGAGTGGGTC GCAACCATTAGTGATGGT | 66 | 208B-327H | EVQLVESGGGLVKPGGSL KLSCAASGFTFSDSYMYW VRQTPDQRLEWVATISDG GSYTFYP DSVKGRFTISR DNAQNNLYLQMSSLKSED TAMYYCASPHAGYFGWFA YWGRGTLVTVSA |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GGTAGTTACACCTTCTAT CCAGACAGTGTGAAGGGA CGATTCACCATCTCCAGA GACAATGCCCAGAACAAC CTGTACCTGCAAATGAGC AGTCTGAAGTCTGAGGAC ACAGCCATGTATTACTGT GCATCCCCCCATGCTGGC TACTTCGGCTGGTTTGCT TACTGGGGCCAGGGACT CTGGTCACTGTCTCTGCA | | | |
| 208B-353H | 67 | GAGGTGCAGCTGGTGGAG TCTGGGGGAGACTTAGTG AAGCCTGGAGGGTCCCTG AAACTCTCCTGTGCAGCC TCTGGATTCACTTTCAAT CACTATGGCATGTCTTGG GTTCGCCAGCCTCCAGAC AAGAGACTGGAGTGGGTC GCAACCATTAGTAGTGGT GGTGGTTACACCTACTAT CCAGACAGTGTGAAGGGG CGCTTCACCATCTCCAGA GACAATGCCAAGGACACC CTGTCCCTGCAAATGAGC AGTCTGAGGTCTGGGGAC ACAGCCGTGTATTACTGT GCAAGCCTATACGGTAGC CTGTTTGCTTACTGGGGC CAAGGGACTCTGGTCACT GTCTCTGCA | 68 | 208B-353H | EVQLVESGGDLVKPGGSL KLSCAASGFTFNHYGMSW VRQPPDKRLEWVATISSG GGYTYYPDSVKGRFTISR DNAKDTLSLQMSSLRSGD TAVYYCASLYGSLFAYWG QGTLVTVSA |
| 208B-178H | 69 | GACGTGAAGCTCGTGGAG TCTGGGGGAGGCTTAGTG AAGCTTGGAGGGTCCCTG AAACTCTCCTGTGCAGCC TCTGGATTCACTTTCAGT AGCTATTACATGTCTTGG GTTCGCCAGACTCCAGAG AAGAGGCTGGAGTTGGTC GCAGCCATTAATAGTAAT GGTGGTAGCACCTACTAT CCAGACACTGTGAAGGGC CGATTCACCATCTCCAGA GACAATGCCAAGAACACC CTGTACCTGCAAATGAGC AGTCTGAAGTCTGAGGAC ACAGCCTTGTATTACTGT GCAAGACATGGGGGACTG GGACGTAGGGACTGGTAC TTCGATGTCTGGGGCGCA GGGACCACGGTCACCGTC TCCTCA | 70 | 208B-178H | DVKLVESGGGLVKLGGSL KLSCAASGFTFSSYYMSW VRQTPEKRLELVAAINSN GGSTYYPDTVKGRFTISR DNAKNTLYLQMSSLKSED TALYYCARHGGLGRRDWY FDVWGAGTTVTVSS |
| 208B-672H | 71 | GAAGTGAAACTGGTGGAG TCTGGGGGAAGTTTAGTG CAGCCTGGAGGGTCCCTG AAACTCTCCTGCGCAGCC TCTGGATTCAATTTCAAT ACCTATGCCATGTCTTGG GTTCGCCAGACTCCAGAG AAGAGGCTGGAGTGGGTC GCATACATTAGTAATGGT GGTGGTAACACCTACTAT GTAGACACTGTAAAGGGC CGATTCACCATCTCCAGA GACAATGCCAAGAACACC CTGTACCTGCAATGAGC AGTCTGAAGTCTGAGGAC ACGGCCATGTATTACTGT GCAAGACATGGGCTCTAC TGGGGCTATTCTATGGAC TACTGGGGTCAAGGAACC TCAGTCACCGTCTCCTCA | 72 | 208B-672H | EVKLVESGGSLVQPGGSL KLSCAASGFNFNTYAMSW VRQTPEKRLEWVAYISNG GGNTYYVDTVKGRFTISR DNAKNTLYLRMSSLKSED TAMYYCARHGLYWGYSMD YWGQGTSVTVSS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-793H | 73 | GAAGTGAAGCTGGTGGAG TCTGGGGGAGGTTTAGTG CAGCCAGGAGGGTCCCTG AAACTCTCCTGTGCAGCC TCTGGATTCACTTTCAGT AGCTATGCCATGTCTTGG GTTCGCCAGACTCCAGAG AGGAGGCTGGAGTGGGTC ACATACATTAGTAATGGT GGTGGTAGCACCTACTAT TCAGACACTGTAAAGGGC CGATTCACCTTCTCCAGA GACAATGCCAAGAACACC CTGTACCTGCAAATGAGC AGTCTGAAGTCTGAGGAC ACGGCCATGTATTACTGT GCAAGACATGGACTGGGA AGGACAGGGTTTGCTTCC TGGGGCCAAGGGACTCTG GTCACTGTCTCTGCA | 74 | 208B-793H | EVKLVESGGGLVQPGGSL KLSCAASGFTFSSYAMSW VRQTPERRLEWVTYISNG GGSTYYSDTVKGRFTFSR DNAKNTLYLQMSSLKSED TAMYYCARHGLGRTGFAS WGQGTLVTVSA |
| 208B-826H | 75 | GATGTGCAGCTGGTGGAG TCTGGGGGAGGCCTAGTG CAGGCTGGAGGGTCCCGG AAACTCTCCTGTGCAGCC TCTGGATTCCCTTTCAGT TCCTTTGGAATGCACTGG GTTCGTCAGGCTCCAGAG AAGGGGCTGGAGTGGGTC GCCTCCATTAGTAGTCGC ACTAGTAAGATCTACTAT GCAGACAACCTGAAGGGC CGATTCACCATCTCCAGA GACAATCCCAAGAACACC CTGTTCCTGCAAATGACC AGTCTTGGATCTGAGGAC ACGGCCATGTATTACTGT GTAAGATCCGTCTTTGGT AATTCTTACTGGTTTTTC GATGTCTGGGGCGCAGGG ACCACGGTCACCGTCTCC TCA | 76 | 208B-826H | DVQLVESGGGLVQAGGSR KLSCAASGFPFSSFGMHW VRQAPEKGLEWVASISSR TSKIYYADNLKGRFTISR DNPKNTLFLQMTSLGSED TAMYYCVRSVFGNSYWFF DVWGAGTTVTVSS |
| 208B-174H | 77 | GAAGTGAAGCTTGAGGAG TCTGGAGGAGGCTTGGTA CAACCTGGGGGATCCATG AAACTCTCCTGTGTAGCC TCTGGATTTTCTTTCAGT AGCTACTGGATGTCTTGG GTCCGCCAGTCTCCAGAG AAGGGGCTTGACTGGGTT GCTGAAATTAGATTGAGA TCTGATAATTATGCAACC CATTATGCGGAGTCTGTG AAAGGGAGGTTCACCATC TCAAGAGATGATTCCATA AGTCGTCTCTACCTGCAA ATGAACACCTTAAGAGCT GAAGACACTGGAATTTAT TACTGTACATGGATGACG TACTGGGGCCAAGGGACT CTGGTCACTGTCTCTGCA ACA | 78 | 208B-174H | EVKLEESGGGLVQPGGSM KLSCVASGFSFSSYWMSW VRQSPEKGLDWVAEIRLR SDNYATHYAESVKGRFTI SRDDSISRLYLQMNTLRA EDTGIYYCTWMTYWGQGT LVTVSA |
| 208B-408H | 79 | GAGGTGAAGCTGGTGGAG TCTGGAGGAGGCTTGGTA CAGCCTGGGGGTTCTCTG AGACTCTCCTGTGCAAGT TCTGGGTTCACCTTCACT GATTACTACATGAGCTGG GTCCGCCAGCCTCCAGGA AAGGCACTTGAGTGGTTG GGTTTTATTAGAAACAAA GCTTATGGTTACACGACC GAGTTCAGTGCATCTGTG AACGGTCGGTTCACCATC | 80 | 208B-408H | EVKLVESGGGLVQPGGSL RLSCASSGFTFTDYYMSW VRQPPGKALEWLGFIRNK AYGYTTEFSASVNGRFTI SRDDSQSVPYLQMNTLRA EDSATYYCARVLYYDYGG FAYWGQGTLVTVST |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | TCCAGAGATGATTCCCAA AGCGTCCCCTATCTTCAA ATGAACACCCTGAGAGCT GAGGACAGTGCCACTTAT TACTGTGCGAGAGTCCTC TACTATGATTACGGGGGA TTTGCTTACTGGGGCCAA GGGACTCTGGTCACTGTC TCTACA | | | |
| 208B-612H | 81 | GAGGTCCAGCTGCAGCAG TCTGGACCTGAGCTGGTA AAGCCTGGGGCTTCAGTG AAGATGTCCTGTAAGGCT TCCGGATACAGATTCACT AGCTATGTTATGCACTGG GTGAGGCAGAAGCCTGGA CAGGGCCTTGAGTGGATT GGATATATTGATCCTCAC AATGATGATACAAAATAC AGTGAGAAGTTCAGAGGT AAGGCCACACTGACTTCA GACAAGTCCTCCACCACA GCCTACATGGAGCTCAGC AGCCTGACCTCTGAGGAC TCTGCGGTCTATTACTGT GTGAGATATTCTTACGAC AGGGATTACAGTCCTATG GACTACTGGGGTCAAGGA ACCTCAGTCACCGTCTCC TCA | 82 | 208B-612H | EVQLQQSGPELVKPGASV KMSCKASGYRFTSYVMHW VRQKPGQGLEWIGYIDPH ND-- DTKYSEKFRGKATLTSDK SSTTAYMELSSLTSEDSA VYYCVRYSYDRDYSPMDY WGQGTSVTVSS |
| 208A-877H | 83 | CAGCTGCAACAGTCTGGA CCTGAGCTGGTGAAGCCT GGGGCTTCAGTGAAAATT TCCTGCAAGACTTCTGGA TACACATTCACTGAAAAC GCCATGCACTGGGTGAAG CAGAGCCGTGGAAAGAGC CTTGAGTGGATTGGAGGT GTTAATCCTAACAATGGT GATACTGTCTACACCCAG AAGTTCAAGGGCAAGGCC ACATTGACTGTAGCCAAG TCTTCCAGCACAGCCTAC ATGGAGCTCCGCACCATG ACATGTGAGGAATCTACA GTGTATTACTGTGCAAGC CGGGAACCGGACTTCTTT GACTACTGGGGCCAAGGC TCCTCTGTCACAGTCTCC TCA | 84 | 208A-877H | QLQQSGPELVKPGASVKI SCKTSGYTFTENAMHWVK QSRGKSLEWIGGVNPNNG DTVYTQKFKGKATLTVAK SSSTAYMELRTMTCEEST VYYCASREPDFFDYWGQG SSVTVSS |
| 208B-251H | 85 | CAGCTGCAACAGTCTGGA CCTGTACTGGTGAAGCCT GGGGCTTCAGTGAAAATT TCCTGCAAGACTTCTGGA TACACATTCACTGAAAAC GCCATGCACTGGGTGAAG CAGAGCCATGGAAAGAGC CTTGAGTGGATTGGAGGT GTTAATCCTAACAATGGT GATACTATCTACAACCAG AAGTTCAAGGGCAAGGCC ACATTGACTGTAGACAAG TCCTCCAGCACAGCCTTC ATGGAGCTCCGCAGCCTG ACATCTGAAGAATCCCCA GTCTATTTCTGTGTAAGA CGGGAACTGGACTTCTTT GACTACTGGGGCCAAGGC ACCTCTGTCACAGTCTCC TCA | 86 | 208B-251H | QLQQSGPVLVKPGASVKI SCKTSGYTFTENAMHWVK QSHGKSLEWIGGVNPNNG DTIYNQKFKGKATLTVDK SSSTAFMELRSLTSEESP VYFCVRRELDFFDYWGQG TSVTVSS |
| 208A-110H 208B- | 87 | CAGCTGCAACAGTCTGGC CCTGTCCTGGTGAAGTCT | 88 | 208A-110H 208B- | QLQQSGPVLVKSGTSVKI SCKTSGYTFTENAMHWVK |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 1070H | | GGGACTTCAGTTAAAATT TCCTGCAAGACTTCTGGA TACACATTCACTGAAAAC GCCATGCACTGGGTGAAA CAGAGCCATGGACAGAGC CTTGAGTGGATTGGAGGT GTTAATCCTAACAATGGT GATACTATCTTCAACCAG AAGTTCAAGGGCAAGGCC ACATTGACTGTAGACAAG TCCTCCAGCACAGCCTTC ATGGAGCTCCGCAGCCTG ACATCTGAAGAATCCACA GTCTATTACTGTGTAAGA CGGGAACTGGACTTCTTT GACTACTGGGGTCAAGGC ACCTCTGTCACAGTCTCC TCA | | 1070H | QSHGQSLEWIGGVNPNNG DTIFNQKFKGKATLTVDK SSSTAFMELRSLTSEEST VYYCVRRELDFFDYWGQG TSVTVSS |
| 208A-334H 208A-920H | 89 | CAGCTGCAACAGTCTGGC CCTGTCCTGGTGAAGCCT GGGACTTCAGTGAAAATT TCCTGCAAGACTTCTGGA TACACATTCACTGAAAAC GCCATGCACTGGGTGAAA CAGAGCCATGAAAGAGC CTTGAGTGGATTGGAGGT GTTAATCCTAACAATGGT GATACTATCTTCAACCAG AAGTTCAAGGGCAAGGCC ACATTGACTGTAGACAAG TCCTCCAGCACAGCCTTC ATGGAGCTCCGCAGCCTG ACATCTGAAGAATCCACA GTCTATTACTGTGTAAGA CGGGAACTGGACTTCTTT GACTACTGGGGCCAAGGC ACCTCTGTCACAGTCTCC TCA | 90 | 208A-334H 208A-920H | QLQQSGPVLVKPGTSVKI SCKTSGYTFTENAMHWVK QSHGKSLEWIGGVNPNNG DTIFNQKFKGKATLTVDK SSSTAFMELRSLTSEEST VYYCVRRELDFFDYWGQG TSVTVSS |
| 208A-159H | 91 | CAGCTGCAACAGTCTGGA CCTGCCCAGGTGAAGCCT GGGGCTTCAGTGATGATT TCCTGCAAGACTTCTGGA TACACATTCACTGAAAAC GCCATGCACTGGGTGAAA CAGAGCCATGAAAGAGC CTTGAGTGGATTGGAGGT GTTAATCCTAACAATGGT GATACTATTTTCAACCAG AAGTTCAAGGACAAGGCC GCATTGACTGTAGACAAG TCCTCCAGCACAGCCTTC ATGGAGCTCCGCAGCCTG ACATCTGAGGAGTCCACA GTCTATTACTGTGTAAGA CGGGAATTGGACTTCTTT GACTACTGGGGCCAAGGC ACCTCTGTCACAGTCTCC TCA | 92 | 208A-159H | QLQQSGPAQVKPGASVMI SCKTSGYTFTENAMHWVK QSHGKSLEWIGGVNPNNG DTIFNQKFKDKAALTVDK SSSTAFMELRSLTSEEST VYYCVRRELDFFDYWGQG TSVTVSS |
| 208A-126H | 93 | CAGCTGCAACAGTCTGGA CCTGTCCTGGTGAAGCCT GGGGCTTCAGTGATGATT TCCTGCAAGACTTCTGGA TACACATTCACTGAAAAC GCCATGCACTGGGTGAAA CAGAGCCATGAAAGAGC CTTGAGTGGATTGGAGGT GTTAATCCTAACAATGGT GATACTATTTTCAACCAG AAGTTCAAGGGCAAGGCC ACATTGACTGTAGACAAG TCCTCCAACACAGCCTTC ACGGAGCTCCGCAGCCTG CCATCTGAAGAATCCACA | 94 | 208A-126H | QLQQSGPVLVKPGASVMI SCKTSGYTFTENAMHWVK QSHGKSLEWIGGVNPNNG DTIFNQKFKGKATLTVDK SSNTAFTELRSLPSEEST VYYCVRRGLDFFDYWGQG TSVTVSS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GTCTATTACTGTGTTAGA CGGGGATTGGACTTCTTT GACTACTGGGGCCAAGGC ACCTCTGTCACAGTCTCC TCA | | | |
| 208A-133H | 95 | CAGCTGCAACAGTCTGGC CCTGTCCTGGTGGGGCCT GGGGCTTCAGTGATGATT TCCTGCAAGACTTCTGGA TACACATTCACTGAAAAC GCCATGCACTGGGTGGAA CAGAGCCATGGAAAGAGC CTTGAGTGGATTGGAGGT GTTAATCCTAACAATGGT GATACTATTTTCAACCAG AAGTTCAAGGGCAAGGCC ACATTGACTGTAGACAAG TCCTCCAGCACAGCCTTC ATGGAGTTCCGCAGCCTG ACATCTGAAGAATCCACA GTCTATTACTGTGTAAGA CGGGAATTGGACTTCTTT GACTACTGGGGCCAAGGC ACCTCTGTCACAGTCTCC TCA | 96 | 208A-133H | QLQQSGPVLVGPGASVMI SCKTSGYTFTENAMHWVE QSHGKSLEWIGGVNPNNG DTIFNQKFKGKATLTVDK SSSTAFMEFRSLTSEEST VYYCVRRELDFFDYWGQG TSVTVSS |
| 208B-556H | 97 | CAGCTGCAACAGTCTGGA CCTGTCCTGGTGAAGCCT GGGGCTTCAGTGATGATT TCCTGCAAGACTTCTGGA TACACATTCACTGAAAAC GCCATGCACTGGGTGAAA CAGAGCCATGGAAAGAGC CTTGAGTGGATTGGAGGT GTTAATCCTAACAATGGT GATACTATTTTCAACCAG AAGTTCAAGGGCAAGGCC ACATTGACTGTAGACAAG TCCTCCAGCACAGCCTTC ATGGAGTTCCGCAGCCTG ACATCTGAAGAATCCACA GTCTATTACTGTGTAAGA CGGGAATTGGACTTCTTT GACTACTGGGGCCAAGGC ACCTCTGTCACAGTCTCC TCAACA | 98 | 208B-556H | QLQQSGPVLVKPGASVMI SCKTSGYTFTENAMHWVK QSHGKSLEWIGGVNPNNG DTIFNQKFKGKATLTVDK SSSTAFMEFRSLTSEEST VYYCVRRELDFFDYWGQG TSVTVSS |
| 208A-741H | 99 | CAGCTGCAACAGTCTGGA CCTGTCCTGGTGAAGCCT GGGGCTTCAGTGATGATT TCCTGCAAGACTTCTGGA TACACATTCACTGAAAAC GCCATGCACTGGGTGAAA CAGAGCCATGGAAAGAGC CTTGAGTGGATTGGAGGT GTTAATCCTAACAATGGT GATACTATTTTCAACCAG AAGTTCAAGGGCAAGGCC ACATTGACTGTAGACAAG TCCTCCAGCACAGCCTTC ATGGAGCTCCGCAGCCTG ACATCTGAAGAATCCACA GTCTATTACTGTGTAAGA CGGGAATTGGACTTCTTT GACTACTGGGGCCAAGGC ACCTCTGTCACAGTCTCC TCA | 100 | 208A-741H | QLQQSGPVLVKPGASVMI SCKTSGYTFTENAMHWVK QSHGKSLEWIGGVNPNNG DTIFNQKFKGKATLTVDK SSSTAFMELRSLTSEEST VYYCVRRELDFFDYWGQG TSVTVSS |
| 208A-1064 CDR H1 208B-1094 CDR H1 208A-293 CDR H1 | 101 | GAATACGCCATGCAC | 102 | 208A-1064 CDR H1 208B-1094 CDR H1 208A-293 CDR H1 | EYAMH |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208A-222 CDR H1 208B-560 CDR H1 | | | | 208A-222 CDR H1 208B-560 CDR H1 | |
| 208A-605 CDR H1 208A-830 CDR H1 | 103 | GAATACGCCATACAC | 104 | 208A-605 CDR H1 208A-830 CDR H1 | EYAIH |
| 208A-134 CDR H1 208A-692 CDR H1 208A-557 CDR H1 208B-281 CDR H1 | 105 | AGTAGTTATATAAGT | 106 | 208A-134 CDR H1 208A-692 CDR H1 208A-557 CDR H1 208B-281 CDR H1 | SSYIS |
| 208A-352 CDR H1 | 107 | AGTAGTTTTATAAGT | 108 | 208A-352 CDR H1 | SSFIS |
| 208A-983 CDR H1 | 109 | AGTAGTTATTTTAGT | 110 | 208A-983 CDR H1 | SSYFS |
| 208B-471 CDRH1 | 111 | AGCAGTACCTATATAAGT | 112 | 208B-471 CDR H1 | STYIS |
| 208A-207 CDR H1 208A-638 CDR H1 208B-515 CDR H1 | 113 | AGCTACTGGATACAC | 114 | 208A-207 CDR H1 208A-638 CDR H1 208B-515 CDR H1 | SYWIH |
| 208A-874 CDR H1 | 115 | AGCTATTGGATGCAC | 116 | 208A-874 CDR H1 | SYWMH |
| 208B-911 CDR H1 | 117 | CCTACTCGATAAAC | 118 | 208B-911 CDR H1 | TYSIN |
| 208B-1096 CDR H1 208B-589 CDR H1 208B-395 CDR H1 208B-189 CDR H1 | 119 | GCCAACAAGATGCAC | 120 | 208B-1096 CDR H1 208B-589 CDR H1 208B-395 CDR H1 208B-189 CDR H1 | ANKMH |
| 208B-547 CDR H1 | 121 | AGCAACAAGATGCAC | 122 | 208B-547 CDR H1 | SNKMH |
| 208A-210 CDR H1 | 123 | AGCTACTATGTACAC | 124 | 208A-210 CDR H1 | SYYVH |
| 208A-422 CDR H1 208A-442 CDR H1 | 125 | AGTGGTTATTACTGGATC | 126 | 208A-422 CDR H1 208A-442 CDR H1 | SGYYWI |
| 208B-862 CDR H1 | 127 | AGTGATTATGCCTGGAAC | 128 | 208B-862 CDR H1 | SDYAWN |
| 208A-967 CDR H1 | 129 | AGCTATGGTGTACAC | 130 | 208A-967 CDR H1 | SYGVH |
| 208B-517 CDR H1 | 131 | ACCCATGGTGTACAC | 132 | 208B-517 CDR H1 | THGVH |
| 208B-822 CDR H1 | 133 | ACCTATGGTGTACAC | 134 | 208B-822 CDR H1 | TYGVH |
| 208B-1024 CDR H1 | 135 | AACTATGGCATGTCT | 136 | 208B-1024 CDR H1 | NYGMS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-327 CDR H1 | 137 | GACTCTTATATGTAT | 138 | 208B-327 CDR H1 | DSYMY |
| 208B-353 CDR H1 | 139 | CACTATGGCATGTCT | 140 | 208B-353 CDR H1 | HYGMS |
| 208B-178 CDR H1 | 141 | AGCTATTACATGTCT | 142 | 208B-178 CDR H1 | SYYMS |
| 208B-672 CDR H1 | 143 | ACCTATGCCATGTCT | 144 | 208B-672 CDR H1 | TYAMS |
| 208B-793 CDR H1 | 145 | AGCTATGCCATGTCT | 146 | 208B-793 CDR H1 | SYAMS |
| 208B-826 CDR H1 | 147 | TCCTTTGGAATGCAC | 148 | 208B-826 CDR H1 | SFGMH |
| 208B-174 CDR F11 | 149 | AGCTACTGGATGTCT | 150 | 208B-174 CDR H1 | SYWMS |
| 208B-408 CDR H1 | 151 | GATTACTACATGAGC | 152 | 208B-408 CDR H1 | DYYMS |
| 208B-612 CDR H1 | 153 | AGCTATGTTATGCAC | 154 | 208B-612 CDR H1 | SYVMH |
| 208A-877 CDR H1<br>208B-251 CDR H1<br>208A-110 CDR H1<br>208B-1070 CDR H1<br>208A-334 CDR H1<br>208A-920 CDR H1<br>208A-159 CDR H1<br>208A-126 CDR H1<br>208A-133 CDR H1<br>208B-556 CDR H1<br>208A-741 CDR H1 | 155 | GAAAACGCCATGCAC | 156 | 208A-877 CDR H1<br>208B-251 CDR H1<br>208A-110 CDR H1<br>208B-1070 CDR H1<br>208A-334 CDR H1<br>208A-920 CDR H1<br>208A-159 CDR H1<br>208A-126 CDR H1<br>208A-133 CDR H1<br>208B-556 CDR H1<br>208A-741 CDR H1 | ENAMH |
| 208A-1064 CDR H2<br>208A-293 CDR H2 | 157 | GGTATCAATCCTACTAAT GGTGATACAATCTACAAC CAGAAGTTCAAGGAC | 158 | 208A-1064 CDR H2<br>208A-293 CDR H2 | GINPTNGDTIYNQKFKD |
| 208B-1094 CDR H2 | 159 | GGTATCAATCCTACTAAT GGTGATACAATCTACAAC CAGAGGTTCAAGGAC | 160 | 208B-1094 CDR H2 | GINPTNGDTIYNQRFKD |
| 208A-222 CDR H2 | 161 | GGTATTAATCCTAACAAT GGCAATGCTATCTACAAC CAGATATTCAAGGAC | 162 | 208A-222 CDR H2 | GINPNNGNAIYNQIFKD |
| 208A-605 CDR H2<br>208B-560 CDR H2 | 163 | GGTATTAATCCTAGCAAT GGCAATGCTATCTACAAC CAAATATTCAAGGAC | 164 | 208A-605 CDR H2<br>208B-560 CDR H2 | GINPSNGNAIYNQIFKD |
| 208A-830 CDR H2 | 165 | GGTATTAATCCTAGCAAT GGCGATCCTATCTATAAC CAGATATTCAAGGAC | 166 | 208A-830 CDR H2 | GINPSNGDPIYNQIFKD |
| 208A-134 CDR H2<br>208A-557 CDR H2 | 167 | TGGATTTATGCTGGAACT GGTAATACTAACTATAAT CAGAAGTTCACAGAC | 168 | 208A-134 CDR H2<br>208A-557 CDR H2 | WIYAGTGNTNYNQKFTD |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208A-352 CDR H2 | | | | 208A-352 CDR H2 | |
| 208A-692 CDR H2 | 169 | TGGATTTTTGCTGGAACT GGTAATACTAATTATAAT CAGAAGTTCACAGAC | 170 | 208A-692 CDR H2 | WIFAGTGNTNYNQKFTD |
| 208A-983 CDR H2 | 171 | TGGATTTATGCTGGAACT GGTAATACTATCTATAAT CAGAAGTTCACAGAC | 172 | 208A-983 CDR H2 | WIYAGTGNTIYNQKFTD |
| 208B-281 CDR H2 | 173 | TGGATTTATGCTGGAACT GGTGGTACTAACTATAAT CAGAAGTTCACAGAC | 174 | 208B-281 CDR H2 | WIYAGTGGTNYNQKFTD |
| 208B-471 CDR H2 | 175 | TGGATTTATGCTGGAACT GGTGCTACTAATTATAAT CAGAAGTTCACAGGC | 176 | 208B-471 CDR H2 | WIYAGTGATNYNQKFTG |
| 208A-207 CDR H2 | 177 | GAAATTGATCCTTCTGAC AGTTATATTAACCAGAAT CAAAAGTTCAGGGGC | 178 | 208A-207 CDR H2 | EIDPSDSYINQNQKFRG |
| 208A-638 CDR H2 | 179 | GAAGTTGATCCTTCTGAC AGTTATATTAACCAGAAT GAAAAGTTCAGGGGC | 180 | 208A-638 CDR H2 | EVDPSDSYINQNEKFRG |
| 208B-515 CDR H2 | 181 | GAGATTGATCCTTCTGAT AGTTATACTAACTACAAT CAAAAGTTCAAGGGC | 182 | 208B-515 CDR H2 | EIDPSDSYTNYNQKFKG |
| 208A-874 CDR H2 | 183 | GAGATTCATCCTTCTGAT AGTTATACTAGCTACAAT CAAAAGTTCAAGGAC | 184 | 208A-874 CDR H2 | EIHPSDSYTSYNQKFKD |
| 208B-911 CDR H2 | 185 | AATATTTATCCTTCTACC AGTCATACTAACTACAAT CAAAAGTTCAGGGAC | 186 | 208B-911 CDR H2 | NIYPSTSHTNYNQKFRD |
| 208B-1096 CDR H2 | 187 | TACATTGATCCTAGCTCT GGTTATACTGAATACAAT CATAAGATCCAGTAC | 188 | 208B-1096 CDR H2 | YIDPSSGYTEYNHKIQY |
| 208B-589 CDR H2 | 189 | TACATTGATCCTAGCTCT GGTTATACTGAATACAAT CATAAGATCCAGGAC | 190 | 208B-589 CDR H2 | YIDPSSGYTEYNHKIQD |
| 208B-395 CDR H2 | 191 | TACATTGATCCTAGCTCT GGTTATACTCAATACAAT CATAAGATCCAGGAC | 192 | 208B-395 CDR H2 | YIDPSSGYTQYNHKIQD |
| 208B-189 CDR H2 | 193 | TACATTGATCCTGCCTCT GGCTATACTGAATACAAT CAGAAGATCAAGGAC | 194 | 208B-189 CDR H2 | YIDPASGYTEYNQKIKD |
| 208B-547 CDR H2 | 195 | TACATTGATCCTAGCTCT GGTTATACTGAATACAAT CAGAAGATCAAGGAC | 196 | 208B-547 CDR H2 | YIDPSSGYTEYNQKIKD |
| 208A-210 CDR H2 | 197 | TGTATTTATCCTGGAGAT GTTAATACTGACTATAAT GAGAAGTTCAAGGGC | 198 | 208A-210 CDR H2 | CIYPGDVNTDYNEKFKG |
| 208A-422 CDR H2 208A-442 CDR H2 | 199 | TACATAAAGTACGACGGT GGCAATAACTACAGCCCA TCTCTCAAAAAT | 200 | 208A-422 CDR H2 208A-442 CDR H2 | YIKYDGGNNYSPSLKN |
| 208B-862 CDR H2 | 201 | TACATAAGCTACAGTGGT ACCACTGTCTACAGCCCA TCTCTCAAAAGT | 202 | 208B-862 CDR H2 | YISYSGTTVYSPSLKS |
| 208A-967 CDR H2 | 203 | GTAATATGGGCTGTTGGA AGTATAAATTATAATTCG GCTCTCATGTCC | 204 | 208A-967 CDR H2 | VIWAVGSINYNSALMS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-517 CDR H2 | 205 | GTGATATGGAGTGGTGGA AGCACAGACTATAATGCA GCTTTCATATCC | 206 | 208B-517 CDR H2 | VIWSGGSTDYNAAFIS |
| 208B-822 CDR H2 | 207 | GTGATATGGGGTGGTGGA AGCACAGGCTATAATGCA GCTTTCGTATCC | 208 | 208B-822 CDR H2 | VIWGGGSTGYNAAFVS |
| 208B-1024 CDR H2 | 209 | ACCATTAGTAGTGGTGGT AGTTATAGCTACTATCCA GACAGTGTAAAGGGG | 210 | 208B-1024 CDR H2 | TISSGGSYSYYPDSVKG |
| 208B-327 CDR H2 | 211 | ACCATTAGTGATGGTGGT AGTTACACCTTCTATCCA GACAGTGTGAAGGGA | 212 | 208B-327 CDR H2 | TISDGGSYTFYPDSVKG |
| 208B-353 CDR H2 | 213 | ACCATTAGTAGTGGTGGT GGTTACACCTACTATCCA GACAGTGTGAAGGGG | 214 | 208B-353 CDR H2 | TISSGGGYTYYPDSVKG |
| 208B-178 CDR H2 | 215 | GCCATTAATAGTAATGGT GGTAGCACCTACTATCCA GACACTGTGAAGGGC | 216 | 208B-178 CDR H2 | AINSNGGSTYYPDTVKG |
| 208B-672 CDR H2 | 217 | TACATTAGTAATGGTGGT GGTAACACCTACTATGTA GACACTGTAAAGGGC | 218 | 208B-672 CDR H2 | YISNGGGNTYYVDTVKG |
| 208B-793 CDR H2 | 219 | TACATTAGTAATGGTGGT GGTAGCACCTACTATTCA GACACTGTAAAGGGC | 220 | 208B-793 CDR H2 | YISNGGGSTYYSDTVKG |
| 208B-826 CDR H2 | 221 | TCCATTAGTAGTCGCACT AGTAAGATCTACTATGCA GACAACCTGAAGGGC | 222 | 208B-826 CDR H2 | SISSRTSKIYYADNLKG |
| 208B-174 CDR H2 | 223 | GAAATTAGATTGAGATCT GATAATTATGCAACCCAT TATGCGGAGTCTGTGAAA GGG | 224 | 208B-174 CDR H2 | EIRLRSDNYATHYAESVK G |
| 208B-408 CDR H2 | 225 | TTTATTAGAAACAAAGCT TATGGTTACACGACCGAG TTCAGTGCATCTGTGAAC GGT | 226 | 208B-408 CDR H2 | FIRNKAYGYTTEFSASVN G |
| 208B-612 CDR H2 | 227 | TATATTGATCCTCACAAT GATGATACAAAATACAGT GAGAAGTTCAGAGGT | 228 | 208B-612 CDR H2 | YIDPHNDDTKYSEKFRG |
| 208A-877 CDR H2 | 229 | GGTGTTAATCCTAACAAT GGTGATACTGTCTACACC CAGAAGTTCAAGGGC | 230 | 208A-877 CDR H2 | GVNPNNGDTVYTQKFKG |
| 208B-251 CDR H2 | 231 | GGTGTTAATCCTAACAAT GGTGATACTATCTACAAC CAGAAGTTCAAGGGC | 232 | 208B-251 CDR H2 | GVNPNNGDTIYNQKFKG |
| 208A-110 CDR H2 208B-1070 CDR H2 208A-334 CDR H2 208A-920 CDR H2 208A-126 CDR H2 208A-133 CDR H2 208B-556 CDR H2 208A-741 CDR H2 | 233 | GGTGTTAATCCTAACAAT GGTGATACTATCTTCAAC CAGAAGTTCAAGGGC | 234 | 208A-110 CDR H2 208B-1070 CDR H2 208A-334 CDR H2 208A-920 CDR H2 208A-126 CDR H2 208A-133 CDR H2 208B-556 CDR H2 208A-741 CDR H2 | GVNPNNGDTIFNQKFKG |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208A-159 CDR H2 | 235 | GGTGTTAATCCTAACAAT GGTGATACTATTTTCAAC CAGAAGTTCAAGGAC | 236 | 208A-159 CDR H2 | GVNPNNGDTIFNQKFKD |
| 208A-1064 CDR H3<br>208B-1094 CDR H3 | 237 | CGGGAACTGGACTACTTT GCCTCC | 238 | 208A-1064 CDR H3<br>208B-1094 CDR H3 | RELDYFAS |
| 208A-293 CDR H3 | 239 | CGGGAACTGGACTACTTT CCCTCC | 240 | 208A-293 CDR H3 | RELDYFPS |
| 208A-222 CDR H3 | 241 | CGACAACTGGACTACTTT GACTAT | 242 | 208A-222 CDR H3 | RQLDYFDY |
| 208A-605 CDR H3<br>208B-560 CDR H3 | 243 | CGACAACTGGACTTCTTT GACTAT | 244 | 208A-605 CDR H3<br>208B-560 CDR H3 | RQLDFFDY |
| 208A-830 CDR H3 | 245 | CGACAACTGGACTACTTT GACTTT | 246 | 208A-830 CDR H3 | RQLDYFDF |
| 208A-134 CDR H3<br>208A-692 CDR H3<br>208A-557 CDR H3<br>208A-352 CDR H3<br>208A-983 CDR H3 | 247 | AGTGGGACGGGGTTTACT TAC | 248 | 208A-134 CDR H3<br>208A-692 CDR H3<br>208A-557 CDR H3<br>208A-352 CDR H3<br>208A-983 CDR H3 | SGTGFTY |
| 208B-281 CDR H3 | 249 | AGTGGGACGGGGTTTATT TAC | 250 | 208B-281 CDR H3 | SGTGFIY |
| 208B-471 CDR H3 | 251 | TCTGGGGCGGGGGTTTAC | 252 | 208B-471 CDR H3 | SGAGVY |
| 208A-207 CDR H3<br>208A-638 CDR H3 | 253 | CATTACTACGGTGTTCTT GACTCC | 254 | 208A-207 CDR H3<br>208A-638 CDR H3 | HYYGVLDS |
| 208B-515 CDR H3 | 255 | CATTACTACGGTGTCTTT GACTCC | 256 | 208B-515 CDR H3 | HYYGVFDS |
| 208A-874 CDR H3 | 257 | GGGGGCTACTATAGGTAC GACGAGTTTGCTTAC | 258 | 208A-874 CDR H3 | GGYYRYDEFAY |
| 208B-911 CDR H3 | 259 | AATGCCTATTCTATGGAC TAC | 260 | 208B-911 CDR H3 | NAYSMDY |
| 208B-1096 CDR H3<br>208B-589 CDR H3<br>208B-395 CDR H3<br>208B-189 CDR H3<br>208B-547 CDR H3 | 261 | TTTGCTTAC | 262 | 208B-1096 CDR H3<br>208B-589 CDR H3<br>208B-395 CDR H3<br>208B-189 CDR H3<br>208B-547 CDR H3 | FAY |
| 208A-210 CDR H3 | 263 | TATTACTACGGTAGTTTT GCTTAC | 264 | 208A-210 CDR H3 | YYYGSFAY |
| 208A-422 CDR H3<br>208A-442 CDR H3 | 265 | GGGTCGGACTCCTTTGAC TAC | 266 | 208A-422 CDR H3<br>208A-442 CDR H3 | GSDSFDY |
| 208B-862 CDR H3 | 267 | AATTAC | 268 | 208B-862 CDR H3 | NY |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208A-967 CDR H3 | 269 | GATCGGACTACGGCTACC CCCTTCTTTGACTAC | 270 | 208A-967 CDR H3 | DRTTATPFFDY |
| 208B-517 CDR H3 | 271 | AATGGGGGGCTACGGCC TTTGACTAC | 272 | 208B-517 CDR H3 | NGGATAFDY |
| 208B-822 CDR H | 273 | AATGGAGGGCTACGGTC TTTGACTAC | 274 | 208B-822 CDR H | NGGATVFDY |
| 208B-1024 CDR H3 | 275 | CTCTACTACGGCTACGGG GACTAC | 276 | 208B-1024 CDR H3 | LYYGYGDY |
| 208B-327 CDR H3 | 277 | CCCCATGCTGGCTACTTC GGCTGGTTTGCTTAC | 278 | 208B-327 CDR H3 | PHAGYFGWFAY |
| 208B-353 CDR H3 | 279 | CTATACGGTAGCCTGTTT GCTTAC | 280 | 208B-353 CDR H3 | LYGSLFAY |
| 208B-178 CDR H3 | 281 | CATGGGGGACTGGGACGT AGGGACTGGTACTTCGAT GTC | 282 | 208B-178 CDR H3 | HGGLGRRDWYFDV |
| 208B-672 CDR H3 | 283 | CATGGGCTCTACTGGGGC TATTCTATGGACTAC | 284 | 208B-672 CDR H3 | HGLYWGYSMDY |
| 208B-793 CDR H3 | 285 | CATGGACTGGGAAGGACA GGGTTTGCTTCC | 286 | 208B-793 CDR H3 | HGLGRTGFAS |
| 208B-826 CDR H3 | 287 | TCCGTCTTTGGTAATTCT TAC | 288 | 208B-826 CDR H3 | SVFGNSYWFFDV |
| 208B-174 CDR H3 | 289 | ATGACGTAC | 290 | 208B-174 CDR H3 | MTY |
| 208B-408 CDR H3 | 291 | GTCCTCTACTATGATTAC GGGGGATTTGCTTAC | 292 | 208B-408 CDR H3 | VLYYDYGGFAY |
| 208B-612 CDR H3 | 293 | TATTCTTACGACAGGGAT TACAGTCCTATGGACTAC | 294 | 208B-612 CDR H3 | YSYDRDYSPMDY |
| 208A-877 CDR H3 | 295 | CGGGAACCGGACTTCTTT GACTAC | 296 | 208A-877 CDR H3 | REPDFFDY |
| 208B-251 CDR H3 208A-110 CDR H3 208B-1070 CDR H3 208A-334 CDR H3 208A-920 CDR H3 208A-159 CDR H3 208A-133 CDR H3 208B-556 CDR H3 208A-741 CDR H3 | 297 | CGGGAATTGGACTTCTTT GACTAC | 298 | 208B-251 CDR H3 208A-110 CDR H3 208B-1070 CDR H3 208A-334 CDR H3 208A-920 CDR H3 208A-159 CDR H3 208A-133 CDR H3 208B-556 CDR H3 208A-741 CDR H3 | RELDFFDY |
| 208A-126 CDR H3 | 299 | CGGGGATTGGACTTCTTT GACTAC | 300 | 208A-126 CDR H3 | RGLDFFDY |
| 208A-1064L | 301 | GACATTGTGCTGACACAG TCTCCTGCTTCCTTAATT GTTTCTCTGGGGCAGACG GCCACCATCTCATGCAGG GCCAGCCAAAGTGTCAGT ACATCTAGGTTTAGTTAT CTGCACTGGATCCAACAG AAACCAGGGCAGCCACCC AAACTCCTCATCAAGTAT GCATCCAACCTTGAATCT | 302 | 208A-1064L | DIVLTQSPASLIVSLGQT ATISCRASQSVSTSRFSY LHWIQQKPGQPPKLLIKY ASNLESGVPVRFSGSGSG TDFTLNIHPVEEEDTATY FCQHSWEFPFTFGSGTKL KIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GGGGTCCCTGTCAGGTTC AGTGGCAGTGGGTCTGGG ACAGACTTCACCCTCAAC ATCCATCCTGTGGAGGAG GAGGATACTGCAACATAT TTCTGTCAGCACAGTTGG GAGTTTCCATTCACGTTC GGCTCGGGGACAAAGTTG AAAATAAAACGGGCTGAT GCTGC | | | |
| 208B-1094L | 303 | GACATTGTGCTGACACAG TCTCCTGCTTCCTTAATT GTTTCTCTGGGGCAGACG GCCACCATCTCATGCAGG GCCAGCCAAAGTCTCAGT ACATCTAGGTTTAGCTAT GTGCACTGGATCCAACAG AAACCAGGGCAGCCACCC AAACTCCTCATCAAGTAT GCATCCAACCTTGAATCT GGGGTCCCTGTCAGGTTC AGTGGCAGTGGGTCTGGG ACAGACTTCACCCTCAAC ATCCATCCTGTGGAGGAG GAGGATACTGCAACATAT TTCTGTCAGCACAGTTGG GAGTTTCCATTCACGTTC GGCTCGGGGACAAAGTTG AAAATAAAACGGGCTGAT GCTGC | 304 | 208B-1094L | DIVLTQSPASLIVSLGQT ATISCRASQSLSTSRFSY VHWIQQKPGQPPKLLIKY ASNLESGVPVRFSGSGSG TDFTLNIHPVEEEDTATY FCQHSWEFPFTFGSGTKL KIKR |
| 208A-293L | 305 | GACATTGTGCTGACACAG TCTCCTGCTTCCTTAATT GTATCTCTGGGGCAGAGG GCCACCATCTCATGTAGG GCCAGCCAAAGTGTCAGT ACATCCAGGTTTAGTTAT GTGCACTGGATCCAACAG AAACCAGGGCAGCCACCC AAACTCCTCATCAAGTAT GCATCCAACCTTGAATCT GGGGTCCCTGTCAGGTTC AGTGGCAGTGGGTCTGGG ACAGACTTCATCCTCAAC ATCCATCCTGTGGAGGAG GAGGATACTGCAACATAT TTCTGTCAGCACAGTTGG GAGTTTCCATTCACGTTC GGCTCGGGGACAAAGTTG GAAATAAAACGGGCTGAT GCTGC | 306 | 208A-293L | DIVLTQSPASLIVSLGQR ATISCRASQSVSTSRFSY VHWIQQKPGQPPKLLIKY ASNLESGVPVRFSGSGSG TDFILNIHPVEEEDTATY FCQHSWEFPFTFGSGTKL EIKR |
| 208A-134L | 307 | GAAGTTTTGATGACCCAA AGTCCACTCTCCCTGCCT GTCAGTCTTGGAGATCAG GCCTCCATCTCTTGCAGA TCTAGTCAGAGCCTTGAA CATACTAATGGAAACACC TATTTAGAGTGGTTCCTG CAGAGACCAGGCCAGCCT CCAAAGCTCCTGATCTAC AAAGTTTCCAGCCGATTT TCTGGGGTCCCAGACAGG TTCAGTGGCAGTGGATCA GGGACAGATTTCACACTC AAGATCAGCAGAGTGGAG GCTGAGGATCTGGGAGTT TATTACTGTTTTCAAGGT TCACATGTTCCATTCACG TTCGGCTCGGGGACAAAG TTGGCAATAAAACGGGCT GATGCTGC | 308 | 208A-134L | EVLMTQSPLSLPVSLGDQ ASISCRSSQSLEHTNGNT YLEWFLQRPGQPPKLLIY KVSSRFSGVPDRFSGSGS GTDFTLKISRVEAEDLGV YYCFQGSHVPFTFGSGTK LAIKR |
| 208A-692L | 309 | GAATTTTGAATGACCCAA AGTCCACTCTCCCTGCCT | 310 | 208A-692L | EVLMTQSPLSLPVSLGDQ ASISCRSSQSLEHSNGNT |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GTCAGTCTTGGAGATCAG GCCTCCATCTCTTGCAGA TCTAGTCAGAGCCTTGAA CATAGTAATGGAAACACC TATTTAGAGTGGTTCCTG CAGAGACCAGGCCAGCCT CCAAAGCTCCTGATCTAC AAAGTTTCCAGCCGATTT TCTGGGGTCCCAGACAGG TTCAGTGGCAGTGGATCA GGGACAGATTTCACACTC AAGATCAGCAGAGTGGAG GCTGAGGATCTGGGAGTT TATTACTGTTTTCAAGGT TCACATGTTCCATTCACG TTCGGCTCGGGGACAAAG TTGGCAATAAACGGGCT CATGCTGC | | | YLEWFLQRPGQPPKLLIY KVSSRFSGVPDRFSGSGS GTDFTLKISRVEAEDLGV YYCFQGSHVPFTFGSGTK LAIKR |
| 208A-352L | 311 | GATGTTTTGATGGCCCAA ACTCCACTCTCCCTGCCT GTCACCCTTGGAGATCAA GCCTCCATCTCTTGCAGA TCTAGTCAGAGCCTTGTA CATAGTAATGGAAACACC TATTTAGAGTGGTTCCTG CAGAAACCAGGCCAGTCT CCAAAGCTCCTGATCTAC AACGTTTCCAACCGATTT TCTGGGGTCCCAGACAGG TTCAGTGGCAGTGGATCA GGGACAGATTTCACACTC AAGATCAGCAGAGTGGAG GCTGAGGATCTGGGAGTT TATTACTGCTTTCAAGGT TCACATGTTCCACTCACG TTCGGCTCGGGGACAAAG TTGGAAATAAACGGGCT GATGCTGC | 312 | 208A-352L | DVLMAQTPLSLPVTLGDQ ASISCRSSQSLVHSNGNT YLEWFLQKPGQSPKLLIY NVSNRFSGVPDRFSGSGS GTDFTLKISRVEAEDLGV YYCFQGSHVPLTFGSGTK LEIKR |
| 208A-983L | 313 | GATGTTTTGATGACCCAA ACTCCACTCTCCCTGCCT GTCAATCTTGGAGATCAG GCCTCCATCTCTTGCAGA TCTAGTCAGAGCCTTCTA CATAGTAATGGAAACACC TATTTAGAGTGGTTCCTG CAGAAACCAGGCCAGTCT CCAAAGCTCCTGATCTAC AATGTTTCCAACCGATTT TCTGGGGTCCCAGACAGG TTCAGTGGCAGTGGATCA GGGACAGATTTCACACTC AAGATCAGCAGAGTGGAG GCTGAGGATCTGGGAGTT TATTACTGCTTTCAAGGT TCACATGTTCCATTCACG TTCGGCTCGGGGACAAAG TTGGCAATAAACGGGCT GATGCTGC | 314 | 208A-983L | DVLMTQTPLSLPVNLGDQ ASISCRSSQSLLHSNGNT YLEWFLQKPGQSPKLLIY NVSNRFSGVPDRFSGSGS GTDFTLKISRVEAEDLGV YYCFQGSHVPFTFGSGTK LAIKR |
| 208B-281L | 315 | GATGTTTTGATGACCCAA ACTCCACTCTCCCTGCCT GTCAGTCTTGGAGATCAA GCCTCCATCTCTTGCAGA TCTAGTCAGAGCCTTGTA CATAATAATGGAAACACC TATTTAGAATGGTTCCTG CAGAAACCAGGCCAGTCT CCAAAGCTCCTGATCTAC AAAGTTTCCAACCGATTT TCTGGGGTCCCAGACAGG TTCAGTGGCAGTGGATCA GGGACAGATTTCACACTC AAGATCAGCAGAGTGGAG GCTGAGGATCTGGGAGTT | 316 | 208B-281L | DVLMTQTPLSLPVSLGDQ ASISCRSSQSLVHNNGNT YLEWFLQKPGQSPKLLIY KVSNRFSGVPDRFSGSGS GTDFTLKISRVEAEDLGV YYCFQGSHVPFTFGSGTK LEIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | TATTACTGCTTTCAAGGT TCACATGTTCCATTCACG TTCGGCTCGGGGACAAAG TTGGAAATAAAACGGGCT GATGCTGC | | | |
| 208B-1024L | 317 | GATGTTTTGATGACCCAA ACTCCACTCTCCCTGCCT GTCAGTCTTGGAGATCAA GCCTCCATCTCTTGCAGA TCTAGTCAGAGCATTGTA CACAGTAATGGAAACACC TATTTAGAGTGGTACCTG CAGAAACTAGGCCAGTCT CCAAAGCTCCTGATCTAC AGAGTTTCCAACCGATTT TCTGGGGTCCCAGACAGG TTCAGTGGCAGTGGATCA GGGACAGATTTCACACTC AAGATCAGCAGAGTGGAG GCTGAGGATCTGGGAGTT TATTACTGCTTTCAAGGT TCACATGTTCCGTGGACG TTCGGTGGAGGCACCAAG CTGGAAATCAAACGGGCT GATGCTGC | 318 | 208B-1024L | DVLMTQTPLSLPVSLGDQ ASISCRSSQSIVHSNGNT YLEWYLQKLGQSPKLLIY RVSNRFSGVPDRFSGSGS GTDFTLKISRVEAEDLGV YYCFQGSHVPWTFGGGTK LEIKR |
| 208B-471L | 319 | GATGTTGTGATGACCCAA ACTCCACTCTCCCTGCCT GTCAGTCTTGGAGATCAA GCCTCCATCTCTTGCAGA TCTAGTCAGAGCCTTCTA CATAGTAATGGAAACACC TATTTAGAATGGTACCTG CAGAAACCTGGCCAGTCT CCAAACCTCCTGATCTAC AATGTTTCCAACCGATTT TCTGGGGTCCCAGACAGG TTCAGTGGCAGTGGATCA GGGACAGATTTCGCACTC AAGATCAGCAGAGTGGGG GCTGAGGATCTGGGAGTT TATTACTGCTTTCAAGGT TCACATGTTCCGCTCACG TTCGGTGCTGGGACCAAG CTGGAGCTGAAACGGGCT GATGCTGC | 320 | 208B-471L | DVVMTQTPLSLPVSLGDQ ASISCRSSQSLLHSNGNT YLEWYLQKPGQSPNLLIY NVSNRFSGVPDRFSGSGS GTDFALKISRVGAEDLGV YYCFQGSHVPLTFGAGTK LELKR |
| 208B-862L | 321 | GATGTTGTGCTGACCCAA ACTCCACTCTCCCTGCCT CTCAGTCTTGGAGATCAG GCCTCCATCTCTTGCAGA TCTAGTCAGACCCTTCTA CACAGTGATGGAGACACC TATTTACATTGGTACCTG CAGAAGCCAGGCCAGTCT CCAAAGCTCCTGATCTAC AAACTTTCCAACCGATTT TCTGGGGTCCCAGACAGG TTCAGTGGCAGTGGATCA GGGACAGATTTCACACTC AAGATCAGCAGAGTGGAG GCTGAGGATCTGGGAGTT TATTTCTGCTCTCAAAGT ACACATGTTCCGTACACG TTCGGAGGGGGGACCAAG CTGGAAATAAAACGGGCT GATGCTGC | 322 | 208B-862L | DVVLTQTPLSLPFSFGNK ASIFCKFSQTLLHRDGNP FLLWYLQKPGQSPKLLIY KLSNRFFGVPKRFRGRGS GTNFPLKISKGEAEDLGV FFCSQSTHVPYTFGGGTK LEIKR |
| 208B-589L 208B-1096L | 323 | GATATTGTGATGACCCAG ACTCCACTCACTTTGTCG GTTACCATTGGACAACCA GCTTCCATCTCTTGCAAG TCAAGTCAGAGCCTCTTA TTTACTAATGGAAAAACC TATTTAAATTGGTTTTTA | 324 | 208B-589L 208B-1096L | DIVMTQTPLTLSVTIGQP ASISCKSSQSLLFTNGKT YLNWFLQRPGQSPKRLIY LLSKLDSGVPDRFSGSGS GTDFTLKISRVEAEDLGV YYCLQSTYFPLTFGAGTK LELKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | CAGAGGCCAGGCCAGTCT CCAAAACGCCTAATCTAT CTGCTGTCTAAATTGGAC TCTGGAGTCCCTGACAGG TTCAGTGGCAGTGGATCA GGGACAGATTTCACACTG AAAATCAGCAGAGTGGAG GCTGAGGATTTGGGAGTT TATTACTGCTTGCAGAGT ACATATTTTCCTCTCACG TTCGGTGCTGGGACCAAG CTGGAGCTGAAACGGGCT GATGCTGC | | | |
| 208B-189L | 325 | GATGTTGTGATGACCCAG ACTCCACTCACTTTGTCG GTTACCATTGGACAACCA GCTTCCATCTCTTGCAAG TCAAGTCAGAGCCTCTTA TATACTAATGGAAAGACC TATTTGAATTGGTTATTA CAGAGGCCAGGCCAGTCT CCAAAACGCCTAATCTAT CTGGTGTCAAAATTGGAC TCTGGAGTCCCTGACAGG TTCAGTGGCAGTGGATCA GGGACAGATTTCACACTG AAAATCAGCAGAGTGGAG GCTGAGGATTTGGGAGTT TATTACTGCTTGCAGAGT ATACATTTTCCGTACACG TTCGGAGGGGGGACCAAG CTGGACATAAAACGGGCT GATGCTGC | 326 | 208B-189L | DVVMTQTPLTLSVTIGQP ASISCKSSQSLLYTNGKT YLNWLLQRPGQSPKRLIY LVSKLDSGVPDRFSGSGS GTDFTLKISRVEAEDLGV YYCLQSIHFPYTFGGGTK LDIKR |
| 208B-327L | 327 | GATATTGTGATGACGCAG GCTGCATTCTCCAATCCA GTCACTCCTGGAACATCA GTTTCCATCTCCTGCAGG TCTAGTAAGAGTCTCCTA CATAGTAATGGCATCACT TATTTGTATTGGTATCTG CAGAAGCCAGGCCAGTCT CCTCAGCTCCTGATTTAT CAGATGTCCAAGATTGCC TCAGGAGTCCCAGACAGG TTCAGGAGCAGTGGGTCA GGAACTGATTTCACACTG AGAATCAGCAGAGTGGAG GCTGCGGATGTGGGTGTT TATTACTGTGCTCAAAAT CTAGAACTTCCGTGGACG TTCGGTGGAGGCACCAAG CTGGAAATCAAACGGGCT GATGCTGC | 328 | 208B-327L | DIVMTQAAFSNPVTPGTS VSISCRSSKSLLHSNGIT YLYWYLQKPGQSPQLLIY QMSKIASGVPDRFRSSGS GTDFTLRISRVEAADVGV YYCAQNLELPWTFGGGTK LEIKR |
| 208A-874L | 329 | GACATTGTGATGACCCAG TCTCACAAATTCATGTCC ACATCAATAGGAGACAGG GTCAGCATCACCTGCAAG GCCAGTCAGAATGTGAGT CCTGCTGTAGCCTGGTAT CAACAGAAACCAGGACAA TCTCCTAAACTACTGATT TACTCGGCATCCTCCCGA TACACTGGAGTCCCTGAT CGCTTCACTGGCAGTGGA TCTGGGACGGCTTTCACT TTCACCATCAGCAGTGTG CAGGCTGAAGACCTGGCA GTTTATTTCTGTCAGCAA CATTTTAGTACTCCGTGG ACGTTCGGTGGAGGCACC ATGCTGGAAATCAAACGG GCTGATGCTGC | 330 | 208A-874L | DIVMTQSHKFMSTSIGDR VSITCKASQNVSPAVAWY QQKPGQSPKLLIYSASSR YTGVPDRFTGSGSGTAFT FTISSVQAEDLAVYFCQQ HFSTPWTFGGGTMLEIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-353L | 331 | GACATTGTGATGACCCAGTCTCAAAAATTCATGTCCACAACAGTTGGGGACAGGGTCAGAGTCACCTGCAAGGCCAGTCAGAATGTGGGTACTGCTGTAGCCTGGTATCAACAGAAACCAGGACAATCTCCTAAACTACTGATTTACTCAGCATCCAATCGGTACACTGGAGTCCCTGATCGCTTCACAGGCAGTGGATCTGGGACAGATTTCACTCTCACCATTACCAATATGCAGTCTGAAGACCTGGCAGATTATTTCTGTCAGCAATATAGCACCTATCCTCTCACGTTCGGCTCGGGGGCAAAGTTGGAAATAAAACGGGCTGATGCTGC | 332 | 208B-353L | DIVMTQSQKFMSTTVGDRVRVTCKASQNVGTAVAWYQQKPGQSPKLLIYSASNRYTGVPDRFTGSGSGTDFTLTITNMQSEDLADYFCQQYSTYPLTFGSGAKLEIKR |
| 208B-793L | 333 | GACATTGTGATGACCCAGTCTCACAAATTCATGTCCACATCAGTAGGAGACAGGGTCAGCATCACCTGCAAGGCCAGTCAGGATGTGGGTACTGCTGTAGCCTGGTATCAACAGAAACCAGGACAATCTCCTAAACTACTGATTTACTGGGCATCCACCCGGCACACTGGAGTCCCTGATCGCTTCACAGGCAGTGGATCTGGGACAGATTTCACTCTCACCATTAGCAATGTGCAGTCTGAAGACTTGGCAGATTATTTCTGTCAGCAATATAGCAACTATCTCACGTTCGGTGCTGGGACCAAGCTGGAGGTGAAACGGGCTGATGCTGC | 334 | 208B-793L | DIVMTQSHKFMSTSVGDRVSITCKASQDVGTAVAWYQQKPGQSPKLLIYWASTRHTGVPDRFTGSGSGTDFTLTISNVQSEDLADYFCQQYSNYLTFGAGTKLEVKR |
| 208B-672L | 335 | GACATCCAGATGACCCAGTCTCCATCCTCCTTATCTGCCTCTCTGGGCGAAAGAGTCAGTCTCACTTGTCGGGCAAGTCAGGACATTGGTGGTAGCATAAACTGGCTTCAGCAGGAACCAGATGGAACTATTAAAGCCTGATCTACGCCACATCCAGTTTAGATTCTGGTGTCCCCAAAAGGTTCAGTGGCAGTAGGTCTGGGTCAGATTATTCTCTCACCATCAGCAGCCTTGAGTCTGAAGATTTTGTAGACTATTACTGTCTACAATATGCTAGTTCTCCTCCGACGTTCGGTGGAGGCACCAAACTGGAAATCAAACGGGCTGATGCTGC | 336 | 208B-672L | DIQMTQSPSSLSASLGERVSLTCRASQDIGGSINWLQQEPDGTIKRLIYATSSLDSGVPKRFSGSRSGSDYSLTISSLESEDFVDYYCLQYASSPPTFGGGTKLEIKR |
| 208B-408L | 337 | GACATCCAGATGACTCAGTCTCCAGCCTCCCTATCTGCATCTGTGGGAGAAACTGTCACCATCACATGTCGAGCAAGTGGGAATATTCACACTTATTTAGCATGGTATCAGCAGAAACAGGGAAAATCTCCTCAGCTCCTGGTCTACAATGCAAACACCTTGGCAGATGGTGTGCCATCAAGGTTCAGTGGCAGTGGATCAGGAACACAATTTTCTCTCAAGATCAACAGTCTGCAGCCTGACGATTTTGGGAGTTATTACTGTCAACATTTTTGGAGTGCTCCGTGG | 338 | 208B-408L | DIQMTQSPASLSASVGETVTITCRASGNIHTYLAWYQQKQGKSPQLLVYNANTLADGVPSRFSGSGSGTQFSLKINSLQPDDFGSYYCQHFWSAPWTFGGGTQLEIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | ACGTTCGGTGGAGGCACC CAGCTGGAAATCAAACGG GCTGATGCTGC | | | |
| 208A-207L 208B-826L | 339 | GATATTGTGTTAACTCAG TCTCCAGCCACCCTGTCT GTGACTCCAGGAGATAGA GTCAGTCTTTCCTGCAGG GCCAGTCAAAGAATTTAC AACTACCTACACTGGTAT CAACAAAAATCACATGAG TCTCCAAGGCTTCTCACC AAGTATGCTTCCCAGTCC ATCTCTGGGATCCCCTCC AGGTTCAGTGGCAGTGGC TCAGGGACAGATTTCATT CTCACTATCAACAGTGTG GAGACTGAAGATTTTGGA ATGTATTTCTGTCAACAG AGTAACAGCTGGCCTCTC ACGTTCGGTGCTGGGACC AAGCTGGAGCTGAGACGG GCTGATGCTGC | 340 | 208A-207L 208B-826L | DIVLTQSPATLSVTPGDR VSLSCRASQRIYNYLHWY QQKSHESPRLLTKYASQS ISGIPSRFSGSGSGTDFI LTINSVETEDFGMYFCQQ SNSWPLTFGAGTKLELRR |
| 208B-395L | 341 | GATATTGTGTTAACTCAG TCTCCAGCCACCCTGTCT GTGACTCCAGGAGATAGA GTCAGTCTTTCCTGCAGG GCCAGTCAAAGAATTTAC AACTACCTACACTGGTAT CAACAAAAATCACATGAG TCTCCAAGGCTTCTCATC AAGTATGCTTCCCAGTCC ATCTCTGGGATCCCCTCC AGGTTCAGTGGCAGTGGC TCAGGGACAGATTTCATT CTCACTATCAACAGTGTG GAGACTGAAGATTTTGGA ATGTATTTCTGTCAACAG AGTAACAGCTGGCCTCTC ACGTTCGGTGCTGGGACC AAGCTGGAGCTGAGACGG GCTGATGCTGC | 342 | 208B-395L | DIVLTQSPATLSVTPGDR VSLSCRASQRIYNYLHWY QQKSHESPRLLIKYASQS ISGIPSRFSGSGSGTDFI LTINSVETEDFGMYFCQQ SNSWPLTFGAGTKLELRR |
| 208B-517L | 343 | GACATTGTGATGACTCAG TCTCCAGCCACCCTGTCT GTGACTCCAGGAGATAGA GTCTCTCTTTCCTGCAGG GCCAGCCAGAGTATTAGC GACTACTTACACTGGTAT CAACAAAAATCACATGAG TCTCCAAGGCTTCTCATC AAATATGCTTCCCAATCC ATCTCTGGGATCCCCTCC AGGTTCCGTGGCAGTGGA TCAGGGTCACATTTCACT CTCAGTATCAACAGTGTG GAACCTGAAGATGTTGGA GTGTATTACTGTCAAAAT GGTCACAGTTTTCCGTGG ACGTTCGGTGGAGGCACC AAGCTGGAAATCAAACGG GCTGATGCTGC | 344 | 208B-517L | DIVMTQSPATLSVTPGDR VSLSCRASQSISDYLHWY QQKSHESPRLLIKYASQS ISGIPSRFRGSGSGSHFT LSINSVEPEDVGVYYCQN GHSFPWTFGGGTKLEIKR |
| 208B-822L | 345 | GACATTGTGATGACTCAG TCTCCAGCCACCCTGTCT GTGACTCCAGGAGATAGA GTCTCTCTTTCCTGCAGG GCCAGCCAGACTATTAGC GACTACTTACACTGGTAT CAACAAAAATCGCATGAG TCTCCAAGGCTTCTCATC AAATATGCTTCCCAATCC ATCTCTGGGATCCCCTCC AGGTTCAGTGGCAGTGGA TCAGGGTCACATTTCACT | 346 | 208B-822L | DIVMTQSPATLSVTPGDR VSLSCRASQTISDYLHWY QQKSHESPRLLIKYASQS ISGIPSRFSGSGSGSHFT LSINSVEPEDVGVYYCQN GHSFPWTFGGGTKLEIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | CTCAGTATCAACAGTGTG GAACCTGAAGATGTTGGA GTGTATTACTGTCAAAAT GGTCACAGTTTTCCGTGG ACGTTCGGTGGAGGCACC AAGCTGGAAATCAAACGG GCTGATGCTGC | | | |
| 208A-210L | 347 | GAGATTGTGCTCACTCAG TCTCCAGCCATCACAGCT GCATCTCTGGGGCAAAAC GTCACCATCACCTGCAGA GCCAGCTCAAGTGTAAGT TACATGCATTGGTACCGG CAGAAGTCCGGCACCTCC CCCCAACTATGGATTTAT GAGATATCAGACGGGCT TCTGGAGTCCCAGCTCGC TTCCGTGCCAGTGGGTCT GGGACCTCTTATTCTCTC ACAATCAGCAGCATGGAG GCTGAAGATGCTGCCATT TATTACTGCCAGCAGTGG AATTATCCTCTCACGTTC GGTGCTGGGACCAAGCTG GAGGTGAAACGGGCTGAT GCTGC | 348 | 208A-210L | EIVLTQSPAITAASLGQN VTITCRASSSVSYMHWYR QKSGTSPQLWIYEISRRA SGVPARFRASGSGTSYSL TISSMEAEDAAIYYCQQW NYPLTFGAGTKLEVKR |
| 208B-547L | 349 | GAAGTTGTGCTCACTCAG TCTCCAGCCATCACAGCT GCATCTCTGGGGCAAAAG GTCACCATCACCTGCAGA GCCAGCTCAAGTGTAAGT TACATGCACTGGTACCGG CAGAAGTCAGGCACCTCC CCCCAGCCATGGATTTAT GAAATATCCACACTGGCT TCTGGAGTCCCAACTCGC TTCCGTGCCAGTGGGTCT GGGACCTCTTATTCTCTC ACAATCAGCAGCATGGAG GCTGAAGATGCTGCCATT TATTACTGCCAGCAGTGG AATTATCCTCTCACGTTC GGTGCTGGGACCAAGCTG GAACTGAAACGGGCTGAT GCTGC | 350 | 208B-547L | EVVLTQSPAITAASLGQK VTITCRASSSVSYMHWYR QKSGTSPQPWIYEISTLA SGVPTRFRASGSGTSYSL TISSMEAEDAAIYYCQQW NYPLTFGAGTKLELKR |
| 208A-638L | 351 | CAAATTGTTCTCACCCAG TCTCCAACAATCATGTCT GCATCTCTAGGGGAACGG GTCACCATGACCTGCACT GCCAGCTCAAGTGTGAGT TCCAGTTACTTGCACTGG TTCCAGCAGAAGCCAGGA TCCTCCCCCAAACTCTGG ATTTATAGCACATCCAAC CTGGCTTCTGGAGTCCCA CCTCGCTTCAGTGGCAGT GGGTCTGGGACCTCTTAC TCTCTCTCAATCAGCAGC GTGGAGGCTGAAGATGTT GCCACTTATTACTGCCTC CAGTTTCATCGTTCCCCG TGGACGTTCGGTGGAGGC GCCAAGTTGGAAATCAAA CGGGCTGATGCTGC | 352 | 208A-638L | QIVLTQSPTIMSASLGER VTMTCTASSSVSSSYLHW FQQKPGSSPKLWIYSTSN LASGVPPRFSGSGSGTSY SLSISSVEAEDVATYYCL QFHRSPWTFGGGAKLEIK R |
| 208B-515L | 353 | CAAATTGTTTTCACCCAG TATCCAGCAATAATGTCT GCATCTCTAGGGGAACGG GTCACCATGACCTGCACA GCCAGCTCAAGTGTAACT TCCAGTTACTTGCACTGG TTCCAGCAGAAGCCAGGA TCCTCCCCCAAACTCTGG | 354 | 208B-515L | QIVFTQYPAIMSASLGER VTMTCTASSSVTSSYLHW FQQKPGSSPKLWIYSTSN PGSGVPARFSGRGSGTSY SLSISSMEAEDAATYYCL QFHRSPWTFGGGTKLEIR R |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | ATTTATAGCACGTCCAAC CCGGGTTCTGGAGTCCCA GCTCGCTTCAGTGGCAGA GGATCTGGGACCTCTTAC TCTCTCTCAATCAGCAGC ATGGAGGCTGAAGATGCT GCCACTTATTACTGCCTC CAGTTTCATCGTTCCCCG TGGACGTTCGGTGGAGGC ACCAAGCTGGAAATCAGA CGGGCTGATGCTGC | | | |
| 208A-877L | 355 | CAAATTGTTCTCACCCAG TCTCCAGCAATCATGTCT GTATCTCCAGGGGAGAAG GTCTCCATGACCTGCAGT GCCAGCTCAAGTGTCACT TACATGCACTGGTATCAG CAGAAGTCAGGCACCTCC CCCAAAAGATGGATTTAT GACACATCCGAGCTGGCT TCTGGAGTCCCTGCTCGC TTCAGTGGCAGTGGGTCT GGGACCACTTACTCTCTC ACAATCAGCAGCATGGAG GCTGAAGATGCTGCCACT TATTACTGCCAGCAGTGG AGTAATAAACCGCTCACG TTCGGTGCTGGGACCAAG CTGGAGCTGAAACGGGCT GATGCTGC | 356 | 208A-877L | QIVLTQSPAIMSVSPGEK VSMTCSASSSVTYMHWYQ QKSGTSPKRWIYDTSELA SGVPARFSGSGSGTTYSL TISSMEAEDAATYYCQQW SNKPLTFGAGTKLELKR |
| 208B-174L | 357 | CAAAATGTTCTCACCCAG TCTCCAGCAATCATGTCT GCATCTCCAGGGGAGAAG GTCACCATGTCCTGCAGT GCCAGCTCAAGTGTCACT TACATGTTCTGGTACCAG CTGAAGCCAGAATCCTCC CCCAGACTCCTGATTTAT GACACATCCAATTTGGCT TCTGGCGTCCCTGTTCGC TTCAGTGGCAGTGGGTCT GGGACCTCTTACTCTCTC ACAATCAGCCGTATGGAG GCTGAAGATGCTGCCACT TATTACTGCCAGGAGTGG AGTAGTTACCCACTCACG TTCGGTGCTGGGACCAAG CTGGACCTGAAACGGGCT GATGCTGC | 358 | 208B-174L | QNVLTQSPAIMSASPGEK VTMSCSASSSVTYMFWYQ LKPESSPRLLIYDTSNLA SGVPVRFSGSGSGTSYSL TISRMEAEDAATYYCQEW SSYPLTFGAGTKLDLKR |
| 208B-612L | 359 | CAAATTGTTCTCACCCAG TCTCCAACACTCATGTCT GCATCGCCAGGAGAAAAG GTCACCATGACCTGCAGT GCCAGCTCAACTGTGACT TACATTTACTGGTACCAA CAGAAGCCCGGCTCCTCC CCCAGACTCTGGATGTAT GACACATTCAACCTGGTT TCTGGAGTCCCTGCTCGC TTCAGTGGCAGTAGGTCT GGGACCTCTTATTTTCTC ACAATCAGTAGCATGGAG GGTGAAGATGCTGCCACT TATTACTGCCAACAGTAC AGTGATTCCCCGTACACG TTCGGAGGGGGGACCAAG CTGGAGATAAAACGGGCT GATGCTGC | 360 | 208B-612L | QIVLTQSPTLMSASPGEK VTMTCSASSTVTYIYWYQ QKPGSSPRLWMYDTFNLV SGVPARFSGSRSGTSYFL TISSMEGEDAATYYCQQY SDSPYTFGGGTKLEIKR |
| 208B-911L | 361 | CAAATTGTTCTCACCCAG TCTCCAGAGATCATGTCT GCATCTCCAGGGGAGAAG GTCACCATAACCTGCAGT | 362 | 208B-911L | QIVLTQSPEIMSASPGEK VTITCSASSSVSFMYWFQ QKPGTSPKLWIYITSNLA SGVPTRFSGSGSGTSYSL |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GCCAGCTCAAGTGTAAGT<br>TTCATGTATTGGTTCCAG<br>CAGAAGCCAGGCACTTCT<br>CCCAAACTCTGGATTTAT<br>ATCACATCCAACCTGGCT<br>TCTGGAGTCCCTACTCGC<br>TTCAGTGGCAGTGGATCT<br>GGGACCTCTTACTCTCTC<br>ACAATCAGCCGAATGGAG<br>GCTGAAGATGCTGCCACT<br>TATTACTGCCAGCAAAGG<br>AGTAGTTTCCCGTACACG<br>TTCGGAGGGGGGACCAAA<br>CTGGAAATGAAACGGGCT<br>GATGCTGC | | | TISRMEAEDAATYYCQQR<br>SSFPYTFGGGTKLEMKR |
| 208A-422L<br>208A-442L | 363 | GACATTGTGCTGACCCAA<br>TCTCCAGCTTCTTTGGCT<br>GTGTCTCTAGGGCAGAGG<br>GCCATCATCTCCTGCAAG<br>GCCAGCCAAAGTGTCAGT<br>TTTGCTGGTACTAATTTA<br>ATGCACTGGTACCAACAG<br>AAACCAGGACAGCAACCC<br>AAACTCCTCATCTATCGT<br>GCATCCAACCTAGAAACT<br>GGGGTTCCTACCAGGTTT<br>AGTGGCAGTGGGTCTAGG<br>ACAGACTTCACCCTCAAT<br>ATCCATCCTGTGGAGGAA<br>GATGATGCTGCAACCTAT<br>TACTGTCAGCAAAGTAGG<br>GAATATTACACGTTCGGA<br>GGGGGGACCAAGCTGGAA<br>ATAAAACGGGCTGATGCT<br>GC | 364 | 208A-422L<br>208A-442L | DIVLTQSPASLAVSLGQR<br>AIISCKASQSVSFAGTNL<br>MHWYQQKPGQQPKLLIYR<br>ASNLETGVPTRFSGSGSR<br>TDFTLNIHPVEEDDAATY<br>YCQQSREYYTFGGGTKLE<br>IKR |
| 208A-967L | 365 | GACATTGTGCTGACCCAA<br>TCTCCAGCTTCTTTGGCT<br>GGGTCTCTAGGGAAAAGG<br>GCCCCCATCTCCTGCAAA<br>GCCAGCGAAAGTGTCAAT<br>TTTTTTGGTACTAATTTA<br>ATACACTGGTACCAACAA<br>AAACCAGGACAGCCCCCC<br>AAACTCCTCATCTATCAT<br>GCATCCAACCTAAAAACT<br>GGAGTCCCTGCCAGGTTC<br>AGGGGCAGGGGGTCTAAA<br>ACAAACTTCCCCCCTCCCC<br>ATTGATCCTGTGGAGGAA<br>AATGATGTTGCAATCTAT<br>TACTGTCTGCAAAATAGG<br>AAAATTCCTCTCACGTTC<br>GGGGTTGGGACCAAGCTG<br>GAGCTGAAACGGGCTGAT<br>GCTGC | 366 | 208A-967L | DIVLTQSPASLAGSLGKR<br>APISCKASESVNFFGTNL<br>IHWYQQKPGQPPKLLIYH<br>ASNLKTGVPARFRGRGSK<br>TNFPLPIDPVEENDVAIY<br>YCLQNRKIPLTFGVGTKL<br>ELKR |
| 208B-178L | 367 | GACATTGTGCTGACCCAA<br>TCTCCAGCTTCTTTGGCT<br>GTGTCTCTAGGGCAGAGG<br>GCCACCATCTCCTGCAGA<br>GCCAGCGAAAGTGTTGAT<br>AATTATGGCATTAGTTTT<br>ATGCACTGGTACCAGCAG<br>AAACCAGGACAGCCACCC<br>AAACTCCTCATCTATCGT<br>GCATCCAACCTAGAATCT<br>GGGATCCCTGCCAGGTTC<br>AGTGGCAGTGGGTCTAGG<br>ACAGACTTCACCCTCACC<br>ATTAATCCTGTGGAGACT<br>GATGATGTTGCAACCTAT<br>TACTGTCAGCAAAGTAAT<br>AAGGATCCATTCACGTTC<br>GGCTCGGGGGCAAAGTTG | 368 | 208B-178L | DIVLTQSPASLAVSLGQR<br>ATISCRASESVDNYGISF<br>MHWYQQKPGQPPKLLIYR<br>ASNLESGIPARFSGSGSR<br>TDFTLTINPVETDDVATY<br>YCQQSNKDPFTFGSGAKL<br>EIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GAAATAAAACGGCTGAT GCTGC | | | |
| 208A-222L 208A-605L 208B-560L | 369 | GACATTGTGGTGACACAG TCTCCTGCTTCCTTAGCT GTATCTCTGGGGCAGAGG GCCACCATCTCATGCAGG GCCAGCCAAAGTGTCAGT ACATCTAGATATAGTTAT CTGCACTGGTACCAACAG AAACCAGGACAACCTCCC AAACTCCTCATCAAGTAT GCATCCAACCTAGAATCT GGGGTCCCTGCCAGGTTC AGTGGCAGTGGGTCTGGG ACAGACTTCACCCTCAAT ATCCATCCTGTGGGGGAG GAGGATACTGCAACATAT TACTGTCAGCACAGTTGG GAGTTTCCATTCACGTTC GGCTCGGGGACAAAGTTG GAAATAAAACGGCTGAT GCTGC | 370 | 208A-222L 208A-605L 208B-560L | DIVVTQSPASLAVSLGQR ATISCRASQSVSTSRYSY LHWYQQKPGQPPKLLIKY ASNLESGVPARFSGSGSG TDFTLNIHPVGEEDTATY YCQHSWEFPFTFGSGTKL EIKR |
| 208A-830L | 371 | GACATTGTACTGACACAG TCTCCTGCTTCCTTAGCT GTATCTCTGGGGCAGAGG GCCACCATCTCATGCAGG TCCAGCCAAAGTGTCAGT ACATCTAGATATAGTTAT TTGCACTGGTACCAACAG AAACCAGGACAACCTCCC AAACTCCTCATCAAGTAT GCATCCAACCTAGAATCT GGGGTCCCTGCCAGGTTC AGTGGCAGTGGGTCTGGG ACAGACTTCACCCTCAAC ATCCATCCTGTGGGGAG GAGGATCCTGCAACATAT TACTGTCAGCACAGTTGG GAGTTTCCATTCACGTTC GGCTCGGGGACAAAGTTG GAAATAAAACGGCTGAT GCTGC | 372 | 208A-830L | DIVLTQSPASLAVSLGQR ATISCRSSQSVSTSRYSY LHWYQQKPGQPPKLLIKY ASNLESGVPARFSGSGSG TDFTLNIHPVGEEDPATY YCQHSWEFPFTFGSGTKL EIKR |
| 208A-557L | 373 | GACATTGCCCTGACACAG TCTCCTGCTTCGTTAGCT GTATCTCTGGGGCAGAGG GCCACCATCTCATGCAGG GCCAGCCAAAGTGTCAGT ACATCTAGATATAGTTATT ATGCACTGGTACCAACAG AAACCAGGACAACCACCC GAACTCCTCATCAAGTAT GCATCCAACCTAGAATCT GGGGTCCCTGCCAGGTTC AGTGGCAGTGGGTCTGGG ACAGACTTCACCCTCAAC ATCCATCCTGTGGGGGAG GAGGATACTGCAACATAT TACTGTCAGCACAGTTGG GATTTTCCATTCACGTTC GGCTCGGGGACAAAGTTG GAAATAAAACGGCTGAT GCTGC | 374 | 208A-557L | DIALTQSPASLAVSLGQR ATISCRASQSVSTSRYSY MHWYQQKPGQPPELLIKY ASNLESGVPARFSGSGSG TDFTLNIHPVGEEDTATY YCQHSWDFPFTFGSGTKL EIKR |
| 208A-133L 208B-556L | 375 | GACATTGTGCTGACACAG TCTCCTGCTTCCTTAGCT GTTTCTCTGGGGCAGAGG GCCACCATCTCATGCAGG GCCAGCCAAAGTGTCAGT ACATCTAGGTATAGCTAC ATGCACTGGTACCAACAG AAACCAGGACAGCCACCC AAACTCCTCATCAAGTAT GCATCCAACCTAGAATCT | 376 | 208A-133L 208B-556L | DIVLTQSPASLAVSLGQR ATISCRASQSVSTSRYSY MHWYQQKPGQPPKLLIKY ASNLESGVPARFSGSGSG TDFTLNIHPVAEEDTATY YCQHSWEFPFTFGSGTKL EIKR |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GGGGTCCCTGCCAGGTTC AGTGGCAGTGGGTCTGGG ACAGACTTCACCCTCAAC ATCCATCCTGTGGCGGAG GAGGATACTGCAACATAT TACTGTCAGCACAGTTGG GAGTTTCCATTCACGTTC GGCTCGGGGACAAAGTTG GAAATAAAACGGGCTGAT GCTGC | | | |
| 208B-1070L | 377 | GACATTGTGCTGACACAG TCTCTTGCTTCCTTAGCT GTTTCTCTGGGGCAGAGG GCCACCATCTCATGCAGG GCCAGCCAAAGTGTCAGT ACATCTAGGTATAGTTAT ATGCACTGGTACCAACAG AAACCAGGACAGCCACCC AAACTCCTCATCAAGTAT GCATCCAACCTTGAATGT GGGGTCCGTGCCAGGTTC AGTGGCAGTGGGTGTGGG ACAGACTTCACCCTCAAC ATCCATCCTGTGGAGGAG GAGGATACTGCAGCATAT TACTGTCAGCACAGTTGG GAGTTTCCATTCACGTTC GGCTCGGGGACAAAATTG GAAATAAAACGGGCTGAT GCTGC | 378 | 208B-1070L | DIVLTQSLASLAVSLGQR ATISCRASQSVSTSRYSY MHWYQQKPGQPPKLLIKY ASNLECGVRARFSGSGCG TDFTLNIHPVEEEDTAAY YCQHSWEFPFTFGSGTKL EIKR |
| 208A-159L | 379 | GACATTGTACTGACACAG TCTCCTGCTTCCTTAGCT GTTTCTCTGGGGCAGAGG GCCACCATCTCCTGCAGG GCCAGCCAAAGTGTCAGT ACATCTAGGTATAGTTAT GTGCACTGGTATCAACAG AAACCAGGACAGCCACCC AAACTCCTCATCAAGTAT GCAGCCAACCTAGAATCT GGGGTCCCTGCCAGGTTC AGTGGCAGTGGGTCTGGG ACAGACTTCACCCTCAAC ATCCATCCTGTGGCGGAG GAGGATGCTGCAGCATAT TACTGTCAGCACAGTTGG GAGTTTCCATTCACGTTC GGCTCGGGGACAAAGTTG GAAATAAAACGGGCTGAT GCTGC | 380 | 208A-159L | DIVLTQSPASLAVSLGQR ATISCRASQSVSTSRYSY VHWYQQKPGQPPKLLIKY AANLESGVPARFSGSGSG TDFTLNIHPVAEEDAAAY YCQHSWEFPFTFGSGTKL EIKR |
| 208A-741L | 381 | GACATTGTGCTGACACAG TCTCCTGCTTCCTTAGCT GTTTCTCTGGGGCAGAGG ACCACCATCTCATGCGGG GCCAGCCAAAGTGTCAGT ACATCTAGGTTTAGTTAT ATGCACTGGTACCAACAG AAACCAGGACAGCCACCC AAACTCCTCATCAAGTAT GCATCCAACCTAGAATCT GGGGTCCCTGCCAGGTTC AGTGGCAGTGGGTCTGGG ACAGACTTCACCCTCAAC ATCCATCCTGTGGCGGAG GAGGATACTGCAGCATAT TACTGTCAGCACAGTTGG GAGTTTCCATTCACGTTC GGCTCGGGGACAAAGTTG GAAATAAAACGGGCTGAT GCTGC | 382 | 208A-741L | DIVLTQSPASLAVSLGQR TTISCGASQSVSTSRFSY MHWYQQKPGQPPKLLIKY ASNLESGVPARFSGSGSG TDFTLNIHPVAEEDTAAY YCQHSWEFPFTFGSGTKL EIKR |
| 208A-334L | 383 | GACATTGTGCTGACACAG TCTCCTGCTTCCTTAGCT | 384 | 208A-334L | DIVLTQSPASLAVSLGQR ATISCRASQSVSTSRYSY |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| | | GTTTCTCTGGGGCAGAGG<br>GCCACCATCTCATGCAGG<br>GCCAGCCAAAGTGTCAGT<br>ACATCTAGGTATAGTTAT<br>ATGCACTGGTACCAACAG<br>AAACCAGGACAGCCACCC<br>AAACTCCTCATCAAGTAT<br>GCATCCAACCTAGAATCT<br>GGGGTCCCTGCCAGGTTC<br>AGTGGCAGTGGGTCTGGG<br>ACAGACTTCACCCTCAAC<br>ATCCATCCTGTGGCGGAG<br>GAGGATACTGCAGCATAT<br>TACTGTCAGCACAGTTGG<br>GGGTTTCCATTCACGTTC<br>GGCTCGGGGACAAAGTTG<br>GAAATAAAGCGGGCTGAT<br>GCTGC | | | MHWYQQKPGQPPKLLIKY<br>ASNLESGVPARFSGSGSG<br>TDFTLNIHPVAEEDTAAY<br>YCQHSWGFPFTFGSGTKL<br>EIKR |
| 208B-251L | 385 | GACATTGTGCTGACACAG<br>TCTCCTGCTTCCTTAGCT<br>GTATCTTTGGGAAAAAAG<br>GCCACCATCTCATGCAGG<br>GCCAGCCAAAGTGTCAGT<br>ACATCTAGGTATAGTTAT<br>ATGCACTGGTACCAACAG<br>AAACCAGGACACCCACCC<br>AAACTCCTCATCAAATAT<br>GCATCCAACCTAGAATCT<br>GGGGTCCCTGCCAGGTTC<br>AGTGGCAGTGGGTCTGGG<br>ACAGACTTCACCCTCAAC<br>ATCCATCCTGTGGCGGAG<br>GAGGATACTGCAGCATAT<br>TACTGTCAGCACAGTTGG<br>GAGTTTCCATTCACGTTC<br>GGCTCGGGGACAAAGTTG<br>GAAATAAAACGGGCTGAT<br>GCTGC | 386 | 208B-251L | DIVLTQSPASLAVSLGKK<br>ATISCRASQSVSTSRYSY<br>MHWYQQKPGHPPKLLIKY<br>ASNLESGVPARFSGSGSG<br>TDFTLNIHPVAEEDTAAY<br>YCQHSWEFPFTFGSGTKL<br>EIKR |
| 208A-110L<br>208A-126<br>208A-920L | 387 | GACATTGTGCTGACACAG<br>TCTCCTGCTTCCTTAGCT<br>GTTTCTCTGGGGCAGAGG<br>GCCACCATCTCATGCAGG<br>GCCAGCCAAAGTGTCAGT<br>ACATCTAGGTATAGTTAT<br>ATGCACTGGTACCAACAG<br>AAACCAGGACAGCCACCC<br>AAACTCCTCATCAAGTAT<br>GCATCCAACCTTGAATCT<br>GGGGTCCCTGCCAGGTTC<br>AGTGGCAGTGGGTCTGGG<br>ACAGACTTCACCCTCAAC<br>ATCCATCCTGTGGCGGAG<br>GAGGATACTGCAGCATAT<br>TACTGTCAGCACAGTTGG<br>GAGTTTCCATTCACGTTC<br>GGCTCGGGGACAAAATTG<br>GAAATAAAACGGGCTGAT<br>GCTGC | 388 | 208A-110L<br>208A-126<br>208A-920L | DIVLTQSPASLAVSLGQR<br>ATISCRASQSVSTSRYSY<br>MHWYQQKPGQPPKLLIKY<br>ASNLESGVPARFSGSGSG<br>TDFTLNIHPVAEEDTAAY<br>YCQHSWEFPFTFGSGTKL<br>EIKR |
| 208A-692CDRL1 | 389 | AGATCTAGTCAGAGCCTT<br>GAACATAGTAATGGAAAC<br>ACCTATTTAGAG | 390 | 208A-692CDRL1 | RSSQSLEHSNGNTYLE |
| 208A-352CDRL1 | 391 | AGATCTAGTCAGAGCCTT<br>GTACATAGTAATGGAAAC<br>ACCTATTTAGAG | 392 | 208A-352CDRL1 | RSSQSLVHSNGNTYLE |
| 208A-983CDRL1<br>208B-471CDRL1 | 393 | AGATCTAGTCAGAGCCTT<br>GTACATAGTAATGGAAAC<br>ACCTATTTAGAG | 394 | 208A983CDRL1<br>208B-471CDRL1 | RSSQSLLHSNGNTYLE |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-1024CDRL1 | 395 | AGATCTAGTCAGAGCATT GTACACAGTAATGGAAAC ACCTATTTAGAG | 396 | 208B-1024CDRL1 | RSSQSIVHSNGNTYLE |
| 208A-134CDRL1 | 397 | AGATCTAGTCAGAGCCTT GAACATACTAATGGAAAC ACCTATTTAGAG | 398 | 208A-134CDRL1 | RSSQSLEHTNGNTYLE |
| 208B-281CDRL1 | 399 | AGATCTAGTCAGAGCCTT GTACATAATAATGGAAAC ACCTATTTAGAA | 400 | 208B-281CDRL1 | RSSQSLVHNNGNTYLE |
| 208B-372CDRL1 | 401 | AGGTCTAGTAAGAGTCTC CTACATAGTAATGGCATC ACTTATTTGTAT | 402 | 208B-372CDRL1 | RSSKSLLHSNGITYLY |
| 208B-862CDRL1 | 403 | AGATCTAGTCAGACCCTT CTACACAGTGATGGAGAC ACCTATTTACAT | 404 | 208B-862CDRL1 | KFSQTLLHRDGNPFLL |
| 208B-589CDRL1 208B-1096CDRL1 | 405 | AAGTCAAGTCAGAGCCTC TTATTTACTAATGGAAAA ACCTATTTAAAT | 406 | 208B-589CDRL1 208B-1096CDRL1 | KSSQSLLFTNGKTYLN |
| 208B-189CDRL1 | 407 | AAGTCAAGTCAGAGCCTC TTATATACTAATGGAAAG ACCTATTTGAAT | 408 | 208B-189CDRL1 | KSSQSLLYTNGKTYLN |
| 208A-874CDRL1 | 409 | AAGGCCAGTCAGAATGTG AGTCCTGCTGTAGCC | 410 | 208A-874CDRL1 | KASQNVSPAVA |
| 208B-353CDRL1 | 411 | AAGGCCAGTCAGAATGTG GGTACTGCTGTAGCC | 412 | 208B-353CDRL1 | KASQNVGTAVA |
| 208B-793CDRL1 | 413 | AAGGCCAGTCAGGATGTG GGTACTGCTGTAGCC | 414 | 208B-793CDRL1 | KASQDVGTAVA |
| 208B-672CDRL1 | 415 | CGGGCAAGTCAGGACATT GGTGGTAGCATAAAC | 416 | 208B-672CDRL1 | RASQDIGGSIN |
| 208B-408CDRL1 | 417 | CGAGCAAGTGGGAATATT CACACTTATTTAGCA | 418 | 208B-408CDRL1 | RASGNIHTYLA |
| 208A-207CDRL1 208B-826CDRL1 208B-395CDRL1 | 419 | AGGGCCAGTCAAAGAATT TACAACTACCTACAC | 420 | 208A-207CDRL1 208B-826CDRL1 208B-395CDRL1 | RASQRIYNYLH |
| 208B-517CDRL1 | 421 | AGGGCCAGCCAGAGTATT AGCGACTACTTACAC | 422 | 208B-517CDRL1 | RASQSISDYLH |
| 208B-822CDRL1 | 423 | AGGGCCAGCCAGACTATT AGCGACTACTTACAC | 424 | 208B-822CDRL1 | RASQTISDYLH |
| 208A-210CDRL1 | 425 | AGAGCCAGCTCAAGTGTA AGTTACATGCAT | 426 | 208A-210CDRL1 | RASSSVSYMH |
| 208B-547CDRL1 | 427 | AGAGCCAGCTCAAGTGTA AGTTACATGCAT | 428 | 208B-547CDRL1 | RASSSVSYMH |
| 208A-638CDRL1 | 429 | ACTGCCAGCTCAAGTGTG AGTTCCAGTTACTTGCAC | 430 | 208A-638CDRL1 | TASSSVSSSYLH |
| 208B-515CDRL1 | 431 | ACAGCCAGCTCAAGTGTA ACTTCCAGTTACTTGCAC | 432 | 208B-515CDRL1 | TASSSVTSSYLH |
| 208A-877CDRL1 | 433 | AGTGCCAGCTCAAGTGTC ACTTACATGCAC | 434 | 208A-877CDRL1 | SASSSVTYMH |
| 208B-174CDRL1 | 435 | AGTGCCAGCTCAAGTGTC ACTTACATGTTC | 436 | 208B-174CDRL1 | SASSSVTYMF |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-612CDRL1 | 437 | AGTGCCAGCTCAACTGTGACTTACATTTAC | 438 | 208B-612CDRL1 | SASSTVTYIY |
| 208B-911CDRL1 | 439 | AGTGCCAGCTCAAGTGTAAGTTTCATGTAT | 440 | 208B-911CDRL1 | SASSSVSFMY |
| 208A-422CDRL1 208A-442CDRL1 | 441 | AAGGCCAGCCAAAGTGTCAGTTTTGCTGGTACTAATTTAATGCAC | 442 | 208A-422CDRL1 208A-442CDRL1 | KASQSVSFAGTNLMH |
| 208A-967CDRL1 | 443 | AAAGCCAGCGAAAGTGTCAATTTTTTTGGTACTAATTTAATACAC | 444 | 208A-967CDRL1 | KASESVNFFGTNLIH |
| 208B-178CDRL1 | 445 | AGAGCCAGCGAAAGTGTTGATAATTATGGCATTAGTTTTATGCAC | 446 | 208B-178CDRL1 | RASESVDNYGISFMH |
| 208A-222CDRL1 208A-605CDRL1 208B-560CDRL1 | 447 | AGGGCCAGCCAAAGTGTCAGTACATCTAGATATAGTTATCTGCAC | 448 | 208A-222CDRL1 208A-605CDRL1 208B-560CDRL1 | RASQSVSTSRYSYLH |
| 208A-557CDRL1 208A-133CDRL1 208B-556CDRL1 208B-1070CDRL1 208B-251CDRL1 208A-110CDRL1 208A-126CDRL1 208A-920CDRL1 208A-334CDRL1 | 449 | AGGGCCAGCCAAAGTGTCAGTACATCTAGGTATAGTTATATGCAC | 450 | 208A-557CDRL1 208A-133CDRL1 208B-556CDRL1 208B-1070CDRL1 208B-251CDRL1 208A-110CDRL1 208A-126CDRL1 208A-920CDRL1 208A-334CDRL1 | RASQSVSTSRYSYMH |
| 208A-741CDRL1 | 451 | GGGGCCAGCCAAAGTGTCAGTACATCTAGGTTTAGTTATATGCAC | 452 | 208A-741CDRL1 | GASQSVSTSRFSYMH |
| 208A-830CDRL1 | 453 | AGGTCCAGCCAAAGTGTCAGTACATCTAGATATAGTTATTTGCAC | 454 | 208A-830CDRL1 | RSSQSVSTSRYSYLH |
| 208A-1064CDRL1 | 455 | AGGGCCAGCCAAAGTGTCAGTACATCTAGGTTTAGTTATCTGCAC | 456 | 208A-1064CDRL1 | RASQSVSTSRFSYLH |
| 208A-159CDRL1 | 457 | AGGGCCAGCCAAAGTGTCAGTACATCTAGGTATAGTTATGTGCACTGG | 458 | 208A-159CDRL1 | RASQSVSTSRYSYVH |
| 208A-293CDRL1 | 459 | AGGGCCAGCCAAAGTGTCAGTACATCCAGGTTTAGTTATGTGCAC | 460 | 208A-293CDRL1 | RASQSVSTSRFSYVH |
| 208B-1094CDRL1 | 461 | AGGGCCAGCCAAAGTCTCAGTACATCTAGGTTTAGCTATGTGCAC | 462 | 208B-1094CDRL1 | RASQSLSTSRFSYVH |
| 208A-692CDRL2 208A-134CDRL2 | 463 | AAAGTTTCCAGCCGATTTTCT | 464 | 208A-692CDRL2 208A-134CDRL2 | KVSSRFS |
| 208B-281CDRL2 | 465 | AAAGTTTCCAACCGATTTTCT | 466 | 208B-281CDRL2 | KVSNRFS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-862CDRL2 | 467 | AAACTTTCCAACCGATTTTCT | 468 | 208B-862CDRL2 | KLSNRFF |
| 208A-352CDRL2 208A-983CDRL2 208B-471CDRL2 | 469 | AATGTTTCCAACCGATTTTCT | 470 | 208A-352CDRL2 208A-983CDRL2 208B-471CDRL2 | NVSNRFS |
| 208B-1024CDRL2 | 471 | AGAGTTTCCAACCGATTTTCT | 472 | 208B-1024CDRL2 | RVSNRFS |
| 208B-327CDRL2 | 473 | CAGATGTCCAAGATTGCCTCA | 474 | 208B-327CDRL2 | QMSKIAS |
| 208B-589CDRL2 208B-1096CDRL2 | 475 | CTGCTGTCTAAATTGGACTCT | 476 | 208B-589CDRL2 208B-1096CDRL2 | LLSKLDS |
| 208A-189CDRL2 | 477 | CTGGTGTCAAAATTGGACTCT | 478 | 208A-189CDRL2 | LVSKLDS |
| 208B-874CDRL2 | 479 | TCGGCATCCTCCCGATACACT | 480 | 208B-874CDRL2 | SASSRYT |
| 208B-353CDRL2 | 481 | TCAGCATCCAATCGGTACACT | 482 | 208B-353CDRL2 | SASNRYT |
| 208B-793CDRL2 | 483 | TGGGCATCCACCCGGCACACT | 484 | 208B-793CDRL2 | WASTRHT |
| 208B-672CDRL2 | 485 | GCCACATCCAGTTTAGATTCT | 486 | 208B-672CDRL2 | ATSSLDS |
| 208B-408CDRL2 | 487 | AATGCAAACACCTTGGCAGAT | 488 | 208B-408CDRL2 | NANTLAD |
| 208A-207CDRL2 208B-826CDRL2 208B-395CDRL2 208B-517CDRL2 | 489 | GCTTCCCAGTCCATCTCTGGG | 490 | 208A-207CDRL2 208B-826CDRL2 208B-395CDRL2 208B-517CDRL2 | ASQSISG |
| 208B-822CDRL2 | 491 | TATGCTTCCCAATCCATCTCT | 492 | 208B-822CDRL2 | YASQSIS |
| 208A-210CDRL2 | 493 | GAGATATCCAGACGGGCTTCT | 494 | 208A-210CDRL2 | EISRRAS |
| 208B-547CDRL2 | 495 | GAAATATCCACACTGGCTTCT | 496 | 208B-547CDRL2 | EISTLAS |
| 208A-638CDRL2 | 497 | AGCACATCCAACCTGGCTTCT | 498 | 208A-638CDRL2 | STSNLAS |
| 208B-515CDRL2 | 499 | AGCACGTCCAACCCGGGTTCT | 500 | 208B-515CDRL2 | STSNPGS |
| 208A-877CDRL2 | 501 | GACACATCCGAGCTGGCTTCT | 502 | 208A-877CDRL2 | DTSELAS |
| 208B-174CDRL2 | 503 | GACACATCCAATTTGGCTTCT | 504 | 208B-174CDRL2 | DTSNLAS |
| 208B-612CDRL2 | 505 | GACACATTCAACCTGGTTTCT | 506 | 208B-612CDRL2 | DTFNLVS |
| 208B-911CDRL2 | 507 | ATCACATCCAACCTGGCTTCT | 508 | 208B-911CDRL2 | ITSNLAS |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208A-422CDRL2<br>208A-442CDRL2 | 509 | CGTGCATCCAACCTAGAAACT | 510 | 208A-422CDRL2<br>208A-442CDRL2 | RASNLET |
| 208A-967CDRL2 | 511 | CATGCATCCAACCTAAAAACT | 512 | 208A-967CDRL2 | HASNLKT |
| 208B-178CDRL2 | 513 | CGTGCATCCAACCTAGAATCT | 514 | 208B-178CDRL2 | RASNLES |
| 208A-222CDRL2<br>208A-605CDRL2<br>208B-560CDRL2<br>208A-557CDRL2<br>208A-133CDRL2<br>208B-556CDRL2<br>208B-251CDRL2<br>208A-110CDRL2<br>208A-126CDRL2<br>208A-920CDRL2<br>208A-334CDRL2<br>208A-741CDRL2<br>208A-830CDRL2<br>208A-1064CDRL2<br>208A-159CDRL2<br>208A-293CDRL2<br>208B-1094CDRL2 | 515 | TATGCATCCAACCTAGAATCT | 516 | 208A-222CDRL2<br>208A-605CDRL2<br>208B-560CDRL2<br>208A-557CDRL2<br>208A-133CDRL2<br>208B-556CDRL2<br>208B-251CDRL2<br>208A-110CDRL2<br>208A-126CDRL2<br>208A-920CDRL2<br>208A-334CDRL2<br>208A-741CDRL2<br>208A-830CDRL2<br>208A-1064CDRL2<br>208A-159CDRL2<br>208A-293CDRL2<br>208B-1094CDRL2 | YASNLES |
| 208B-1070CDRL2 | 517 | TATGCATCCAACCTTGAATGT | 518 | 208B-1070CDRL2 | YASNLEC |
| 208A-692CDRL3<br>208A-983CDRL3<br>208B-281CDRL3<br>208A-134CDRL3 | 519 | TTTCAAGGTTCACATGTTCCATTCACG | 520 | 208A-692CDRL3<br>208A-983CDRL3<br>208B-281CDRL3<br>208A-134CDRL3 | FQGSHVPFT |
| 208A-352CDRL3<br>208B-471CDRL3 | 521 | TTTCAAGGTTCACATGTTCCACTCACG | 522 | 208A-352CDRL3<br>208B-471CDRL3 | FQGSHVPLT |
| 208B-1024CDL3 | 523 | TTTCAAGGTTCACATGTTCCGTGGACG | 524 | 208B-1024CDL3 | FQGSHVPWTF |
| 208B-327CDRL3 | 525 | GCTCAAAATCTAGAACTTCCGTGGACG | 526 | 208B-327CDRL3 | AQNLELPWT |
| 208B-862CDRL3 | 527 | TCTCAAAGTACACATGTTCCGTACACG | 528 | 208B-862CDRL3 | SQSTHVPYT |
| 208B-589CDRL3<br>208B-1096CDRL3 | 529 | TTGCAGAGTACATATTTTCCTCTCACG | 530 | 208B-589CDRL3<br>208B-1096CDRL3 | LQSTYFPLT |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-189CDRL3 | 531 | TTGCAGAGTATACATTTTCCGTACACG | 532 | 208B-189CDRL3 | LQSIHFPYT |
| 208B-672CDRL3 | 533 | CTACAATATGCTAGTTCTCCTCTCACG | 534 | 208B-672CDRL3 | LQYASSPPT |
| 208A-638CDRL3<br>208B-515CDRL3 | 535 | CTCCAGTTTCATCGTTCCCCGTGGACG | 536 | 208A-638CDRL3<br>208B-515CDRL3 | LQFHRSPWT |
| 208A-967CDRL3 | 537 | CTGCAAAATAGGAAAATTCCTCTCACG | 538 | 208A-967CDRL3 | LQNRKIPLT |
| 208A-874CDRL3 | 539 | CAGCAACATTTTAGTACTCCGTGGACG | 540 | 208A-874CDRL3 | QQHFSTPWT |
| 208B-353CDRL3 | 541 | CAGCAATATAGCACCTATCCTCTCACG | 542 | 208B-353CDRL3 | QQYSTYPLT |
| 208B-793CDRL3 | 543 | CAGCAATATAGCAACTATCTCACG | 544 | 208B-793CDRL3 | QQYSNYLT |
| 208A-207CDRL3<br>208B-826CDRL3<br>208B-395CDRL3 | 545 | CAACAGAGTAACAGCTGGCCTCTCACG | 546 | 208A-207CDRL3<br>208B-826CDRL3<br>208B-395CDRL3 | QQSNSWPLT |
| 208A-210CDRL3<br>208B-547CDRL3 | 547 | CAGCAGTGGAATTATCCTCTCACG | 548 | 208A-210CDRL3<br>208B-547CDRL3 | QQWNYPLT |
| 208A-877CDRL3 | 549 | CAGCAGTGGAGTAATAAACCGCTCACG | 550 | 208A-877CDRL3 | QQWSNKPLT |
| 208B-612CDRL3 | 551 | CAACAGTACAGTGATTCCCCGTACACG | 552 | 208B-612CDRL3 | QQYSDSPYT |
| 208B-911CDRL3 | 553 | CAGCAAAGGAGTAGTTTCCCGTACACG | 554 | 208B-911CDRL3 | QQRSSFPYT |
| 208A-422CDRL3<br>208A-442CDRL3 | 555 | CAGCAAAGTAGGGAATATTACACG | 556 | 208A-422CDRL3<br>208A-442CDRL3 | QQSREYYT |
| 208B-178CDRL3 | 557 | CAGCAAAGTAATAAGGATCCATTCACG | 558 | 208B-178CDRL3 | QQSNKDPFT |
| 208B-517CDRL3<br>208B-822CDRL3 | 559 | CAAAATGGTCACAGTTTTCCGTGGACG | 560 | 208B-517CDRL3<br>208B-822CDRL3 | QNGHSFPWT |
| 208B-408CDRL3 | 561 | CAACATTTTTGGAGTGCTCCGTGGACG | 562 | 208B-408CDRL3 | QHFWSAPWT |
| 208B-174CDRL3 | 563 | CAGGAGTGGAGTAGTTACCCATTCACG | 564 | 208B-174CDRL3 | QEWSSYPLT |
| 208A-222CDRL3<br>208A-605CDRL3<br>208B-560CDRL3<br>208A-133CDRL3<br>208B-556CDRL3<br>208B-1070CDRL3 | 565 | CAGCACAGTTGGGAGTTTCCATTCACG | 566 | 208A-222CDRL3<br>208A-605CDRL3<br>208B-560CDRL3<br>208A-133CDRL3<br>208B-556CDRL3<br>208B-1070CDRL3 | QHSWEFPFT |

APPENDIX A-continued

DESCRIPTION OF SEQUENCES

| mAb Clone | SEQ ID | Nucleic Acid Seq | SEQ ID | mAb Clone | Amino Acid Seq |
|---|---|---|---|---|---|
| 208B-251CDRL3 | | | | 208B-251CDRL3 | |
| 208A-110CDRL3 | | | | 208A-110CDRL3 | |
| 208A-126CDRL3 | | | | 208A-126CDRL3 | |
| 208A-920CDRL3 | | | | 208A-920CDRL3 | |
| 208A-741CDRL3 | | | | 208A-741CDRL3 | |
| 208A-830CDRL3 | | | | 208A-830CDRL3 | |
| 208A-1064CDRL3 | | | | 208A-1064CDRL3 | |
| 208A-159CDRL3 | | | | 208A-159CDRL3 | |
| 208A-293CDRL3 | | | | 208A-293CDRL3 | |
| 208B-1094CDRL3 | | | | 208B-1094CDRL3 | |
| 208A-557CDRL3 | 567 | CAGCACAGTTGGGATTTTCCATTCACG | 568 | 208A-557CDRL3 | QHSWDFPFT |
| 208A-334CDRL3 | 569 | CAGCACAGTTGGGATTTTCCATTCACG | 570 | 208A-334CDRL3 | QHSWGFPFT |
| HCV core 1-169 amino acid sequence | 571 | ATGTCTACCAACCCGAAACCGCAGAAAAAAAACAAACGTAACACCAACCGTCGTCCGCAGGACGTTAAATTCCCGGGTGGTGGTCAGATCGTTGGTGGTGTTTACCTGCTGCCGCGTCGTGGTCCGCGTCTGGGTGTTCGTGCTACGCGTAAAACCTCTGAACGTTCTCAGCCGCGTGGGCGTCGTCAGCCGATCCCGAAAGCTCGTCGTCCGGAAGGTCGTACCTGGGCTCAGCCGGGTTACCCGTGGCCGCTGTACGGTAACGAAGGTTGCGGTTGGGCTGGTTGGCTGCTGTCTCCGCGTGGATCTCGTCCGTCTTGGGGTCCGACCGACCCGCGTCGTCGTTCTCGTAACCTTGGTAAAGTTATCGATACCCTGACCTGCGGTTTCGCTGACCTGATGGGTTACATACCGCTGGTTGGAGCTCCGCTGGGTGGTGCTGCTCGTGCTCTGGCGCATGGCGTGCGTGTTCTGGAAGATGGCGTCAACTATGCCACCGGTAATCTG | 572 | HCV core 1-169 amino acid sequence | MSTNPKPQKKNKRNTNRRPQDVKFPGGGQIVGGVYLLPRRGPRLGVRATRKTSERSQPRGRRQPIPKARRPEGRTWAQPGYPWPLYGNEGCGWAGWLLSPRGSRPSWGPTDPRRRSRNLGKVIDTLTCGFADLMGYIPLVGAPLGGAARALAHGVRVLEDGVNYATGNL |
| | | | 573 | HCV 134-154 Peptide 1 | MGYIPLVGAPLGGAARALAHG |
| | | | 574 | HCV 141-161 Peptide 2 | GAPLGGAARALAHGVRVLEDG |
| | | | 575 | HCV 151-171 Peptide 3 | LAHGVRVLEDGVNYATGNLPG |
| | | | 576 | ALRZ-8 | MGYIPLVGAPLGGAARALAHGVRVLEDGVNYATGNLPGC |
| | | | 577 | ALRZ-9 | MGYIPLVGAPLGGAARALAHGVRVLEDGVNYATGNLPGQYIKANSKFIGITEL |

The invention claimed is:

1. A monoclonal antibody that is specifically immunoreactive with the lipid binding domain of HCV core antigen, wherein said monoclonal antibody has a heavy chain variable domain of SEQ ID NO: 6; and a light chain of SEQ ID NO: 306.

2. An immunoassay reagent comprising a monoclonal antibody of claim 1 wherein said antibody is labeled with a detectable label.

3. An immunoassay reagent comprising a monoclonal antibody of claim 1 wherein said antibody is bound to a solid phase.

4. The immunoassay reagent of claim 2 further comprising an additional antibody against an HCV antigen.

5. The immunoassay reagent of claim 4 wherein said additional antibody is an additional anti-core antibody.

6. An immunoassay for the detection of HCV in a test sample, said immunoassay comprising:
   (i) contacting a test sample suspected of containing HCV with a first antibody directed against HCV core antigen to form a complex between said first antibody and antigen located within said test sample;
   (ii) contacting said complex formed in step (i) with an antibody of claim 5, to form a complex between said antibody and antigen in the complex formed in step (i) wherein said antibody is detectably labeled and
   (iii) detecting the labeled of the complex formed in step (ii).

7. The immunoassay of claim 6, wherein said first antibody is directed to the DNA binding domain of HCV core antigen.

8. The immunoassay of claim 6 wherein said antibody of step (ii) is labeled with a fluorescent label.

9. The immunoassay of claim 8 wherein said label is acridinium.

10. The immunoassay of claim 6 wherein said antibody of step (i) is bound to a solid phase.

11. The immunoassay of claim 6 wherein said antibody of step (i) comprises a monoclonal antibody that is specifically immunoreactive with the lipid binding domain of HCV core antigen and that is distinct from the antibody of step (ii).

12. The immunoassay of claim 6 wherein said antibody of step (i) comprises a monoclonal antibody that is specifically immunoreactive with the lipid binding domain of HCV core antigen and that is the same as the antibody of step (ii).

13. The immunoassay method of claim 6, wherein the test sample was obtained from a patient and the method further comprises diagnosing, prognosticating, or assessing the efficacy of a therapeutic/prophylactic treatment of the patient, wherein, if the method further comprises assessing the efficacy of a therapeutic/prophylactic treatment of the patent, the method optionally further comprises modifying the therapeutic/prophylactic treatment of the patient as needed to improve efficacy.

14. The immunoassay method of claim 13, wherein the method is adapted for use in an automated system or a semi-automated system.

15. A kit comprising the immunodiagnostic reagent of claim 1 and instructions for the use of the immunodiagnostic reagent in the immunoassay for detection HCV in a test sample.

16. The immunoassay reagent of claim 3 further comprising an additional antibody against an HCV antigen.

* * * * *